(12) United States Patent
Tsai et al.

(10) Patent No.: US 11,382,924 B2
(45) Date of Patent: *Jul. 12, 2022

(54) COMPOUNDS AND PHARMACEUTICAL USES THEREOF

(71) Applicant: SyneuRx International (Taiwan) Corp., New Taipei (TW)

(72) Inventors: Guochuan Emil Tsai, Pasadena, CA (US); Yi-Wen Mao, New Taipei (TW); Lu-Ping Lu, New Taipei (TW); Wei-Hua Chang, New Taipei (TW); Han-Yi Hsieh, New Taipei (TW); Jhe Wei Hu, New Taipei (TW); Tsai-Miao Shih, New Taipei (TW); ChanHui Huang, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/377,829

(22) Filed: Jul. 16, 2021

(65) Prior Publication Data

US 2022/0054516 A1 Feb. 24, 2022

Related U.S. Application Data

(63) Continuation of application No. PCT/CN2021/075789, filed on Feb. 7, 2021, which is a continuation of application No. 17/014,774, filed on Sep. 8, 2020, now Pat. No. 11,154,531.

(60) Provisional application No. 63/014,448, filed on Apr. 23, 2020, provisional application No. 62/977,219, filed on Feb. 15, 2020, provisional application No. 62/971,972, filed on Feb. 8, 2020.

(51) Int. Cl.
| | | |
|---|---|---|
| A61K 31/7032 | (2006.01) | |
| A61K 9/00 | (2006.01) | |
| A61P 31/14 | (2006.01) | |
| A61K 45/06 | (2006.01) | |

(52) U.S. Cl.
CPC ......... *A61K 31/7032* (2013.01); *A61K 9/008* (2013.01); *A61K 45/06* (2013.01); *A61P 31/14* (2018.01)

(58) Field of Classification Search
None
See application file for complete search history.

(56) References Cited

U.S. PATENT DOCUMENTS

| 5,571,551 | A | 11/1996 | Fusi et al. |
| 6,489,287 | B1 | 12/2002 | Gauthier et al. |
| 8,652,533 | B2 | 2/2014 | Hara et al. |
| 10,105,378 | B2 | 10/2018 | Tsai et al. |
| 10,265,336 | B2 | 4/2019 | Tsai et al. |
| 2007/0197610 | A1 | 8/2007 | Kennis et al. |
| 2008/0096959 | A1 | 4/2008 | Hara et al. |
| 2009/0118202 | A1 | 5/2009 | Thekkumkara |
| 2009/0170928 | A1 | 7/2009 | Bruno et al. |
| 2011/0287109 | A1 | 11/2011 | Bagley et al. |
| 2017/0362394 | A1 | 12/2017 | Chigurupati et al. |
| 2018/0092935 | A1 | 4/2018 | Tsai et al. |
| 2018/0133237 | A1 | 5/2018 | Tsai et al. |
| 2019/0201427 | A1 | 7/2019 | Tsai et al. |
| 2019/0367549 | A1 | 12/2019 | Tsai et al. |
| 2020/0390791 | A1 | 12/2020 | Tsai et al. |

FOREIGN PATENT DOCUMENTS

| CN | 1398871 | A | | 2/2003 | |
| CN | 1450077 | A | | 10/2003 | |
| CN | 1454599 | A | | 11/2003 | |
| CN | 1560077 | A | | 1/2005 | |
| CN | 1568968 | A | | 1/2005 | |
| CN | 1602853 | A | * | 4/2005 | ............. A61K 31/28 |
| CN | 101618066 | A | | 1/2010 | |
| CN | 102127125 | A | | 7/2011 | |
| CN | 102180917 | A | | 9/2011 | |
| CN | 102250159 | A | | 11/2011 | |
| CN | 102743419 | A | | 10/2012 | |
| CN | 105687226 | A | * | 6/2016 | ........... A61K 31/353 |
| EP | 0413056 | A1 | | 2/1991 | |
| JP | 2012-116791 | A | | 6/2012 | |
| KR | 2009-0072527 | A | | 7/2009 | |
| WO | WO 2000/015044 | A1 | | 3/2000 | |
| WO | WO 2008/131047 | A2 | | 10/2008 | |
| WO | WO 2009/000864 | A1 | | 12/2008 | |
| WO | WO 2010/056413 | A2 | | 5/2010 | |
| WO | WO 2011/085454 | A1 | | 7/2011 | |
| WO | WO 2012/144754 | A2 | | 10/2012 | |
| WO | WO 2013/096182 | A2 | | 6/2013 | |
| WO | WO 2017/167168 | A1 | | 10/2017 | |
| WO | WO 2019/228408 | A1 | | 12/2019 | |

OTHER PUBLICATIONS

Chiou, W. C., Chen, J. C., Chen, Y. T., Yang, J. M., Hwang, L. H., Lyu, Y. S., . . . & Huang, C. (2021). The inhibitory effects of PGG and EGCG against the SARS-CoV-2 3C-like protease. Biochemical and Biophysical Research Communications. (Year: 2021).*
U.S. Appl. No. 17/058,920, filed Nov. 25, 2020, Tsai et al.
U.S. Appl. No. 17/014,774, filed Sep. 8, 2020, Tsai et al.

(Continued)

*Primary Examiner* — Dale R Miller

(74) *Attorney, Agent, or Firm* — McDermott Will & Emery LLP

(57) ABSTRACT

A method of treating coronavirus infection, comprising administering to a subject in need thereof an effective amount of a composition, wherein the composition comprises one or more compounds of Formula (I):

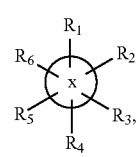

(I)

or a pharmaceutically acceptable salt thereof.

24 Claims, 19 Drawing Sheets

(56) References Cited

OTHER PUBLICATIONS

[No Author Listed], Nuts and Seeds in Health and Disease Prevention, 1st Edition. Preedy, Ed. Academic Press. Apr. 14, 2011:506.
[No Author Listed], The use of tannic acid in the local treatment of burn wounds: intriguing old and new perspectives. Wounds. 2001;13(4):1-19.
Abdelwahed et al., Study of antimutagenic and antioxidant activities of gallic acid and 1,2,3,4,6-pentagalloylglucose from Pistacia lentiscus. Confirmation by microarray expression profiling. Chem Biol Interact. Jan. 5, 2007;165(1):1-13. Epub Oct. 21, 2006.
Fan et al., Inhibitory effects of tannic acid on fatty acid synthase and 3T3-L1 preadipocyte. Biochim Biophys Acta. Jul. 2013;1831(7):1260-6.
Hu et al., Mitogenic activity of (−)epigallocatechin gallate on B-cells and investigation of its structure-function relationship. Int J Immunopharmacol. Nov. 1992;14(8):1399-407.
Jeyaseelan et al., Antibacterial activity of sequentially extracted organic solvent extracts of fruits, flowers and leaves of *Lawsonia inermis* L. from Jaffna. Asian Pac J Trop Biomed. Oct. 2012;2(10):798-802.
Karas et al., Galloylation of polyphenols alters their biological activity. Food Chem Toxicol. Jul. 2017;105:223-240. doi: 10.1016/j.fct.2017.04.021. Epub Apr. 18, 2017.
Lavoie et al., Complete (1)H and (13)C NMR assignments of a series of pergalloylated tannins. Magn Reson Chem. Feb. 2016;54(2):168-74. Epub Sep. 9, 2015.
Liou et al., Optimal operating conditions on batch extraction. J Nat Chiao Tung Univ. Dec. 1976;2:83-94.
Liu et al., In Vivo and In Vitro Anti-Arthritic Effects of Cardenolide-Rich and Caffeoylquinic Acid-Rich Fractions of Periploca forrestii. Molecules. Aug. 9, 2018;23(8):1988(1-16).
Liu et al., Tannic acid stimulates glucose transport and inhibits adipocyte differentiation in 3T3-L1 cells. J Nutr. Feb. 2005;135(2):165-71.
Nakazono et al., Chemiluminescence enhancement of 1,2-di[3,4,5-tri(3,4,5-trihydroxybenzoyloxy)benzoyloxy] benzene in the presence of quaternary ammonium ions. Luminescence. Sep.-Oct. 2010;25(5):360-3.
Niemetz et al., Ellagitannin biosynthesis: oxidation of pentagalloylglucose to tellimagrandin II by an enzyme from Tellima grandiflora leaves. Chem Commun. Dec. 11, 2000:35-36.
Nishizawa et al., Structure of Gallotannins in Paeoniae Radix. Chem Pharm Bull. Dec. 31, 1980;28(9):2850-2.
Nishizawa et al., Tannins and related compounds. Part 5. Isolation and characterization of polygalloylglucoses from Chinese gallotannin. J Chem Soc, Perkin Trans 1. 1982;(0):2963-8.
Ono et al., Anti-amyloidogenic activity of tannic acid and its activity to destabilize Alzheimer's beta-amyloid fibrils in vitro. Biochim Biophys Acta. Nov. 5, 2004;1690(3):193-202.
Qiao et al., Research progress in Galla chinensis and gallic tannins. Sci Tech Food Industry. Jul. 31, 2011:458-462.
Ren et al., Synthesis and structure-activity relationship study of antidiabetic penta-O-galloyl-D-glucopyranose and its analogues. J Med Chem. May 4, 2006;49(9):2829-37.
Sancheti et al., 1,2,3,4,6-penta-O-galloyl-β-d-glucose: A cholinesterase inhibitor from Terminalia chebula. S Afr J Bot. Apr. 2010;76(2):285-8.
Sekowski et al., Interaction of α-synuclein with Rhus typhina tannin—Implication for Parkinson's disease. Colloids Surf B Biointerfaces. Jul. 1, 2017;155:159-165. Epub Apr. 10, 2017.
Sylla et al., Gallotannins and Tannic Acid: First Chemical Syntheses and In Vitro Inhibitory Activity on Alzheimer's Amyloid β-Peptide Aggregation. Angew Chem Int Ed Engl. Jul. 6, 2015;54(28):8217-21. Epub May 26, 2015.
Theisen et al., Tannins from Hamamelis virginiana bark extract: characterization and improvement of the antiviral efficacy against influenza A virus and human papillomavirus. PLoS One. Jan. 31, 2014;9(1):e88062(1-14).
Tian et al., Antioxidant and antimicrobial activities of consecutive extracts from Galla chinensis:The polarity affects the bioactivities. Food Chem. Mar. 1, 2009;113(1):173-9.
Toda et al., Inhibitory effects of ellagi- and gallotannins on rat intestinal alpha-glucosidase complexes. Biosci Biotechnol Biochem. Mar. 2001;65(3):542-7.
Viswanatha et al., Anticonvulsant activity of 1,2,3,4,6-penta-O-galloyl-β-D-glucopyranose isolated from leaves of Mangifera indica. Naunyn Schmiedebergs Arch Pharmacol. Jul. 2013;386(7):599-604. Epub Apr. 9, 2013.
Wu et al., Preparation of gallnut tannins liposome and its quality evaluation. Sci Tech Food Industry. Mar. 31, 2015;36(3):74-77, 81.
Chen et al., Inhibition of SARS-CoV 3C-like Protease Activity by Theaflavin-3,3'-digallate (TF3). Evid Based Complement Alternat Med. Jun. 2005;2(2):209-215, Epub Apr. 7, 2005.
Crabtree et al., 1274. Gallotannins. Part XI. Synthesis of m-digallic and m-trigallic acids and their derivatives. J Chem Soc. Dec. 31, 1965;0:6888-93.
Fiuza et al., Phenolic acid derivatives with potential anticancer properties—a structure-activity relationship study. Part 1: methyl, propyl and octyl esters of caffeic and gallic acids. Bioorg Med Chem. Jul. 1, 2004;12(13):3581-9.
Hatano et al., Gallotannins having a 1,5-anhydro-D-glucitol core and some ellagitannins from *Acer* species. Chem Pharm Bull. Dec. 31, 1990;38(7):1902-6.
Park et al., Dieckol, a SARS-CoV 3CL(pro) inhibitor, isolated from the edible brown algae *Ecklonia cava*. Bioorg Med Chem, Jul. 1, 2013;21(13):3730-7. Epub Apr. 22, 2013.
Venter et al., Comprehensive analysis of tara tannins by reversed-phase and hydrophilic interaction chromatography coupled to ion mobility and high-resolution mass spectrometry. Anal Bioanal Chem. Sep. 2019;411(24):6329-6341. Epub Jun. 19, 2019.

* cited by examiner

| SNB01 (μM) | 31.25 | 62.5 | 125 | 250 | 500 | 500 | 0 |
| 3CLPro (μM) | 20 | 20 | 20 | 20 | 20 | 0 | 20 |

| β-10G (μM) | 31.25 | 62.5 | 125 | 250 | 500 | 500 | 0 |
| 3CLPro (μM) | 20 | 20 | 20 | 20 | 20 | 0 | 20 |

Figure 20
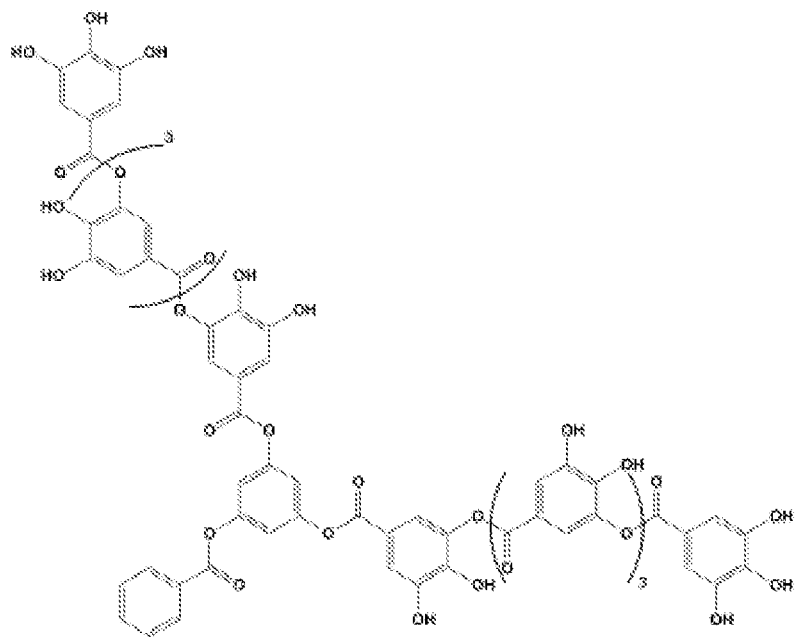
Compound 103
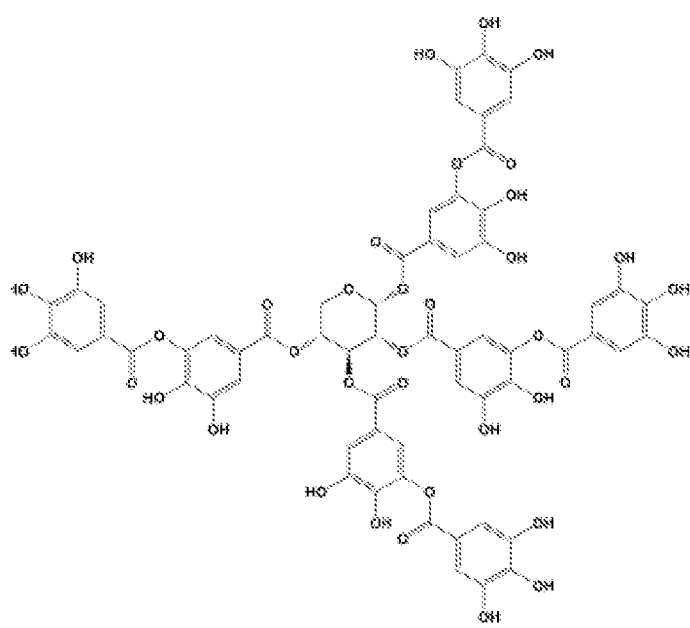
Compound 117

Figure 20 (cont'd)
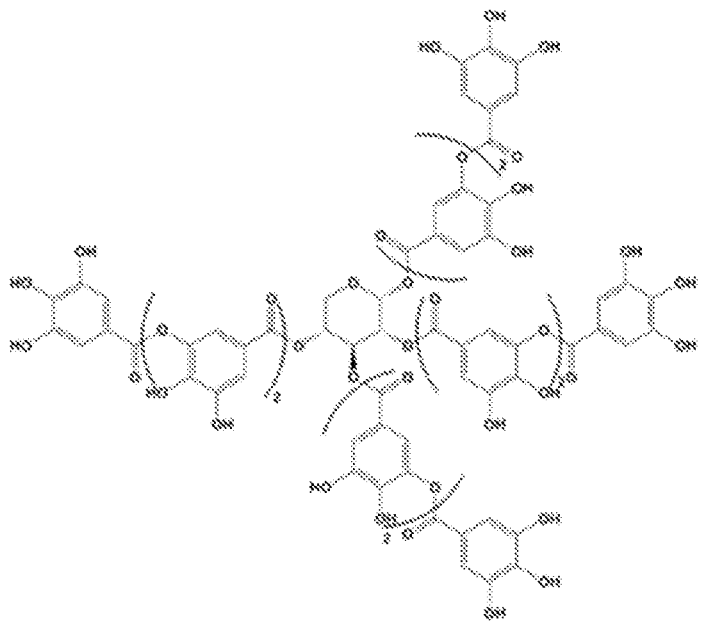
Compound 119
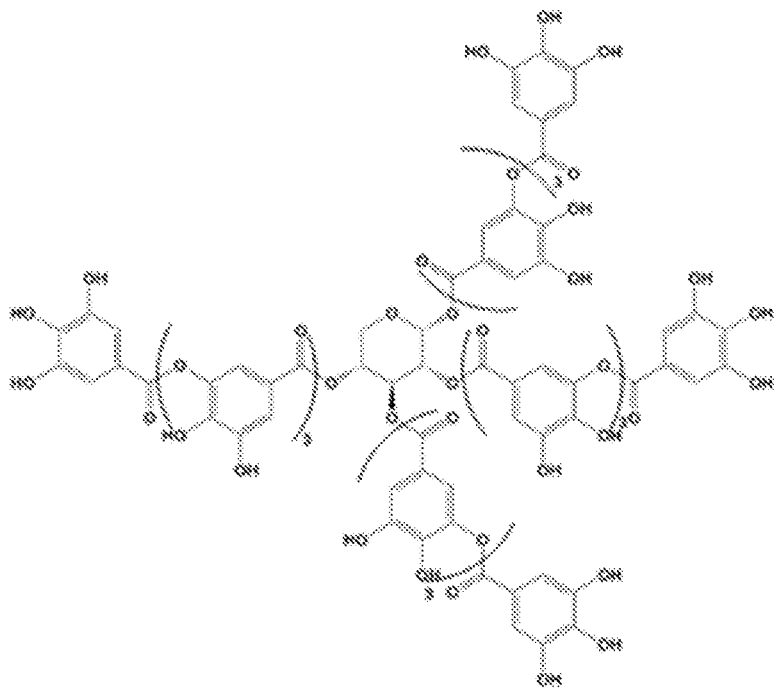
Compound 121

Figure 20 (cont'd)
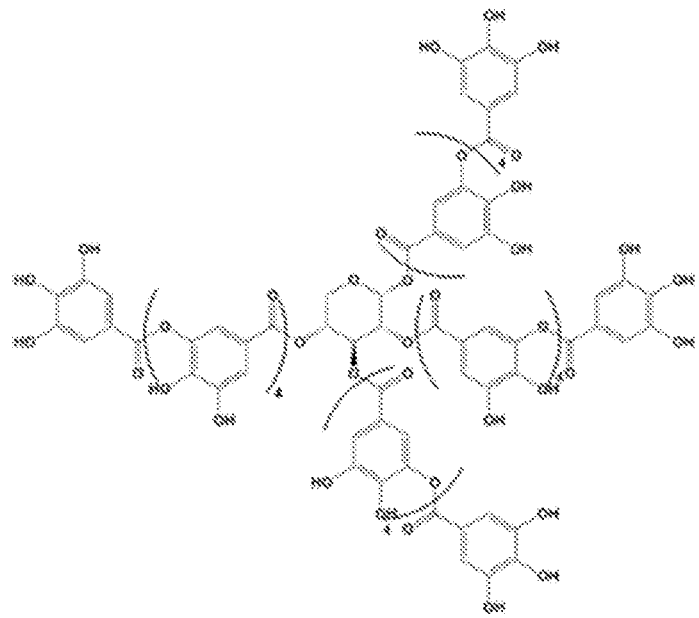
Compound 123
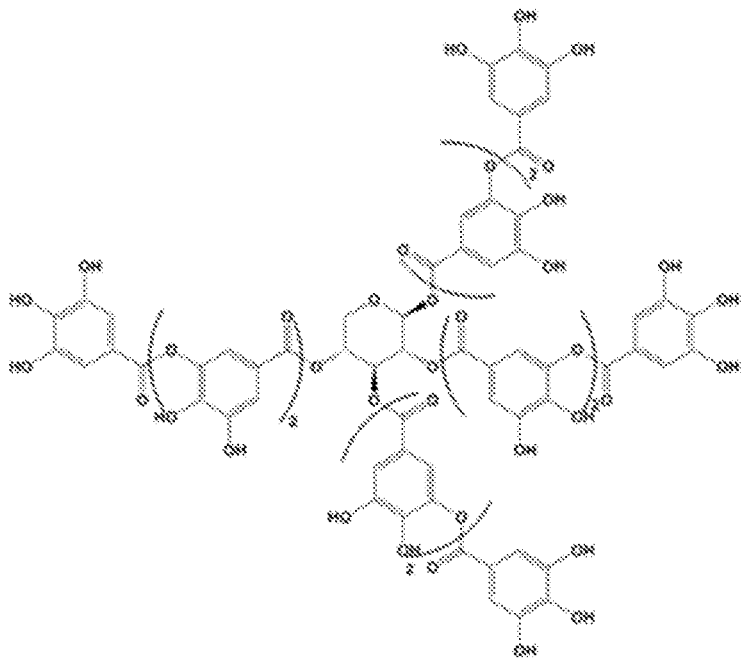
Compound 126

Figure 20 (cont'd)
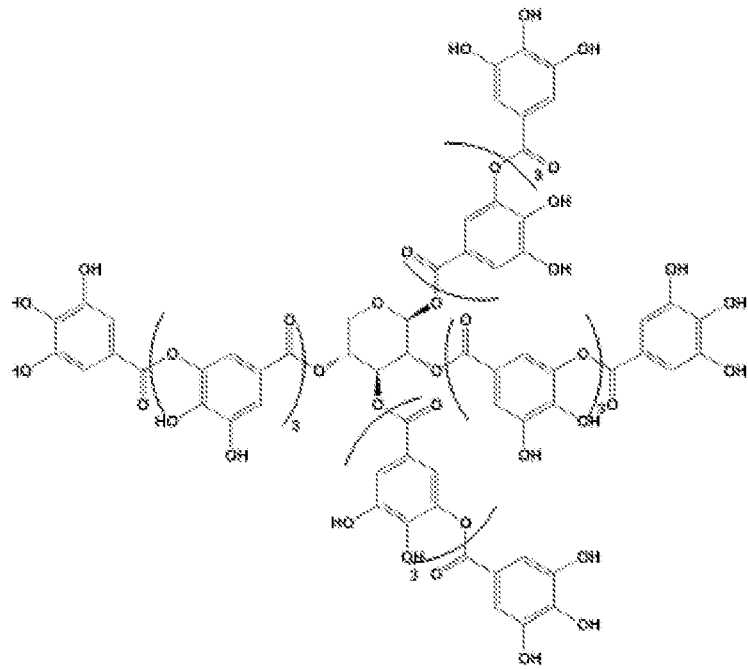
Compound 128
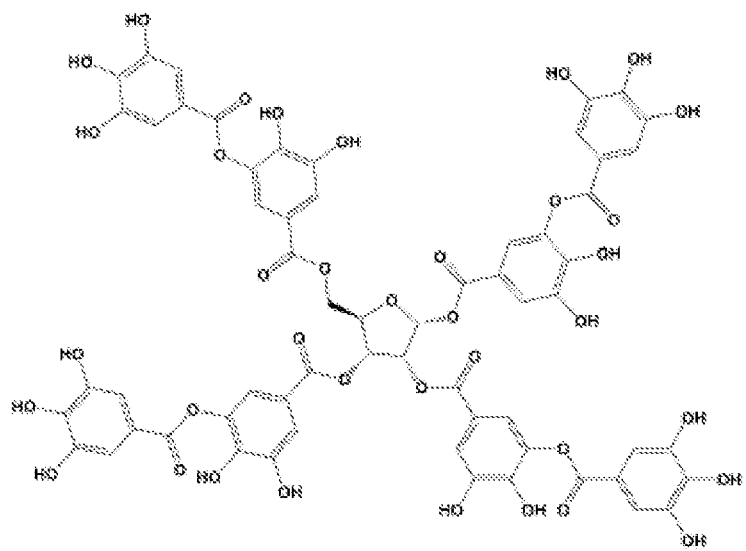
Compound 134

Figure 20 (cont'd)
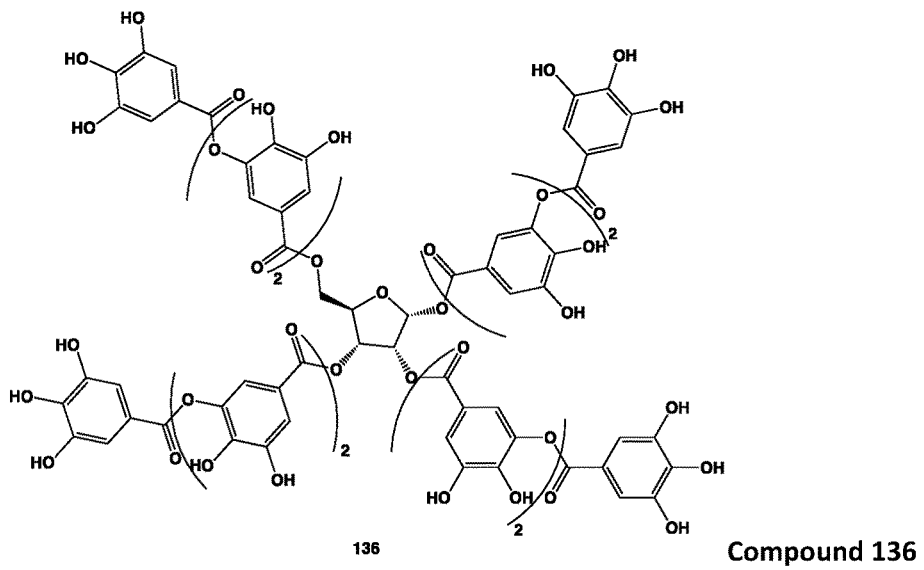
Compound 136
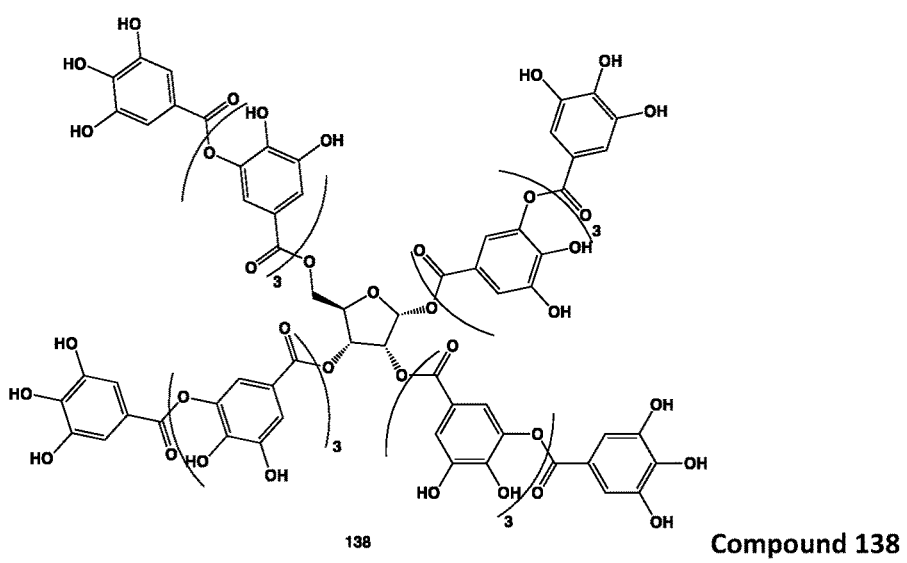
Compound 138
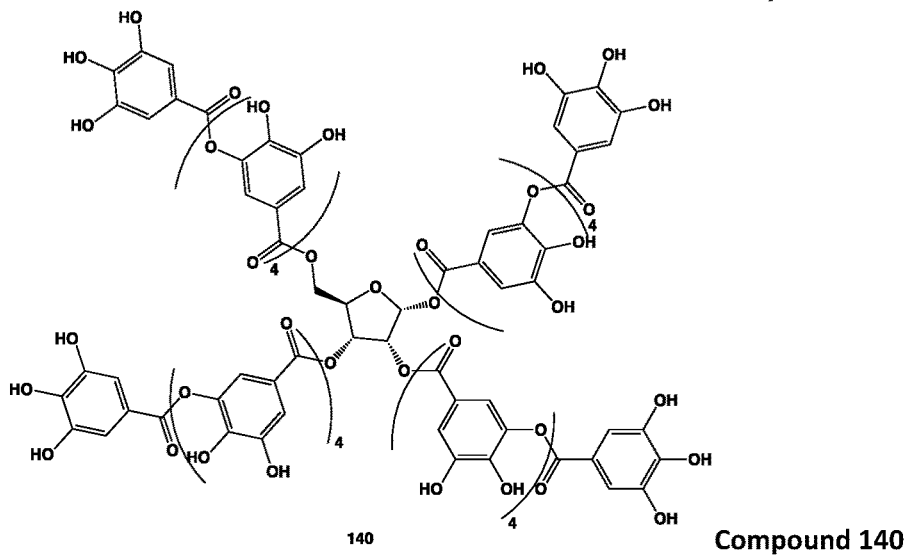
Compound 140

Figure 20 (cont'd)
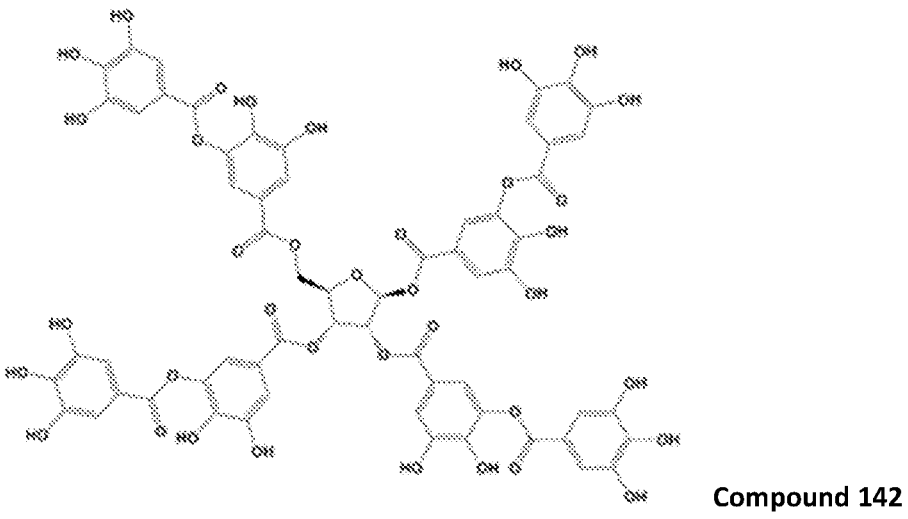
Compound 142
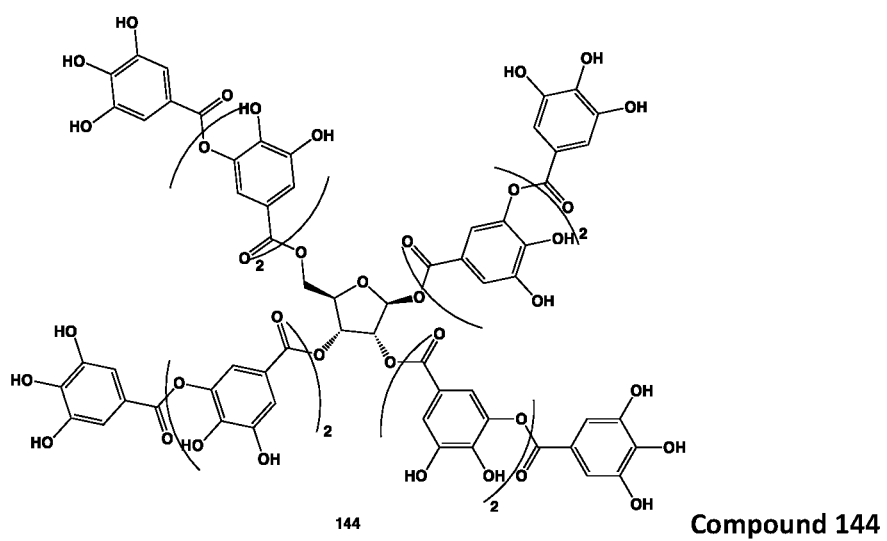
Compound 144
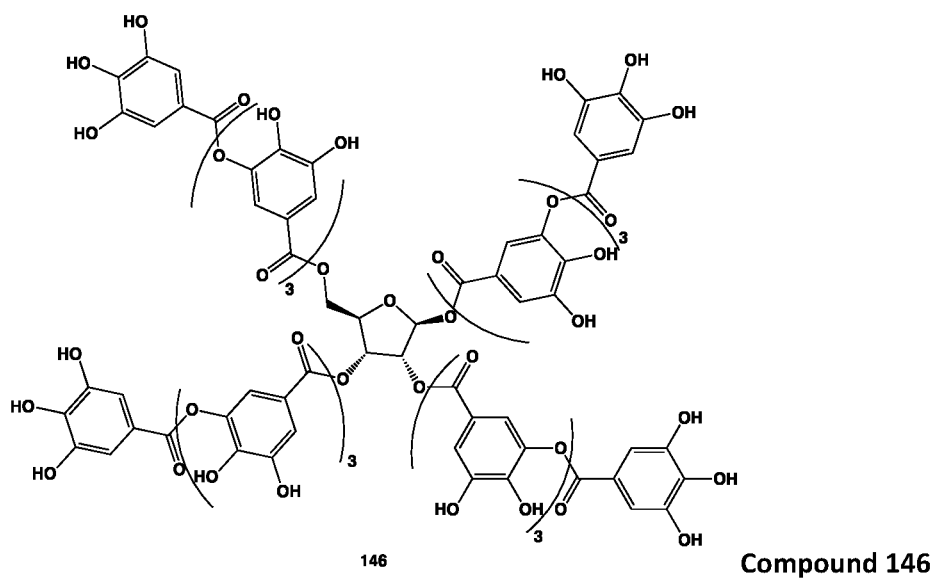
Compound 146

Figure 20 (cont'd)
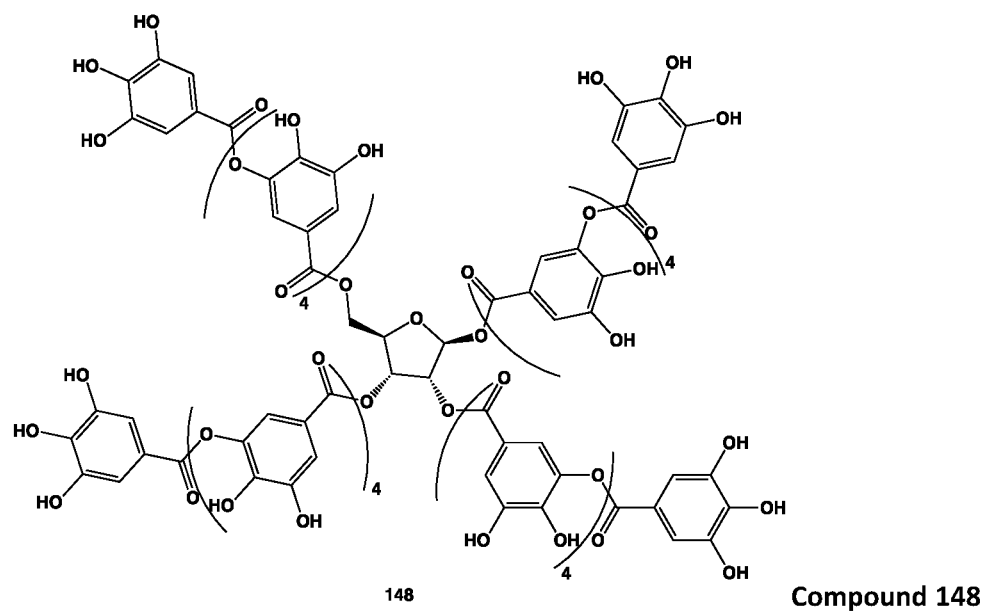
Compound 148
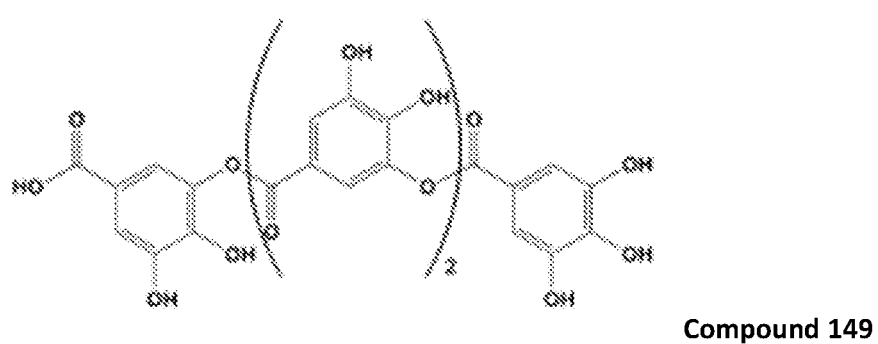
Compound 149

COMPOUNDS AND PHARMACEUTICAL USES THEREOF

CROSS-REFERENCE TO RELATED APPLICATIONS

This application is a continuation of International Patent Application No. PCT/CN2021/075789, filed Feb. 7, 2021, which claims the benefit of priority to U.S. Provisional Patent Application No. 62/971,972, filed Feb. 8, 2020, U.S. Provisional Patent Application No. 62/977,219, filed Feb. 15, 2020, and U.S. Provisional Patent Application No. 63/014,448, filed Apr. 23, 2020, and U.S. patent application Ser. No. 17/014,774, filed Sep. 8, 2020. Each of the priority applications is hereby incorporated by reference in its entirety.

BACKGROUND OF THE INVENTION

A virus is a small infectious agent that replicates only inside the living cells of a host organism. Viruses can infect all types of life forms, from animals and plants to microorganisms, including bacteria and archaea. While not inside an infected cell or in the process of infecting a cell, viruses exist in the form of independent particles, or virions, consisting of: (i) the genetic material, i.e. long molecules of DNA or RNA that encode the structure of the proteins by which the virus acts; (ii) a protein coat, the capsid, which surrounds and protects the genetic material; and in some cases (iii) an outside envelope of lipids.

Antiviral drugs are a class of medications designed to treat viral infections. As the human body is able to deal with the majority of viruses by immunity itself, these drugs target some specific virulent and life-threatening illnesses that the body either cannot fight by itself, or struggles to win against. Researchers working on "rational drug design" strategies for developing antivirals have tried to attack viruses at every stage of their life cycles (e.g., before cell entry, entry inhibition, uncoating inhibition), during viral synthesis, assembly and release phase.

Coronaviruses, members of the family Coronaviridae and subfamily Coronavirinae, are enveloped viruses containing single-strand, positive-sense RNA genome ranging from 26 to 32 kilobases in length. Coronaviruses have been identified in several vertebrate hosts including bird, bat, pig, rodent, camel and human. Human can acquire coronavirus infection from other host of mammals. Human coronavirus infection are one of the major causes of detrimental upper respiratory tract illness in human. Besides encoding structural proteins, majority part of the coronavirus genome is transcribed and translated into a polyprotein, which encodes proteins essential for viral replication and gene expression. The functional polypeptides are released from the polyproteins by extensive proteolytic processing which is one of the crucial steps in the life cycle of coronaviruses. The virus will not be packaged without the proteolysis. This is primarily achieved by the 33.1-kDa main protease (MPro), which is also known as 3C-like protease (3CLPro).

Members of the coronavirus's family include virus strains having different phylogenetic origin (thelancet.com; doi.org/10.1016/S0140-6736 (20)30251-8) and causing different severity in mortality and morbidity. As such, treatment for coronavirus infection varies depending on the specific strains that causes the infection. So far, there is no approved antiviral drug treatment for any coronavirus. Because of the conservation of the critical residues and its functional importance, we consider 3CLPro can be an important target for the design of ubivquitous anti-coronaviral drugs for the infection.

SUMMARY OF THE INVENTION

The present disclosure is based on the unexpected observation that exemplary compounds having the structure of Formula (I) described herein successfully inhibited the protease activity of 3CLPro of SARS-CoV-2 and inhibited SARS-CoV-2 replication in cells. Further, it was observed that compounds of Formula (I) with high numbers of galloyl moieties showed better inhibitory activity against 3CLPro of SARS-CoV-2 that those having lower numbers of galloyl moieties. Moreover, exemplary Formula (I) compounds (e.g., SNB01) showed presence in pulmonary tissues upon oral administration in an animal model. All the discoveries reported herein show that compounds of Formula (I) would be expected to be effective in inhibiting coronavirus such as SARS-CoV-2 and thus alleviating conditions caused by coronavirus infection.

Accordingly, one aspect of the present disclosure features a method of inhibiting coronavirus and/or treating coronavirus infection, the method comprising administering to a subject in need thereof an effective amount of a composition, wherein the composition comprises one or more compounds of Formula (I):

or a pharmaceutically acceptable salt thereof. In Formula (I):

Ring X is a 5 or 6 membered monocyclic ring, which optionally has one or two heteroatoms selected from the group consisting of N, O, P, and S;

at least one of $R_1$, $R_2$, $R_3$, $R_4$, $R_5$, and $R_6$, independently is of the formula:

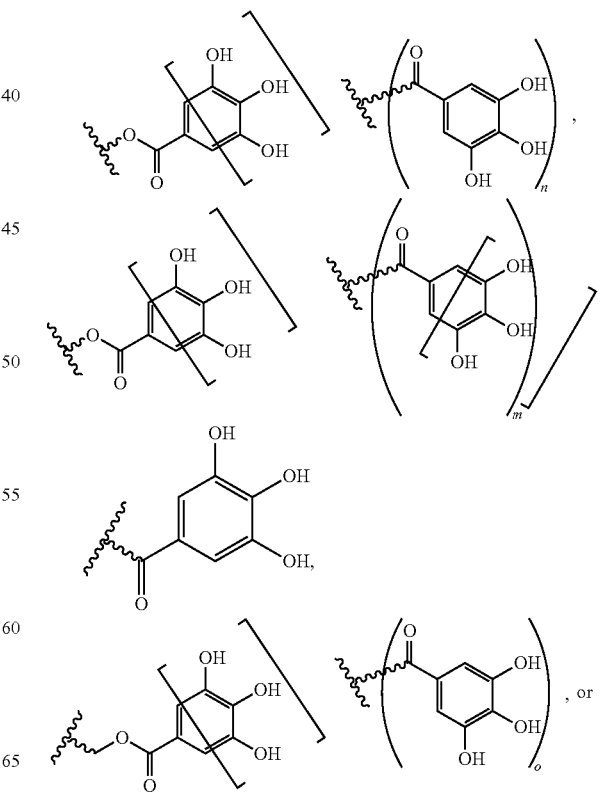

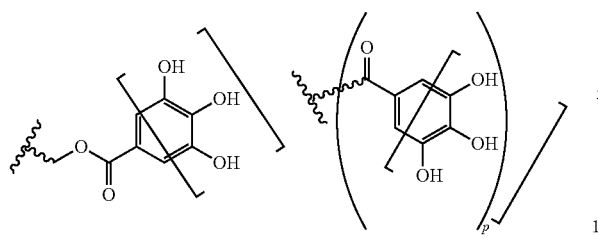
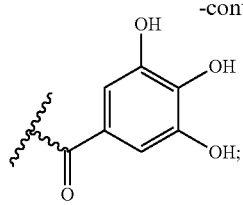
and the remaining $R_1$, $R_2$, $R_3$, $R_4$, $R_5$, and $R_6$ each, independently, is selected from the group consisting of —OH, —COOH,
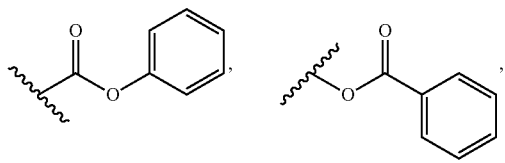
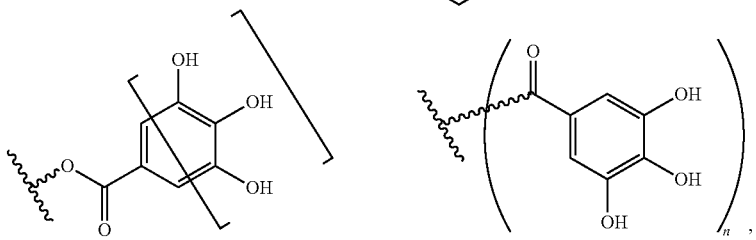
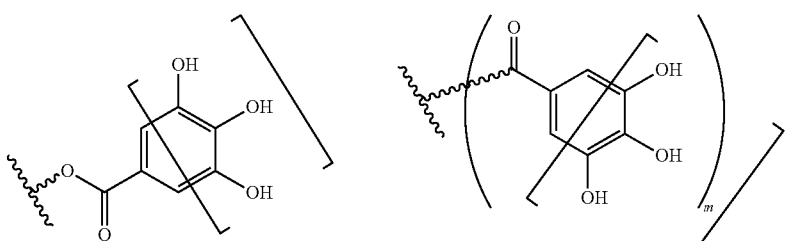
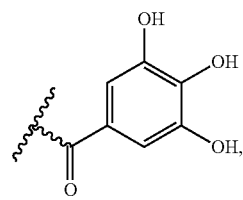
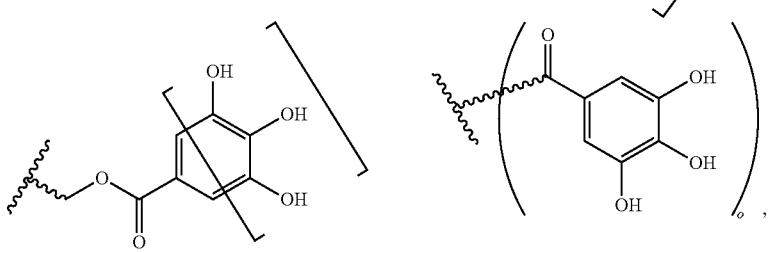
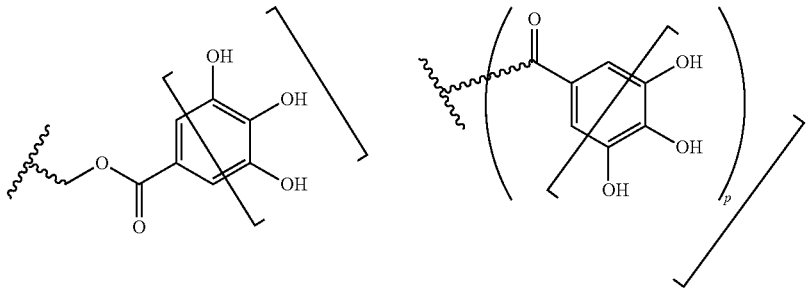
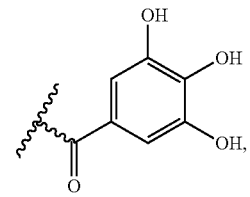
and absent;
n and o are, independently, 0 or 1;
m and p are, independently, 1, 2, 3, 4, or 5.
The compound of Formula (I) has 2 to 35 galloyl moieties, inclusive.

In some embodiments, $R_1$, $R_2$, $R_3$, $R_4$, $R_5$, or $R_6$ may be unsubstituted. In other embodiments, $R_1$, $R_2$, $R_3$, $R_4$, $R_5$, or $R_6$ may be substituted with 1, 2, 3, 4, or 5 substituents. Exemplary substitutents include, but are not limited to, $C_{1-3}$ alkyl, halogen, —$CF_3$, —CN, —$NO_2$, —SH, —OH, —S($C_{1-3}$ alkyl), —$NH_2$, NH($C_{1-3}$ alkyl), N($C_{1-3}$ alkyl)$_2$, and —O($C_{1-3}$ alkyl). In other embodiments, one or more $R_1$, $R_2$, $R_3$, $R_4$, $R_5$, and $R_6$ may be absent. At least one of $R_1$, $R_2$, $R_3$, $R_4$, $R_5$, and $R_6$ is present.

In some embodiments, Ring X is a 6 membered monocyclic ring, which optionally has one or two heteroatom of N, O, P, and/or S. In some examples, Ring X is a 6 membered monocyclic ring having one heteroatom, e.g., N, O, P, or S. In specific examples, the heteroatom in Ring X is O. In other examples, Ring X can be a 6 membered monocyclic ring having two heteroatoms, which can be N, O, P, or S. The two heteroatoms may be identical. Alternatively, the two heteroatoms can be different.

In some embodiments, Ring X is a 5 membered monocyclic ring, which optionally has one or two heteroatom of N, O, P, and/or S. In some examples, Ring X is a 5 membered monocyclic ring having one heteroatom, e.g., N, O, P, or S. In specific examples, the heteroatom in Ring X is O. In other examples, Ring X can be a 5 membered monocyclic ring having two heteroatoms, which can be N, O, P, or S. The two heteroatoms may be identical. Alternatively, the two heteroatoms can be different.

In some examples, Ring X is

In some examples, Ring X is

In some examples, Ring X is

In some embodiments, each of $R_1$, $R_2$, $R_3$, $R_4$, $R_5$, and $R_6$, independently, can be of the formula:

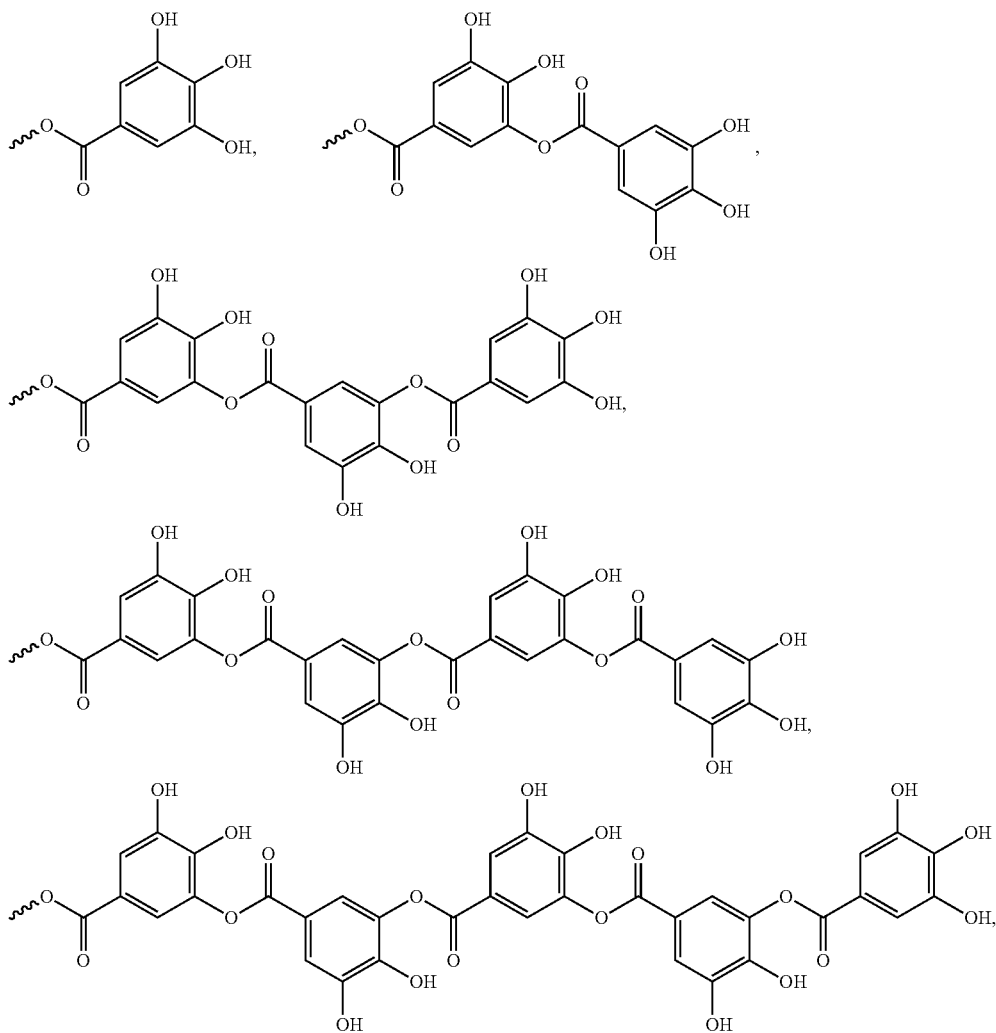

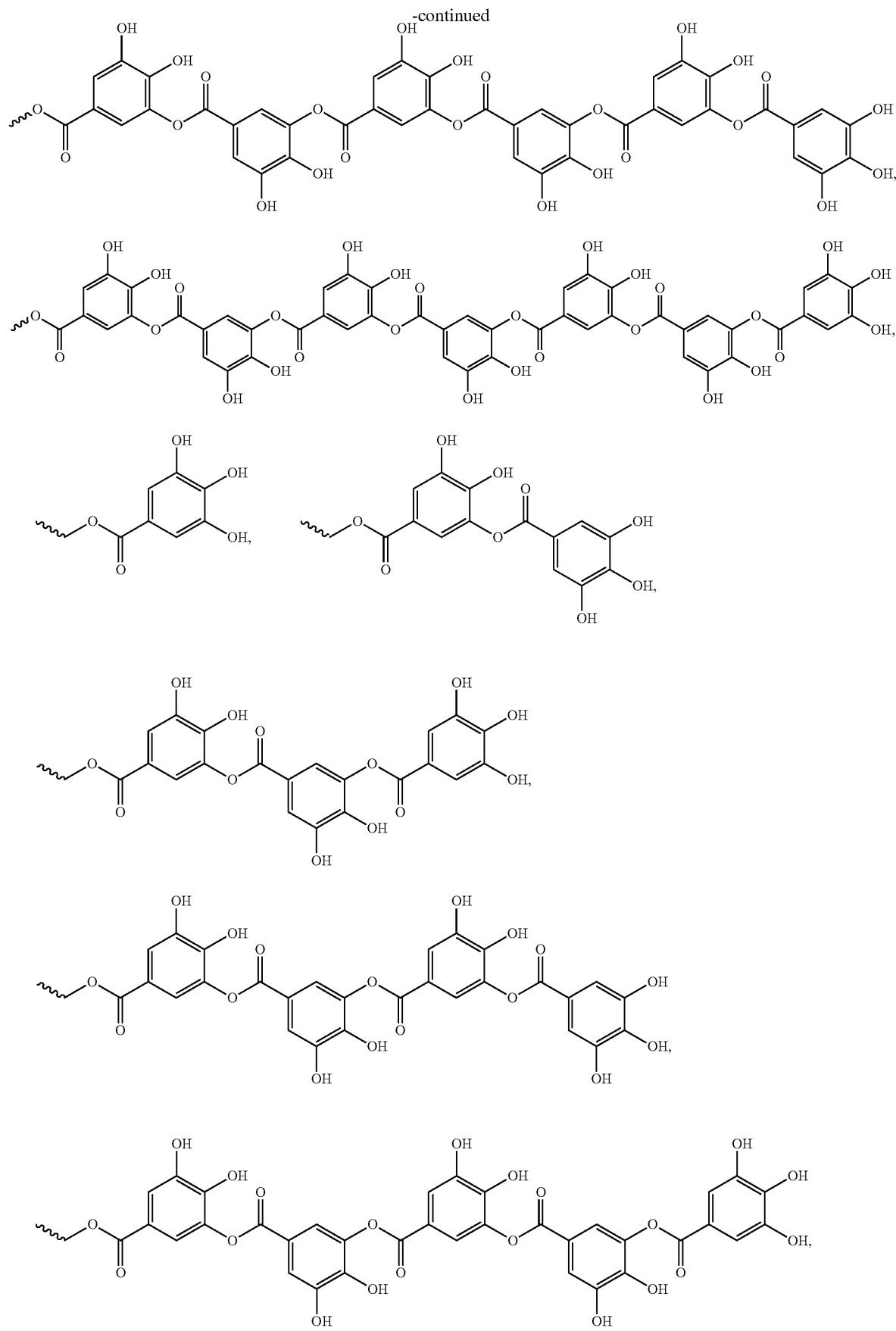
-continued

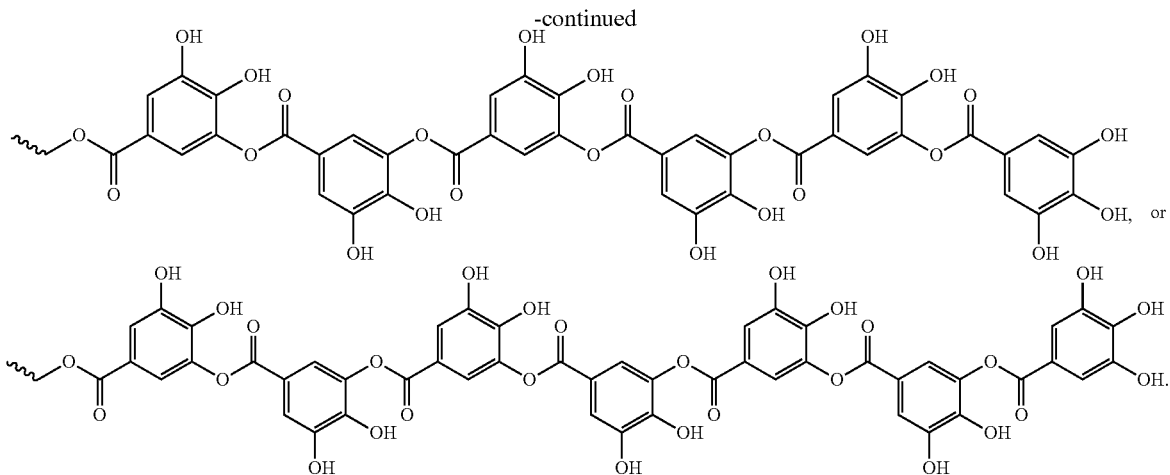

, or

In some embodiments, the Formula (I) compounds have the structure of (Ia),

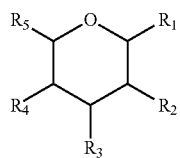

in which each of $R_1$, $R_2$, $R_3$, $R_4$, $R_5$, and $R_6$, independently can be of the formula:

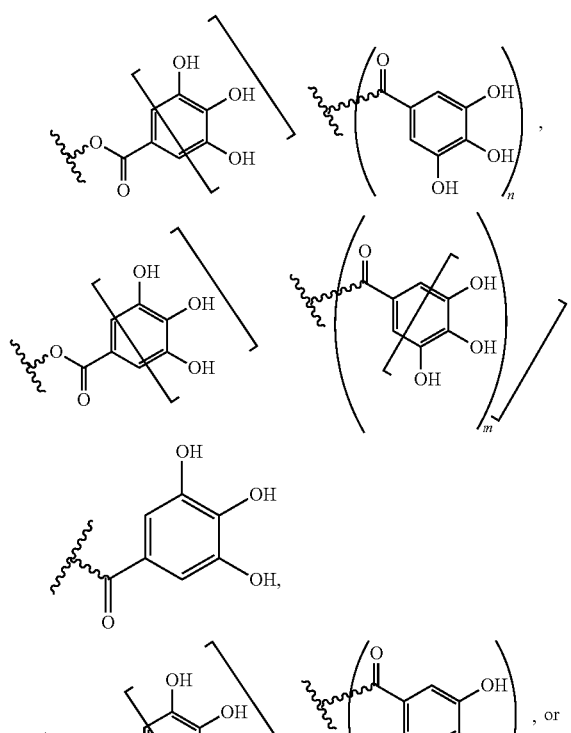

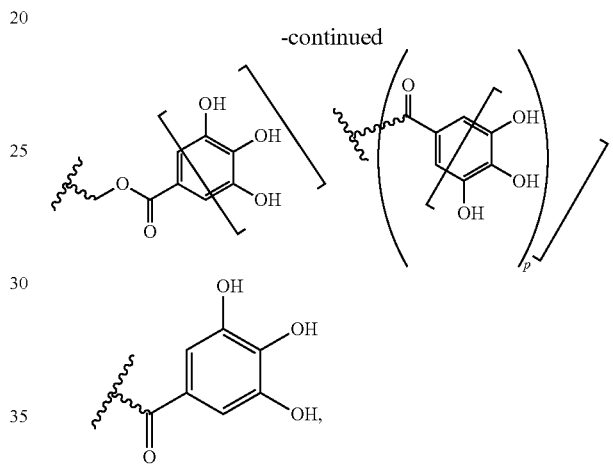

in which n, m, o and p are as defined herein. In some examples, the compound of Formula (Ia) may have the structure of (Ib)

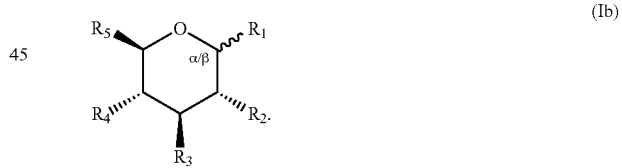

Exemplary compounds include, but are not limited to, α5G, α5G, α10G, β10G, α15G, β15G, α20G, β20G, α25G, or β25G.

In some embodiments, the Formula (I) compounds have the structure of (Ic)

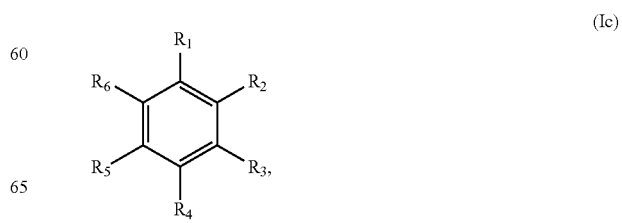

in which each of the $R_1$, $R_2$, $R_3$, $R_4$, $R_5$, and $R_6$, independently can be of the formula:
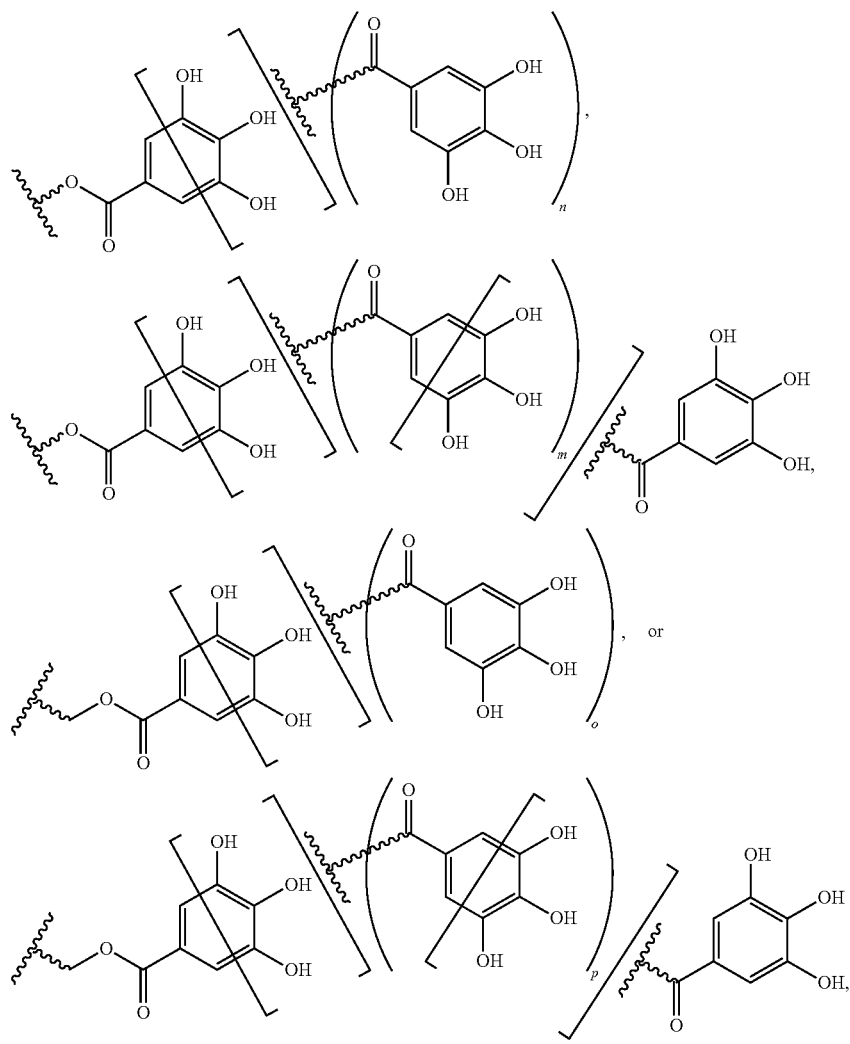
n, m, o and p are as defined herein.
In some embodiments, the compounds of Formula (I) can be of the structure
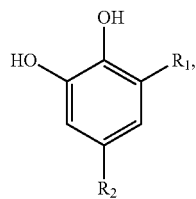
(Id)
in which $R_1$ can be
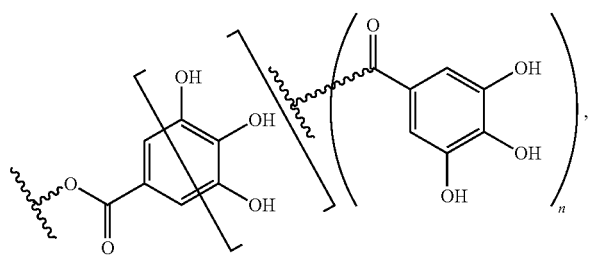

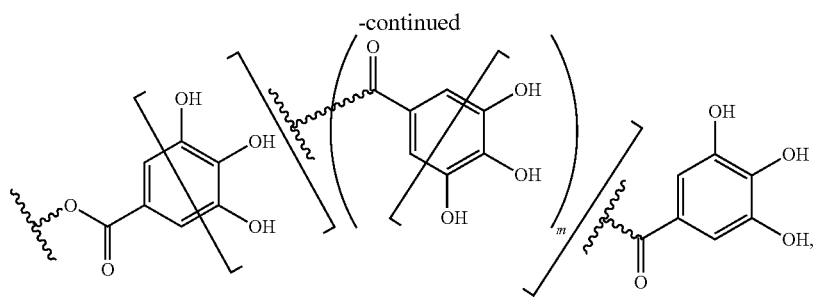
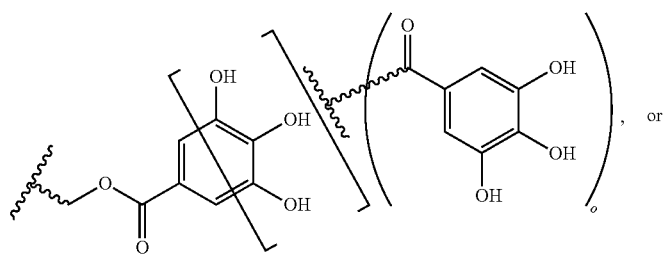
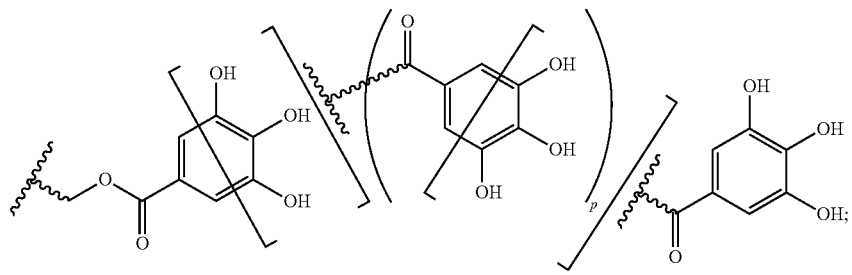
and $R_2$ can be —COOH or
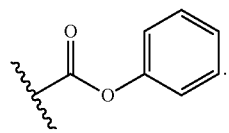 [SMILES: *C(=O)Oc1ccccc1]
Exemplary compounds include phenol 3G, phenol 5G, phenol 7G, Compound 14, Compound 18, and Compound 149.
In some embodiments, the compounds of Formula (I) can have the structure
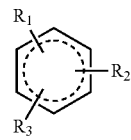 (Ie)
(e.g., 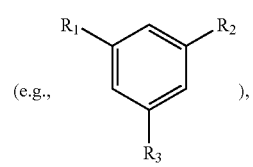 ), (Ie-1)
in which at least one of $R_1$, $R_2$, and $R_3$ is
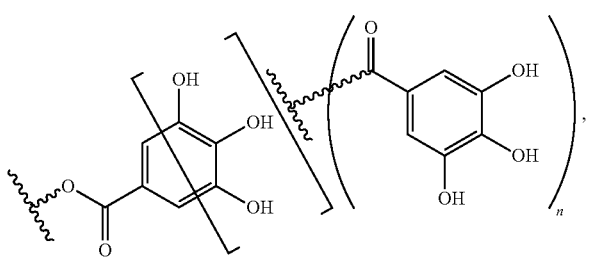

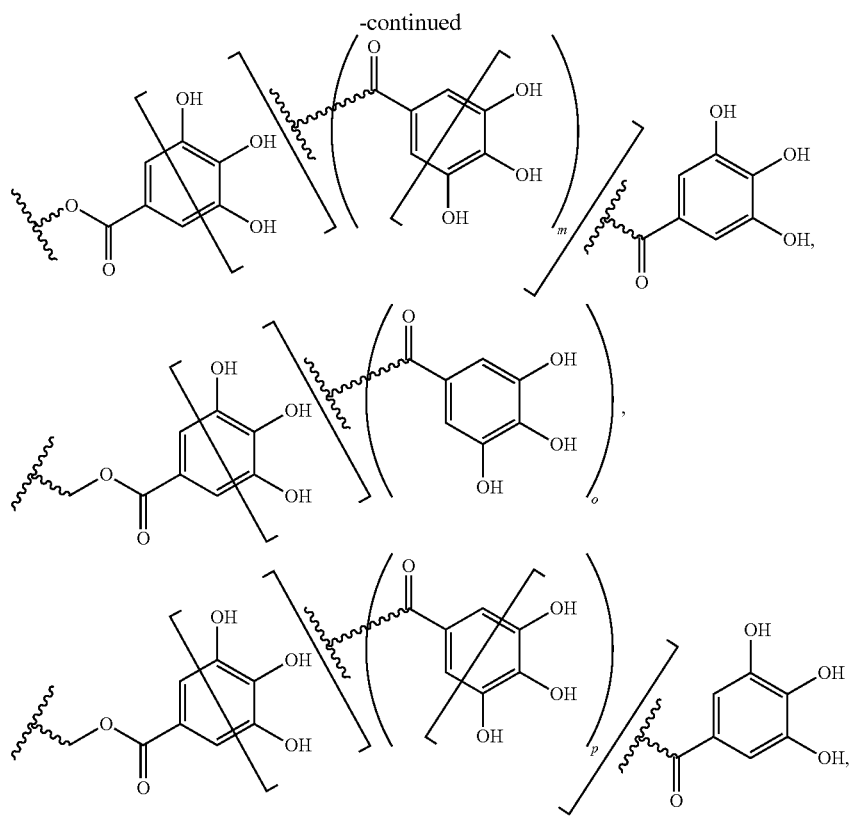
and the remaining $R_1$, $R_2$, and $R_3$ each independently are
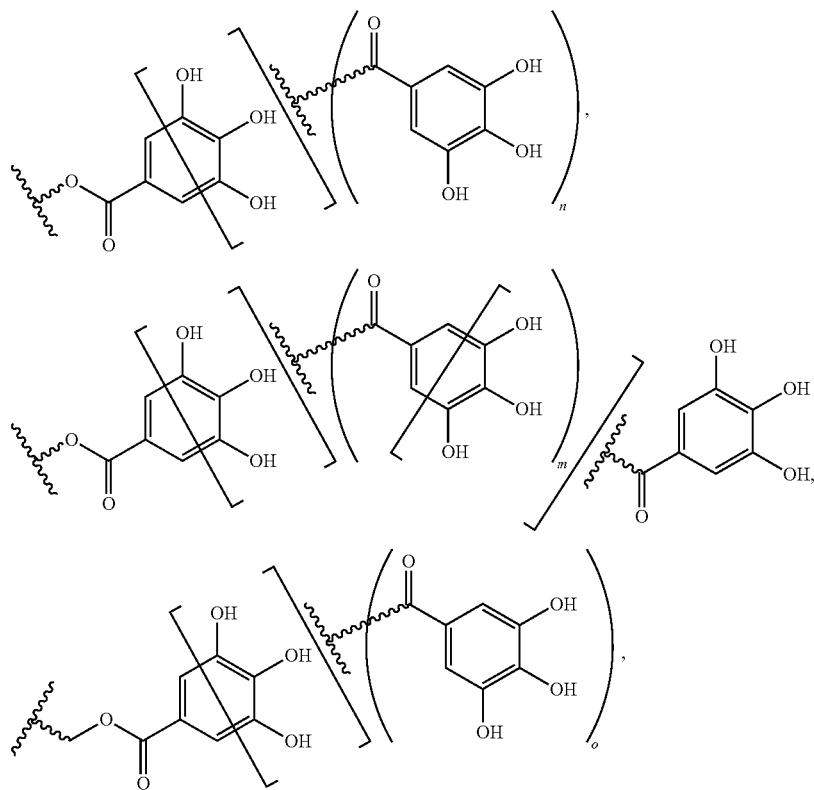

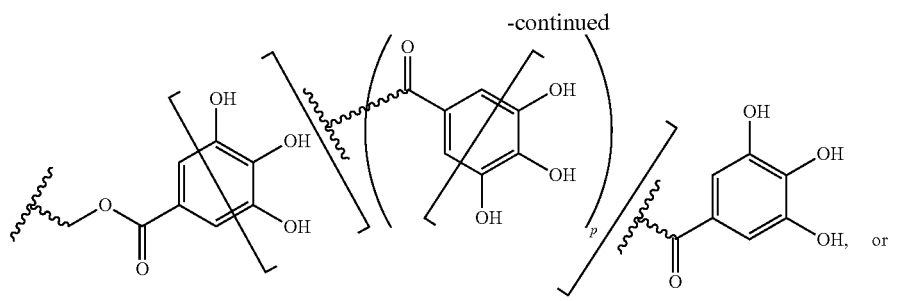
Exemplary compounds include phloroglucinol 6G, phloroglucinol 9G, phloroglucinol 12G, phloroglucinol 15G, phloroglucinol 21G, or Compound 103.
In some embodiments, the compounds of Formula (I) can have the structure of
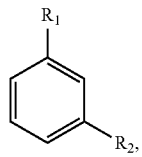
(If)
in which each of $R_1$ and $R_2$ independently is
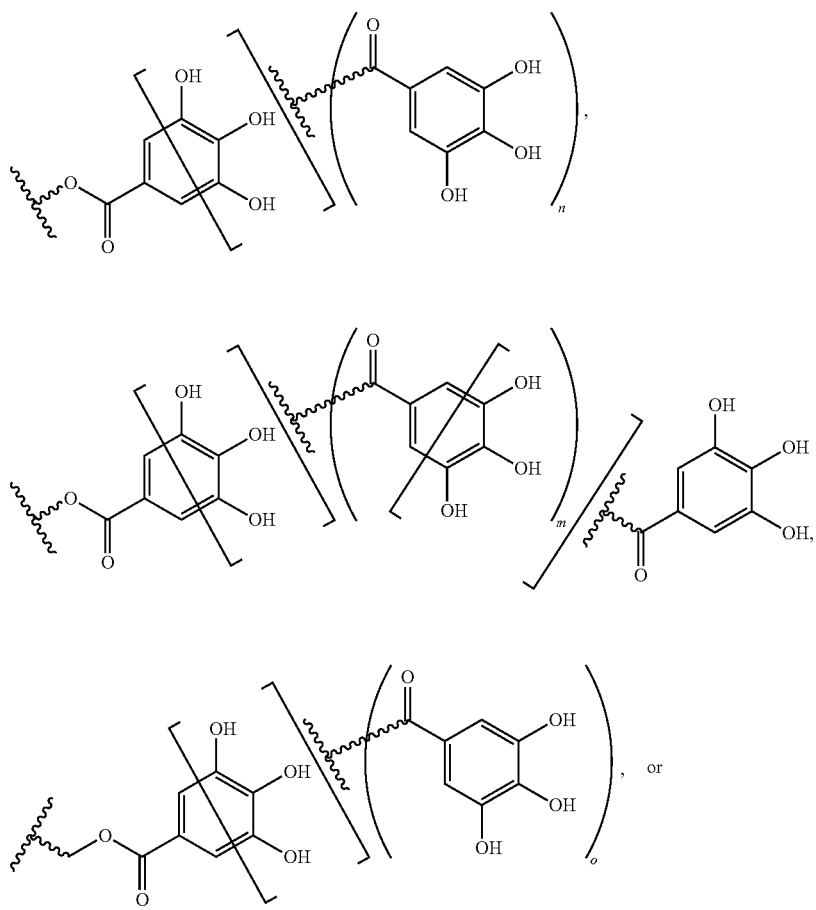

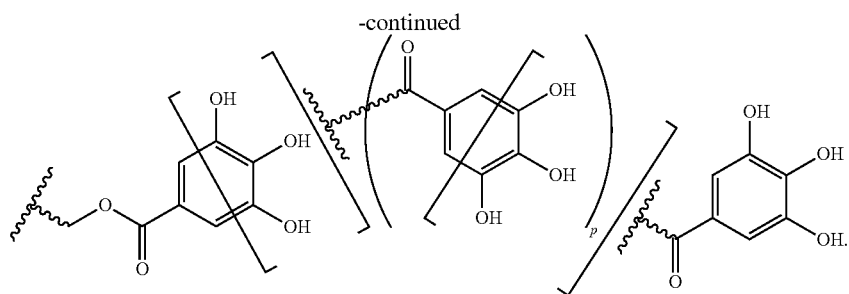
Exemplary compounds include Resorcin 10G or Resorcin 14G.
In some embodiments, the compounds of Formula (I) may have the structure of
(Ig)
in which each of $R_1$, $R_2$, $R_3$, and $R_4$ independently is
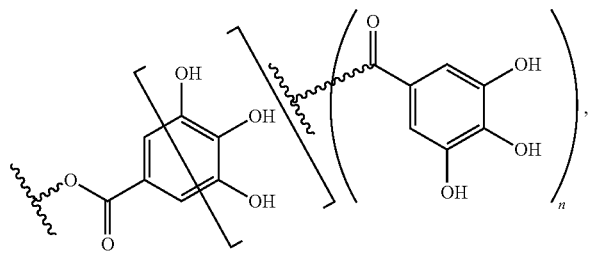
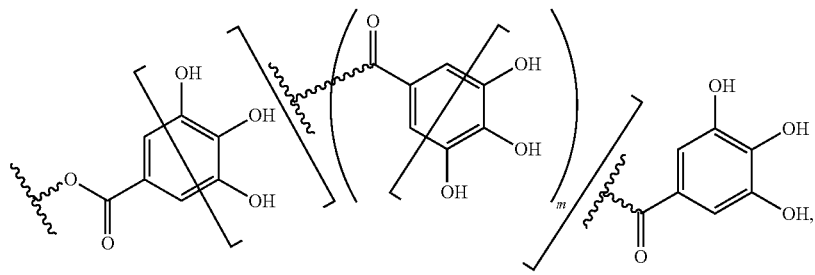
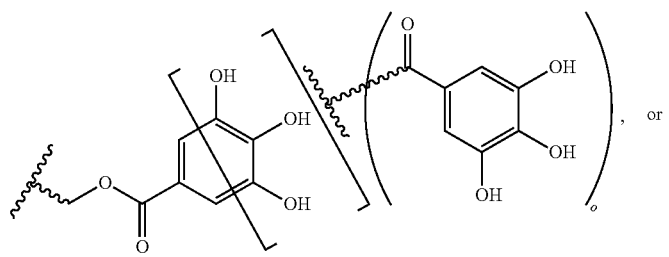
, or -continued
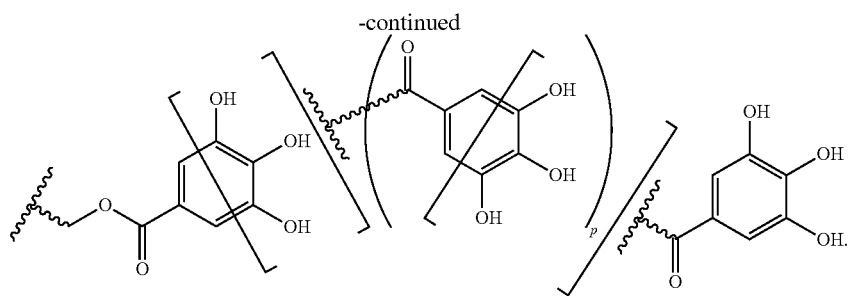
Exemplary compounds include Compound 117, 119, 121, 123, 126, or 128.
In some embodiments, the compound of Formula (I) may have the structure of
(Ih)
in which each of $R_1$, $R_2$, $R_3$, and $R_4$ independently is
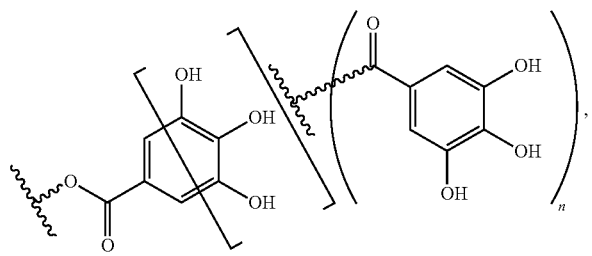
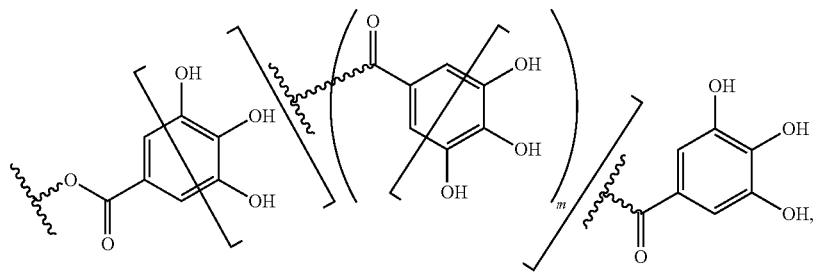
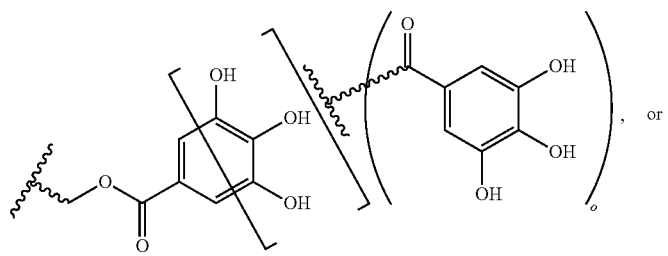

-continued

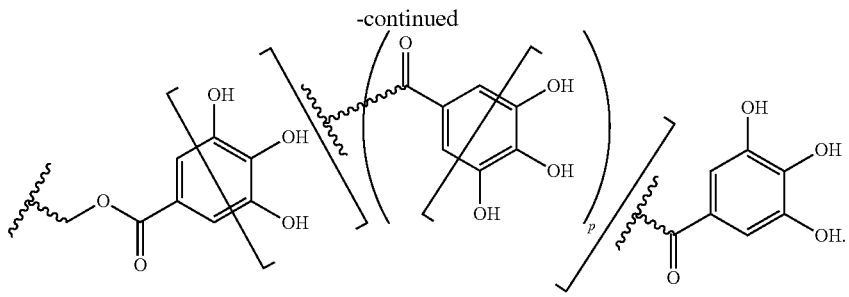

Exemplary compounds include Compound 134, 136, 138, 140, 142, 144, 146, or 148.

In some embodiments, the composition for use in any of the methods disclosed herein may comprise a mixture of compounds of Formula (I), each of which contains 2 to 35 (e.g., 4 to 35) galloyl moieties, inclusive.

In some embodiments, about 1-25% of the Formula (I) compounds in the composition have 5 galloyl moieties. Alternatively or in addition, about 10-40% of the Formula (I) compounds in the composition have 6-7 galloyl moieties. Alternatively or in addition, about 20-85% of the Formula (I) compounds in the composition have 8-12 galloyl moieties.

In some embodiments, the composition for use in any of the methods disclosed herein may comprise a substantially homogenous population of compounds of Formula (I). In this substantially homogenous population of compounds of Formula (I), the majority Formula (I) compounds are identical, i.e., having the same number of galloyl moeities ranging from 2-35, inclusive. In some examples, the majority Formula (I) compounds in the substantially homogenous population has 5 galloyl moieties. In some examples, the majority Formula (I) compounds in the substantially homogenous population has 6 galloyl moieties. In some examples, the majority Formula (I) compounds in the substantially homogenous population has 7 galloyl moieties. In some examples, the majority Formula (I) compounds in the substantially homogenous population has 8 galloyl moieties. In some examples, the majority Formula (I) compounds in the substantially homogenous population has 9 galloyl moieties. In some examples, the majority Formula (I) compounds in the substantially homogenous population has 10 galloyl moieties. In some examples, the majority Formula (I) compounds in the substantially homogenous population has 11 galloyl moieties. In some examples, the majority Formula (I) compounds in the substantially homogenous population has 12 galloyl moieties. In some examples, the majority Formula (I) compounds in the substantially homogenous population has 13 galloyl moieties. In some examples, the majority Formula (I) compounds in the substantially homogenous population has 14 galloyl moieties. In some examples, the majority Formula (I) compounds in the substantially homogenous population has 15 galloyl moieties. In some examples, the majority Formula (I) compounds in the substantially homogenous population has 16 galloyl moieties. In some examples, the majority Formula (I) compounds in the substantially homogenous population has 17 galloyl moieties. In some examples, the majority Formula (I) compounds in the substantially homogenous population has 18 galloyl moieties. In some examples, the majority Formula (I) compounds in the substantially homogenous population has 19 galloyl moieties. In some examples, the majority Formula (I) compounds in the substantially homogenous population has 20 galloyl moieties. In some examples, the majority Formula (I) compounds in the substantially homogenous population has 21 galloyl moieties. In some examples, the majority Formula (I) compounds in the substantially homogenous population has 22 galloyl moieties. In some examples, the majority Formula (I) compounds in the substantially homogenous population has 23 galloyl moieties. In some examples, the majority Formula (I) compounds in the substantially homogenous population has 24 galloyl moieties. In some examples, the majority Formula (I) compounds in the substantially homogenous population has 25 galloyl moieties. In some examples, the majority Formula (I) compounds in the substantially homogenous population has a number of galloyl moieties ranging from 26-30. In some examples, the majority Formula (I) compounds in the substantially homogenous population has a number of galloyl moieties ranging from 31-35.

In some embodiments, the compound of Formula (I) is

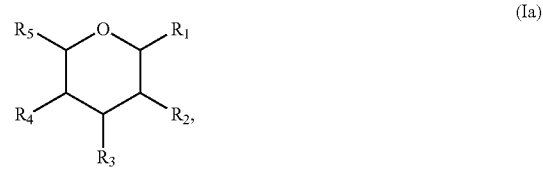

(Ia)

and none of $R_1$, $R_2$, $R_3$, $R_4$, and $R_5$ is absent (i.e., all present). In some examples, about 1-25% of the Formula (Ia) compounds in the composition for use in any of the methods disclosed herein have 5 galloyl moieties. Alternatively or in addition, about 10-40% of the Formula (Ia) compounds in the composition have 6-7 galloyl moieties. Alternatively or in addition, about 20-85% of the Formula (Ia) compounds in the composition have 8-12 galloyl moieties.

In some embodiments, the Formula (I) compounds in the composition for use in any of the methods disclosed herein has the structure of is Formula (I)

(Ia)

as disclosed herein. In such a composition, about 1-8% of the Formula (Ia) compounds have 5 galloyl moieties, about 15-35% of the Formula (Ia) compounds have 6-7 galloyl moieties, and about 60-80% of the Formula (Ia) compounds have 8-12 galloyl moieties.

In some embodiments, the composition for use in any of the methods disclosed herein can be a nutraceutical composition. In some embodiments, the composition can be a health food. In some embodiments, the composition can be a medical food. In other embodiments, the composition can be a pharmaceutical composition. Any of the compositions disclosed herein may be placed in a medical device. Examples include, but are not limited to, an inhaler, a nebulizer, a nasal spray, and a vaporization aerosol device for administration to the subject.

In some embodiments, the coronavirus infection is an infection caused by a coronavirus. Examples include SARS-CoV-2, severe acute respiratory syndrome coronavirus (SARS-CoV), middle east respiratory syndrome coronavirus (MERS-CoV), 229E alpha coronavirus, NL63 alpha coronavirus, OC43 beta coronavirus, and HKU1 beta coronavirus. In specific examples, the coronavirus is SARS-CoV-2.

In some embodiments, the compound or composition is administered to the subject by oral administration, by injections, by topical administration, or by inhalation.

In some embodiments, the subject is a human subject. In some embodiments, the subject is administered the composition continuously or at a frequency of every five minutes to one time every three months. In some embodiments, the human subject is treated concurrently with, prior to, or subsequent to, one or more additional anti-viral agents.

In some embodiments, the one or more additional antiviral agents may comprise a viral entry inhibitor, a viral uncoating inhibitor, a viral reverse transcriptase inhibitor, a viral protein synthesis inhibitor, a viral protease inhibitor, a viral polymerase inhibitor, a viral integrase inhibitor, an interferon, or a combination thereof.

Exemplary viral entry inhibitors include, but are not limited to, maraviroc, enfuvirtide, ibalizumab, fostemsavir, plerixafor, epigallocatechin gallate, vicriviroc, aplaviroc, maraviroc, tromantadine, nitazoxanide, umifenovir, and podofilox.

Exemplary viral uncoating inhibitors include, but are not limited to, amantadine, rimantadine, and pleconaril.

Exemplary viral reverse transcriptase inhibitors include, but are not limited to, zidovudine, didanosine, zalcitabine, stavudine, lamivudine, abacavir, emtricitabine, entecavir, truvada, nevirapine, raltegravir, and tenofovir disoproxil.

Exemplary viral protease inhibitors include, but are not limited to, fosamprenavir, ritonavir, atazanavir, nelfinavir, indinavir, saquinavir, saquinavir, famciclovir, fomivirsen, lopinavir, ribavirin, darunavir, oseltamivir, and tipranavir. Exemplary viral polymerase inhibitors include, but are not limited to, amatoxins, rifamycin, cytarabine, fidaxomicin, tagetitoxin, foscarnet sodium, idoxuridine, penciclovir, sofosbuvir, trifluridine, valacyclovir, valganciclovir, vidarabine, and remdesivir.

Exemplary viral integrase inhibitors include, but are not limited to, raltegarvir, elvitegravir, dolutegravir, bictegravir, and cabotegravir.

Exemplary interferons include, but are not limited to, type I interferon, type II interferon, type III interferon, and peginterferon alfa-2a.

In other aspects, the present disclosure provides an aerosol dispenser for treating coronavirus infection. The aerosol dispenser may comprise a container, in which a composition comprising any of the Formula (I) compounds or the mixture of the Formula (I) compounds disclosed herein are placed. The Formula (I) compounds or the mixture thereof are suspended in a liquid propellant. Exemplary aerosol dispenser includes, but are not limited to, an inhaler, a nebulizer, a nasal spray, or a vaporization aerosol device. In some embodiments, the composition comprises microparticles that comprise the one or more Formula (I) compounds, and optionally wherein the microparticles have a mass median diameter ($D_{50}$) of about 1 μM to about 5 μM.

Also within the scope of the present disclosure are compositions comprising one or more compounds of Formula (I) as disclosed herein for use in inhibiting coronavirus and/or treating coronavirus infection (e.g., infection caused by SARS-CoV-2), as well as such compositions for manufacturing a medicament for use in treating the coronavirus infection.

The details of one or more embodiments of the invention are set forth in the description below. Other features or advantages of the present invention will be apparent to from the following drawings and detailed description of several embodiments, and also from the appended claims.

BRIEF DESCRIPTION OF THE DRAWINGS

FIG. 7A: a chart showing inhibitory activity of SNB01. $EC_{50}$=0.585 μM; $EC_{90}$=8.307 μM; $EC_{99}$=12.900 μM of SNB01. FIG. 7B: a chart showing inhibitory activity of Remdesivir (left) and $EC_{99}$=15.000 μM. The $EC_{50}$, $EC_{90}$ and $EC_{99}$ were interpolated from the non-linear regression using asymmetric (five-parameters) logistic dose-response curve, as described in Example 7 below.

FIG. 8A: a chart showing inhibitory activity of SNB01. EC50=0.515 μM; EC90=10.540 μM; EC99=19.130 μM. FIG. 8B: a chart showing inhibitory activity of Remdesivir. EC99=15.000 μM. The EC50, EC90 and EC99 were interpolated from the non-linear regression using asymmetric (five-parameters) logistic dose-response curve, as described in Example 7 below.

FIG. 15A: linear regression of the peak area ratios versus concentrations over the range of 1.25 to 20 µg/mL. FIG. 15B: linear regression of the peak area ratios versus concentrations over the range of and 0.078 to 1.25 µg/mL.

FIG. 20 shows chemical structures of the exemplary Formula (I) compounds listed in Table 35.

DETAILED DESCRIPTION

Figure 1:
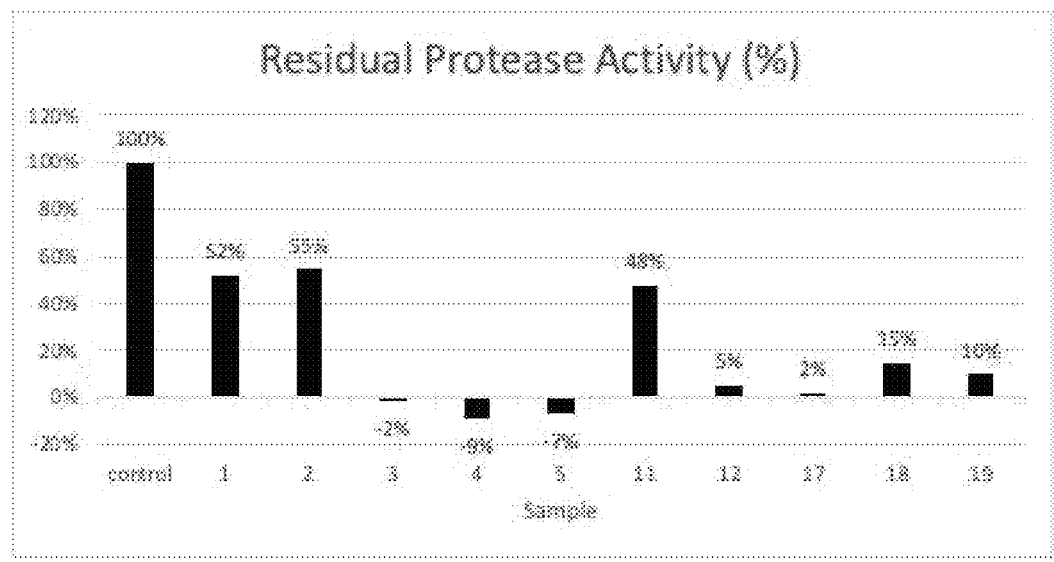
FIG. 1 is a chart showing the protease activity of 2019-nCoV 3CLPro in response to exemplary Formula (I) compounds at the concentration of 3 μM.

The present disclosure is based, at least in part, on the unexpected discoveries that compounds of Formula (I) showed inhibitory activity against 3CLPro protease of SARS-CoV-2 and thus would be expected to be effective in treating infection caused by coronavirus such as SARS-CoV-2. Moreover, Formula (I) compounds (e.g., Formula (Ib) compounds, either in alpha form or beta form, having high numbers of galloly moieties (e.g., 10G), showed better inhibitory activity relative to those counterparts having low numbers of galloyl moieties (e.g., 5G). Accordingly, the present disclosure provides methods of inhibiting coronavirus proliferation and/or treating infection caused by a coronavirus such as SARS-CoV-2, the method comprising administering to a subject who needs the treatment a composition comprising one or more compounds of Formula (I) and kits for use in the intended treatment.

Because of the conservation of the critical residues and its functional importance, it is contemplated that 3CLPro is an important target for treating coronavirus infection, e.g., infection caused by any of the coronavirus strains as disclosed herein. Accordingly, provided herein are methods for treating coronavirus infection comprising administering to a subject in need of the treatment (e.g., a human patient having infection caused by a coronavirus) an effective amount of any of the compositions disclosed herein, which comprise one or more of compounds of Formula (I). Such compounds are expected to inhibit 3CLPro activity, thereby benefiting treatment of coronavirus infection.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group or a saturated carbocyclyl ring having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl or substituted $C_{1-3}$ alkyl, e.g., —CF$_3$ or —CH$_2$OH).

The term "monocyclic ring" refers to a single cyclic ring wherein the atoms on the ring are selected from the group consisting of C, N, O, P and S. In some embodiments, a "monocyclic ring" is a carbocyclyl with 3 to 10 carbon atoms ($C_{3-10}$ carbocyclyl). In some embodiments, a "monocyclic ring" is a heterocyclic ring with 3-10 atoms, including at least one atom from the group consisting of N, O, P and S. In some embodiments, a "monocyclic ring" is

In some embodiments, a "monocyclic ring" is

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or Spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholilanyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C6 aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl. In some embodiments, the aralkyl is a subset of heteroaryl and aryl, optionally linked by alkyl groups.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

"Halo" or "halogen" refers to fluorine (fluoro, —F), chlorine (chloro, —Cl), bromine (bromo, —Br), or iodine (iodo, —I).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "inhibition", "inhibiting", "inhibit," or "inhibitor" refer to the ability of a compound to reduce, slow, halt or prevent activity of a particular biological process in a cell relative to vehicle.

When a compound, pharmaceutical composition, method, use, or kit is referred to as "selectively," "specifically," or "competitively" binding a first protein, the compound binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a compound is referred to as "selectively," "specifically," or "competitively" modulating (e.g., increasing or inhibiting) the activity of a protein, the compound modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject", "individual," or "patient" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "subject" may be human, but also include other mammals, particularly those mammals useful as laboratory models for human disease, e.g. mouse, rat, rabbit, dog, etc. A "patient" refers to a human subject in need of treatment of a disease. In certain embodiments, a subject is a human of having, or at risk for a central nervous system (CNS) disorder, obesity, diabetes, or hyperlipidemia.

The terms "administer," "administering," or "administration" refers to implanting, absorbing, ingesting, injecting, inhaling, or otherwise introducing a compound described herein, or a composition thereof, in or on a subject.

"Oral administration" or "adminiderted orally" is a route of administration where a substance is taken through the mouth. Many medications are taken orally because they are intended to have a systemic effect, reaching different parts of the body via the bloodstream.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

"Injection" is the act of putting a drug into a person's body using a needle (usually a hypodermic needle) and a syringe. Injection is a technique for delivering drugs by parenteral administration, that is, administration via a route other than through the digestive tract. Parenteral injection includes intravenous injection, intramuscular injection, subcutaneous injection, intradermal injection and depot injection.

Administration by "topical administration" refers to applying a drug on the surface of a body, for example, applied to the skin or mucosal surfaces, such as the vagina, penis, eyes and ears and so on. Topical medicines usually avoid contact with the mouth and do not eat. Topical administration may include, but not limited to, ointments, creams, gels, pastes, poultices, topical powders, and medicated plasters.

Administration by "inhalation" refers to the administration of a substance in the form of a gas, aerosol, or fine powder via the respiratory tract, usually by oral or nasal inhalation, for local or systemic effect.

Mouth inhalation: in Inhaled medications can be absorbed quickly and act both locally and systemically. Proper technique with inhaler devices is necessary to achieve the correct dose. Some medications can have an unpleasant taste or irritate the mouth. In general, only 20-50% of the pulmonary-delivered dose rendered in powdery particles will be deposited in the lung upon mouth inhalation. The remainder of 50-70% undeposited aerosolized particles are cleared out of lung as soon as exhalation. An inhaled powdery particle that is >8 μm is structurally predisposed to depositing in the central and conducting airways (conducting zone) by inertial impaction. An inhaled powdery particle that is between 3 and 8 μm in diameter tend to largely deposit in the transitional zones of the lung by sedimentation. An inhaled powdery particle that is <3 μm in diameter is structurally predisposed to depositing primarily in the respiratory regions of the peripheral lung via diffusion. Particles that deposit in the upper and central airways are rarely absorbed systemically because they are going to be removed by mucociliary clearance in an efficient and rapid fashion.

Nasal inhalation: Inhalation by smoking a substance is likely the most rapid way to deliver drugs to the brain, as the substance travels directly to the brain without being diluted in the systemic circulation. The severity of dependence on psychoactive drugs tends to increase with more rapid drug delivery.

The term "continuously" refers to an administration uninterrupted for a period according to medically or therapeutically need, for example, but not limited to, infusion with or without pump, respiratory therapy, inhalation therapy.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a composition herein may be administered to a subject in need of the treatment via a suitable route.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "health food" or "health food product" refers to any kind of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

I. Compounds of Formula (I)

The present disclosure is related to method of treating coronavirus infection, comprising administering to a subject in need thereof an effective amount of a composition, wherein the composition comprises one or more compounds of Formula (I):

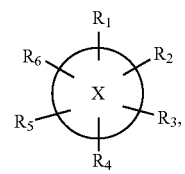

(I)

or a pharmaceutically acceptable salt thereof. Ring X can be a 5-membered or 6-membered monocyclic ring, which optionally may include one or two heteroatoms, such as N, O, P, or S. Among $R_1$-$R_6$, at least one is of the formula

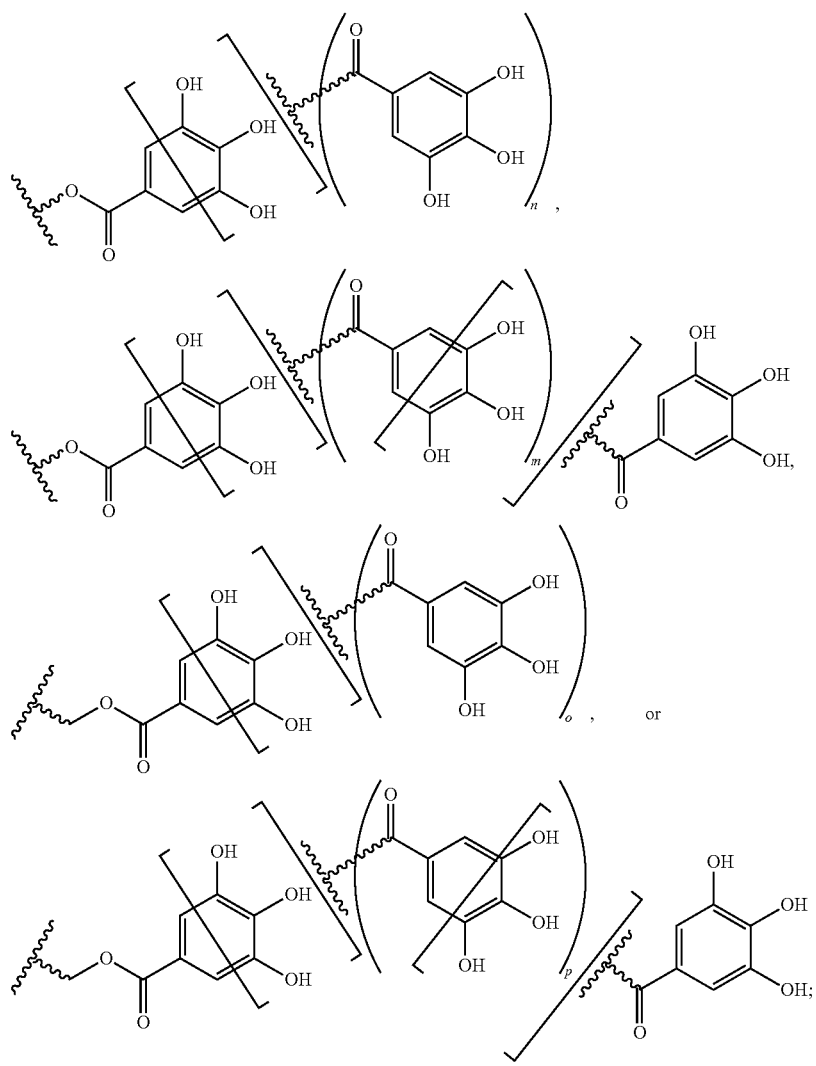
and each of the remaining $R_1$-$R_6$, independently, is —OH, —COOH,
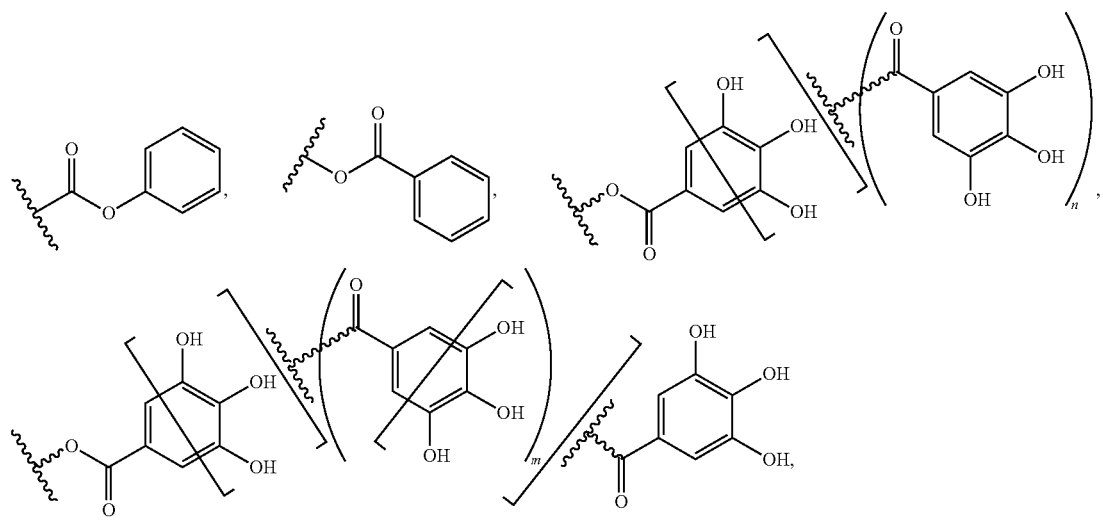

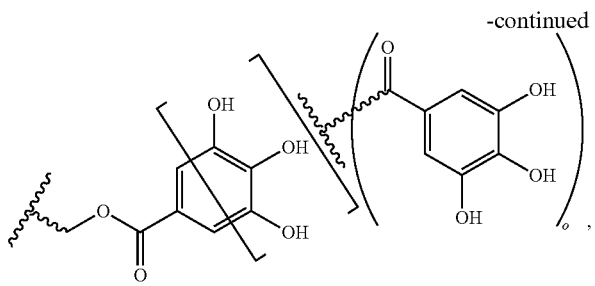

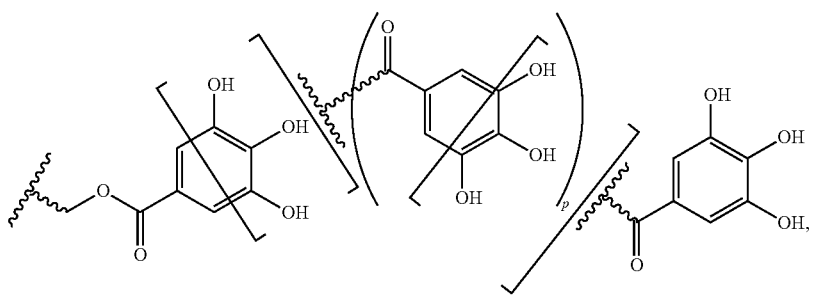

or absent.

Any of the compounds of Formula (I) may have 2 to 35 galloyl moieties, inclusive (e.g., 4-35, inclusive). In some embodiments, one of $R_1$, $R_2$, $R_3$, $R_4$, $R_5$, or $R_6$ is present Ring X in a compound of Formula (I). In some embodiments, two of $R_1$, $R_2$, $R_3$, $R_4$, $R_5$, or $R_6$ are present in Ring X in a compound of Formula (I). In some embodiments, three of $R_1$, $R_2$, $R_3$, $R_4$, $R_5$, or $R_6$ are present Ring X in a compound of Formula (I). In some embodiments, four of $R_1$, $R_2$, $R_3$, $R_4$, $R_5$, or $R_6$ are present in Ring X in a compound of Formula (I). In some embodiments, five of $R_1$, $R_2$, $R_3$, $R_4$, $R_5$, or $R_6$ are present in Ring X in a compound of Formula (I). In some embodiments, all of $R_1$, $R_2$, $R_3$, $R_4$, $R_5$, or $R_6$ are present in Ring X in a compound of Formula (I).

In some examples, each of $R_1$, $R_2$, $R_3$, $R_4$, $R_5$, or $R_6$ can be unsubstituted. In other examples, each of $R_1$, $R_2$, $R_3$, $R_4$, $R_5$, or $R_6$ may be substituted with 1, 2, 3, 4, or 5 substituents selected from the group consisting of $C_{1-3}$ alkyl, halogen, —CN, —$NO_2$, —SH, —S($C_{1-3}$ alkyl), —$NH_2$, NH($C_{1-3}$ alkyl), N($C_{1-3}$alkyl)$_2$, and —O($C_{1-3}$ alkyl); wherein n and o are, independently, 0 or 1; m and p are, independently, 1, 2, 3, 4, or 5.

In some embodiments, Ring X can be a 6-membered monocarbocylic ring, e.g.,

In other examples, Ring X can be a 6-membered monoheterocylic ring. In some examples, the monoheterocyclic ring contains one N atom. In some examples, the monoheterocyclic ring contains one 0 atom. In some examples, the monoheterocyclic ring contains one P atom. In some examples, the monoheterocyclic ring contains one S atom. Examples include

In some embodiments, Ring X can be a 6-membered heterocyclic ring having two heteroatoms, which may be O, N, S, or P. In some examples, the two heteroatoms are identical. In other examples, the two heteroatoms are different. In some examples, the two heteroatoms are both N. In some examples, the two heteroatoms are N and O.

In some embodiments, Ring X can be a 5-membered monocarbocylic ring. In other examples, Ring X can be a 5-membered monoheterocylic ring. In some examples, the monoheterocyclic ring contains one N atom. In some examples, the monoheterocyclic ring contains one O atom. In some examples, the monoheterocyclic ring contains one P atom. In some examples, the monoheterocyclic ring contains one S atom. Example include

In some embodiments, Ring X can be a 5-membered heterocyclic ring having two heteroatoms, which may be O, N, S, or P. In some examples, the two heteroatoms are identical. In other examples, the two heteroatoms are different. In some examples, the two heteroatoms are both N. In some examples, the two heteroatoms are N and O.

In some embodiments, one or more of $R_1$, $R_2$, $R_3$, $R_4$, $R_5$, and $R_6$, where applicable, is of the formula:

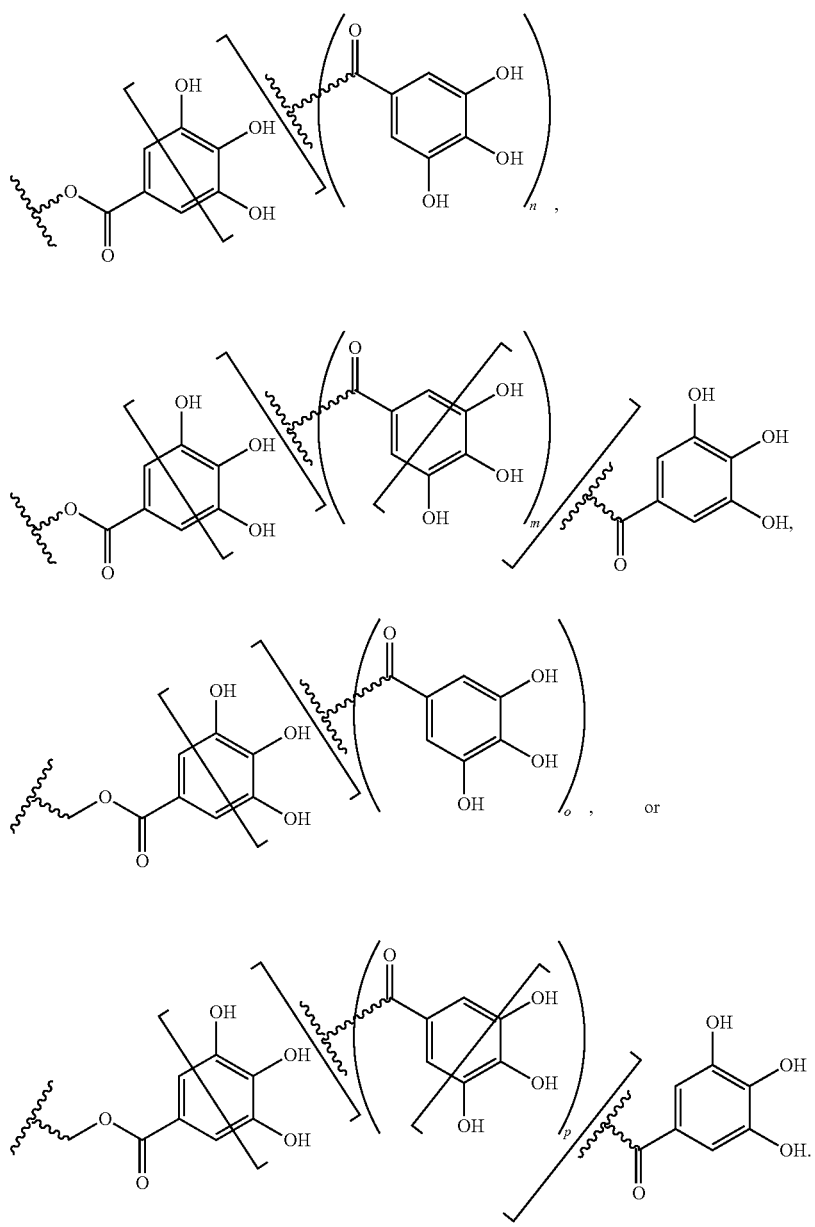

In some instances, these groups are unsubstituted. In other instances, one or more of these groups can be substituted can be substituted with 1, 2, 3, 4, or 5 substituents selected from the group consisting of $C_{1-3}$ alkyl, halogen, —CN, —$CF_3$, —$NO_2$, —SH, —S($C_{1-3}$ alkyl), —$NH_2$, NH($C_{1-3}$ alkyl), N($C_{1-3}$ alkyl)$_2$, —OH, and —O($C_{1-3}$ alkyl); wherein n and o are, independently, 0 or 1; m and p are, independently, 1, 2, 3, 4, or 5.

In some examples, one or more of $R_1$, $R_2$, $R_3$, $R_4$, $R_5$, and $R_6$, where applicable, can be of the formula:

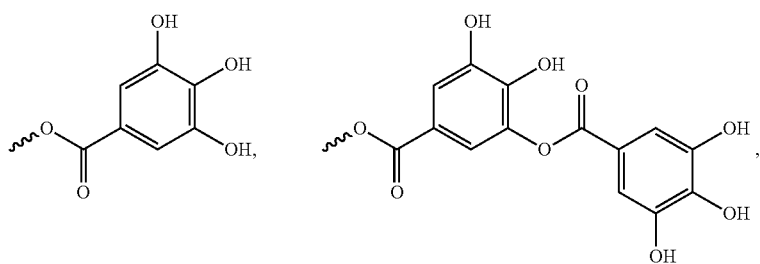

-continued
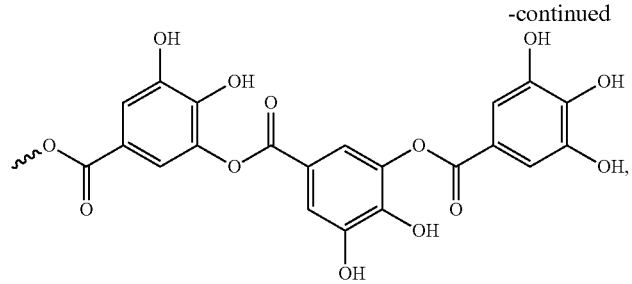
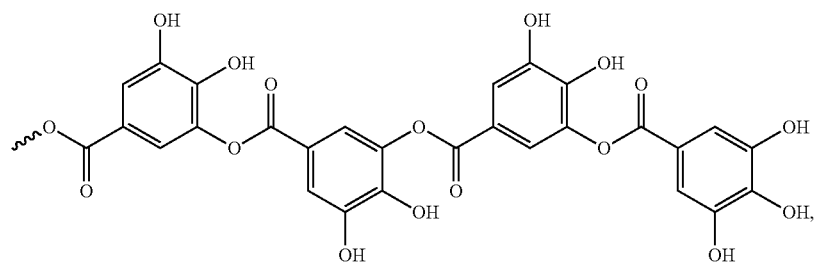
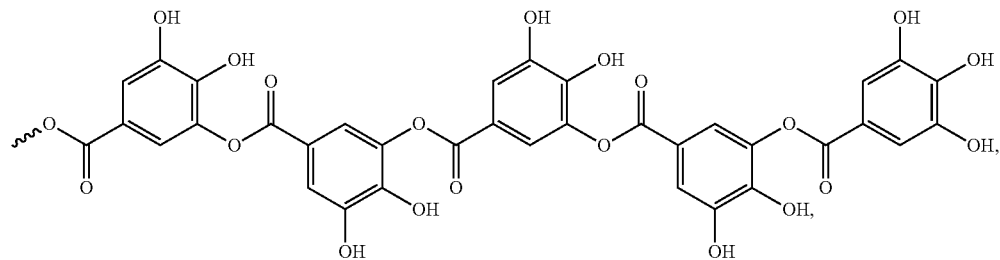
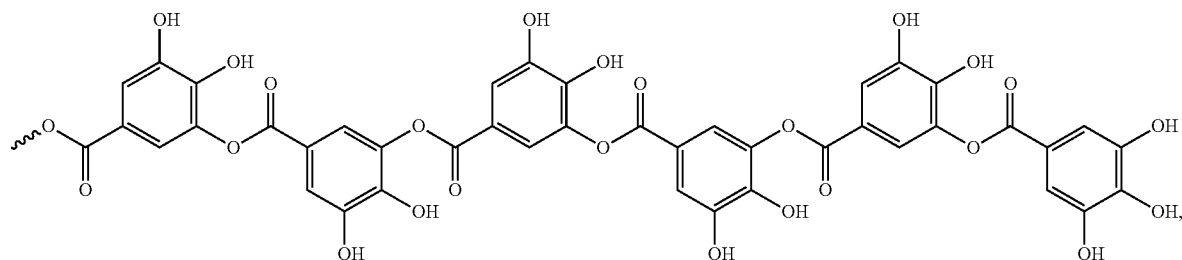
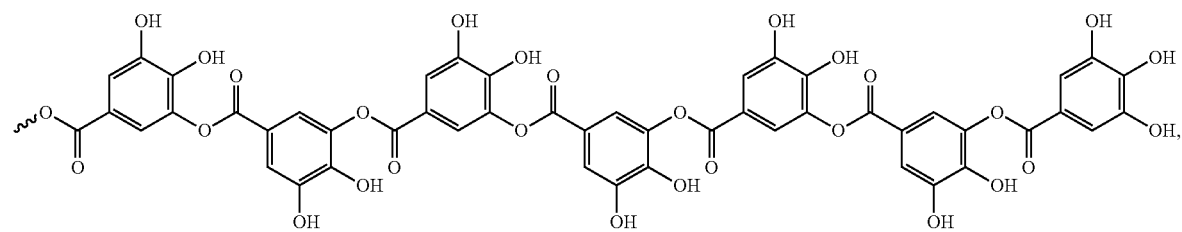
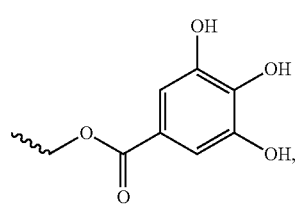
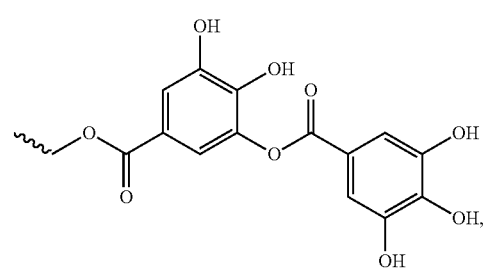

-continued

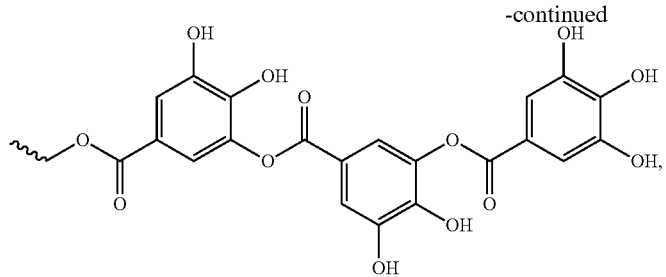

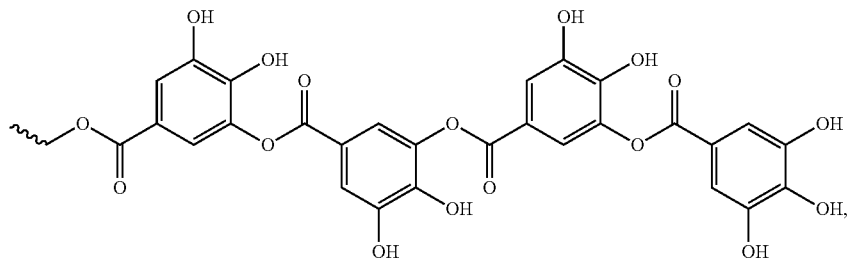

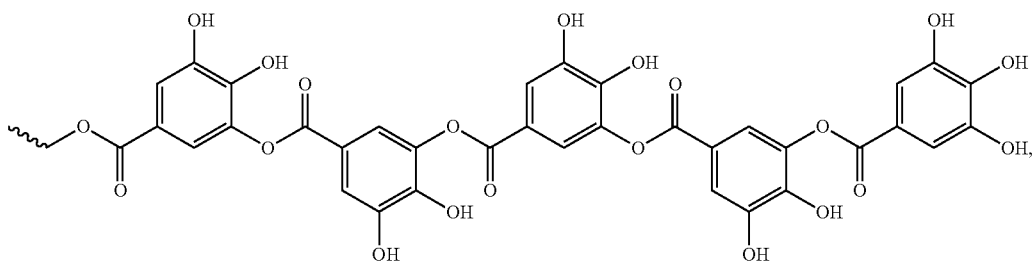

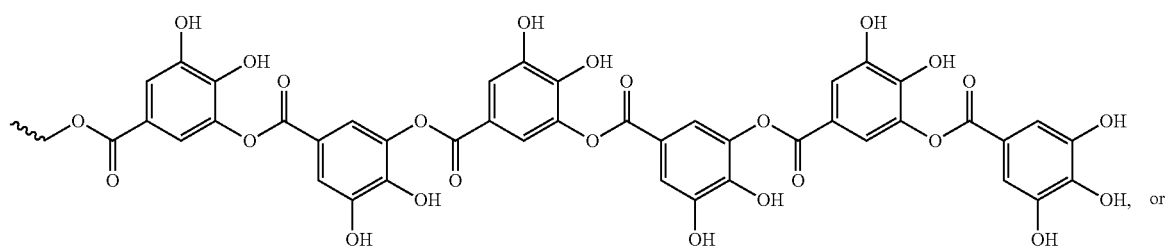

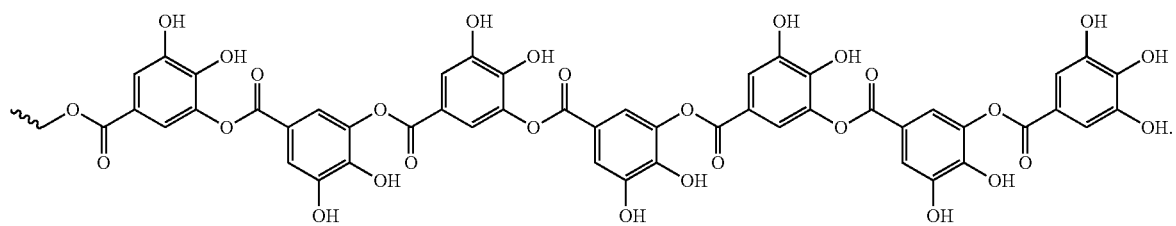

In some embodiments, a compound of Formula (I) may contain Ring X to which all of $R_1$-$R_6$ are attached. In other embodiments, a compound of Formula (I) may contain Ring X, to which one or more of $R_1$-$R_6$ are absent but at least one of the $R_1$-$R_6$ moieties is attached. In some embodiments, a compound of Formula (I) disclosed herein may contain 2-35 galloyl moieties, inclusive. For example, a compound of Formula (I) may contain 4-35 galloyl moieties.

In some examples, a compound of Formula (I) is a compound having the structure of Formula (I)

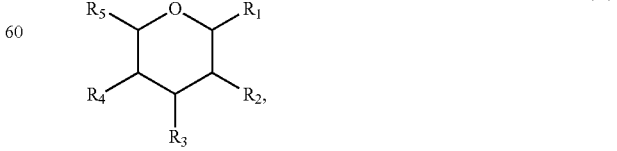

(Ia)

in which all of $R_1$, $R_2$, $R_3$, $R_4$, and $R_5$ are present and as defined herein. Compounds of Formula (Ia) may be in any stereo configuration (e.g., in alpha form or in beta form), or contain mixtures of compounds with different stereo configuration. For example, a compound of Formula (Ia) may have the structure of

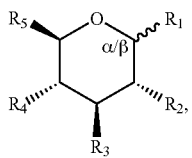

in which $R_1$, $R_2$, $R_3$, $R_4$, and $R_5$ are present and as defined herein. A Formula (Ia) compound (e.g., a Formula (Ib) compound) may have 4-35 galloyl moieties, for example, 6-35 galloyl moieties; 8-35 galloyl moieties, 10-35 galloyl moieties, 15-35 galloyl moieties, 20-35 galloyl moieties, 25-35 galloyl moieties, or 30-35 galloyl moieties. In some instances, A Formula (Ia) compound (e.g., a Formula (Ib) compound) may have ≥15 galloyl moieties. Exemplary Formula (Ia) compound (e.g., Formula (Ib) compounds) include α5G, β5G, α10G, β10G, α15G, β15G, α20G, β20G, α25G, or β25G. See structures in Table 1 and Table 34 below.

In some examples, a compound of Formula (I) is a compound having the structure of

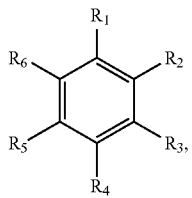

in which each of $R_1$, $R_2$, $R_3$, $R_4$, $R_5$, and $R_6$ is as defined herein. In some instances, all of $R_1$, $R_2$, $R_3$, $R_4$, $R_5$, and $R_6$ are present. In some instances, five of $R_1$, $R_2$, $R_3$, $R_4$, $R_5$, and $R_6$ are present. In some instances, four of $R_1$, $R_2$, $R_3$, $R_4$, $R_5$, and $R_6$ are present. In some instances, three of $R_1$, $R_2$, $R_3$, $R_4$, $R_5$, and $R_6$ are present. In some instances, two of $R_1$, $R_2$, $R_3$, $R_4$, $R_5$, and $R_6$ are present. In some instances, one of $R_1$, $R_2$, $R_3$, $R_4$, $R_5$, and $R_6$ is present. A Formula (Ic) compound may have 4-35 galloyl moieties, for example, 6-35 galloyl moieties; 8-35 galloyl moieties, 10-35 galloyl moieties, 15-35 galloyl moieties, 20-35 galloyl moieties, 25-35 galloyl moieties, or 30-35 galloyl moieties. In some instances, A Formula (Ia) compound (e.g., a Formula (Ib) compound) may have ≥15 gallolyl moieties.

In some examples, a compound of Formula (I) is a compound having the structure of

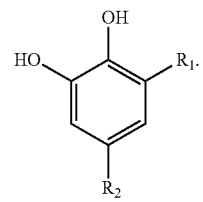

In Formula (Id), $R_1$ can be

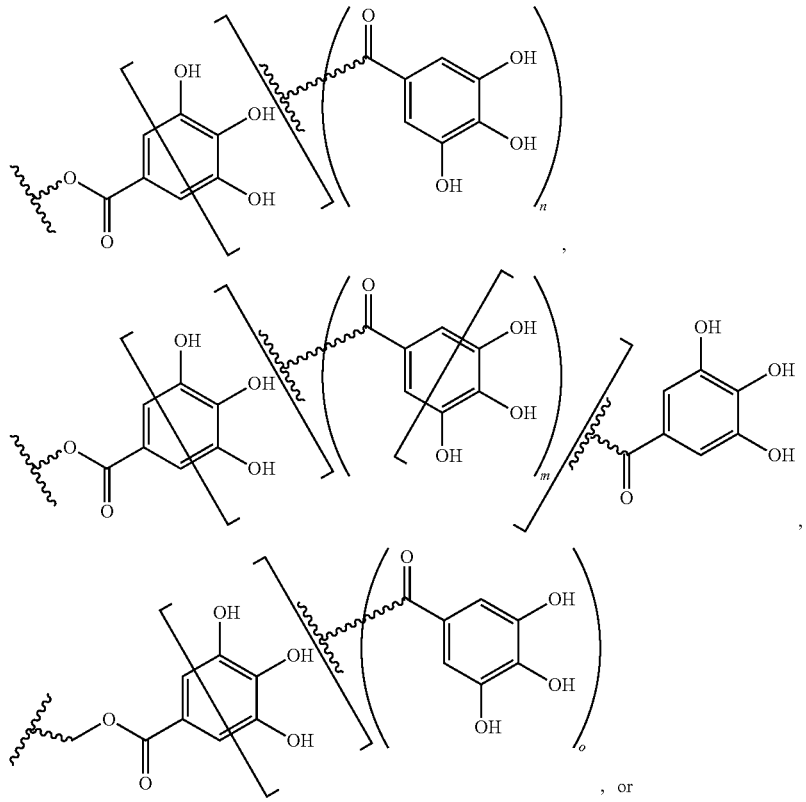

, or

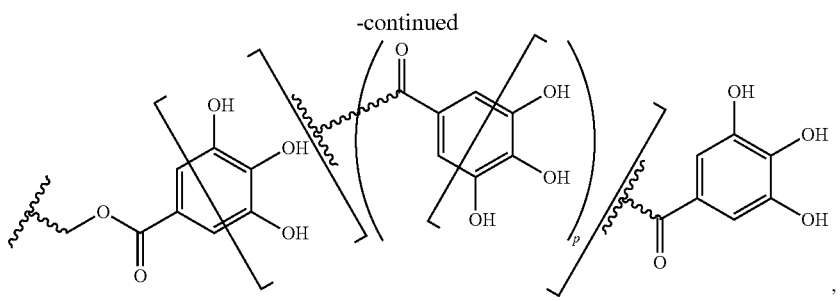

for example, the groups containing one or more galloyl moieties disclosed herein. In some instances, $R_2$ can be —COOH (e.g., Compound 14, Compound 18, or Compound 149; see Table 35 below and FIG. 20). In other instances, $R_2$ can be

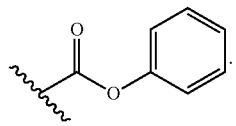 [SMILES: *C(=O)Oc1ccccc1]

A Formula (Id) compound may have 2-15 galloyl moieties, for example, 2, 3, 4, 5, 6, 7, 8, 9, 10, 11, 12, 13, 14, or 15 galloyl moieties. A Formula (Id) compound having $R_2$ as

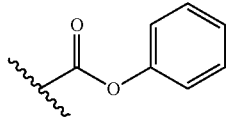 [SMILES: *C(=O)Oc1ccccc1]

is designed herein as phenol nG compounds, wherein G represents galloyl moiety and n refers to the number of galloyl moieties. Examples include Compounds phenol 3G, phenol 5G, and phenol 7G listed in Table 1 below.

In some examples, a compound of Formula (I) is a compound having the structure of

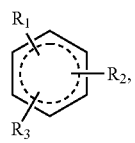
(Ie)

in which at least one of $R_1$, $R_2$, and $R_3$ is

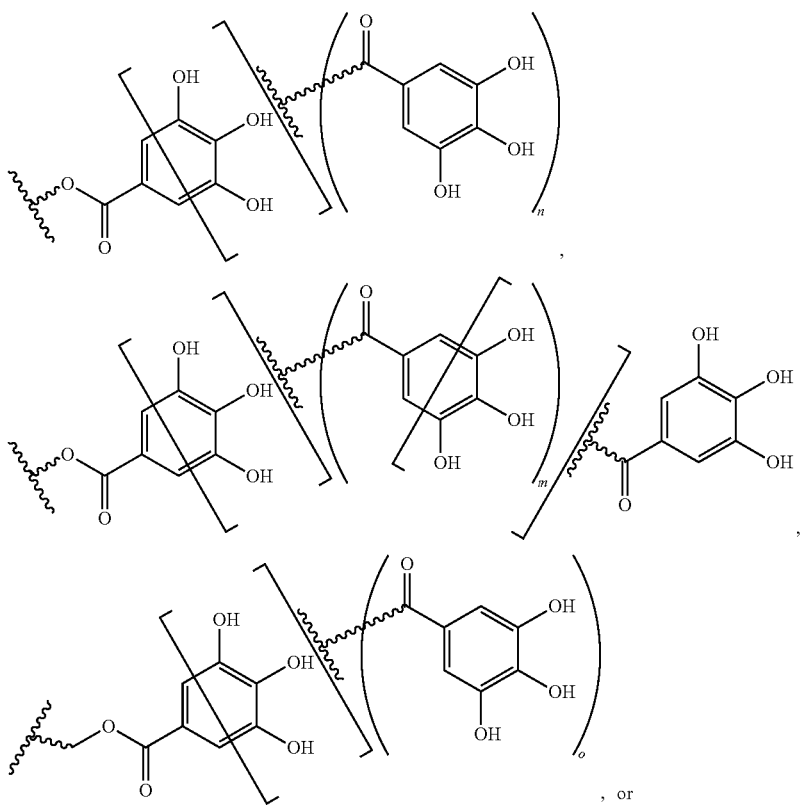

, or

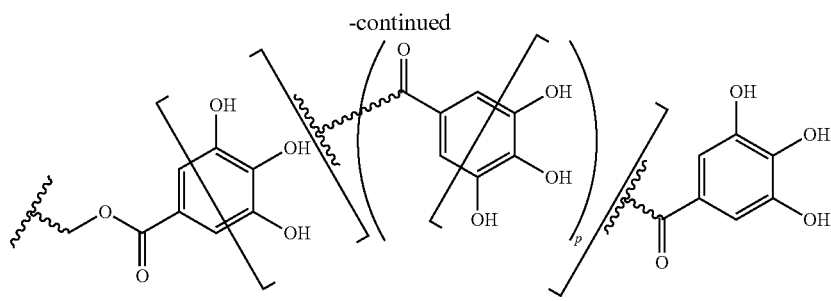
(e.g., those examples provided above), and the remaining of $R_1$, $R_2$, and $R_3$ can be
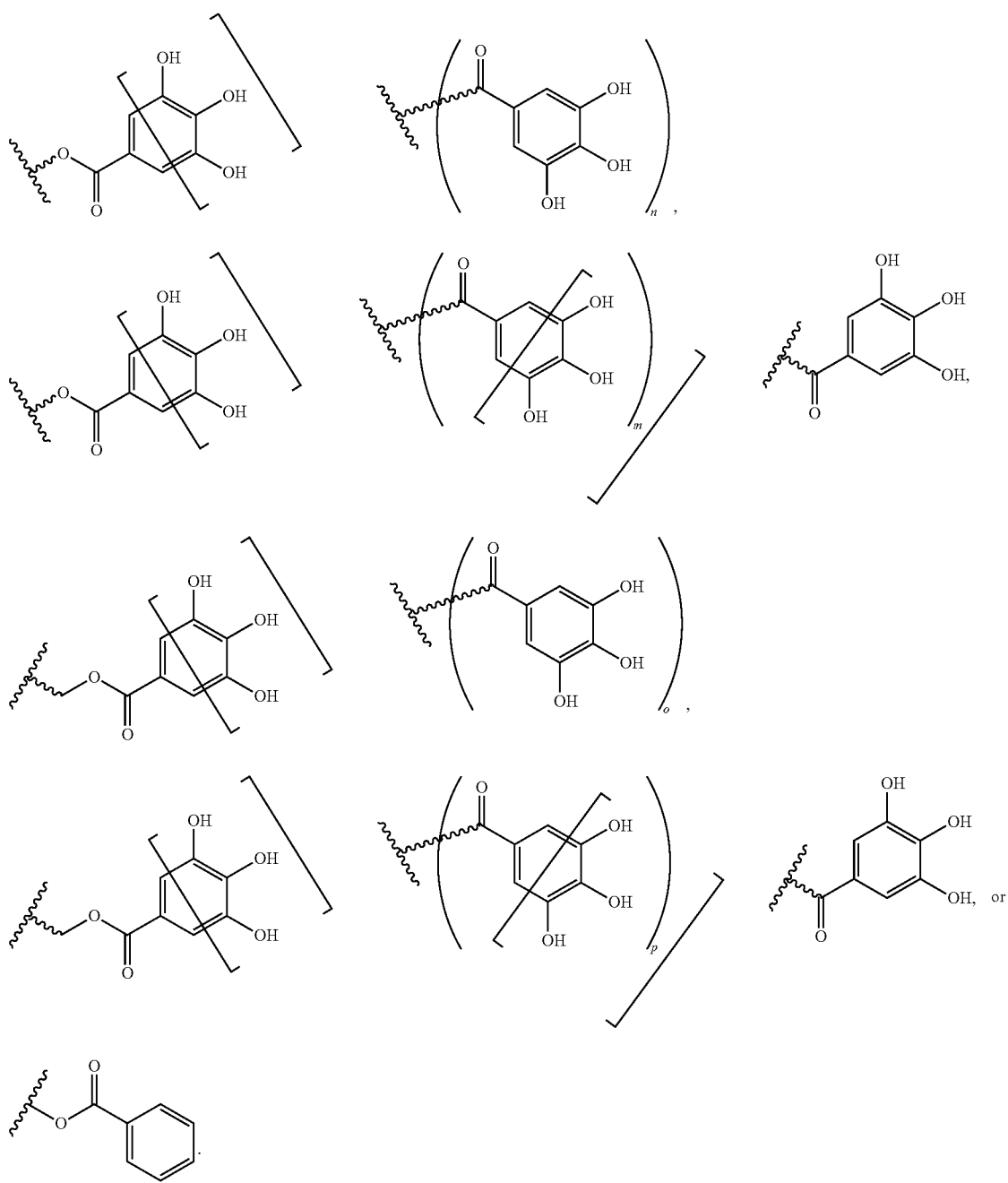

In some instances, the Formula (Ie) compounds may have the structure of

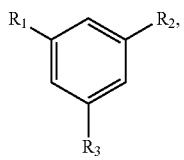  (Ie-1)

in which each of $R_1$-$R_3$ is as defined herein.

A Formula (Ie) (e.g., Ie-1) compound may have 4-35 galloyl moieties, for example, 6-35 galloyl moieties; 8-35 galloyl moieties, 10-35 galloyl moieties, 15-35 galloyl moieties, 20-35 galloyl moieties, 25-35 galloyl moieties, or 30-35 galloyl moieties. In some instances, A Formula (Ie) compound may have ≥15 galloyl moieties.

In some instances, all of $R_1$, $R_2$, and $R_3$ in Formula (Ie) (e.g., Ie-1) are (e.g., those examples above). Such Formula (Id) compounds are also named phloroglucinol nG compounds, wherein G represents gallolyl moiety and n refers to the number of gallolyl moieties. Examples include phloroglucinol 6G, phloroglucinol 9G, phloroglucinol 12G, phloroglucinol 15G, or phloroglucinol 21G (see Table 1 and Table 34 below). In some instances one of $R_1$, $R_2$, and $R_3$ is

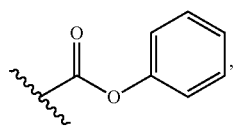 [SMILES: *C(=O)Oc1ccccc1]

e.g., Compound 103 (see Table 35 and FIG. 20).

In some examples, a compound of Formula (I) is a compound having the structure of

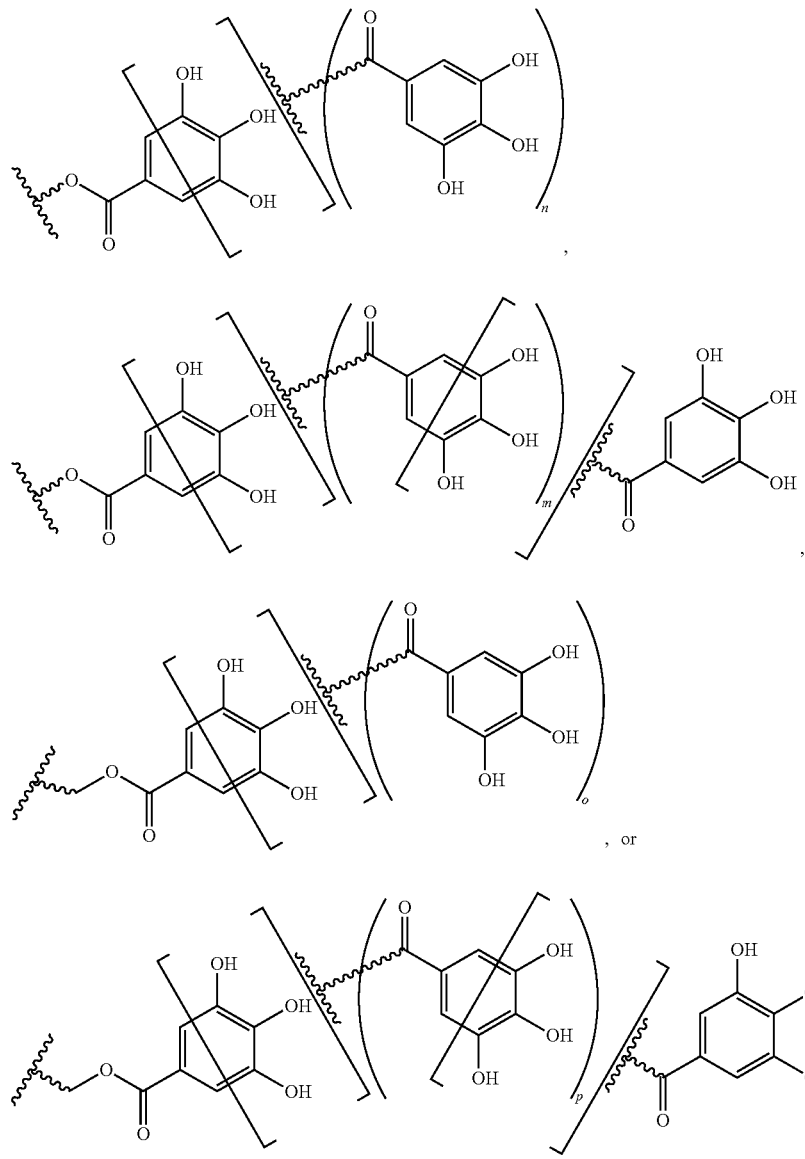

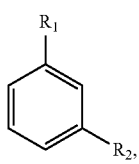

(If)

in which each $R_1$ and $R_2$ independently is

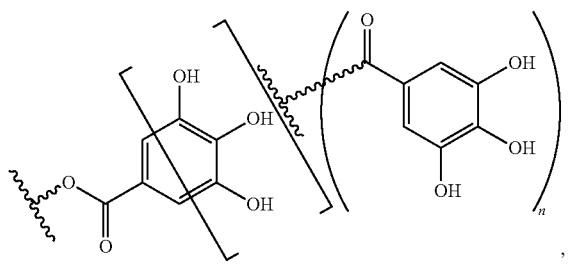

,

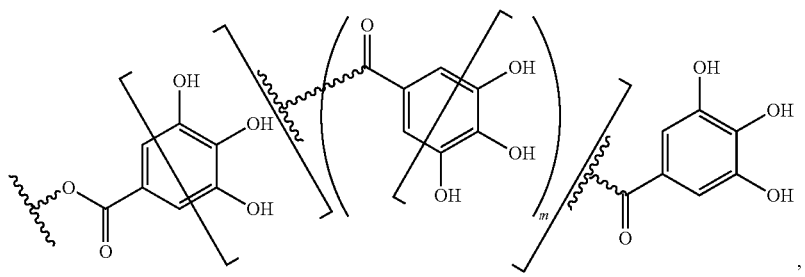

,

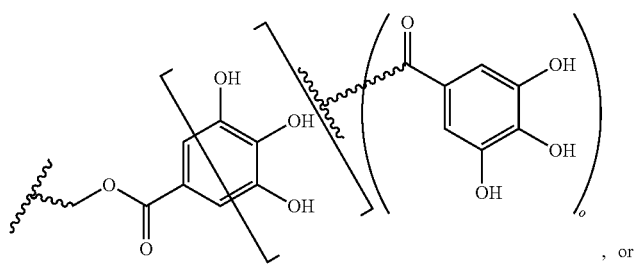

, or

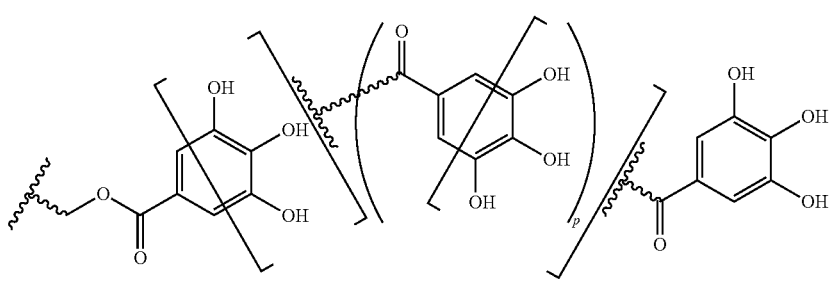

(e.g, those examples above). A Formula (If) compound may have 4-35 galloyl moieties, for example, 6-35 galloyl moieties; 8-35 galloyl moieties, 10-35 galloyl moieties, 15-35 galloyl moieties, 20-35 galloyl moieties, 25-35 galloyl moieties, or 30-35 galloyl moieties. In some instances, A Formula (If) compound may have ≥10 gallolyl moieties. Such compounds are also named Resorcin nG compounds, wherein G represents gallolyl moiety and n refers to the number of gallolyl moieties. Examples include Resorcin 10G and Resorcin 14G listed in Table 1 below.

In some instances, a compound of Formula (I) is a compound having the structure of

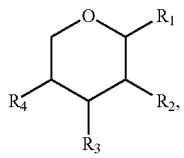

in which one or more of $R_1$, $R_2$, $R_3$, and $R_4$, independently, is (e.g., those examples provided herein). A Formula (Ig) compound may have 4-35 galloyl moieties, for example, 6-35 galloyl moieties; 8-35 galloyl moieties, 10-35 galloyl moieties, 15-35 galloyl moieties, 20-35 galloyl moieties, 25-35 galloyl moieties, or 30-35 galloyl moieties. In some instances, A Formula (Ig) compound may have ≥15 gallolyl moieties. In some instances, all of $R_1$, $R_2$, $R_3$, and $R_4$ are present in Formula (Ig). In some instances, three of $R_1$, $R_2$, $R_3$, and $R_4$ are present in Formula (Ig). In some instances, two of $R_1$, $R_2$, $R_3$, and $R_4$ are present in Formula (Ig). In some instances, one of $R_1$, $R_2$, $R_3$, and $R_4$ are present in Formula (Ig). A Formula (Ig) compound may be of any stereo configuration or a mixture of different stereo configu-

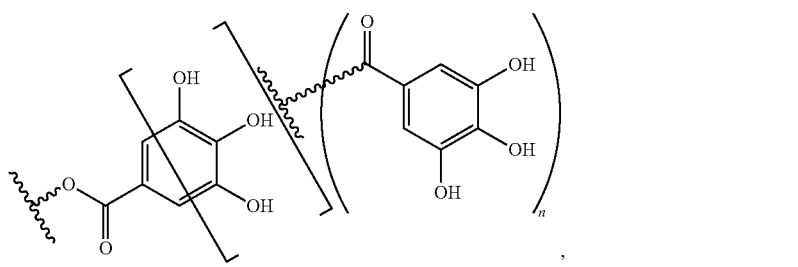

,

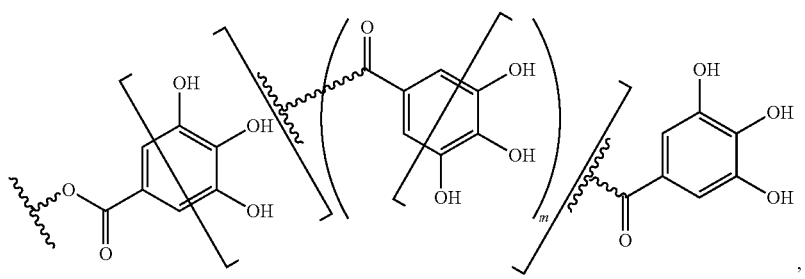

,

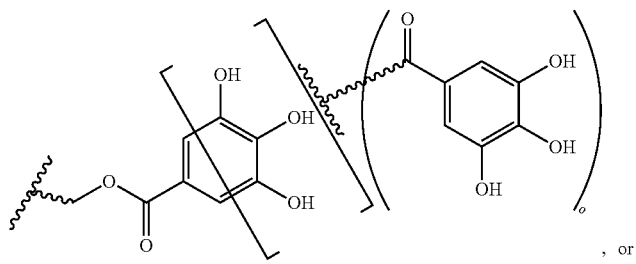

, or

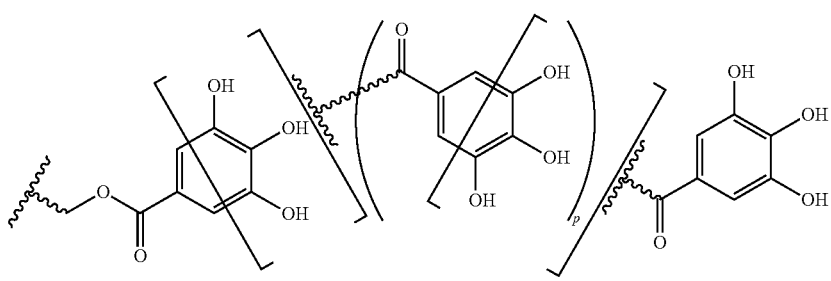

ration. Exemplary Formula (Ig) compounds include Compound 117, 119, 121, 123, 126, or 128 shown in Table 35 below and FIG. 20.

In some instances, a compound of Formula (I) is a compound having the structure of

(Ih)

in which one or more of $R_1$, $R_2$, $R_3$, and $R_4$, independently, is

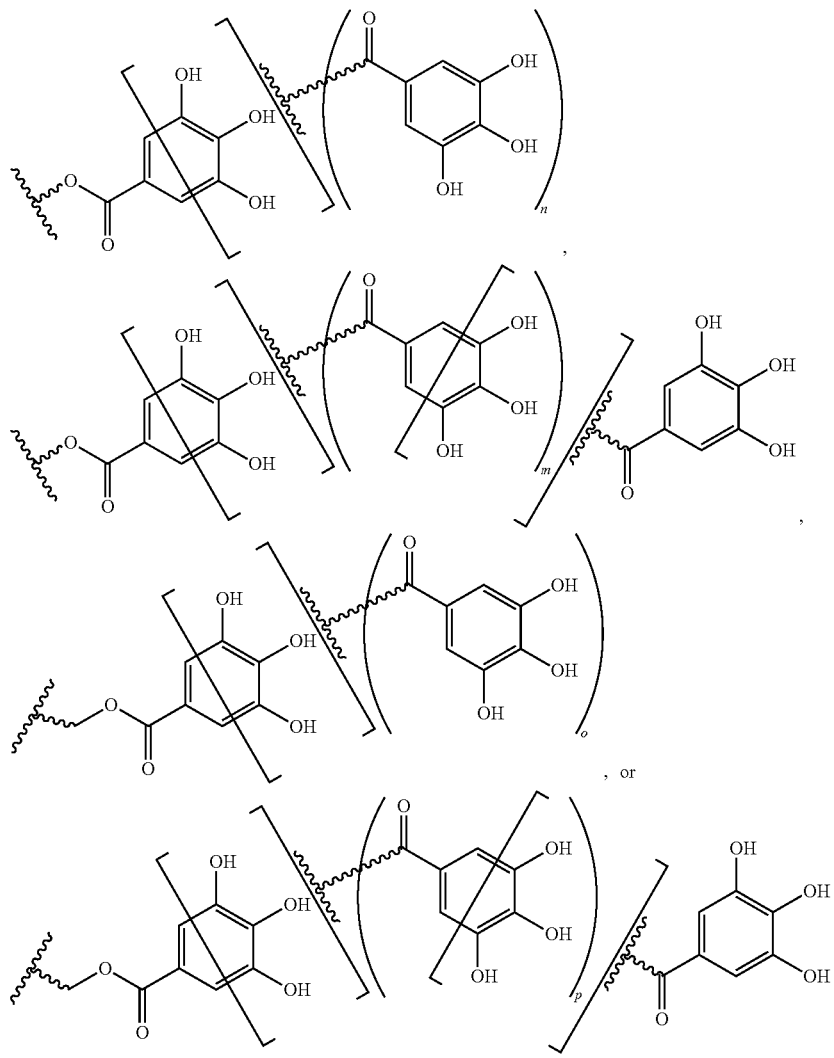

(e.g., those examples provided herein). A Formula (Ih) compound may have 4-35 galloyl moieties, for example, 6-35 galloyl moieties; $-35 galloyl moieties, 10-35 galloyl moieties, 15-35 galloyl moieties, 20-35 galloyl moieties, 25-35 galloyl moieties, or 30-35 galloyl moieties. In some instances, A Formula (Ih) compound may have ≥15 galloyl moieties. In some instances, all of $R_1$, $R_2$, $R_3$, and $R_4$ are present in Formula (N. In some instances, three of $R_1$, $R_2$, $R_3$, and $R_4$ are present in Formula (Ih). In some instances, two of $R_1$, $R_2$, $R_3$, and $R_4$ are present in Formula (Ih). In some instances, one of $R_1$, $R_2$, $R_3$, and $R_4$ are present in Formula (Ih). A Formula (Ih) compound may be of any stereo configuration or a mixture of different stereo configuration. Exemplary Formula (Ih) compounds include Compound 134, 136, 138, 140, 142, 144, 146, or 148 shown in Table 35 below and FIG. 20.

In some embodiments, a population of any of the Formula (I) compounds are for use in the methods disclosed herein. In some examples, the Formula (I) compounds may have the structure of Formula (Ia). In some examples, the Formula (I) compounds may have the structure of Formula (Ib), which may be in alpha form, in beta form, or a combination thereof. In some examples, the Formula (I) compounds may have the structure of Formula (Ic). In some examples, the Formula (I) compounds may have the structure of Formula (Id). In some examples, the Formula (I) compounds may have the structure of Formula (Ie) (e.g., Ie-1). In some examples, the Formula (I) compounds may have the structure of Formula (If). In some examples, the Formula (I) compounds may have the structure of Formula (Ig). In some examples, the Formula (I) compounds may have the structure of Formula (Ih).

In some examples, about 1-25% of the Formula (I) compounds in the population have 5

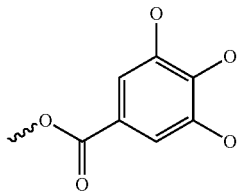

moieties. In some examples, about 10-40% of the Formula (I) compounds in the population have 6-7

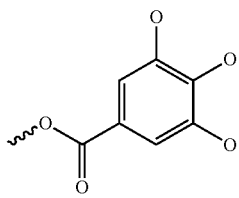

moieties. In some examples, about 20-85% of the Formula (I) compounds in the population have 8-12

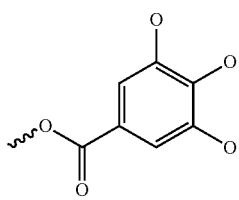

moieties. In some embodiments, the Formula (I) compounds contain the

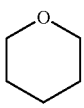

central ring, to which the galloyl moieites are attached.

In some embodiments, about 1-25% of the Formula (I) compounds in the population have 5 galloyl moieties. In some embodiments, about 4-15% of the Formula (I) compounds in the population have 5 galloyl moieties. In some embodiments, about 4-10% of the Formula (I) compounds in the population have 5 galloyl moieties. In some embodiments, about 4-8% of the Formula (I) compounds in the composition have 5 galloyl moieties. In some embodiments, about 1-4% of the Formula (I) compounds in the population have 5 galloyl moieties. In some embodiments, about 10-40% of the Formula (I) compounds in the composition have 6-7 galloyl moieties. In some embodiments, about 20-35% of the Formula (I) compounds in the population have 6-7 galloyl moieties. In some embodiments, about 25-35% of the Formula (I) compounds in the composition have 6-7 galloyl moieties. In some embodiments, about 28-33% of the Formula (I) compounds in the population have 6-7 galloyl moieties. In some embodiments, about 15-28% of the Formula (I) compounds in the population have 6-7 galloyl moieties. In some embodiments, about 15-20% of the Formula (I) compounds in the population have 6-7 galloyl moieties. In some embodiments, about 20-85% of the Formula (I) compounds in the population have 8-12 galloyl moieties. In some embodiments, about 55-85% of the Formula (I) compounds in the population have 8-12 galloyl moieties. In some embodiments, about 55-75% of the Formula (I) compounds in the population have 8-12 galloyl moieties. In some embodiments, about 55-65% of the Formula (I) compounds in the population have 8-12 galloyl moieties. In some embodiments, about 75-85% of the Formula (I) compounds in the population have 8-12 galloyl moieties. In some embodiments, about 78-83% of the Formula (I) compounds in the population have 8-12 galloyl moieties. In some embodiments, about 63-75% of the Formula (I) compounds in the population have 8-12 galloyl moieties. In some embodiments, about 58-63% of the Formula (I) compounds in the population have 8-12 galloyl moieties.

In some embodiments, the population of Formula (I) compounds disclosed herein comprises a substantially homogenous population of compounds of Formula (I), i.e., at least 80% (e.g., at least 85%, at least 90%, at least 95%, at least 98%, at least 99%, or higher) of the Formula (I) compounds are identical. The Formula (I) compounds in the population contain 2-35 galloyl moieties. In some examples, the Formula (I) compounds in the population may have any number of galloyl moieties between 4-35, for example, between 6-35, between 8-35, between 10-35, between 15-35, between 20-35, between 25-35, or between 30-35 galloyl moieties. In some instances, The Formula (I) compounds in the population may have ≥15 gallolyl moieites.

In some embodiments, the substantially homogenous population of compounds of Formula (I) may have the control ring (Ring X) of

.

The majority compounds of Formula (I) in the substantially homogeneous population may contain the

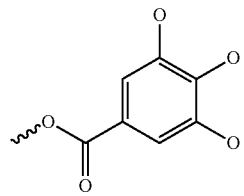

moiety at a certain total number ranging from 2-35, for example ranging from 5-15. In some examples, the majority compound of Formula (I) in the population contain 5

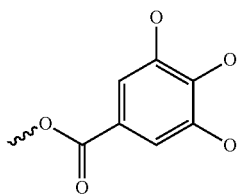

moieties. In some examples, the majority compound of Formula (I) in the population contain

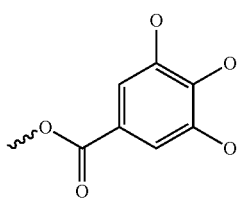

moieties. In some examples, the majority compound of Formula (I) in the population contain 7

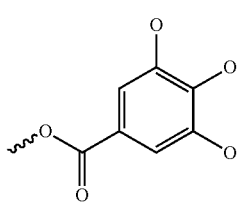

moieties. In some examples, the majority compound of Formula (I) in the population contain 8

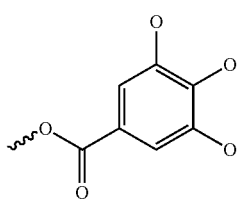

moieties. In some examples, the majority compound of Formula (I) in the population contain 9

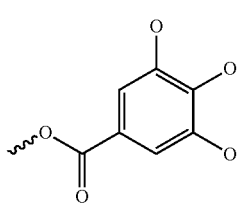

moieties. In some examples, the majority compound of Formula (I) in the population contain 10

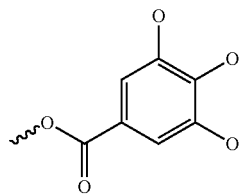

moieties. In some examples, the majority compound of Formula (I) in the population contain 11

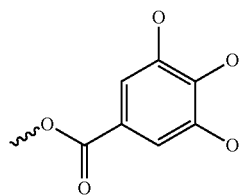

moieties. In some examples, the majority compound of Formula (I) in the population contain 12

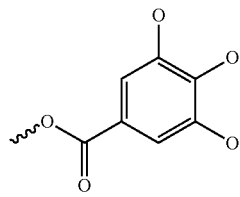

moieties. In some examples, the majority compound of Formula (I) in the population contain 13

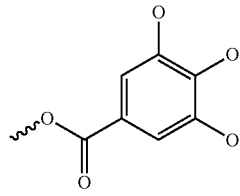

moieties. In some examples, the majority compound of Formula (I) in the population contain 14

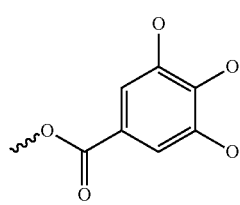

moieties. In some examples, the majority compound of Formula (I) in the population contain 15

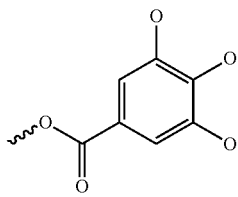

moieties.

Any of the Formula (I) compound disclosed above may have the structure of

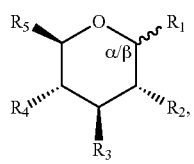

in which each of $R_1$-$R_6$ may contain one or more galloyl moieties. In some instances, the central ring is in α format. In other instances, the central ring is in β format. When the Formula (I) compound composition contains a mixture of Formula (I) compounds, it may contain compounds in both α and β format.

Any of the compounds of Formula (I) or compositions thereof, may be prepared via, e.g., chemical synthesis or isolation from a suitable nature source. See, e.g., U.S. Ser. No. 10/265,336 and U.S. Ser. No. 10/105,378, the relevant disclosures of each of which are incorporated by reference for the purpose and subject matter referenced herein.

Any of the Formula (I) compounds or a population comprising such as disclosed herein is also within the scope of the present disclosure.

II. Composition Comprising Formula (I) Compounds and Kit Containing Such

One aspect of the present disclosure relates to compositions, for example, pharmaceutical compositions, health food product such as nutraceutical compositions, and medical food that comprise one or more compound of Formula (I) and a carrier, e.g., a pharmaceutically acceptable carrier and/or an edible carrier. Such carriers, either naturally occurring or non-naturally occurring (synthetic), may confer various benefits to the compound of Formula (I) in the composition, for example, improving in vitro and/or in vivo stability of the Formula (I) compound, enhancing bioavailability of the compound of Formula (I), increasing the associated bioactivity and/or reducing side effects. Suitable carriers include, but are not limited to, diluents, fillers, salts, buffers, stabilizers, solubilizers, buffering agents, preservatives, or a combination thereof.

(A) Pharmaceutical Compositions

One or more of the Formula (I) compounds disclosed herein can be mixed with one or more suitable carriers to form the compositions as disclosed herein.

In some embodiments, the composition disclosed herein may comprise a mixture of the Formula (I) compounds having various numbers of the

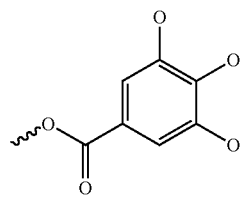

moiety (e.g., 2-35 collectively, for example, 4-35). In some instances, the mixture of Formula (I) compounds may have 4-15 galloyl moeities collectively. For example, at least 60% of the Formula (I) compounds in the composition have 6-12

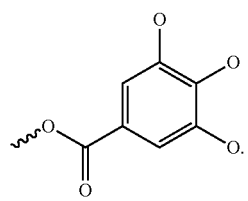

In other examples, at least 50% of the Formula (I) compounds in the composition have 8-12

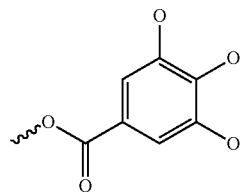

moieties. In yet other examples, ≥98% of the Formula (I) compounds in the composition have 4-12

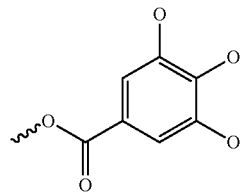

moieties. Alternatively, ≥97% of the Formula (I) compounds in the composition have 5-12

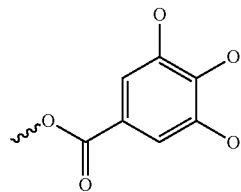

moieties. In some examples, ≥90% of the Formula (I) compounds in the composition have 6-12

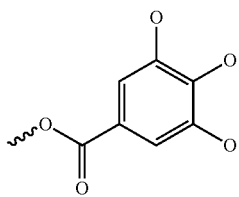

moieties. In other examples, or ≥60% of the Formula (I) compounds in the composition have 8-12

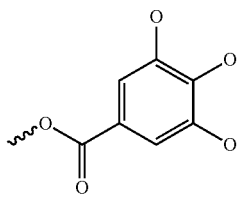

moieties. Further, in some examples, about 1-25% of the Formula (I) compounds in the composition have 5

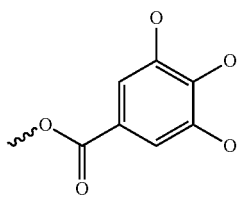

moieties, or about 10-40% of the Formula (I) in the composition have 6-7

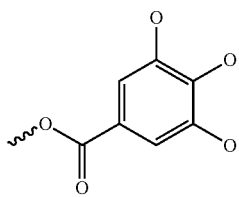

moieties. In still other examples, about 20-85% of the Formula (I) in the composition have 8-12

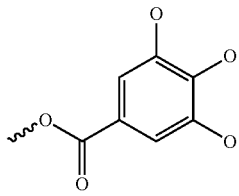

moieties.

In other embodiments, the composition disclosed herein comprises a substantially homogeneous population of any of the Formula (I) compounds disclosed herein. As used herein, "a substantially homogenous population of a Formula (I) compound" refers to a population, in which a majority of the Formula (I) compounds is the same, i.e., having the same Ring X and the same total number of the

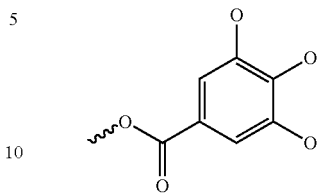

moiety. For example, at least 80% (e.g., at least 85%, at least 90%, at least 95%, at least 98%, or more) of the Formula (I) compounds in a substantially homogenous population are the same.

In some examples, the composition disclosed herein comprises a substantially homogeneous population of any of the Formula (I) compounds, the majority of which has 2, 3, 4, 5, 6, 7, 8, 9, 10, 11, 12, 13, 14, 15, 16, 17, 18, 19, 20, 21, 22, 23, 24, 25 26, 27, 28, 29, 30, 31, 32, 33, 34, or 35

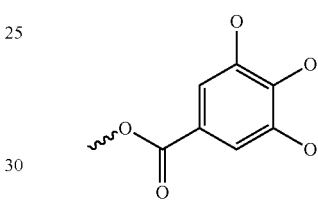

moieties. In some instances, the substantially homogeneous population of Formula (I) compounds comprise at least 80% (e.g., at least 85%, at least 90%, at least 95%, at least 98%, or more) identical Formula (I) compounds having a total number of

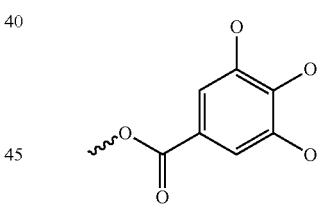

moiety within the range of 6-30, 8-25, 10-25, or 15-25. See above disclosures.

The compositions as described herein, e.g., a pharmaceutical composition comprising a pharmaceutically acceptable carrier, can be used for treating any of the target diseases as described herein. Pharmaceutically acceptable carriers include diluents, fillers, salts, buffers, stabilizers, solubilizers and other material which are well-known in the art. Exemplary pharmaceutically acceptable carriers in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from a suitable inorganic base, (e.g., sodium hydroxide, barium hydroxide, iron (ii) hydroxide, iron (III) hydroxide, magnesium hydroxide, calcium hydroxide, aluminium hydroxide, ammonium hydroxide, potassium hydroxide, caesium hydroxide, or lithium hydroxide) or a suitable organic base (e.g., pyridine, methyl amine, imidazole, benzimidazole, histidine, phosphazene bases, or a hydroxide of an organic cation such as quaternary ammonium hydroxide and phosphonium hydroxide). Also, pharmaceutically-acceptable salts can be prepared as alkaline metal or alkaline earth salts, such as lithium, sodium, potassium or calcium salts.

The pharmaceutical compositions as described herein can comprise pharmaceutically acceptable carriers, excipients, or stabilizers in the form of lyophilized formulations or aqueous solutions. Remington: The Science and Practice of Pharmacy 20th Ed. (2000) Lippincott Williams and Wilkins, Ed. K. E. Hoover. Such carriers, excipients or stabilizers may enhance one or more properties of the active ingredients in the compositions described herein, e.g., bioactivity, stability, bioavailability, and other pharmacokinetics and/or bioactivities.

Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (nonionic surfactants), or polyethylene glycol (PEG).

In some examples, the pharmaceutical composition described herein includes pulmonary compatible excipients. Suitable such excipients include, but not limited to, richloromono-fluoromethane, dichloro-difluoromethane, dichloro-tetrafluoroethane, chloropenta-fluoroethane, monochloro-difluoroethane, difluoroethane, tetrafluoroethane, heptafluoropropane, octafluoro-cyclobutane, purified water, ethanol, propylene glycol, glycerin, PEG (e.g. PEG400, PEG 600, PEG 800 and PEG 1000), sorbitan trioleate, soya lecithin, lecithin, oleic acid, Polysorbate 80, magnesium stearate and sodium laury sulfate, methylparaben, propylparaben, chlorobutanol, benzalkonium chloride, cetylpyridinium chloride, thymol, ascorbic acid, sodium bisulfite, sodium metabisulfite, EDTA, sodium hydroxide, tromethamine, ammonia, HCl, $H_2SO_4$, $HNO_3$, citric acid, $CaCl_2$, $CaCO_3$, sodium citrate, sodium chloride, disodium EDTA, saccharin, menthol, ascorbic acid, glycine, lysine, gelatin, povidone K25, silicon dioxide, titanium dioxide, zinc oxide, lactose, lactose monohydrate, lactose anhydrate, mannitol, and dextrose.

In other examples, the pharmaceutical composition described herein can be formulated in sustained-release format. Suitable examples of sustained-release preparations include semipermeable matrices of solid hydrophobic polymers which matrices are in the form of shaped articles, e.g., films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle or a sealed container to be manually accessed.

The pharmaceutical compositions described herein can be in unit dosage forms such as solids, solutions or suspensions, or suppositories, for administration by inhalation or insufflation, intrathecal, intrapulmonary or intracerebral routes, oral, parenteral or rectal administration.

For preparing solid compositions, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as powder collections, tablets, pills and capsules. This solid preformulation composition is then subdivided into unit dosage forms of the type described above containing from 0.1 to about 5 grams of the active ingredient of the present invention. Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

In some examples, the pharmaceutical composition described herein include a liposome composition. Liposomes are artificially prepared spherical vesicle composition consisting of a lamellar phase lipid bilayer. Liposomes or lipid vesicles are usually composed of phosphatidylcholine-enriched phospholipids and may also contain mixed lipid chains with surfactant properties such as egg phosphatidyl ethanolamine. Preferably, the liposomal composition is composed of one or more vesicle forming lipid, selected from di-aliphatic chain lipid, such as phospholipids; diglycerides; di-aliphatic glycolipids; single lipids such as sphingomyelin or glycosphingolipid; steroidal lipids; hydrophilic polymer derivatised lipids, or mixtures thereof. Preferably, the vesicle forming lipid comprises one or more phospholipids, one or more steroidal lipids, and one or more hydrophilic polymer derivatized lipids. The one or more phospholipids that may be used in the liposome composition comprises phospholipids that form bilayer vesicular structure. The phospholipids that may be used include, but are not limited to, phospholipid such as phosphatidyl choline (PC); phosphatidyl ethanolamine (PE); phosphatidyl serine (PS), phosphatidylglycerol (PG), phosphatidylionositol (PI), sphingomyelin, phosphatidic acid (PA), lecithin; phosphatidylcholine lipid derivatives such as dipalmitoylphosphatidylcholine (DPPC), egg phosphatidylcholine (EPC), hydrogenated egg phosphatidylcholine (HEPC), partially hydrogenated egg phosphatidylcholine (PHEPC), distearylphosphatidyl choline (DSPC), dipalmitoyl phosphatidyl choline (DPPC), soy phosphatidyl choline (SPC), hydrogenated soy phosphatidyl choline (HSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), diarachidoyl phosphatidyl ethanolamine (DAPE) and dipalmitoyl phosphatidyl glycerol (DPPG) and the like.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. In some embodiments, the compositions are composed of particle sized between 10 nm to 100 mm.

Compositions in preferably sterile pharmaceutically acceptable solvents may be nebulized by use of gases. Nebulized solutions may be breathed directly from the nebulizing device or the nebulizing device may be attached to a face mask, tent, endotracheal tube and/or intermittent positive pressure breathing machine (ventilator). Solution, suspension or powder compositions may be administered, preferably orally or nasally, from devices which deliver the formulation in an appropriate manner.

In some embodiments, any of the pharmaceutical compositions herein may further comprise a second therapeutic agent based on the intended therapeutic uses of the composition.

(B) Health Food Product

In some embodiments, the compositions described herein can be a health food product, which can be any kinds of liquid and solid/semi-solid materials that are used for nourishing humans and animals, for treatment of virus infection, or in particular, coronavirus infection. The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein may comprise one or more edible carriers, which confer one or more of the benefits to the composition in the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, flax seed oil, and/or benzoate.

In some examples, the healthy food product is a nutraceutical composition, which refers to compositions containing components from food sources and conferring extra health benefits in addition to the basic nutritional value found in foods. A nutraceutical composition as described herein comprises the composition described herein and additional ingredients and supplements that promote good health and/or enhance stability and bioactivity.

The actions of nutraceutical compositions may be fast or/and short-term or may help achieve long-term health objectives as those described herein, e.g., improving health conditions, in, e.g., human subjects who have or are at risk for virus infection. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pre-gelatinised maize starch, polyvinylpyrrolidone or hydroxypropyl methylcellulose); fillers (for example, lactose, microcrystalline cellulose or to calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

The health food products described herein may further comprise one or more second therapeutic agents, including those described herein.

(C) Medical Food Products

The present disclosure also provides compositions of medical food products, use in improving basic condition during or in the risk of virus infection. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management.) In some examples, a medical food composition described herein is not one of those that would be simply recommended by a physician as part of an overall diet to manage the symptoms or reduce the risk of a disease or condition.

Any of the medical food compositions described herein, comprising one or more compounds of Formula (I) or salts thereof and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

(D) Kits

The present disclosure also provides kits for use in improving basic medical condition. Such kits can include one or more containers comprising the composition as described herein and optionally one or more of the second therapeutic agents as also described herein.

In some embodiments, the kit can comprise instructions for use in accordance with any of the methods described herein. The included instructions can comprise, for example, a description of administration of the composition of Formula (I) and optionally a description of administration of the second therapeutic agent(s) to improve medical conditions of virus infection or in the rick of virus infection. The kit may further comprise a description of selecting an individual suitable for treatment based on identifying whether that individual has the disease or is at risk for the disease. In still other embodiments, the instructions comprise a description of administering one or more agents of the disclosure to an individual at risk of virus infection.

The instructions relating to the use of the composition of Formula (I) to achieve the intended therapeutic effects generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk, or QR code) are also acceptable.

The label or package insert may indicate that the composition is used for the intended therapeutic utilities. Instructions may be provided for practicing any of the methods described herein.

The kits of this invention are in suitable packaging. Suitable packaging includes, but is not limited to, chambers, vials, bottles, jars, flexible packaging (e.g., sealed Mylar or plastic bags), and the like. Also contemplated are packages for use in combination with a specific device, such as an inhaler, nebulizer, ventilator, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Metered-dose inhaler is a device that delivers a measured amount of medication as a mist the patient can inhale. The drug is dissolved or suspended in the low-boiling solvent is stored in a pressurized bottle, the bottle is connected to a pressure switch. The low boiling point solvent makes the pressurized bottle maintain a high internal air pressure at room temperature. Once the switch is pressed, the liquid in the bottle will be released quantitatively, and the medicine will be sprayed into the air in the form of aerosol. The medicine is inhaled into the airways.

In some embodiments, the size of metering chamber in the valve of metered-dose inhaler (MDI) may comprise 25 uL, 50 uL, 75 uL, or 100 uL.

In some embodiments, the MDI canister surface was modified by multiples of one or more of a variety of monomers to improve drug stability and drug delivery. Particularly preferred coating tend to be pure perfluoroalkoxyalkylene (PFA), and blends of polytetrafluoroethylene (PTFE) and polyethersulphone (PES).

Kits may optionally provide additional components such as buffers and interpretive information. Normally, the kit comprises a container and a label or package insert(s) on or associated with the container. In some embodiments, the invention provides articles of manufacture comprising contents of the kits described above.

III. Applications of Composition of Formula (I)

The present disclosure provides a pharmaceutical composition and method of treating certain disorders, diseases, and/or mitigating symptoms of which on subjects.

In some embodiments, the present disclosure provides a composition able to effectively inhibit 3C-like protease (3CLPro) and use thereof in inhibiting, treating, reducing the viral load, and/or reducing morbidity or mortality in the clinical outcomes, in patients suffering from the viral infection. The method comprises administering to a subject in need thereof an effective amount of a composition, which comprises (1) one or more compounds of Formula (I) or a pharmaceutically acceptable salt thereof and (2) a pharmaceutically acceptable carrier; In some embodiments, the effective amount is a prophylactically effective amount (e.g., amount effective for inhibiting viral 3CLPro in a subject in need thereof or amount effective in treating or reducing the viral load, and/or reducing morbidity or mortality in the clinical outcomes in subjects suffering from the viral infection).

In some embodiments, the target viral infection to be treated by the method disclosed herein is a pneumonia caused by the infection of genus Coronavirus, which may include the novel coronavirus (2019-nCoV), severe acute respiratory syndrome coronavirus (SARS-CoV), and middle east respiratory syndrome coronavirus (MERS-CoV). In some embodiments, the target viral infection to be treated by the method disclosed herein is caused by alpha coronavirus strain 229E and NL63, beta coronavirus strain OC43 and HKU1 and coronavirus strains caused by novel transmission from other mammals to human that share the protein homology and the proteolytic functioning of 3CLPro.

In yet another aspect, the present disclosure further provides methods of reducing the risk that an individual will develop a pathological coronavirus infection that has clinical sequelae. The methods generally involve administering a therapeutically effective amount of 3CLPro) inhibitor a composition comprising a therapeutically effective amount of the composition herein.

Determination of whether an amount of the composition as described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration, genetic factors and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration and/or route of administration may be determined and adjusted over the course of therapy, and is generally, but not necessarily, based on treatment and/or suppression and/or amelioration and/or delay of a target disease/disorder. Alternatively, sustained continuous release formulations of a composition as described herein may be appropriate. Various formulations and devices for achieving sustained release are known in the art.

Generally, for administration of any of the compositions, an exemplary daily dosage might range from about any of 0.1 µg/kg to 3 µg/kg to 30 µg/kg to 300 µg/kg to 3 mg/kg, to 30 mg/kg to 100 mg/kg, to 300 mg/kg, to 1 gram/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering one or more initial doses at a suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to twenty four times a day or a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, about 3 mg/kg, about 30 mg/kg, and about 300 mg/kg) may be used. In some embodiments, dosing frequency can be continuously for the period medically or therapeutically needed, every one hour, every two hour, four times a day, three times a day, twice a day, once a day, once every other day, once every week, once every 2 weeks, once every 4 weeks, once every 2 months, once every 3 months or only given once. The dosing regimen can vary over time.

In some embodiments, for an adult patient of normal weight, doses ranging from about 0.3 to 500.00 mg/kg/day (e.g., 0.5 to 400 mg/kg/day, 1-300 mg/kg/day, 5-300 mg/kg/day, or 10-200 mg/kg/day) may be administered. The particular dosage regimen, i.e., dose, timing and repetition, will depend on the particular individual and that individual's medical history, as well as the properties of the individual agents (such as the half-life of the agent, and other considerations well known in the art).

Conventional methods, known to those of ordinary skill in the art of medicine, can be used to administer the composition (e.g., a pharmaceutical composition, a health food composition, a nutraceutical composition or a medical food composition) to the subject, depending upon the type of viral infection disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The composition can be administered by pulmonary delivery system, that is, the active pharmaceutical ingredient is administered into lung. The pulmonary delivery system can be an inhaler system. In some embodiments, the inhaler system is a pressurized metered dose inhaler, a dry powder inhaler, or a nebulizer. In some embodiments, the inhaler system is with a spacer.

In some embodiments, the pressurized metered dose inhaler includes a propellant, a co-solvent, and/or a surfactant. In some embodiments, the propellant is selected from the group comprising of fluorinated hydrocarbons such as trichloromono-fluoromethane, dichloro-difluoromethane, dichloro-tetrafluoroethane, chloropenta-fluoroethane, monochloro-difluoroethane, difluoroethane, tetrafluoroethane, heptafluoropropane, octafluoro-cyclobutane. In some embodiments, the co-solvent is selected from the group comprising of purified water, ethanol, propylene glycol, glycerin, PEG400, PEG 600, PEG 800 and PEG 1000. In some embodiments, the surfactant or lubricants is selected from the group comprising of sorbitan trioleate, soya lecithin, lecithin, oleic acid, Polysorbate 80, magnesium stearate and sodium laury sulfate. In some embodiments, the preservatives or antioxidants is selected from the group comprising of methyparaben, propyparaben, chlorobutanol, benzalkonium chloride, cetylpyridinium chloride, thymol, ascorbic acid, sodium bisulfite, sodium metabisulfite, sodium bisulfate, EDTA. In some embodiments, the pH adjustments or tonicity adjustments is selected from the group comprising of sodium oxide, tromethamine, ammonia, HCl, $H_2SO_4$, $HNO_3$, citric acid, $CaCl_2$, $CaCO_3$.

In some embodiments, the dry powder inhaler includes a disperse agent. In some embodiments, the disperse agent or carrier particle is selected from the group comprising of lactose, lactose monohydrate, lactose anhydrate, mannitol, dextrose which their particle size is about 1-100 μm.

In some embodiments, the nebulizer may include a co-solvent, a surfactant, lubricant, preservative and/or antioxidant. In some embodiments, the co-solvent is selected from the group comprising of purified water, ethanol, propylene glycol, glycerin, PEG (e.g. PEG400, PEG600, PEG800 and/or PEG 1000).

In some embodiments, the surfactant or lubricant is selected from the group comprising of sorbitan trioleate, soya lecithin, lecithin, oleic acid, magnesium stearate and sodium laury sulfate.

In some embodiments, the preservative or antioxidant is selected from the group comprising of sodium benzoate, potassium benzoate, calcium benzoate, methyparaben, propyparaben, chlorobutanol, benzalkonium chloride, cetylpyridinium chloride, thymol, ascorbic acid, sodium bisulfite, sodium metabisulfite, sodium bisulfate, EDTA.

In some embodiments, the nebulizer further includes a pH adjustment or a tonicity adjustment, which is selected from the group comprising of sodium oxide, tromethamine, ammonia, HCl, $H_2SO_4$, $HNO_3$, citric acid, $CaCl_2$, $CaCO_3$.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water-soluble antibodies can be administered by the drip method, whereby a pharmaceutical formulation the composition described herein and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the composition herein, can be dissolved and administered in a pharmaceutical excipient such as Water-for-Injection, 0.9% saline, or 5% glucose solution.

In one embodiment, the composition is administered via a site-specific or targeted local delivery technique. Examples of site-specific or targeted local delivery techniques include various implantable depot sources of the compositions or local delivery catheters, such as infusion catheters, an indwelling catheter, or a needle catheter, endotracheal tube, endobronchial catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568. Treatment efficacy for a target disease/disorder can be assessed by methods well-known in the art.

In some embodiments, the invention is related to a method of treating coronavirus infection, comprising administering to a subject in need thereof an effective amount of the compound or the composition disclosed herein.

In some embodiments, the coronavirus virus is selected from the group consisting of SARS-CoV-2, severe acute respiratory syndrome coronavirus (SARS-CoV), middle east respiratory syndrome coronavirus (MERS-CoV), 229E alpha coronavirus, NL63 alpha coronavirus, OC43 beta coronavirus, and HKU1 beta coronavirus. In some embodiments, the subject to be treated by the method discloses has COVID-19, a disease caused by SARS-CoV-2 infection.

In some embodiments, the composition is placed in a medical device selected from the group consisting of an inhaler, a nebulizer, a nasal spray, and a vaporization aerosol device for administration to the subject.

In some embodiments, the subject is a human subject, for example, a human subject having infection or suspected of having infection by a coronavirus. In some examples, the human subject has COVID-19 or suspected of having COVID-19 (e.g., having one or more symptoms associated with COVID-19).

In some embodiments, the human subject is treated concurrently with, prior to, or subsequent to, one or more additional anti-viral agents. In some examples, the additional anti-viral agents comprise a viral entry inhibitor, a viral uncoating inhibitor, a viral reverse transcriptase inhibitor, a viral protein synthesis inhibitor, a viral protease inhibitor, a viral polymerase inhibitor, a viral integrase inhibitor, an interferon, and/or the combination thereof.

Exemplary viral entry inhibitors include maraviroc, enfuvirtide, ibalizumab, fostemsavir, plerixafor, epigallocatechin gallate, vicriviroc, aplaviroc, maraviroc, tromantadine, nitazoxanide, umifenovir, and podofilox. Exemplary viral uncoating inhibitors include amantadine, rimantadine, and pleconaril. Exemplary viral reverse transcriptase inhibitors include zidovudine, didanosine, zalcitabine, stavudine, lamivudine, abacavir, emtricitabine, entecavir, truvada, nevirapine, raltegravir, and tenofovir disoproxil. Exemplary viral protease inhibitors include fosamprenavir, ritonavir, atazanavir, nelfinavir, indinavir, saquinavir, saquinavir, famciclovir, fomivirsen, lopinavir, ribavirin, darunavir, oseltamivir, and tipranavir. Exemplary viral polymerase inhibitors include amatoxins, rifamycin, cytarabine, fidaxomicin, tagetitoxin, foscarnet sodium, idoxuridine, penciclovir, sofosbuvir, trifluridine, valacyclovir, valganciclovir, vidarabine, and remdesivir. Exemplary viral integrase inhibitors include raltegarvir, elvitegravir, dolutegravir, bictegravir, and cabotegravir. Exemplary interferons include type I interferon, type II interferon, type III interferon, and peginterferon alfa-2a.

In some embodiments, the subject is administered the composition continuously or at a frequency of every five minutes to one time every three months.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introuction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); Nucleic Acid Hybridization (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1. Identification of Coronavirus' 3C-Like Protease (3CLPro) and Papain-Like Protease (PLPro) Domains Protein Sequence in 2019-nCoV and Comparison of the Proteases Between SARS-CoV and 2019-nCoV To identify the 3CLPro and PLPro protein sequences of coronaviruses, 2019-nCoV, SARS-CoV 3CLPro and SARS-CoV PLPro sequences (Accession: 1UK3_A and 4MM3_B, respectively) were aligned to 2019-nCoV polyprotein ORFlab sequence (Accession: QH062111.1) using BLAST. The results showed that the domain of 2019-nCoV 3CLPro is located at $Ser^{3264}$-$Gln^{3569}$, and the protein sequences of SARS-CoV 3CLPro and 2019-nCoV 3CLPro are 96% identical.

The critical catalytic residues, $His^{41}$ and $Cys^{144}$, and the sequence signature $Tyr^{160}$-$Met^{161}$-$His^{162}$ of SARS-CoV 3CLPro are conserved in 2019-nCoV 3CLPro.

The domain of 2019-nCoV PLPro is from $Glu^{1564}$-$Lys^{1878}$, and protein sequences of SARS-CoV PLPro and 2019-nCoV PLPro are 83% identical. However, the catalytic triad, $cys^{1651}$-$His^{1812}$-$Asp^{1826}$, and the zinc-binding residues, $Cys^{1729}$, $Cys^{1732}$, $Cys^{1764}$ and $Cys^{1766}$ of SARS-CoV PLPro are conserved in 2019-nCoV PLPro. Therefore, 3CLPro is more conserved across the coronavirus family than PLPro, indicating that 3CLPro plays an important role in the purulence of the family of coronaviruses.

Example 2. Comparison of Coronavirus' 3C-Like Protease (3CLPro) and Papain-Like Protease (PLPro) Domains Protein Sequence Between 2019-nCoV and the Other Human Coronavirus The protein sequences of MERS-CoV polyprotein ORFlab (Accession: AFS88944.1), beta coronaviruses OC43 polyprotein ORFlab (Accession: AAR01012.1) and HKU1 polyprotein ORFlab (Accession: AZS52616.1) were obtained from GenBank (http://www.ncbi.nlm.nih.gov). To compare the sequence homology between 2019-nCoV 3CLPro and the other three human coronavirus strains, MERS-CoV, OC43 and HKU1, the 2019-nCoV 3CLPro sequence ($Ser^{3264}$-$Gln^{3569}$) was aligned with the protein sequence of MERS-CoV polyprotein ORFlab, OC43 polyprotein ORFlab, or HKU1 polyprotein ORFlab using the BLAST® method. The 3CLPro sequence identities between 2019-nCoV 3CLPro and MERS-CoV, OC43 and HKU1 were 51%, 48%, and 48%, respectively. However, the catalytic residues, $His^{41}$ and $Cys^{144}$, and the sequence signature $T_y e60\_m_{et}161\_His^{162}$ are conserved among all of the coronavirus strains tested, which underline the functional importance of 3CLPro.

The PLPro amino acid sequence identity between 2019-nCoV and the other three coronaviruses (MERS-CoV, OC43, and HKU1) was also determined by sequence alignment. 2019-nCoV PLPro sequence ($Glu^{1564}$-$Lys^{1878}$) was aligned with MERS-CoV polyprotein ORFlab, OC43 polyprotein ORFlab, and HKU1 polyprotein ORFlab using BLAST method. The results showed that the sequence identities between 2019-nCoV PLPro and MERS-CoV, OC43 and HKU1 were 31%, 29% and 30%, respectively. However, the catalytic triad, $Cys^{1651}$-$His^{1812}$-$Asp^{1826}$, and the zinc-binding residues, $Cys^{1729}$, $Cys^{1732}$, $Cys^{1764}$ and $Cys^{1766}$ of 2019-nCoV PLPro were conserved among coronavirus strains.

The sequence identities among these coronaviruses are consistently higher in 3CLPro than in PLPro, suggesting the importance of the 3CLPro in viral replication. These results suggest that 3CLPro could be a critical therapeutic target for developing anti-viral drug candidates.

Example 3. Comparison of Protein Sequences Between 2019-nCoV and Influenza a Virus To investigate the homology between 2019-nCoV and Influenza A Virus, the protein sequences of 2019-nCoV polyprotein ORFlab (Accession: QH062111.1), the sequences of influenza A virus (H1N1) A/swine/Korea/61/2016 (Accession: AXU05463.1 to AXU05472.1), the avian influenza A virus (H1N1) A/wild bird/Korea/SK14/2014 (Accession: ANC28540.1 to ANC28551.1), and influenza A (H7N9) virus A/Anhui/1/2013 (Accession: AGO51387.1 to AGO51410.1) were obtained from GenBank (http://www.ncbi.nlm.nih.gov). The results showed that no significant homology was found between the 2019-nCov polypeptide and any of the Influenza A viral proteins.

Example 4. Inhibition Activity of the Test Compounds Against 2019-nCoV 3CL Protease (2019-nCoV 3CLPro)

The proteolytic activity of 2019-nCoV 3CLPro was determined in vitro by measuring the enhanced fluorescence due to cleavage of the fluorogenic substrate (Dabcyl-KT-SAVLQSGFRKME-Edans). For analyzing the inhibition potential, various compounds shown in Table 1 below were mixed with a reaction mixture containing 20 mM Bis-Tris buffer (pH 7.0), 35 nM 2019-nCoV 3CL protease and 6 μM fluorogenic substrate. The fluorescence change resulting from the enzymatic reaction was measured at 538 nm with excitation at 355 nm using a fluorescence plate reader at certain time points. The proteolytic activity in the presence of compounds was calculated using the following equation:

Protease activity (%)=(fluorescence$_{sample,\ 300\ sec}$−fluorescence$_{sample,\ 0\ sec}$)/(fluorescence$_{DMSO,\ 300\ sec}$−fluorescence$_{DMSO,\ 0\ min}$)×100%.

Inhibition activity (%)=100%−Protease Activity. All reactions were carried out in duplicates in 96-well plates.

In this assay study, Samples 1-5, 11-12, 17-19 listed in Table 1 (column of 3 μM) below were analyzed. Descriptions of Samples 17 and 19 can be found in U.S. Ser. No. 10/265,336 and U.S. Ser. No. 10/105,378, the relevant disclosures of each of which are incorporated by reference for the purpose and subject matter referenced herein. Among these samples, Samples 1, 2 and 11 displayed approximately half maximal inhibition (IC$_{50}$) at the concentration of 3 μM, resulting in proteolytic activities decreased to 52%, 55% and 48%, respectively. In addition, Samples 3, 4, 5, 12 and 17 showed good inhibitory activities against 2019-nCoV 3CLPro at the concentration of 3 μM, as the protease activity declined to 0 to 15% (FIG. 1). In sum, samples 3, 4, 5, 12, and 17 showed complete inhibitory activities against 2019-nCoV 3CLPro at the concentration of 3 μM and the results are statistically significant.

To further study the correlation between compound structure/composition and the inhibitory activities against 2019-nCoV 3CLPro, a assay study using 1 μM of each sample listed in Table 1 (the column of 1 μM) was performed.

1 μM of each sample was (2 μl) pre-incubate with 48 μl reaction mixture (50 nM SARS-CoV-2 viral 3CL protease in 20 mM Bis-Tris, pH 7.4) at 37° C. for 30 minutes. Afterwards, 50 μl of the fluorogenic peptide substrate (6 μM) was added into the mixture and gently mixed. The fluorescence change resulting from the reaction was measured at 485 nm with excitation at 360 nm using a fluorescence plate reader at 37° C. for 4 min. The proteolytic activity in the presence of compounds was calculated using the following equation:

Protease activity (%)=(fluorescence$_{sample,\ 4\ min}$−fluorescence$_{sample,\ 0\ min}$)/(fluorescence$_{DMSO,\ 4\ min}$−fluorescence$_{DMSO,\ 0\ min}$)×100%.

Inhibition activity (%)=100%−Protease Activity. All reactions were carried out in duplicate in 96-well plates.

The results are shown in Table 1 (the column of 1 μM) below and in FIG. 2.

TABLE 1

Inhibitory Activities of Exemplary Formula (I) Compounds Against 2019-nCoV 3CLPro

| Sample | Structure | Residual Protease Activity (%) 3 μM | 1 μM |
|---|---|---|---|
| 1 | 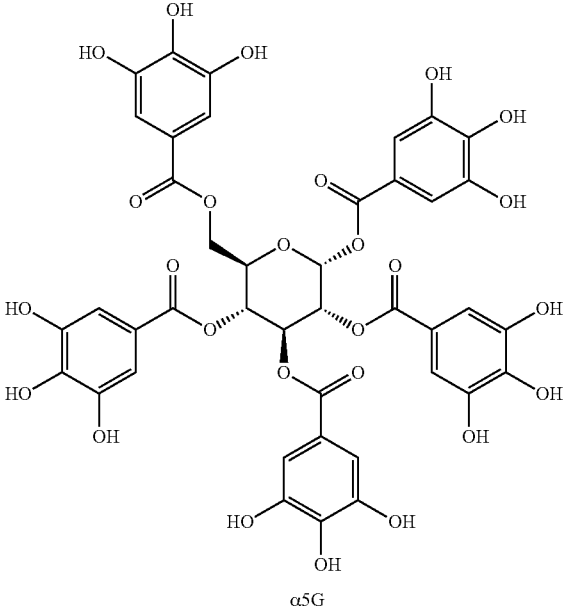 [SMILES: O=C(OC[C@H]1O[C@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1] α5G | 52% | N/A |

TABLE 1-continued

Inhibitory Activities of Exemplary Formula (I) Compounds Against 2019-nCoV 3CLPro

| Sample | Structure | Residual Protease Activity (%) | |
|---|---|---|

TABLE 1-continued

Inhibitory Activities of Exemplary Formula (I) Compounds Against 2019-nCoV 3CLPro

| Sample | Structure | Residual Protease Activity (%) 3 μM | 1 μM |
|---|---|---|---|
| 4 | β10G | −9% | 43% |
| 5 | α15G | −7% | 32% |

TABLE 1-continued

Inhibitory Activities of Exemplary Formula (I) Compounds Against 2019-nCoV 3CLPro

| Sample | Structure | Residual Protease Activity (%) 3 μM | Residual Protease Activity (%) 1 μM |
| --- | --- | --- | --- |
| 6 | 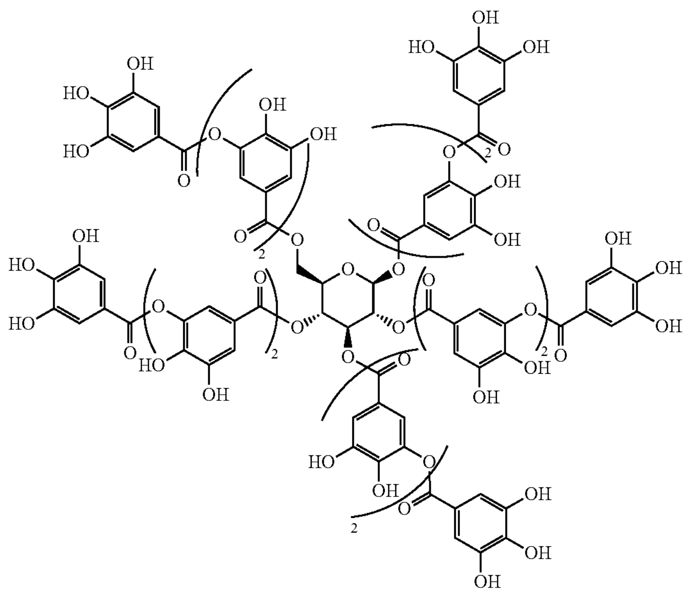 <br>β15G | N/A | 39% |
| 7 | 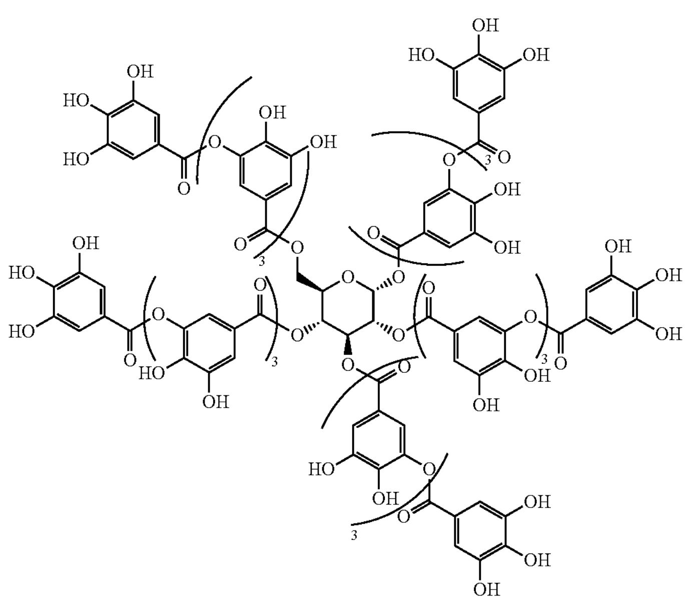 <br>α20G | N/A | 25% |

TABLE 1-continued

Inhibitory Activities of Exemplary Formula (I) Compounds Against 2019-nCoV 3CLPro

| Sample | Structure | Residual Protease Activity (%) 3 μM | Residual Protease Activity (%) 1 μM |
|---|---|---|---|
| 8 | 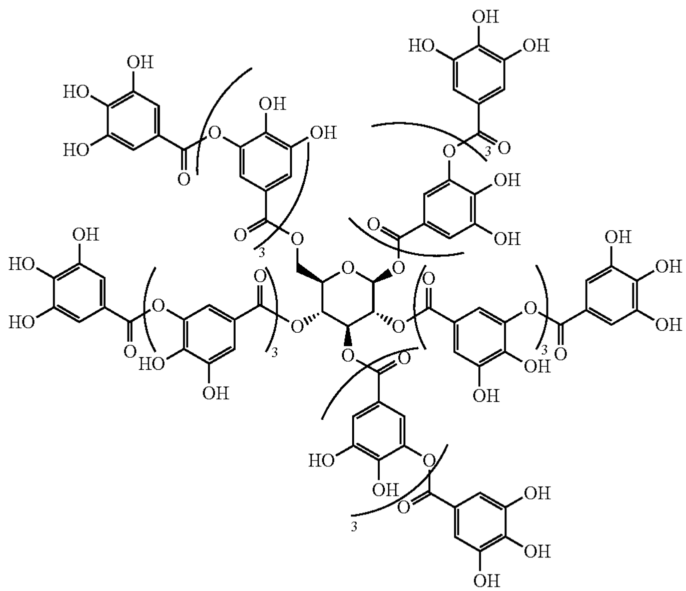  β20G | N/A | 29% |
| 9 | 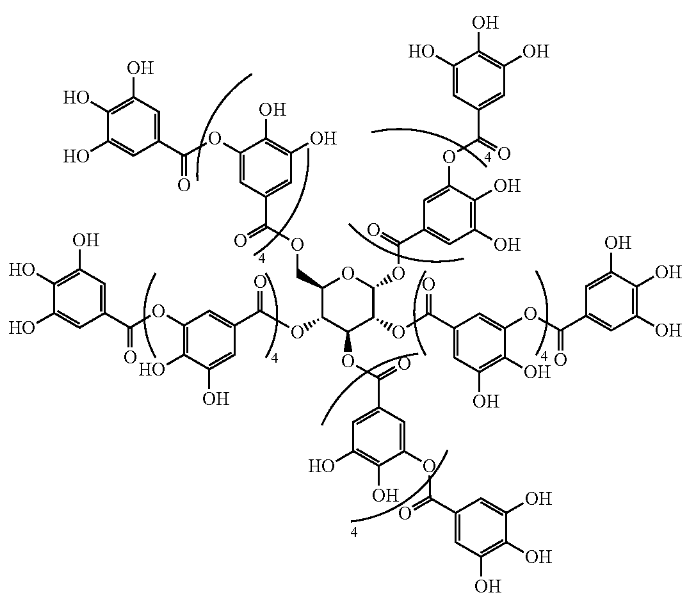  α25G | N/A | 10% |

TABLE 1-continued

Inhibitory Activities of Exemplary Formula (I) Compounds Against 2019-nCoV 3CLPro

| Sample | Structure | Residual Protease Activity (%)

TABLE 1-continued

Inhibitory Activities of Exemplary Formula (I) Compounds Against 2019-nCoV 3CLPro

| Sample | Structure | Residual Protease Activity (%) 3 μM | 1 μM |
|---|---|---|---|
| 12 | Resorcin 10G | 5% | 42% |
| 13 | Phloroglucinol 15G | N/A | 31% |

TABLE 1-continued

Inhibitory Activities of Exemplary Formula (I) Compounds Against 2019-nCoV 3CLPro

| Sample | Structure | Residual Protease Activity (%) 3 μM | 1 μM |
|---|---|---|---|
| 14 | phenol 7G | N/A | 62% |
| 15 | Resorcin 14G | N/A | 36% |

TABLE 1-continued

Inhibitory Activities of Exemplary Formula (I) Compounds Against 2019-nCoV 3CLPro

| Sample | Structure | Residual Protease Activity (%) 3 μM | 1 μM |
|---|---|---|---|
| 16 | Phloroglucinol 21G | N/A | 18% |
| 17 | The Enriched tannic acid (SNB01) | 2% | 26% |
| 18 | Merck tannic acid Product No.: 1.00773.1000 | 15% | 50% |
| 19 | CCBiotech tannic acid | 10% | 44% |

Figure 2:
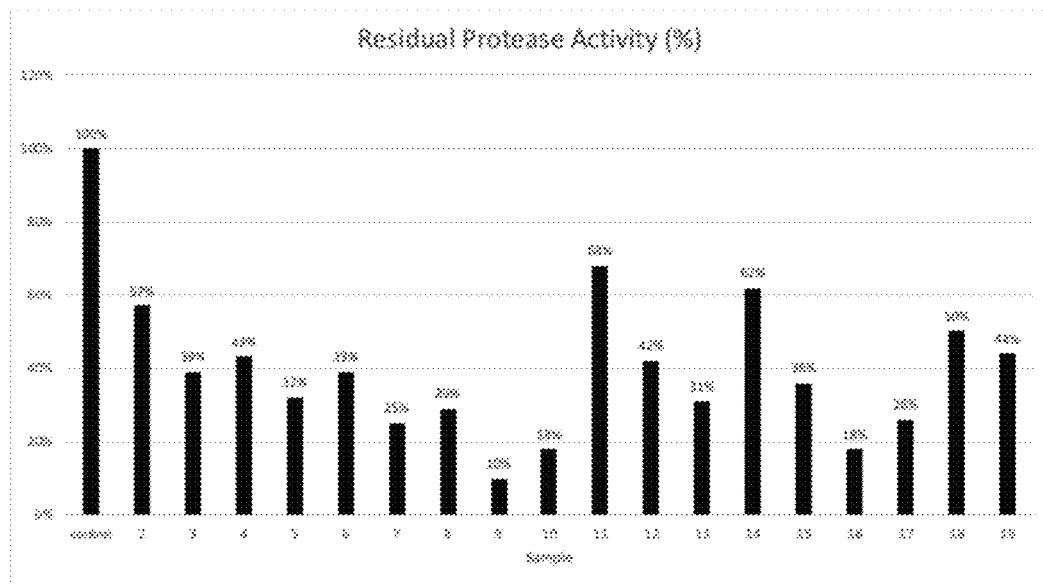
FIG. 2 shows inhibitory activities of exemplary Formula (I) compounds against 2019-nCoV 3CLPro at the concentration of 1 μM

As shown in FIG. 2, compounds having a high number of galloyl moieties showed better inhibitory activity against 2019-nCoV 3CLPro. In addition, compounds having an alpha core showed better inhibitory activities than the corresponding compounds having a beta core. (e.g., sample 1>sample 2, sample 3>sample 4, etc.). In the groups of mixed composition (samples 17-19), enriched tannic acid sample 17 showed better inhibitory activities than samples 18 and 19. As noted above, the enriched tannic acid sample 17 has a higher average galloyl moiety number relative to that of samples 18 and 19.

Figure 3:
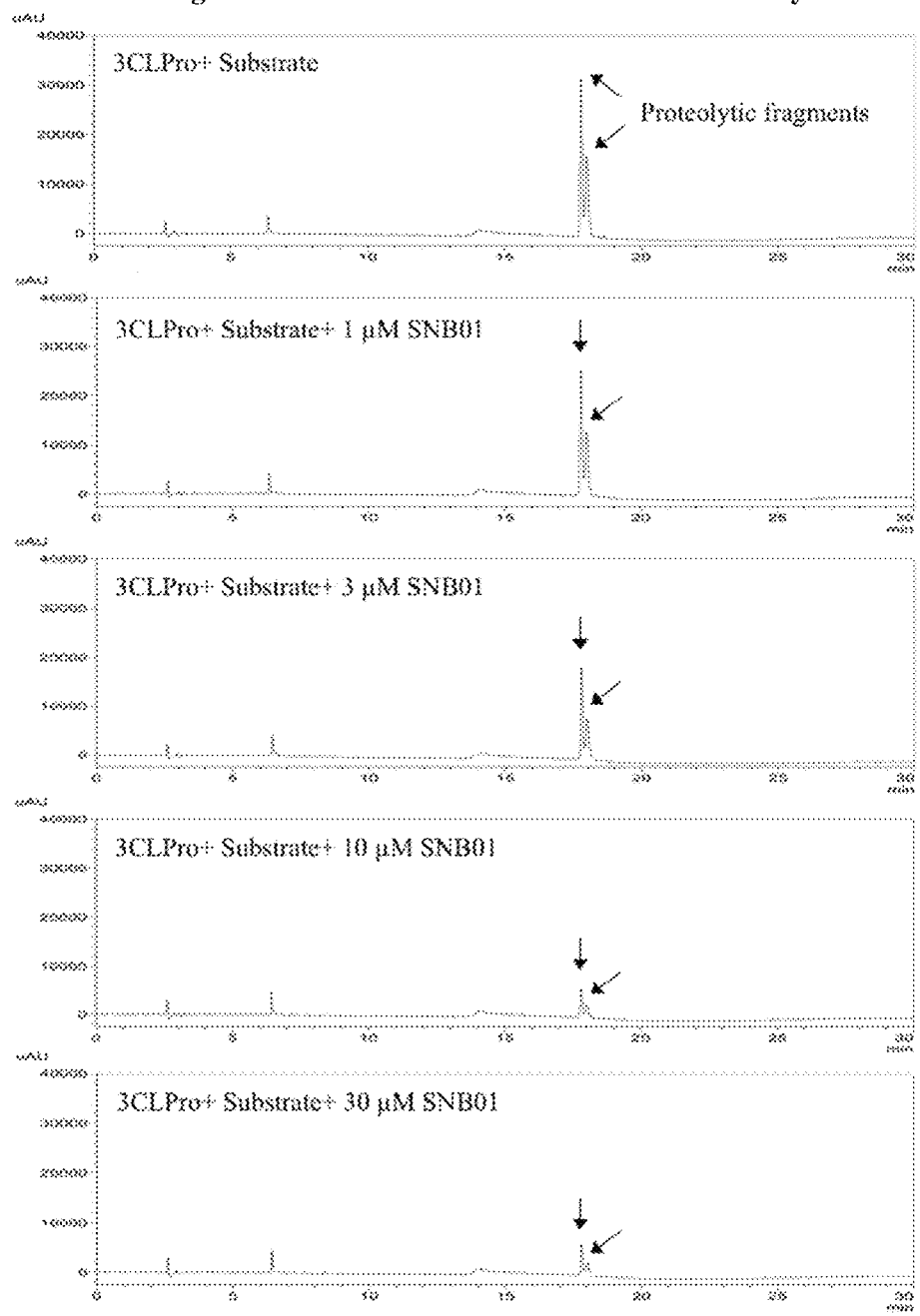
FIG. 3 shows inhibition of 3CLPro of SARS-CoV-2 by SNB01 at various concentrations as indicated. SNB01 (1-30 μM) was incubated with 3CLPro (1 μM) and the substrates of fluorogenic peptide (Dabcyl-TSAVLQSGFRKM-Edans, 10 μM) at 37° C. before subjected to HPLC separation by a C18 column with mobile phase of 0.1% trifluoroacetic acid and acetonitrile. Two proteolytic fragments were detected by UV absorbance at 510 nm (shown in arrows). A dose-dependent inhibitory pattern was observed.

Example 5. Inhibition of 3-Chymotrypsin-Like Protease (3CLPro) of SARS-CoV-2 by SNB01 Compounds 3CLPro is a pivotal enzyme in regulating proteolytic process of polyprotein, an essential replication machinery of SARS-CoV-2. The inhibition of 3CLPro is considerate a high-potential therapeutic treatment for the development of anti-SARS-CoV-2 medications. Numerous compounds were screened for the discovery of drug candidates having inhibitory activity against 3CLPro. SNB01 (the Enriched tannic acid) exhibits a high potency against 3CLPro as assayed by HPLC (FIG. 3). Different concentrations of SNB01 consistently block the proteolytic of 3CLPro, and shows a linear concentration-response relationship ($R^2$=0.97). Based on our preliminary finding, this study is to confirm and evaluate the inhibition of SNB01 on the proteolytic activity of SARS-CoV-2 3CLPro. The objective of this study is to evaluate the inhibition of SNB01 on the proteolytic activity of SARS-CoV-2 viral 3-Chymotrypsin-like Protease (3CL-Pro or 3CL Protease).

Test Article and Control Article Information
Test Article

| Code Name: | SNB01 |
|---|---|
| Content: | 99.65% |
| Physical Properties and Characterization: | Yellowish-white powder |
| Storage: | Stored in a shady area (not exceeding 25° C.) with protection from light, in desiccation. |
| Special Handling: | Standard safety precautions (use of personal protective clothing, gloves, and mask) were taken when handling the test article. |

Vehicle Control

| Name: | Sterile Double distilled water (ddH$_2$O) |
|---|---|
| Equipment of ddH$_2$O production: | Barnstead Smart2pure, Thermo Scientific |
| Appearance: | Colorless clear liquid |
| Storage: | Stored in a sealed container. |
| Justification: | ddH$_2$O will be used for the preparation of test article's formulation and vehicle control in the 3CL protease activity assay. |

Reagent Preparation
Substrate

The fluorogenic substrate, prepared by Genomics (Taiwan), is a 12-mer amino acid peptide (TSAVLQSGFRKM) plus Lys at the N-terminal and Glu at the C-terminal for the attachment of fluorophores 4-(4-dimethylaminophenylazo) benzoic acid (Dabcyl) and 5-[(2-aminoethyl)amino]naphthalene-1-sulfonic acid (Edans), respectively.

Reaction Buffer

An appropriate amount of Bis-Tris was weighed, dissolved in ddH$_2$O to have 20 mM, pH 7.4 reaction buffer and stored at room temperature.

SARS-CoV-2 Viral 3CL Protease

The viral RNA of SARS-CoV-2 was obtained from the clinical specimen of the Department of Pathology and Laboratory Medicine at Taipei Veterans General Hospital. Reverse transcription (RT)-PCR was applied to amplify the cDNA of SARS-CoV-2 3CLPro with 3CL-forward primer (5'-AGT GGT TTT AGA AAA ATG GCA TTC CC-3', SEQ ID NO: 1) and 3CL-reverse primer (5'-C TCC GGT ATT GAG GGA CGC-3', SEQ ID NO: 2). The amplified cDNA product was sequenced, confirmed and showed 100% identity with the reported SARS-CoV-2 3CLPro by BLAST search (http://www.ncbi.nlm.nih.gov/BLAST/).

For protein expression, the amplified cDNA product was inserted into the pET42b vector and subsequently transformed into *Escherichia coli* strain BL21. The transformed cells with pET42b-SARS-CoV-2 3CLPro were incubated on Luria-Bertani (LB) agar plates with 100 µg/ml kanamycin for selection (37° C.; 14-16 hours). Kanamycin-resistant clones were isolated and cultured in a 250 ml flask. When the culture density reached 0.8 Optic Density at 600 nm, protein expression was induced by the addition of 0.4 mM isopropyl-b-D-1-thiogalactopyranoside (IPTG) at 16° C. After 22 hours, cultured cells were harvested by centrifugation and lysis. Finally, SARS-CoV-2 3CLPro was purified from bacterial lysates using Glutathione Sepharose® 4B column before incubated with 1% Factor Xa protease solution to remove Glutathione S-transferase tag. The untagged 3CLPro was dialyzed in buffer of 12 mM Tris(hydroxymethyl)aminomethane hydrochloride, 120 mM sodium chloride, 0.1 mM ethylenediaminetetraacetic and 2 mM dithiothreitol, pH 7.4 before storage.

Preparation of the Test Article and Control Samples

Preparation of the Test Article

The test article (SNB01) is a composition comprising a mixture of compounds of Formula (Ib),

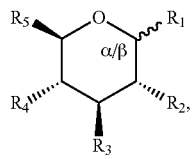

in which each of $R_1$-$R_5$ is present and set forth herein. About 4-8% of the Formula (Ib) compounds in SNB01 have 5 galloyl moieties, about 28-33% of the Formula (Ib) compounds in SNB01 have 6-7 galloyl moieties, and about 58-63% of the Formula (Ib) compounds in SNB01 have 8-12 galloyl moieties 5 milligrams (±10%) of test article (SNB01) were dissolved in ddH$_2$O to obtain a 10 mM stock solution. Serial dilution of the stock solution with ddH$_2$O was shown in the following Table 2. SNB01-1 to SNB01-12 were used for the protease activity assay.

TABLE 2

Samples Evaluated in 3CLPro Protease Inhibitory Assay

| Samples | Volume (µL) | ddH$_2$O (µL) | Total volume (µL) | Concentration (µM) |
|---|---|---|---|---|
| SNB01-1 | 20 | 80 | 100 | 2000 |
| SNB01-2 | 50 | 50 | 100 | 1000 |
| SNB01-3 | 50 | 50 | 100 | 500 |
| SNB01-4 | 50 | 50 | 100 | 250 |
| SNB01-5 | 50 | 50 | 100 | 125 |
| SNB01-6 | 50 | 50 | 100 | 62.5 |
| SNB01-7 | 25 | 75 | 100 | 15.62 |
| SNB01-8 | 50 | 50 | 100 | 7.81 |
| SNB01-9 | 50 | 50 | 100 | 3.90 |
| SNB01-10 | 50 | 50 | 100 | 1.95 |
| SNB01-11 | 50 | 50 | 100 | 0.97 |
| SNB01-12 | 50 | 50 | 100 | 0.48 |

Control ddH$_2$O without SNB01 was used as the negative control.

Procedure of 3CL Protease Activity Assay

The fluorogenic peptide substrate was used to monitor the proteolytic reaction of 3CL protease. The variable concentration of test article samples (SNB01-1 to SNB01-12) were added 2 µl and pre-incubate with 48 µl reaction mixture (50 nM SARS-CoV-2 viral 3CL protease in 20 mM Bis-Tris, pH 7.4) at 37° C. for 30 minutes. Afterward, 50 µl of the fluorogenic peptide substrate (6 µM) was added into the mixture and gently mixed. The fluorescence change from the protease reaction was immediately monitored on a fluorescence microplate reader at 37° C. for 4 min. The fluorescence excitation and emission wavelengths were 360 and 485 nm, respectively. The protease activity was presented as fluorescence intensity and calculated by the following equation:

$$\text{Inhibition (\%)} = 1 - [(\text{fluorescence}_{sample,\ 4\ min} - \text{fluorescence}_{sample,\ 0\ min}) / (\text{fluorescence}_{ddH_2O,\ 4\ min} - \text{fluorescence}_{ddH_2O,\ 0\ min})] \times 100\%.$$

Result

Figure 4:
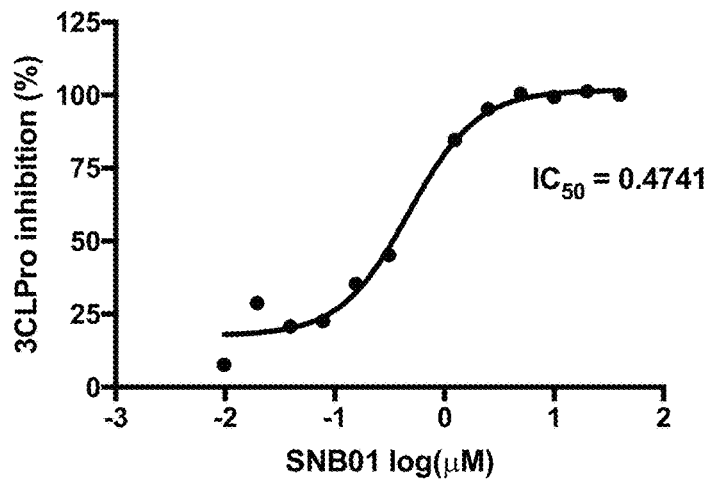
FIG. 4 shows the inhibition of SNB01 on 3CL Protease Activity of SARS-CoV-2. Each data represents mean percentage of 3CLPro inhibition by SNB01 as measured by a fluorescent enzymatic assay. A variable-slope, four parameters, sigmoid model by GraphPad 7.0 fitting was applied to determine the $IC_{50}$.

Results obtained from this study demonstrated a potent inhibitory activity of SNB01 on 3CLPro as observed in the protease enzymatic assay. The 50% inhibition concentration (IC$_5$O) of SNB01 against 3CLPro was determined to be about 0.474 µM (FIG. 4).

3C-like protease (3CLPro) plays a critical role in the enzymatic hydrolysis of the viral polyprotein to produce functional viral proteins. The processing of the polyprotein is essential for replication and maturation of SARS-CoV-2. The polyprotein contains, at least, 14 cleavage sites (Grum-Tokars et al., 2008). Since most proteolytic processing of these sites were conducted by 3CLPro, inhibition of this proteolytic enzyme is considerate a prime target for the therapy against SARS-CoV-2 infection. It was also known in the fact that 3CLPro is conserved across coronavirus. For example, the 3CLPro of SAR-CoV2 shares approximately 40-50% sequence identity with orthocoronavirinae, including MERS-CoV (52.0%), HCoV-OC43 (49.0%), HCoV-NL63 (48.4%), HCoV-HKU1 (45.2%), and HCoV-229E (41.9%). Moreover, the 3CLPro of SAR-CoV2 shares about 96.1% sequence identity to that of SARS. Sequences of the 3CLPro sequences from these viruses can be found, e.g., in Genbank, for example, SARS-CoV-2 (YP_009742612.1), SARS-CoV (NP_828863), MERS-CoV (YP_009047233.1), HCoV-NL-63 (5GWY_B), HCoV-229E (2ZU2_B), HCoV-OC43 (YP_009555250) and HCoV-HKU1 (YP_459936.1) and their activity dyads located in both the histidine-41 (His[41]) and cysteine-145 (Cys[145]). In addition, the cleavage sites in the polyprotein substrates of 3CLPro also share high homology among SARS-CoV-2, SARS-CoV and other human coronavirus as known in the art. Therefore, inhibition of 3CLPro is likely a reliable therapeutic approach for the SARS-CoV-2 infected patients.

The results reported herein show that SNB01 inhibits SARS-CoV-2 replication via the inhibition of 3CLPro, a pivot cysteine protease in the viral replication.

SNB01 shows a significantly low $IC_{50}$ value (0.4741 μM) as compared to other antiviral candidates. Up to now, several antiviral agents have been investigated as a potential inhibitor to block SARS 3CLPro and some of the drugs have been in clinical development (Table 3). For example, Lopinavir-Ritonavir combination treatment improves clinical outcomes of a coronavirus infection, including mortality and rate of intubation, in SARS-CoV infected patients (Chan et al., 2003). However, the combination therapy of Lopinavir-Ritonavir fails to improve the clinical outcomes, including mortality rate, in severe SARS-CoV-2 patients (Cao et al., 2020). These two anti-viral compounds, among others (Saquinavir, Nelfinavir, and Tipranavir), are not potent in the inhibition of 3CLPro (see Table 3). Their $IC_{50}$ were shown to be all above 100 μM. The findings indicated that SNB01 can be a promising candidate for use in treating coronavirus infection (e.g., infection caused by SARS-CoV-2) and associated diseases (e.g., COVID-19).

TABLE 3

The $IC_{50}$ of 3C-like Protease of the Antiviral Candidate Drugs of SARS-CoV-2

| Viral protease inhibitor | $IC_{50}$ of the 3CLPro | Reference |
| --- | --- | --- |
| Lopinavir | 486 ± 2 μM | (Vatansever et al., 2020) |
| | 20 μM, failed to inhibit | (Ma et al., 2020) |
| Ritonavir | 20 μM, failed to inhibit | (Ma et al., 2020) |
| Saquinavir | 411 ± 6 μM | (Vatansever et al., 2020) |
| Nelfinavir | 234 ± 15 μM | (Vatansever et al., 2020) |
| Tipranavir | 180 ± 20 μM | (Vatansever et al., 2020) |

Example 6. Pulmonary and Plasma Concentrations of Exemplary Formula (I) Compounds after Inhalation or Oral Administration (i) Pulmonary and Plasma Concentration of Tannic Acid after Single Inhalation Treatment The C57BL/6J mice were placed in nebulizing device of inhalation of the enriched tannic acid of 200 mg/mL for 100 minutes. Total amount of tannic acid was determined by HPLC after tannase treatment (commercial Tannase: 167 U/g, Analysis grade, E. Merck KGaA, Germany, same below). The data presented in Table 4 below show good bioavailability of tannic acid in both the plasma and lung after the inhalation treatment.

TABLE 4

Lung and Plasma Concentrations of Tannic Acid in Mice After Inhalation of Tannic Acids

| | Lung (μg/g) | Plasma (μg/mL) |
| --- | --- | --- |
| Mice-2 | 4.31 | 8.16 |
| Mice-4 | 4.34 | 7.69 |
| Mice-6 | 3.66 | 5.78 |
| Average | 4.10 | 7.21 |

(ii) Pulmonary Concentration of Tannic Acid after Repeated Inhalations

The C57BL/6J mice were placed in nebulizing device for inhalation for different dosages and durations daily for 14 days. Total amount of enriched tannic acid was determined by HPLC after tannase treatment. The results shown in Table 5 below indicate good bioavailability of tannic acid in lung after repeated inhalation administration of the enriched tannic acide.

TABLE 5

Lung Concentration of Tannic Acids After Repeated Inhalation

| | Lung (μg/g) |
| --- | --- |
| 3.13 mg/kg (36 mg/mL, 60 min) | 49.08 |
| 8.5 mg/kg (200 mg/mL, 60 min) | 45.06 |
| 9.36 mg/kg (108 mg/mL, 60 min) | 61.51 |
| 12.75 mg/kg (200 mg/mL, 60 min) | 28.84 |

(iii) Pulmonary Concentrations of Tannic Acid after Single Oral Administration

The Sprague-dawley rats were administered with the enrich tannic acid orally at 1000 mg/kg. Total amount of tannic acid was determined by HPLC after tannase treatment. As shown in Tables 6 and 7 below, good bioavailability of tannic acid in lung was observed after the oral administration either by a single dose or by a seven-day repeated daily administration.

TABLE 6

Lung Concentrations of Tannic Acid After a Single Oral Dose

| Single dose | Lung-1 (mg/g) | Lung-2 (μg/g) | Lung-3 (μg/g) | Average (μg/g) |
| --- | --- | --- | --- | --- |
| 4 h | 1.14 | 0.67 | 2.81 | 1.54 (~1.04 μM) |

TABLE 7

Lung Concentrations of Tannic Acids After 7-Day Reported Daily Doses

| 7 Days repeat doses | Lung-1 (μg/g) | Lung-2 (μg/g) | Average (μg/g) |
| --- | --- | --- | --- |
| 4 h | 4.20 | 4.63 | 4.42 (~3.00 μM) |
| 7 h | 1.96 | 1.05 | 1.50 (~1.02 μM) |

Example 7. The Cytotoxicity and SARS-CoV-2 Virucidal Assay of SNB01

The objective of this study is to evaluate the cytotoxicity and the virucidal activity of SNB01 against SARS-CoV-2.
Test Article and Vehicle Control Article
Test Article

| Code Name | SNB01 |
| --- | --- |
| Content | 99.65% |
| Physical Properties and Characterization | Yellowish-white powder |
| Storage | Stored in a shady area (not exceeding 25° C.) protected from light in desiccation |
| Special Handling | Standard safety precautions (use of personal protective clothing, gloves, and mask) were taken when handling the test article. |

Vehicle Control

| Name | Dimethyl sulfoxide (DMSO) |
|---|---|
| Specification | 500 mL/bottle |
| Appearance | Colorless liquid |
| Storage | Stored in a sealed container at room temperature |

Preparation of the Cell Line and SARS-COV-2 Virus

Vero E6 Cell Line

Vero E6 cells (ATCC #CRL-1586) were maintained in Dulbecco's modified Eagle medium (DMEM, Cat #11995040, Thermo Fisher Scientific) supplemented with 10% fetal bovine serum (FBS, Cat #10437028, Thermo Fisher Scientific) in a humidified incubator at 37° C. with 5% $CO_2$ atmosphere. Cultured cells with 80-90% confluence were treated with 0.25% trypsin for cell detachment and passage. The treated cells were mixed with DMEM medium and centrifuged at 1000 rpm for 5 minutes for cell isolation and trypsin removal. After cell counting, Vero E6 cells were dispensed at a density of $10^4$ cell per 0.1 mL per well in a 96-well microplate and incubated for 24 hours before experimentation. For virucidal assay, infection medium had 2% FBS (Choy et al., 2020).

SARS-CoV-2 Virus

The virus was obtained from Center for Disease Control, Taiwan.

Preparation of the Test Article and Control Samples

Test Article Solution for Cytotoxicity Assay

The test article was prepared on the day when the experiment was conducted and kept at room temperature. The remaining test article was discarded as general waste following the completion of experiment.

136.1 mg of SNB01 was dissolved in DMSO or double-distilled water ($ddH_2O$) to obtain an 80 mM stock solution. Serial dilution of the stock solution was performed with DMEM medium for 8.59-8800 µM solutions as shown in the following Table 8. The test article with the serial concentrations were named SNB01-1 to -11 for the cytotoxicity test. The final concentration of the vehicle (DMSO or $ddH_2O$) was 1%.

TABLE 8

Samples Evaluated in Cytotoxicity Assay

| Samples | Volume (µL) | DMSO or ddH$_2$O (µL) | Culture medium with 2 or 10% FBS (µL) | Total volume (µL) | Conc. (µM) |
|---|---|---|---|---|---|
| SNB01-1 | 11 | 0 | 89 | 100 | 8800 |
| SNB01-2 | 60 | 6.6 | 53.4 | 120 | 4400 |
| SNB01-3 | 60 | 6.6 | 53.4 | 120 | 2200 |
| SNB01-4 | 60 | 6.6 | 53.4 | 120 | 1100 |
| SNB01-5 | 60 | 6.6 | 53.4 | 120 | 550 |
| SNB01-6 | 60 | 6.6 | 53.4 | 120 | 275 |
| SNB01-7 | 60 | 6.6 | 53.4 | 120 | 137.5 |
| SNB01-8 | 60 | 6.6 | 53.4 | 120 | 68.75 |
| SNB01-9 | 60 | 6.6 | 53.4 | 120 | 34.38 |
| SNB01-10 | 60 | 6.6 | 53.4 | 120 | 17.19 |
| SNB01-11 | 60 | 6.6 | 53.4 | 120 | 8.59 |

Vehicle Control for the Cytotoxicity Assay

One percent (V/V) vehicle (DMSO or $ddH_2O$) in DMEM medium (with 2% or 10% FBS) was applied as the vehicle control.

Preparation of the Test Article Solutions for the SARS-CoV-2 Virucidal Assay

The test article was prepared on the day of the experiment and kept at room temperature. The remaining samples were discarded as general waste after the experiment.

8.5 mg of SNB01 were dissolved in DMSO to obtain a 5 mM stock solution. Serial dilution with culture media was performed to obtain the test article with concentrations ranging from 0.002 to 100 µM SNB01 with 2% DMSO as shown in the following Table 9. These samples were labelled as SNB01-12 to -23 for the cell-based SARS-CoV-2 virucidal assay.

TABLE 9

Samples Evaluated in SARS-CoV-2 Virucidal Assay

| Code | Volume (µL) | DMSO or ddH$_2$O (µL) | Culture medium with 2 or 10% FBS (µL) | Total volume (µL) | Conc. (µM) |
|---|---|---|---|---|---|
| SNB01-12 | 14 | 0 | 686 | 700 | 100 |
| SNB01-13 | 350 | 7 | 343 | 700 | 50 |
| SNB01-14 | 350 | 7 | 343 | 700 | 25 |
| SNB01-15 | 350 | 7 | 343 | 700 | 12.5 |
| SNB01-16 | 350 | 7 | 343 | 700 | 6.25 |
| SNB01-17 | 350 | 7 | 343 | 700 | 3.125 |
| SNB01-18 | 350 | 7 | 343 | 700 | 1.562 |
| SNB01-19 | 350 | 7 | 343 | 700 | 0.781 |
| SNB01-20 | 350 | 7 | 343 | 700 | 0.390 |
| SNB01-21 | 350 | 7 | 343 | 700 | 0.195 |
| SNB01-22 | 350 | 7 | 343 | 700 | 0.098 |
| SNB01-23 | 20 | 19.6 | 940.4 | 980 | 0.002 |

Positive Control and Vehicle Control for the SARS-CoV-2 Virucidal Assay

Final concentration of 15 µM Remdesivir (Cat #S8923, Selleckchem), which exhibits inhibitory activity against SARS-CoV-2 infection, and 1% DMSO were applied as positive and vehicle controls, respectively.

Cytotoxicity and SARS-COV-2 Virucidal Assay

Cytotoxicity Assay

Vero E6 cells were seeded at the density of $10^4$ cells/well onto 96-well plates before maintained at 37° C. and 5% $CO_2$ in a humidified cell culture incubator. After 24 hours, the culture medium was removed before 10 µL of the test articles (SNB01-1 to -11) was mixed with 100 µL culture medium of DMEM with 2% FBS and added into the Vero E6 cells in the wells. The cells were incubated for another 24-hour before the day of experiment when the supernatant was removed before the cells were added 110 µL. of cell counting solution with 100 µL medium and 10 µL CCK8 solution (Cat #CK04-05, Dojindo Molecular Technologies, Inc.) and incubated for 2 hours.

The cell viability was determined following the formazan formed and measured at the absorbance of 450 nm on the Sunrise™ absorbance microplate reader (Cat #INSTSUN-1, Tecan).

SARS-CoV-2 Virucidal Assay

Vero E6 cells were seeded ($10^4$ cells/100 μL/well) and incubated in 96-well microplates before maintained at 37° C. in a humidified cell culture incubator with 5% $CO_2$. After 24 hours, the supernatant of Vero E6 cells was refreshed with infection medium (with 2% FBS) containing different concentrations of the test article, SNB01-12 to -23. Subsequently, 100 μL of SARS-CoV-2 virus-containing medium with 2% FBS [multiplicity of infection (MOI)=0.01] were added to each well of 96-well microplates to reach the final concentrations of test article ranging from 0.001 to 50.00 μM in 200 μL medium containing 1% DMSO and 2% FBS.

Twenty-four hours after the virus inoculation, the supernatant of each well was transferred and subjected to RNA extraction by QIAamp Viral RNA mini kit (Cat #52906, QIAGEN), and the cell layer of each well was subjected to RNA extraction using TRIzol™ reagent (Cat #15596026, Thermo Fisher Scientific). Reverse transcription of cDNA was completed using HiScript II Q RT SuperMix kit for qPCR (Cat #R223, Vazyme Biotech).

SARS-CoV-2 viral genome was quantified using two-step quantitative PCR on the StepOnePlus™ Real-Time PCR System (Applied Biosystems) with the SensiFAST™ SYBR® Hi-ROX kit (#BIO-92006, BIOLINE). SARS-CoV-2 RdRP gene was amplified using the forward (5'-GTGARATGGTCATGTGTGGCGG-3'; SEQ ID NO: 3) and reverse (5'-CARATGTTAAASACACTATTAGCATA-3'; SEQ ID NO: 4) primers (Corman et al., 2020). Serial dilutions of SARS-CoV-2 cDNA with a known viral PFU (plaque forming unit) were subjected to the same quantitative PCR and served to develop a standard curve to interpolate the viral counts of the test article-treated cells. The SARS-CoV-2 virucidal activity was presented as percentage of inhibition and calculated using the following equation:

$$\text{Inhibition (\%)} = [1 - (PFU_{sample}/PFU_{mean\ of\ vehicle})] \times 100\%.$$

Percentage of inhibition of the samples were plotted (Y axis) against logarithmic concentrations of the test article (X-axis). The concentration-inhibition plot was fitted with non-linear regression using asymmetric (five-parameters) logistic dose-response curve; $EC_{50}$, $EC_{90}$ and $EC_{99}$ (concentration that inhibits 50, 90 and 99% SARS-CoV-2 viral counts, respectively) were derived from the equation.

Results

Cytotoxicity Assay

Figure 5:
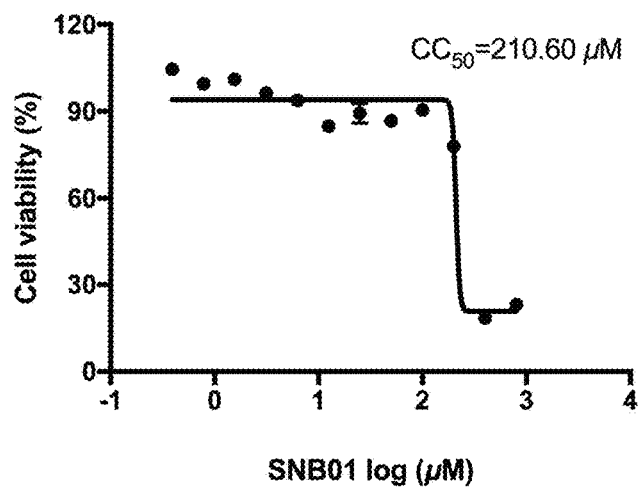
FIG. 5 shows the cytotoxicity of SNB01 in Vero E6 cells cultured in DMEM supplemented with 10% FBS and incubated for 24 hours. CC50 was found to be around 210.60 μM.
Figure 6:
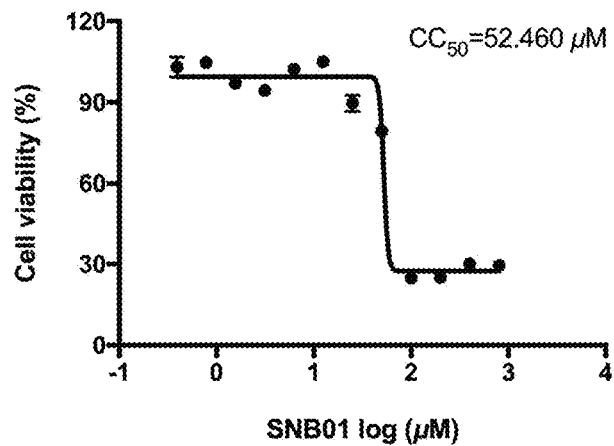
FIG. 6 shows the cytotoxicity of SNB01 in Vero E6 cells cultured in DMEM supplemented with 2% FBS and incubated for 24 hours. The final concentration of the DMSO vehicle is 1% (V/V). The CC50 was found to be around 52.460 μM.

The 50% cytotoxic concentration ($CC_{50}$) of SNB01 (using dd$H_2O$ as the vehicle) was determined to be 210.60 μM when the Vero E6 cells were maintained in DMEM supplemented with 10% FBS (FIG. 5). $CC_{50}$ of SNB01 (using DMSO as the vehicle) in DMEM supplemented with 2% FBS was 52.46 μM (FIG. 6).

SARS-CoV-2 Virucidal Assay

Figure 7A:
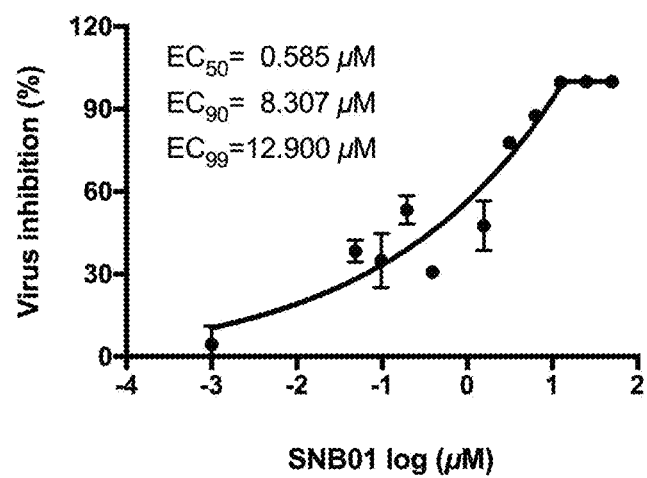
FIGS. 7A and 7B include diagrams showing inhibitory activity of SNB01 against SARS-CoV-2 infection as relative to remdesivir as determined in the supernatant of a Vero E6 cellular system.
Figure 7B:
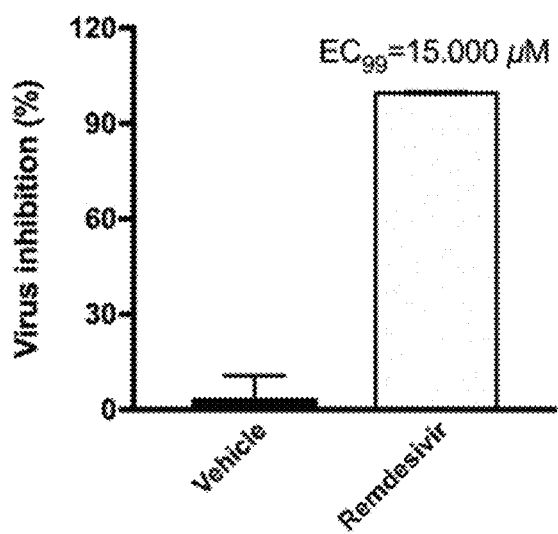
Figure 8A:
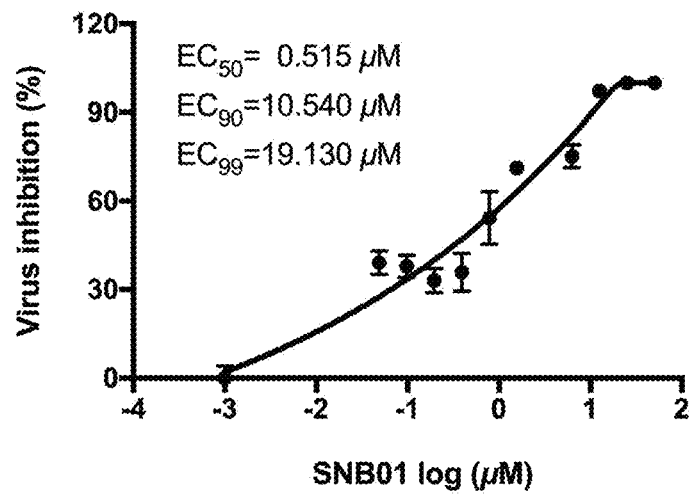
FIGS. 8A and 8B shows inhibitory activity of SNB01 against SARS-CoV-2 as relative to remdesvisir as observed in the cell layer of a Vero E6 cellular system.
Figure 8B:
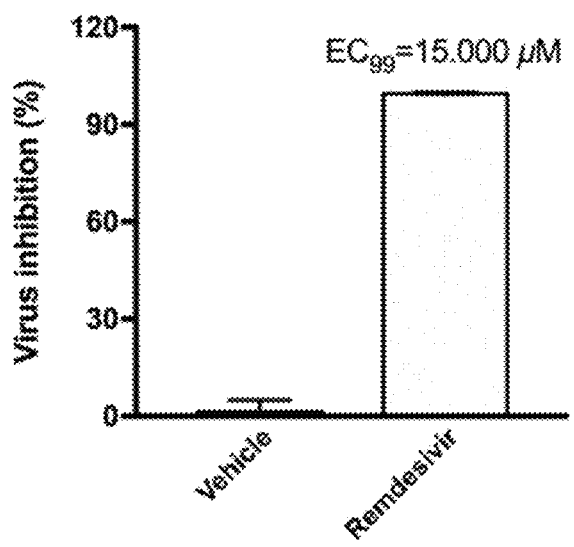

The effective concentrations ($EC_{50}$, $EC_{90}$ and $EC_{99}$) determined from the supernatant of SNB01 treatment against SARS-CoV-2 infection in Vero E6 cells were 0.585, 8.307 and 12.900 μM, respectively (FIG. 7A). The effective concentrations ($EC_{50}$, $EC_{90}$ and $EC_{99}$) determined from the cell layer were 0.515, 10.540 and 19.130 μM, respectively (FIG. 8A). Remdesivir exhibited 99% inhibitory activity (EC99) against SARS-CoV-2 at 15 μM in both supernatant and cell layer (FIG. 7B; and FIG. 8B).

Therapeutic indices of SNB01 were 101.9 in the cells ($CC_{50}$=52.460 μM/$EC_{50}$=0.515 μM) and 89.7 in the supernatant ($CC_{50}$=52.460 μM/$EC_{50}$=0.585 μM), while 10% FBS in the culture media would further raise the therapeutic indices to 408.9 and 360.0 for the cells and supernatant, respectively.

The results obtained from this study showed that the potency of SNB01 against SARS-CoV-2 infection is equivalent to that of Remdesivir (Table 8). Also, as a SARS-CoV-2 3CLPro inhibitor, SNB01 demonstrates a much better therapeutic index than Lopinavir (1.906) and Ritonavir (0.489) (Table 10). In addition, the $CC_{50}$ of SNB01 in Vero E6 is as high as 210.60 μM (in 10% FBS media), which provides an ample safety margin to support its clinical development.

TABLE 10

The Therapeutic Index of Lopinavir, Ritonavir and Remdesivir against SARS-CoV-2 Infection

| Reference Study | Compound | Method and Source | $CC_{50}$ (μM) | $EC_{50}$ (μM) | Therapeutic Index ($CC_{50}$/$EC_{50}$) |
|---|---|---|---|---|---|
| (Choy et al., 2020) | Lopinavir | qRT-PCR, supernatant | 49.75 | 26.10 | 1.906 (MOI = 0.02) |
| (Choy et al., 2020) | Ritonavir | qRT-PCR, supernatant | 48.91 | >100 | 0.489 (MOI = 0.02) |
| (Choy et al., 2020) | Remdesivir | qRT-PCR, supernatant | >100 | 26.9 | 3.717 (MOI = 0.02) |
| (Jeon et al., 2020) | Remdesivir | Immuno-fluorescence | >25 | 11.41 | 2.191 (MOI = 0.01) |
| (Pruijssers et al., 2020) | Remdesivir | qRT-PCR, supernatant | >10 | 1.49 | 6.711 (MOI = 0.01) |
| (Runfeng et al., 2020) | Remdesivir | Cytopathic effect | 110.8 | 0.65 | 170.46 (unknown MOI) |
| (Wang et al., 2020) | Remdesivir | qRT-PCR, supernatant | >100 | 0.77 | 129.87 (MOI = 0.05) |

(MOI, multiplicity of infection)

In sum, SNB01 showed potent $EC_{50}$ along with a high therapeutic index ($CC_{50}$/$EC_{50}$) for the virucidal activity against SARS-CoV-2, indicating that SNB01 would be effective in inhibiting infection by SARS-CoV-2, as well as other coronavirus, for example, those share a high sequence homology in their 3CLPro protease, and thus effective in treating disease associated with the infection, for example, COVID-19. Without being bound by theory, the results reported herein indicate that SNB01 can not only inhibit the intracellular viral replication, but also impede the spreading of the virus extracellularly, thereby leading to superior anti-viral effects.

Example 8. Binding of SNB01 with the SARS-CoV-2 Viral 3CL Protease

The objective of this study is to investigate the binding of SNB01 with the SARS-CoV-2 viral 3-chymotrypsin-like protease (3CL Protease, 3CLPro).

Test Article and Control Article

Test Article

| Code Name: | SNB01 |
|---|---|
| Content: | 99.65% |
| Physical Properties and Characterization: | Yellowish-white powder |
| Storage: | Stored in a shady area (not exceeding 25° C.), in desiccation, and protected from light. |
| Special Handling: | Standard safety precautions (use of personal protective clothing, gloves, and mask) were taken when handling the test article. |

(2S,3R,4S,5R,6R)-3,4,5-tris(3,4-dihydroxy-5-(3,4,5-tri-hydroxybenzoyloxy)benzoyloxy)-6-((3,4-dihydroxy-5-(3,4,5-trihydroxybenzoyloxy)benzoyloxy)methyl)oxan-2-yl 3,4-dihydroxy-5-(3,4,5-trihydroxybenzoyloxy)benzoate (abbreviated as β-10G) was identified as one of the main components in SNB01. This molecule was evaluated in this example. Furthermore, a synthetic analogue (2S,3R,4S,5R,6R)-6-(((3-((3,4-dihydroxy-5-((3,4,5-trihydroxybenzoyl)oxy)benzoyl)oxy)-4,5-dihydroxybenzoyl)oxy)methyl)tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (abbreviated as β-15G) was also tested. β-15G has the similar conformation as β-10G but has five more gallic acid (GA) moieties. Single moiety of gallic acid (GA; Sigma-Aldrich) was also analyzed as a control.

The structures of β-10G and β-15G are provided in Table 1 above, and the structure of GA is shown below:

TABLE 11

| | |
|---|---|
| | Vehicle Control |
| Name: | Sterile Double distilled water (DDW) |
| Equipment of DDW production: | Barnstead Smart2pure, Thermo Scientific |
| Appearance: | Colorless clear liquid |
| Storage: | Stored in a sealed container |
| Justification: | DDW will be used for the preparation of test article's formulation and also used as the vehicle control in the assay. |

Materials
Reaction Buffer
Appropriate amount of Tris(hydroxymethyl)aminomethane hydrochloride (Tris-HCl), sodium chloride, ethylenediaminetetraacetic acid and dithiothreitol were weighted and dissolved in DDW to have 12 mM, 120 mM, 0.1 mM and 2 mM solutions. The reaction buffer was adjusted to pH 7.4 and stored at room temperature.
Native Polyacrylamide Gel Electrophoresis (Native-PAGE)
For Native-PAGE Stacking Gel:

| Components | Volume (mL) |
|---|---|
| 0.375 M Tris-HCl (pH = 8.8) | 4.275 |
| Acrylamide/Bis-acrylamide (30%/0.8% w/v) | 0.67 |
| 10% (w/v) ammonium persulfate | 0.05 |
| Tetramethylethylenediamine | 0.005 |

For Native-PAGE Separating Gel:

| Components | Volume (mL) |
|---|---|
| 0.375 M Tris-HCl (pH = 8.8) | 6.49 |
| Acrylamide/Bis-acrylamide (30%/0.8% w/v) | 3.4 |
| 10% (w/v) ammonium persulfate | 0.1 |
| Tetramethylethylenediamine | 0.01 |

Running Buffer for Native-PAGE
Appropriate amount of Tris-HCl and glycine were weighted and dissolved in DDW to obtain 25 mM and 192 mM running buffer and stored at room temperature for the native-PAGE.
Sample Buffer (2×) for Native-PAGE 62.5 mM Tris-HCl (pH 6.8), 25% glycerol and 1% bromophenol blue were dissolved in DDW and stored at room temperature.
Fixing Solution for Native-PAGE
50% methanol and 10% glacial acetic acid were dissolved in DDW and stored at room temperature.
Staining Solution for Native-PAGE
0.1% Coomassie Brilliant Blue R-250, 50% methanol and 10% glacial acetic acid were dissolved in DDW and stored at room temperature.
SARS-CoV-2 Viral 3CL Protease
The viral RNA of SARS CoV2 was obtained from the clinical specimen of the Department of Pathology and Laboratory Medicine at Taipei Veterans General Hospital. Reverse transcription (RT)-PCR was applied to amplify the complementary DNA (cDNA) of SARS-CoV-2 3CLPro with 3CL-forward primer (5'-AGT GGT TTT AGA AAA ATG GCA TTC CC-3'; SEQ ID NO: 1) and 3CL-reverse primer (5'-C TCC GGT ATT GAG GGA CGC-3'; SEQ ID NO: 2). The amplified cDNA product was sequenced confirmed and showed 100% identity of the reported SARS-CoV-2 3CLPro by BLAST search (ncbi.nlm.nih.gov/BLAST/).

For protein expression, the amplified cDNA product was inserted into the pET42b vector and subsequently transformed *Escherichia coli* strain BL21. The transformed cells with pET42b-SARS-CoV-2 3CLPro was incubated on Luria-Bertani (LB) agar plates with 100 ug/ml kanamycin for selection (37° C.; 14-16 hours). Kanamycin-resistant clones were isolated and culture in 250 ml flask. When the culture density reached 0.8 OD at 600 nm, protein expression was induced by the addition of 0.4 mM isopropyl-b-D-1-thiogalactopyranoside (IPTG) at 16° C. After 22 hours, cultured cells were harvested by centrifugation and lysis. Finally, SARS-CoV-2 3CLPro was purified from bacterial lysates using Glutathione Sepharose® 4B column before incubated with 1% Factor Xa protease solution to remove Glutathione S-transferase tag. The untagged 3CLPro was dialyzed in buffer with 12 mM Tris(hydroxymethyl)aminomethane hydrochloride, 120 mM sodium chloride, 0.1 mM ethylenediaminetetraacetic and 2 mM dithiothreitol, pH 7.4 before storage.
Preparation of Test Article and Control Samples
Preparation of the Solutions for Test Article
The test article was prepared on the day of experiment and kept at room temperature. The remaining solutions were discarded as general waste after the experiment.

Five milligrams of SNB01, β-10G, β-15G and GA were dissolved in reaction buffer to obtain 10 mM stock solution. The stock solution was further diluted with reaction buffer as shown in the following tables for the assay of the interaction between test compounds and SARS-CoV-2 3CLPro by native-PAGE. Test conditions for each SNB01 sample are provided in Table 12 below.

TABLE 12

Serial Dilution of the Test Article

| Sample | Volume (μL) | Reaction buffer | Total volume | Concentration |
|---|---|---|---|---|
| SNB01-1 | 10 | 90 | 100 | 1000 |
| SNB01-2 | 50 | 50 | 100 | 500 |
| SNB01-3 | 50 | 50 | 100 | 250 |
| SNB01-4 | 50 | 50 | 100 | 125 |
| SNB01-5 | 50 | 50 | 100 | 62.5 |
| β-10G-1 | 10 | 90 | 100 | 1000 |
| β-10G-2 | 50 | 50 | 100 | 500 |
| β-10G-3 | 50 | 50 | 100 | 250 |
| β-10G-4 | 50 | 50 | 100 | 125 |
| β-10G-5 | 50 | 50 | 100 | 62.5 |
| β-15G-1 | 10 | 90 | 100 | 1000 |
| β-15G-2 | 50 | 50 | 100 | 500 |
| β-15G-3 | 50 | 50 | 100 | 250 |
| β-15G-4 | 50 | 50 | 100 | 125 |
| β-15G-5 | 50 | 50 | 100 | 62.5 |
| GA-1 | 10 | 90 | 100 | 1000 |
| GA-2 | 50 | 50 | 100 | 500 |
| GA-3 | 50 | 50 | 100 | 250 |
| GA-4 | 50 | 50 | 100 | 125 |
| GA-5 | 50 | 50 | 100 | 62.5 |

Negative Control

Reaction buffer was used as negative control.
Procedure of Running Native-Page

Figure 9:
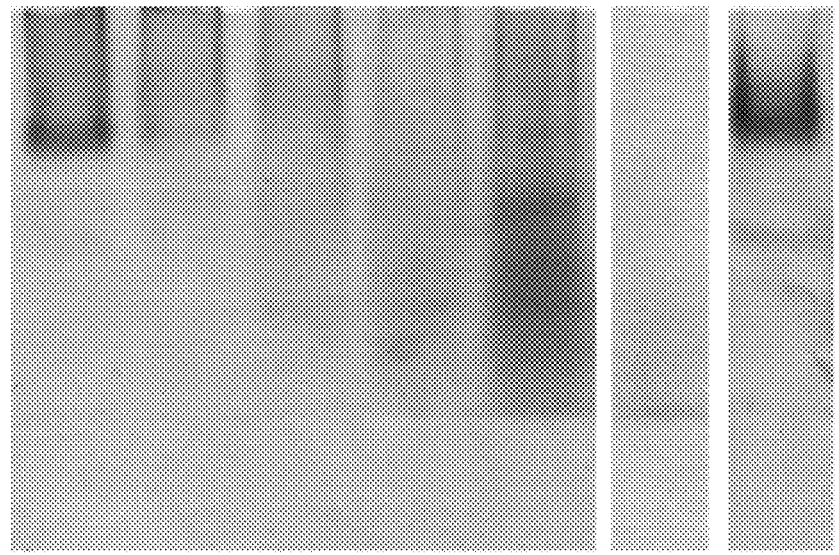
FIG. 9 shows Native-PAGE of SNB01 and SARS-CoV-2 Viral 3CLPro. 3CLpro exhibited more than one band (far right lane). After complexation, the bands became smear in a SNB01-dependent manner with higher amount of SNB01 shift the mobility of the complex more (left five lanes).
Figure 10:
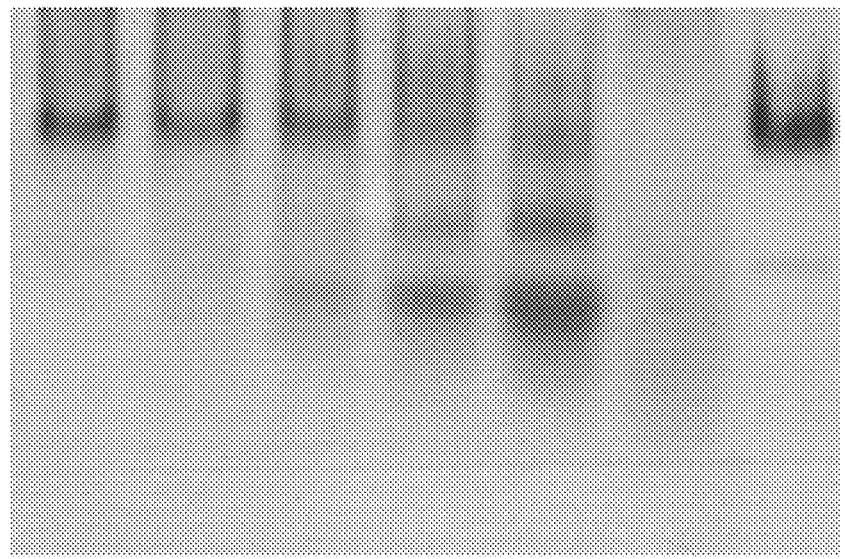
FIG. 10 shows Native-PAGE of β-10G and SARS-CoV-2 Viral 3CLPro. The complexation 3CLpro with β-10G affected its mobility. The bands shifted in a dose-dependent manner with increased amount of β-10G.
Figure 11:
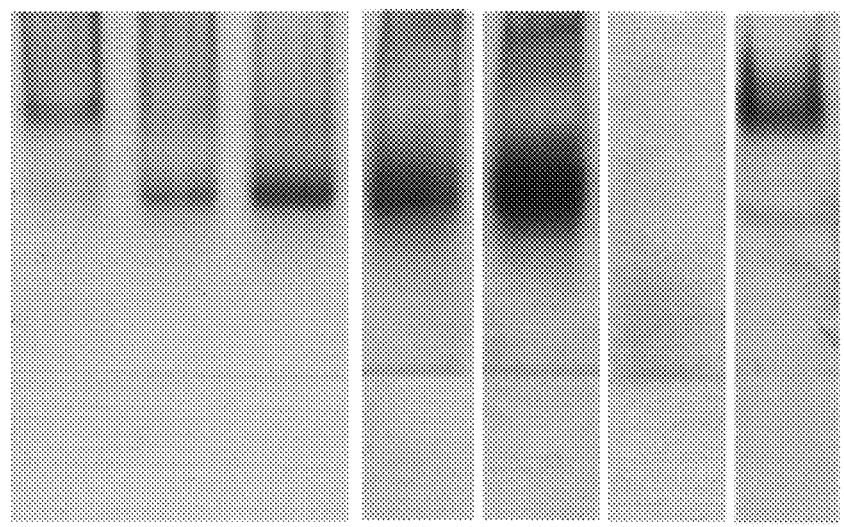
FIG. 11 shows Native-PAGE of β-15G and SARS-CoV-2 Viral 3CLPro. The complexation 3CLpro with β-15G affected its mobility. The bands shifted in a dose-dependent manner with increased amount of β-15G.
Figure 12:
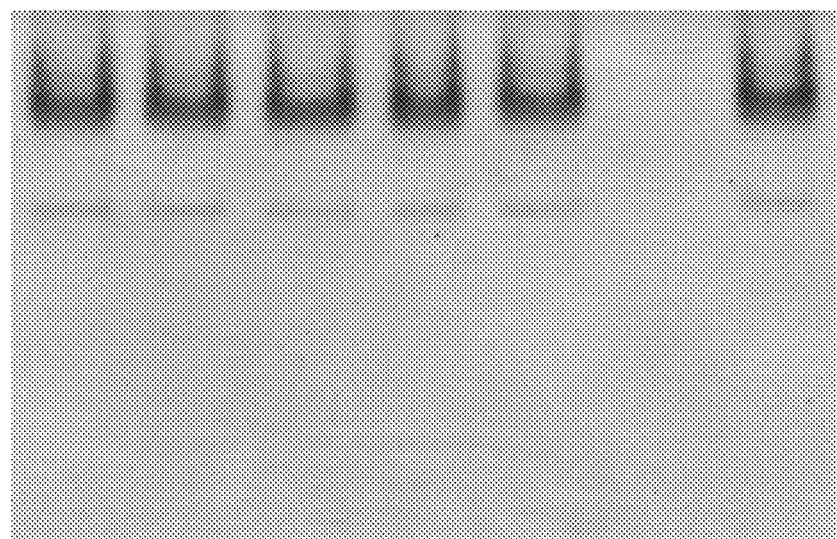
FIG. 12 shows Native-PAGE of Gallic Acid and SARS-CoV-2 Viral 3CLPro. No shift of the bands of 3CLpro, suggesting no complexation with gallic acid (GA).

10 μL of the samples (see Table 12, SNB01-1 to GA-5) were mixed with 10 μL of 40 μM SARS-CoV-2 3CLPro. All the reaction mixture was shaken at 99 rpm by program 61 (RM-2L Intelli-mixer, ELMI Ltd.) at 4° C. for 3 hours. Afterwards, 10 μL of the reaction mixture were mixed with the same volume of sample buffer (2×), respectively. Besides, 10 μL of 20 μM SARS-CoV-2 3CLPro, SNB01-2, β-10G-2, β-15G-2 or GA-2 were mixed with 10 μL of sample buffer (2×), respectively. All samples were run native-PAGE at 80V at 4° C. for 100 minutes. The gels were soaked in fixing solution and shaken at 100 rpm for 30 minutes. Afterwards, the gels were removed into staining solution and shaken at 100 rpm for 30 minutes. Finally, the gels were replenished by DDW several times and shaken at 120 rpm until the background of the gels was fully de-stained.
Result Results obtained this study demonstrated significant binding between SNB01, β-10G, or β-15G and SARS-CoV-2 3CLPro as determined by the native-PAGE. After incubation of SNB01 with 3CLPro (complexation), the band of 3CLPro on PAGE became smear and shifted position, indicating formation of complex between the protease and SNB01. (FIG. 9) FIG. 10 showed the β-10G and 3CLPro complex-ation also affected the mobility of 3CLPro on PAGE. The bands shifted and broadened, dependent on the amount of β-10G. FIG. 11 illustrated the bands changed their position and expanded after β-15G and 3CLPro complexed. The interaction was also dependent on the amount of β-15G. FIG. 12 showed GA has no significant binding to shift the mobility of 3CLPro.

In summary, SNB01 (comprising β-10G), β-10G, and its analogue β-15G all displayed remarkable dose dependent complexation with 3CLPro that changed the mobility of 3CLPro on the native-PAGE. However, incubation of GA with 3CLPro did not lead to mobility change of the protease on the native-PAGE, indicating no binding between the two components.

In conclusion, all of SNB01, β-10G and β-15G displayed prominent binding activity to 3CLPro of SARS-CoV-2, a pivotal enzyme in the viral replication. This result further demonstrates that SNB01, β-10G and β-15G are potent inhibitors of 3CLPro protease, which is expected to lead to anti-viral activity.

Example 9. Preliminary Study of Interaction Between SNB01 and SARS-CoV-2 Viral 3CL Protease by Isothermal Titration Calorimetry The objective of this study is to confirm the binding target of SNB01 with SARS-CoV-2 viral 3-chymotrypsin-like protease (3CL protease, 3CLPro).
Test Article and Control Article
Test Article

| | |
|---|---|
| Code Name: | SNB01 |
| Content: | 99.65% |
| Supplier | SyneuRx International (Taiwan) Corp. |
| Physical Properties and Characterization: | Yellowish-white powder |
| Storage: | Stored in a shady area (not exceeding 25° C.), in desiccation, and protected from light. |
| Special Handling: | Standard safety precautions (use of personal protective clothing, gloves, and mask) were taken when handling the test article. |

Vehicle Control

| | |
|---|---|
| Name: | Sterile Double distilled water (DDW) |
| Equipment of DDW Production: | Barnstead Smart2pure, Thermo Scientific |
| Appearance: | Colorless clear liquid |
| Storage: | Stored in a sealed container. |
| Justification: | DDW will be used for the preparation of test article's formulation and also used as the vehicle control in the assay. |

Reagent Preparation
Reaction Buffer

Appropriate amount of Tris(hydroxymethyl)aminomethane hydrochloride, sodium chloride, ethylenediaminetetraacetic acid and dithiothreitol were weighted and dissolved in DDW to have 12 mM, 120 mM, 0.1 mM and 2 mM solutions, respectively. The pH value of reaction buffer was adjusted to 7.4 and stored at room temperature.
SARS-CoV-2 Viral 3CL Protease The viral RNA of SARS CoV2 was obtained from the clinical specimen of the Department of Pathology and Laboratory Medicine at Taipei Veterans General Hospital. Reverse transcription (RT)-PCR was applied to amplify the complementary DNA (cDNA) of SARS-CoV-2 3CLPro with 3CL-forward primer (5'-AGT GGT TTT AGA AAA ATG GCA TIC CC-3', SEQ ID NO: 1) and 3CL-reverse primer (5'-CTCC GGT ATT GAG GGA CGC-3'; SEQ ID NO: 2). The amplified cDNA product was sequenced confirmed and showed 100% identity of the reported SARS-CoV-2 3CLPro by BLAST search (ncbi.nlm.nih.gov/BLAST/).

For protein expression, the amplified cDNA product was inserted into the pET42b vector and subsequently transformed *Escherichia coli* strain BL21. The transformed cells with pET42b-SARS-CoV-2 3CLPro was incubated on Luria-Bertani (LB) agar plates with 100 ug/ml kanamycin for selection (37° C.; 14-16 hours). Kanamycin-resistant clones were isolated and cultured in 250 ml flasks. When the culture density reached 0.8 OD at 600 nm, protein expression was induced by the addition of 0.4 mM isopropyl-b-D-1-thiogalactopyranoside (IPTG) at 16° C. After 22 hours, cultured cells were harvested by centrifugation and lysis. Finally, SARS-CoV-2 3CLPro was purified from bacterial lysates using Glutathione Sepharose® 4B column before incubated with 1% Factor Xa protease solution to remove Glutathione S-transferase tag. The untagged 3CLPro was dialyzed in buffer with 12 mM Tris(hydroxymethyl)aminomethane hydrochloride, 120 mM sodium chloride, 0.1 mM ethylenediaminetetraacetic and 2 mM dithiothreitol, pH 7.4 before storage.

Preparation of Test Article and Control Samples
Preparation of the Solutions for Test Article The test article was prepared on the day of experiment and kept at room temperature. The remaining solutions were discarded as general waste after the experiment.

Five milligrams of test article (SNB01) were dissolved in reaction buffer to obtain 10 mM stock solution. The stock solution was further diluted with reaction buffer as shown in the following Table 13. Sample SNB01-1 was used for the assay of binding affinity by isothermal titration calorimetry (ITC).

TABLE 13

Dilution of SNB01 Sample

| Sample Code | Volume (μL) | Reaction buffer (μL) | Total volume (μL) | Concentration (μM) |
|---|---|---|---|---|
| SNB01-1 | 100 | 900 | 1000 | 1000 |

Negative Control

Reaction buffer was used as negative control.

Procedure of Isothermal Titration Calorimetry Assay

Isothermal titration calorimetry (ITC) (Malvern Panalytical Ltd) was carried out by using a MicroCal iTC200 system at 25° C. The syringe was filled with 70 μL of the sample SNB01-1. Afterwards, the sample cell was filled with 350 μL of 40 μM SARS-CoV-2 viral 3CLPro in the reaction buffer. The titration was performed by 20 injections of 2 μL sample SNB01-1 into the sample cell. 1 μL of the first injection was performed in titration to minimize the volumetric error of the syringe plunger, and was later discarded in the analysis. The time between each injection was 180 seconds. The data obtained from isothermal titration was analyzed using the NITPIC software package for ITC analysis. The data were fitted using the one-site model (identical and independent binding sites). The binding isotherms were analyzed by nonlinear regression to calculate the number of binding sites (N), the binding constant (Kb or K), and the enthalpy of binding ($\Delta H$). Thermodynamic parameters as changes in free energy ($\Delta G$) and entropy ($\Delta S$) of binding were determined from the Gibbs free energy relation $\Delta G = \Delta H - T\Delta S = -RT \ln(K_b)$, where T is the absolute temperature and R=1.987 cal/mol K.

Result

Figure 13:
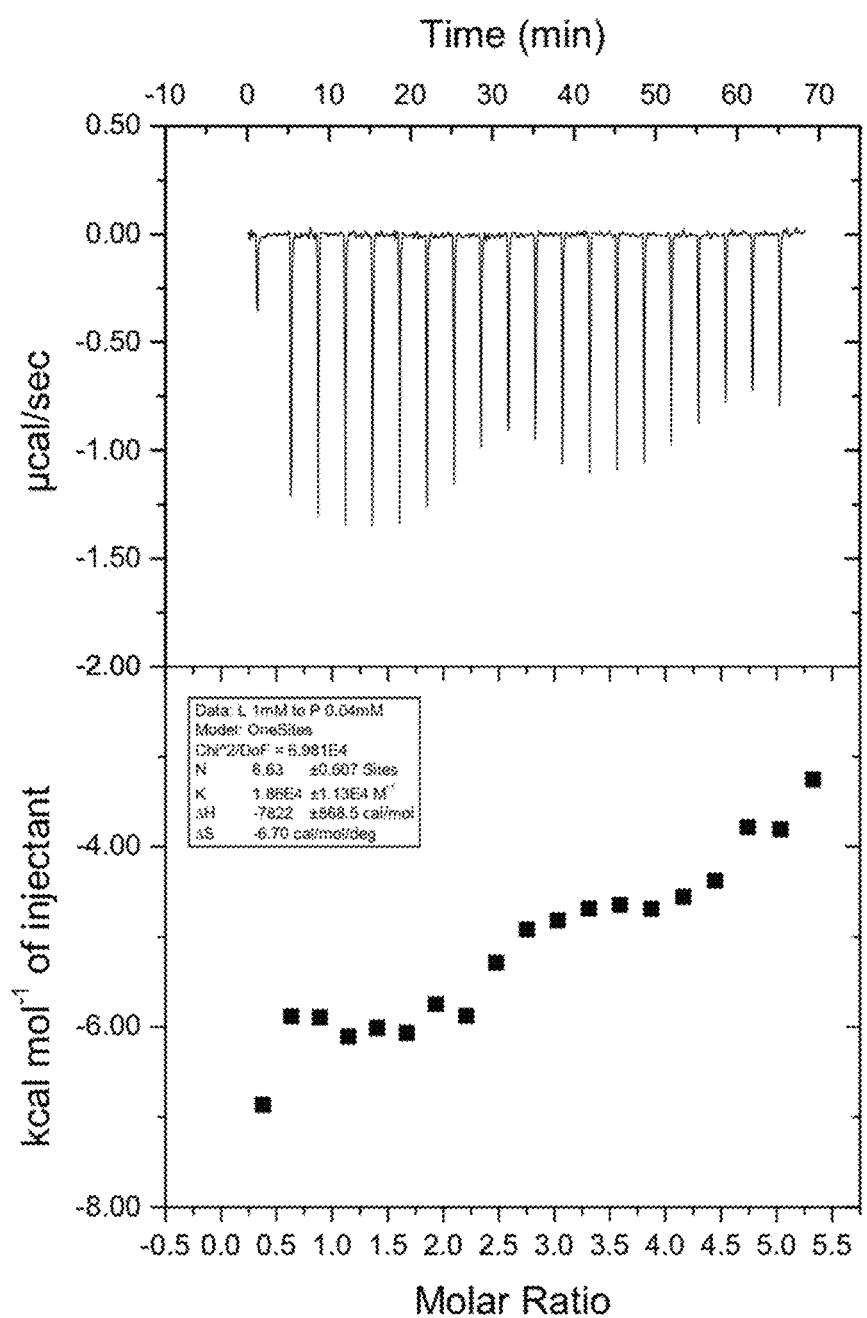
FIG. 13 shows the interactions between SNB01 and SARS-CoV-2 Viral 3CLPro by ITC Analysis. The upper panel shows the calorimetric data. The bottom plot reveals the integrated heat as a function of the SNB01/3CLPro molar ratio.
Figure 14:
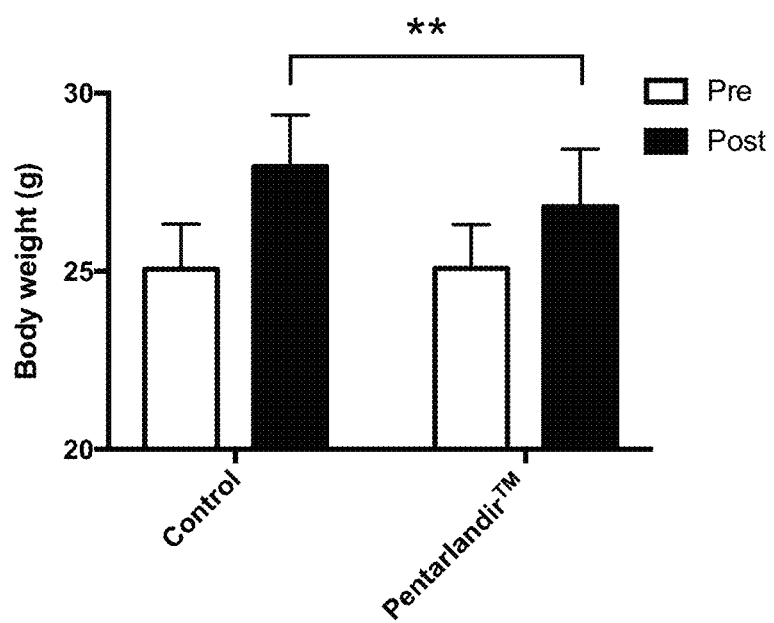
FIG. 14 shows body weight change in SNB01-treated mice. Mice received daily oral-administration of SNB01 or double-distilled water as vehicle control for 6 weeks. In addition, mice was fed ad libitum, supplied by standard chow. Body weight was measured throughout experiment. Data was presented as mean±SEM (n=10). Pre, before the oral administration; Post, after the oral administration is completed. **$p<0.01$, by two-tailed Student's t-test.

This study demonstrated a substantial binding activity of SNB01 with 3CLPro by ITC assay:

$\Delta G$: −5824.395 cal/mol
Number of binding sites: 6.63±0.607
Kb: 1.86E4±1.13E4 $M^{-1}$
$\Delta H$: −7822±868.5 cal/mol
$\Delta S$: −6.70 cal/mol/deg FIG. 13 shows the isothermal titration curves and the heat per injection obtained from the interaction between SNB01 and 3CLPro. The large binding constant, and the negative Gibbs energy from binding suggested a strong interaction between SNB01 and 3CLPro.

The N, Kb, $\Delta H$ and $\Delta S$ could be determined by the one-site model. However, the injection profile showed that the thermodynamic reaction has not saturated. The calorimetric readings were still changing by the injections of SNB01 past an hour. Future study to adjust the concentration of the test compounds and the number of injections to reach a saturated state can be informative.

A six-site model was also used for reference. All the thermodynamic parameters were collated in Table 14 below. Most of the Gibbs free energy were negative and the binding constants were large. The model also suggested the interaction between SNB01 and 3CLPro is strong.

TABLE 14

The Thermodynamic Parameters of the Six-Site Model of the Binding of SNB01 with SARS-CoV-2 Viral 3CLPro by ITC Analysis.

| Site | Kb ($M^{-1}$) | $\Delta H$ (cal/mol) | $\Delta S$ (cal/mol/deg) | $\Delta G$ (cal/mol) |
|---|---|---|---|---|
| 1 | 9.67E4 ± 1.9E4 | −1.277E4 ± 1.14E4 | −20.0 | −6.807E3 |
| 2 | 9.42E4 ± 9.8E3 | 1.248E4 ± 7.67E4 | 64.6 | −6.780E3 |
| 3 | 9.62E4 ± 1.0E4 | −3.344E4 ± 2.38E5 | −89.3 | −6.815E3 |
| 4 | 1.01E5 ± 1.1E4 | 2775 ± 3.79E5 | 13.6 | −6.830E3 |
| 5 | 1.00E5 ± 1.9E4 | 2.021E4 ± 3.24E5 | 90.7 | 7.296E4 |
| 6 | 1.03E5 ± 2.1E4 | −1.887E4 ± 1.42E5 | −40.3 | 1.150E5 |

Kb, binding constant; $\Delta H$, $\Delta S$ and $\Delta G$, changes in the enthalpy, entropy and Gibbs free energy of binding.

In sum, the results from this study show that SNB01 has substantial interaction with SARS-CoV-2 viral 3CLPro. The binding of SNB01 to 3CLPro is an exothermic reaction (negative $\Delta S$) associated with favorable enthalpy change (negative $\Delta H$). The negative $\Delta H$ values are associated with van der Waals interaction and hydrogen bonding, while negative $\Delta S$ values are associated with the net formation of hydrogen bonds (da Silva et al., 2017). Therefore, the binding enthalpy between SNB01 and 3CLPro likely occurs with the formation of hydrogen bonds. This finding is consistent with our molecular modeling study (see Example 13) that also suggests multiple active components of SNB01 can form multiple hydrogen bonds with SARS-CoV-2 viral 3CLPro, and lend support that 3CLPro inhibition is the SNB01's mechanism of action.

Example 10. A 14-Day Repeated Dose Toxicity Study of Orally Administered SNB01 in Rats This study aims at evaluating the toxicity and potential target organ(s) of the toxicity of SNB01, which was orally administered to male Sprague-Dawley (SD) rats once per day for 14 consecutive days. The study can also provide information for dose planning of the future experiment.

Test Article & Control Article
Identity of Test Article

| | |
|---|---|
| Code Name: | SNB01 |
| Physical Properties and Characterization: | Yellowish-white powder |
| Storage condition: | Stored in a sealed container with desiccation, protected from light, and relative humidity (RH) <60%, as recommended by the sponsor. |
| Expiration Date: | 04/20/2022 |
| Manufacturer: | SyneuRx International (Taiwan) Corp. |
| Special Handling: | Standard safety precautions (use of personal protective clothing, gloves, and mask) will be taken when handling the test article. |

Identity of Vehicle/Control Article

| | |
|---|---|
| Name | Double distilled water (DDW) |
| Equipment of DDW production: | Barnstead Smart2pure, Thermo Scientific. |
| Appearance: | Colorless clear liquid |
| Storage: | Stored in a sealed container |
| Special Handling: | Standard safety precautions (use of personal protective clothing, gloves, and mask) will be taken when handling the control article. |
| Justification: | DDW will be used for the preparation of test article's formulation and also used as vehicle control in the animal toxicity studies not to cause hemolysis, sensitization and irritation. |

Preparation of the Formulations

Formulation Preparation: The formulations of test article and vehicle control were freshly prepared before administration.

Test article formulation: Required amount of the test article was accurately weighed, added it into appropriate amounts of DDW, and stirred slowly until totally dissolved. The final concentration of test article was 400 mg/mL. The concentration of the formulation for test article was calculated by Weight/Volume.

Control Vehicle: Double distilled water (DDW) was used as the vehicle control.

Formulation Storage and the Disposition of Formulation

On the day of dosing, the dose formulation was freshly prepared at room temperature and protected from light prior to the dosing. The dosing procedure was finished within 3 hours. The remaining formulations of test article and vehicle control were discarded as medical waste and general waste respectively following the completion of dosing.

Study System

Animals Used in the Study

| | |
|---|---|
| Species & Strain: | Sprague-Dawley (SD) rat |
| Grade: | Specific Pathogen Free (SPF) |
| Supplier: | BIOLASCO TAIWAN CO., LTD |
| Animal age on Day 1: | 10-11 weeks old |
| Weight at pre-dosing on Day 1: | Male: 270-320 grams. Body weights of the tested animals ranged within ±20% of the mean body weight. |
| Number of animals: | Total of 7 rats were used in the study. |

Housing

Animals were housed in singleton in a polycarbonate cage (cage size of 33.2 cm×21.5 cm×21 cm) at an environmentally monitored, well-ventilated room maintained at a temperature of 20-26° C. and a relative humidity of 40%-70%. Fluorescent lighting was provided for illumination and maintaining 12-hour light/12-hour dark cycle. Polycarbonate cages, diet and corn cob bedding were autoclaved before using. All rats in the study had oral intake of water and food ad libitum. Examination of the specific pathogens and its frequency are shown Table 15 below:

TABLE 15

Specific Pathogens, Frequency, and Testing Methods

| Specific Pathogens | Frequency | Method |
|---|---|---|
| I. SEROLOGY | | |
| 1. Sendai virus (SEND) | Year | MFIA |
| 2. Pneumonia virus of mice (PVM) | Year | MFIA |
| 3. Sialodacryoadenitis virus (SDAV) | Year | MFIA |

TABLE 15-continued

Specific Pathogens, Frequency, and Testing Methods

| Specific Pathogens | Frequency | Method |
|---|---|---|
| 4. Kilham rat virus (KRV) | Year | MFIA |
| 5. H-1 virus | Year | MFIA |
| 6. Reovirus 3 | Year | MFIA |
| 7. *Mycoplasma pulmonis* | Year | MFIA |
| 8. Lymph choriomeningitis virus (LCMV) | Year | MFIA |
| 9. Hantavirus (HANT) | Year | MFIA |
| 10. Mouse adenovirus (MAV) 1&2 | Year | MFIA |
| 11. *Encephalitozoon cuniculi* | Year | MFIA |
| 12. Cilia-Associated Respiratory Bacillus | Year | MFIA |
| 13. Rat parvovirus | Year | MFIA |
| 14. Rat Minute virus | Year | MFIA |
| 15. Parvovirus NS-1 | Year | MFIA |
| 16. Theiler virus (GD VII) | Year | MFIA |
| 17. Rat Respiratory Virus | Year | Histopathology |
| 18. *Clostridium piliforme* (CPIL; Tyzzer's Disease) | Year | MFIA + Gross Necropsy |
| II. MICROBIOLOGY | | |
| 1. *Citrobacter rodentium* | Year | CULTURE |
| 2. *Corynebacterium kutscheri* | Year | CULTURE |
| 3. *Salmonella spp.* | Year | CULTURE |
| 4. *Streptobacillus moniliformis* | Year | PCR |
| 5. *Helicobacter hepaticus* | Year | PCR |
| 6. *Helicobacter bilis* | Year | PCR |
| 7. *Helicobacter spp.* | Year | PCR |
| 8. *Pasteurella pneumotropica* | Year | CULTURE |
| 9. *Pasteurella multocida* | Year | CULTURE |
| 10. *Pasteurella sp.* | Year | CULTURE |
| 11. *Streptococcus pneumonia* | Year | CULTURE |
| 12. *Citrobacter spp.* | Year | CULTURE |
| 13. *Klebsiella oxytoca* | Year | CULTURE |
| 14. *Klebsiella pneumoniae* | Year | CULTURE |
| 15. *Bordetella bronchiseptica* | Year | CULTURE |
| 16. *Mycoplasma pulmonis* | Year | PCR |
| III. PARASITOLOGY | | |
| 1. Ectoparasites-direct | | |
| (1) *Lice* | Year | CLINICAL EXAM AND NECROPSY |
| (2) *Mites* | Year | CLINICAL EXAM AND NECROPSY |
| 2. Endoparasites-Helminths | | |
| (1) *Aspiculuris tetraptera* | Year | DIRECT EXAM + FLOTATION TEST |
| (2) *Syphacia muris* | Year | DIRECT EXAM + FLOTATION TEST |
| (3) *Syphacia obvelata* | Year | DIRECT EXAM + FLOTATION TEST |
| 3. Endoparasites-Protozoa | | |
| (1) *Chilomastix sp.* | Year | DIRECT EXAM + FLOTATION TEST |
| (2) *Entamoeba sp.* | Year | DIRECT EXAM + FLOTATION TEST |
| (3) *Giardia spp.* | Year | DIRECT EXAM + FLOTATION TEST |
| (4) *Hexamastix sp.* | Year | DIRECT EXAM + FLOTATION TEST |
| (5) *Monocercomonoides sp.* | Year | DIRECT EXAM + FLOTATION TEST |
| (6) *Retortamonas sp.* | Year | DIRECT EXAM + FLOTATION TEST |
| (7) *Spironucleus spp.* | Year | DIRECT EXAM + FLOTATION TEST |
| (8) *Trichomonads* | Year | DIRECT EXAM + FLOTATION TEST |
| (9) Other *Protozoan* | Year | DIRECT EXAM + FLOTATION TEST |

Quarantine and Acclimation

Animals were quarantined and acclimatized for at least 7 days before the study. The general health conditions of the animals were evaluated by a veterinarian, and a complete health check was performed. Animals with abnormalities, unusual behaviors or 20% over/under average weight were excluded from the study.

Animal and Cage Card Identification

Each rat was singly housed. Thus, animal was identified by the cage cards. The cage card was labeled with the date, project code, experiment, treatment group numbers, and dose level.

Experimental Design

| Group | Control/ Test Article | Dose Level (mg/kg) | Conc. (mg/mL) | Number of Animals/ | Animal ID Female |
|---|---|---|---|---|---|
| 1 Vehicle control | DDW | 0 | 0 | 2 | A and B |
| 2 Dosing group | SNB01 in DDW | 4000 mg/kg | 400 mg/mL | 5 | C, D, E, F and G |

Group Assignment and Dosage

The body weight of animals was measured on Day 0 (the day before dosing). All rats were randomly assigned to vehicle control or SNB01-treated groups. Their body weights were similar. If the morality of animals was observed, unrelated to the test article on the Day 1, the animal was replaced by an extra animal with similar body weight. Data collected from those animals died unrelated to the test article was retained in the study file but not to be reported.

Dosing conditions are provided below:
Dose Route: Oral gavage
Dose Frequency and Duration: Once daily for 14 consecutive days. The first dosing day is defined as Day 1.
Dose Volume: 10 mL/kg
Dosing Method: The vehicle control group A and B and test article group C, D, E, F, and G rats received either vehicle control or test article via oral gavage using a suitable disposable syringe and a 16-gauge ball-tipped stainless-steel tube. Dosage volume were calculated based upon the body weight of the most closely weighed date.

Clinical Observations

Daily Clinical Observations: All rats were observed at least twice daily (a.m. and p.m.) or as often as needed during the quarantine, acclimation and study periods for signs of mortality, morbidity, respiration, secretion, feces, and their water and food intake.

Detailed Clinical Observations: Each rat was removed from its cage and examined closely for any clinical sign of toxicity prior to dosing. The observation included, but not be limited to, evaluation of behavior, skin, fur, eyes, ears, nose, abdomen, external genitalia, anus, limbs, feet and respiration.

Body Weights

Body weight was measured daily at 10 a.m. during the experimental period (Table 7.

Individual Body Weight and Mean Weight Gain of the Animals). Body weight was also recorded when an animal was found dead or euthanized in extremis.

Food consumption (food in/food out) was recorded for animals in both vehicle control and test article groups daily after the first dosing day throughout the study period and reported as gram/rat/day.

Animal Euthanasia

All animals were euthanized after the end of experiment by $CO_2$-inhalation.

Macroscopic and Microscopic Examinations

All animals received complete necropsy examinations. Animals found dead after regular working hours was refrigerated at 2 to 8° C. and the necropsy was conducted as soon as possible within 24 hours. Any lesions or abnormality in tissues or organs were recorded in necropsy and gross visual examination. After 24 hours of final dosing, all survived animals were euthanized for necropsy examination. Collected lung tissues were preserved in 10% neutral buffered formalin solution for histological examination and evaluation. Carcasses was discarded as medical waste following the necropsy examination and the tissue collection.

Result

Mortality and Morbidity

Neither mortality nor morbidity was observed in any group throughout the study

Clinical Observations:

No significant abnormalities were observed in 4000 mg/kg of SNB01-treatment groups during 14-days oral administration.

Body Weight:

Although slight reduction of body weight was observed in four out of five animals in 4000 mg/kg of SNB01-treated group, the mean body weight loss was less than 10 percent on day 14 (−7%) (Table 8. Individual Body Weight and Mean Weight Gain of the Animals.)

This reduction of body weight could be accounted for the weight suppression effect of SNB01, even at very low doses. See below disclosures.

Food Consumption:

Notable reduction of daily food consumption was occasionally observed in several animals. Overall, daily food consumption of all the animals did not show significant, nor persistent decrease during the experimental period.

Water Consumption:

Similar results of water intake were observed as food-consumption. Notable reductions of the water-intake occurred infrequently during the 14-day oral administration, but the reductions were temporary.

Necropsy and Lung Pathology Analysis

After the end of 14-day oral administration, treated animals was housed for 24 hours and subsequently, euthanized for necropsy and analysis of lung pathology.

No gross lesion or abnormality of the test article-treated rats was observed by necropsy.

The lung tissues were fixed and paraffin-embedded before the pathology analysis. In the SNB01-treated rats, no pathological abnormality was observed in the sections with hematoxylin and eosin (H&E) staining.

In sum, no significant side effects were observed in connection with oral administration of SNB01 at a daily dose of as high as 4,000 mg/kg/day.

SNB01 Toxicity Study of Orally Administered SNB01 in Rats

Other than oral administration, inhaled route is also considered as a potential administration approach of SNB01 in view of the pulmonary symptoms in SARS-CoV-2 infected patients. Therefore, the inhalation safety of SNB01 was also evaluated. In the inhalation safety study, a single dose (8.25 mg/kg) of SNB01 was delivered to male 10-week-old Sprague-Dawley (SD) rats by a nebulizer (BlueEchoCare, N.Y., USA). Respiratory function including respiratory frequency and blood-oxygen ratio, general physiological indicators including food and water consumption and body weight were monitored for 24 hours after inhaled SNB01 administration. No significant abnormality and clinical sign was observed.

Example 11. Evaluation of Toxicity of SNB01 in Human Subjects

A toxicity study of SNB01 was performed in human subjects in a 7-day repeated dose treatment at a daily dose of 1100 mg/kg. No clinical or behavioral abnormality was observed in the human subjects treated with SNB01. A slight weight loss (1.5%) was observed at the end of day 7.

Moreover, a necropsy examination did not reveal any significant abnormality and lesions of major organs, including lung, liver, spleen, heart, kidney, and gastrointestinal tract. Thus, the dose of 1100 mg/kg is considered no-observed-adverse-effect level (NOAEL).

Example 12. The Pharmacokinetic Studies of SNB01 in Sprague-Dawley Rats by LC-MS Analysis The objective of this study is to evaluate and determine the pharmacokinetic parameters of SNB01 in Sprague-Dawley rats after either single or 14-day repeated oral administration by LC-MS analysis.

Test Article and Control Article Information
Test Article

| | |
|---|---|
| Code Name: | SNB01 |
| Assay: | 99.65% |
| Supplier | SyneuRx International (Taiwan) Corp. |
| Physical Properties and Characterization: | Yellowish-white powder |
| Storage: | Stored in a shady area (not exceeding 25° C.), in desiccation, and protected from light. |
| Special Handling: | Standard safety precautions (use of personal protective clothing, gloves, and mask) were taken when handling the test article. |

Vehicle

| | |
|---|---|
| Name: | Double distilled water (DDW) |
| Storage: | Stored in a sealed container after sterilization |

Formulation Preparation
Preparation of the Formulation Solutions

The test article's formulation solutions were prepared on Day −1 (one day before dosing). Required amount of the test article was accurately weighed, with addition of appropriate amounts of double distilled water (DDW), and stirred slowly until totally dissolved. DDW was added to the quantum satis level to prepare the final desired volume with the concentrations of 70, 150 and 200 mg/mL. The concentration of the formulation for test article was calculated by weight/volume. The solution was protected from light and stored in a 2-8° C. refrigerator.

Formulation Storage and its Disposition

On the day of dosing, the formulation solutions were transferred and stored at room temperature and protected from light prior to dosing. The dosing procedure was finished within 6 hours. The remaining test article's and vehicle control article's formulation solutions were discarded as general waste following the completion of dosing.

Study System
Animals Used in the Study

| | |
|---|---|
| Species & strain: | Male Sprague-Dawley rats |
| Grade: | Specific Pathogen Free (SPF) |
| Supplier: | BioLASCO Taiwan Co., Ltd. |
| Animal age on the dosing day (Day 1): | 10 weeks |
| Body weight on the dosing day (Day 1): | 300 to 350 grams. All animals in the study had body weight that fell within ± 20% of the mean body weight. |
| Number of animals in this study: | Total 29 male rats |

Housing

Animal were housed in singleton in a polycarbonate cage (cage size of 33.2 cm×21.5 cm×21 cm) and in an environmentally monitored, well-ventilated room maintained at temperature of 20-26° C. and a relative humidity of 40%-70%. Fluorescent lighting was provided for illumination approximately 12 hours per day. Polycarbonate cages, diet and corn cob bedding were autoclaved before use. Specific pathogens, as well as frequency and methods of examination were shown in Table 15.

Quarantine and Acclimation

Animals were quarantined and acclimatized for at least 7 days. The general health of the animals was evaluated by a veterinarian. Animals with abnormality or body weight ≥±20% average weight were excluded from the study.

Animal Identification

Cage identification: The cage cards were labeled with the date, project code, experiment, treatment group number, and dose level.

Experimental Design
Rat Jugular Vein Catheterization

Anesthesia was induced with isoflurane (3-5%) in an anesthesia chamber and maintained with a mask (1-3% isoflurane). A polyethylene catheter was implanted into the jugular vein. Catheters were kept patent by flushing with heparinized saline (100 units/mL). Ketoprofen (5 mg/kg) was administered prior to animals regaining consciousness to alleviate pain. Animals were allowed to recover for 24 hrs after the surgery.

Randomization and Group Assignment

After randomization, rats were assigned to one of five groups as shown in the table below:

| Group | Test Article | Dose Level (mg/kg) | Conc. (mg/mL) | Number | Animal ID |
|---|---|---|---|---|---|
| 1 | Fasting-single oral dose | SNB01 | 1000 | 200 | 7 | #1~7 |
| 2 | Fasting-single oral dose | | 750 | 150 | 5 | #8~12 |
| 3 | Fasting-single oral dose | | 350 | 70 | 6 | #13~18 |
| 4 | Fasting-14-day repeated oral dose | | 1000 | 200 | 6 | #19~24 |
| 5 | Fed-single oral dose | | 1000 | 200 | 5 | #25~29 |

Dosing Procedure:
Dosing route: Oral gavage
Dose frequency and duration: Single and 14-day repeated administration
Dose: 350, 750 or 1000 mg/kg
Dosing volume: 10 mL/kg
Dosing method: Administer the dose by a sterile disposable syringe with a 16-gauge ball-tipped stainless steel tube for oral gavage. The dosing volume was calculated based upon the body weight most recently measured and rounded to 2 decimal places. The division value is 0.02 mL for a 1 mL one-time-use sterile syringe, therefore, when the dosing volume was between two division value lines, the dosing volume was the larger one.

Justification for route of administration: The oral route of administration was selected for test article because it would be the intended clinical route of administration.

Justification for dosage of administration: The dosage for this PK experiments was determined based on our previous research data. Our findings indicated that 2000 mg/kg of SNB01 is well tolerated in mice. Based on the conversion by body surface area, the equivalent dose for SNB01 in rat would be 1000 mg/kg. Furthermore, 1000 mg/kg was chosen for PK study in rats because tannic acid has lower absorption rate in rat (*J. Agric. Food Chem.* 2003, 51, 331-339).

Groups 1-3 of 350, 750 and 1000 mg/kg were chosen for PK study in rats to explore the dosage effect.

Group 4 received 14 days repeated administration to explore the pharmacokinetic effects in long-term.

In addition, Group 5 was fed ad lib to determine the fasting/food effects.

Fasting Requirement

Rats were allocated into 5 groups: animals in the first to third groups were fasted overnight; animals in the fourth group were fasted 3 hrs every day before the administration of the test article during the experiment period; while animals in the fifth group received no fasting prior to the test article administration.

Collection and Processing of the Blood Samples

Blood samples (about 500 µL) were collected from the animals in Groups 1 and 2 at pre-dosing (0 hr), and 0.25, 0.5, 1, 2, 4, 6, 8, and 24 hrs after the dosing. In addition, blood samples were collected from animals in Groups 3 to 5 at pre-dosing (0 hr), and 1, 2, 4, 5, 6, 7, and 24 hrs after dosing. The collected blood samples were transferred into tubes with 5 µL heparin (5000 IU/mL) and centrifuged at 4,000×g for 10 min at 2 to 8° C. The supernatant was transferred into new tubes and stored at −80° C. until analysis.

Introduction of Tannic Acid Analysis

SNB01 is described in Example 5 above. The analytical method for pharmacokinetic studies of SNB01 was modified from the method of Heilongjiang Institute for Food and Drug Control to measure the tannic acid in the rat plasma.

Up to date, an optimal analytical method for detecting the tannic acid content in drug product is described by Heilongjiang Institute for Food and Drug Control, in which tannase was applied to hydrolyze tannic acid to have the total gallic acid determined by high performance liquid chromatography (HPLC). After the determination of the amount of total gallic acid, free gallic acid before tannase treatment was subtracted from the total amount of gallic acid to deduce the amount of polymerized gallic acid that is represented in the tannic acid (Drug Standards of China 2014, Vol. 15, No. 3).

According to the reference above, an assay with enzymatic hydrolysis of tannic acid to determine the amount of total vs. free gallic acid was developed.

Analysis of the Blood Samples by HPLC-MS

Internal Standard (IS)
  Name: 3,5-dihydroxybenzoic acid
  Manufacture: Sigma-Aldrich, Germany
  Purity: 97%
  Storage condition: Stored in a cool place. Kept the container tightly closed in a dry and well-ventilated place.

Instruments and Apparatus
  Mass spectrometer: Shimadzu, LCMS-2020, Japan
  Pump: Shimadzu LC-20AD, Japan
  Mass spectrometer detector: Shimadzu LCMS-2020, Japan
  Photodiode array detector: Shimadzu SPD-M20A, Japan
  Automatic sampler: Shimadzu SIL-20AC HT, Japan
  Column oven: Shimadzu CTO-20AC, Japan
  Column: Kinetex® EVO C18, 5 µm, 150*4.6 mm, Phenomenex, US Solution Preparation 1. Preparation of Mobile Phase Mobile phase A: Accurately transferred 1 mL, of formic acid into a container with 1 L of water and mixed well.

Mobile phase B: Accurately transferred 200 mL of MeOH into a container with 800 mL of ACN and mixed well.

2. Preparation of the Solution of Enzyme Reaction

Acetate buffer (0.02 M): Prepared 0.02 M acetic acid and 0.02 M sodium acetate aqueous solutions. Mixed them together and adjust the pH to 4.7.

Tannase reaction solution (15 mg/mL): Accurately weighed 150 mg of tannase into centrifuge tube to which 10 mL of 0.02 M acetic acid buffer was added. Mixed well by vortex.

3. Preparation of Internal Standard

Internal standard (4.5 mg/mL): Accurately weighed 45 mg of internal standard into a tube containing 10 mL of deionized water ($ddH_2O$) and mixed well.

4. Preparation of Extraction Reagent

Extraction reagent: ACN solution containing 1.5% (w/w) formic acid

5. Preparation of Samples for SNB01 Standard Curve:

Fifteen mg of SNB01 and about 2/3 volume of diluent were added into a 200 mL volumetric flask and vortexed until well-mixed. Then, appropriate amount of diluent was added to the flask to achieve the final desired volume. The same was mixed well to obtain SNB01 stock solution (TA9-1), with the concentration of 75 µg/mL, to prepare for the solutions for standard curve with a serial 1:2 dilution by $ddH_2O$ according to Table 16 below:

TABLE 16

| | SNB01 Samples | | |
| --- | --- | --- | --- |
| Solution name | Volume of $ddH_2O$ (µL) | Final volume (µL) | SNB01 concentration (µg/mL) |
| TA9-1 | — | 400 | 75.0 |
| TA8-1 | 200 | 400 | 37.5 |
| TA7-1 | 200 | 400 | 18.75 |
| TA6-1 | 200 | 400 | 9.38 |
| TA5-1 | 200 | 400 | 4.69 |
| TA4-1 | 200 | 400 | 2.34 |
| TA3-1 | 200 | 400 | 1.17 |
| TA2-1 | 200 | 400 | 0.58 |
| TA1-1 | 200 | 400 | 0.29 |
| Blank-1 | 400 | 400 | — |

6. Enzyme hydrolysis:

The solutions (TA1-1-TA9-1) were used to prepare for the samples of standard curve to analyze the rat plasma according to the scheme shown in Table 17 below. Briefly, 200 µL of tannase reaction solution (15 mg/mL) was added into the standard curve samples and mixed well by vortex. The mixtures were incubated at 30° C. for 4 hours to complete the hydrolysis. The hydrolysate was extracted by 600 µL of extraction reagent (1.5% (w/w) formic acid in ACN), and centrifuged at 15,000×g for 10 min at 2-8° C.

TABLE 17

TA Samples Tested

| Sample name | Volume of rat plasma (μL) | Tannase reaction solution (μL) | Extraction reagent (μL) | Final volume (μL) |
|---|---|---|---|---|
| TA9 | 100 | 200 | 600 | 940 |
| TA8 | 100 | 200 | 600 | 940 |
| TA7 | 100 | 200 | 600 | 940 |
| TA6 | 100 | 200 | 600 | 940 |
| TA5 | 100 | 200 | 600 | 940 |
| TA4 | 100 | 200 | 600 | 940 |
| TA3 | 100 | 200 | 600 | 940 |
| TA2 | 100 | 200 | 600 | 940 |
| TA1 | 100 | 200 | 600 | 940 |
| Blank | 100 | 200 | 600 | 940 |

The supernatant was collected and mixed with 10 μL of internal standard (IS) (4.5 mg/mL), followed by evaporating to dryness under $N_2$. The dried extract was re-constituted in 150 μL mobile phase A and filtered through a 0.22 μm membrane filter. The final concentrations of the samples for SNB01 standard curve were shown in Table 18 below:

TABLE 18

TA Sample Conditions

| Sample name | Reconstituted solution (μL) | SNB01 concentration (μg/mL) |
|---|---|---|
| TA9 | 150 | 20 |
| TA8 | 150 | 10 |
| TA7 | 150 | 5 |
| TA6 | 150 | 2.5 |
| TM | 150 | 1.25 |
| TA4 | 150 | 0.625 |
| TA3 | 150 | 0.313 |
| TA2 | 150 | 0.156 |
| TA1 | 150 | 0.078 |
| Blank | 150 | — |

Extraction Procedure of the Plasma Sample

The frozen plasma samples were completely thawed at room temperature and vortexed well before taking an aliquot. 100 μL of each sample was accurately pipetted in duplicate into two 1.5 mL tubes. One set of samples was to determine free gallic acid in the plasma; the other was to determine the total gallic acid content after hydrolysis in the same plasma. The experimental procedures were shown as the following.

Determination of the Free Gallic Acid Content in Rat Plasma:

Free gallic acid in the rat plasma was analyzed without enzymatic hydrolysis. 100 μL of each plasma sample was extracted by 600 μL of extraction reagent (1.5% (w/w) formic acid in ACN), and centrifuged at 15,000×g for 10 min at 2-8° C. The supernatant was collected and mixed with 10 μL of IS (4.5 mg/mL), followed by evaporating to dryness under $N_2$. The dried extract containing free gallic acid was re-constituted with 150 μL of mobile phase A and filtered through a 0.22 μm membrane filter. The samples were stored at −20° C. prior to HPLC-MS analysis.

Determination of the Total Gallic Acid in the Rat Plasma:

Amount of the total tannic acid in the rat plasma was analyzed after the completion of the enzymatic hydrolysis. 100 μL of each plasma sample was mixed well with 200 μL of tannase reaction solutions (15 mg/mL). The mixtures were incubated at 30° C. for 4 hours to complete the hydrolysis. Then, the hydrolysates were extracted by 600 μL of extraction reagent (1.5% (w/w) formic acid in ACN), and centrifuged at 15,000×g for 10 min at 2-8° C. The supernatant was collected and mixed with 10 μL of IS (4.5 mg/mL), followed by evaporating to dryness under $N_2$. The dried extract containing total gallic acid was re-constituted with 150 μL of mobile phase A and filtered through a 0.22 μm membrane filter. The samples were stored at −20° C. prior to HPLC-MS analysis.

Parameters of the Instruments

HPLC-MS Parameters:
  Flow rate: 0.6 mL/min
  Column temperature: 30° C.
  Sample oven: 4° C.
  Run time: 50 min
  Injection volume: 25 μL
  Mobile phase gradient elution:

| Time (min) | % M.P. A | % M.P. B |
|---|---|---|
| 0 | 98 | 2 |
| 10 | 81 | 19 |
| 25 | 78 | 22 |
| 26 | 75 | 25 |
| 31 | 74 | 26 |
| 44 | 66 | 34 |
| 46 | 2 | 98 |
| 48 | 98 | 2 |
| 50 | 98 | 2 |

HPLC-MS Conditions

Ionization mode: Electrospray ionization, negative

Scan mode: Selected-ion monitoring chromatogram (SIM) scanning

Figure 15A:
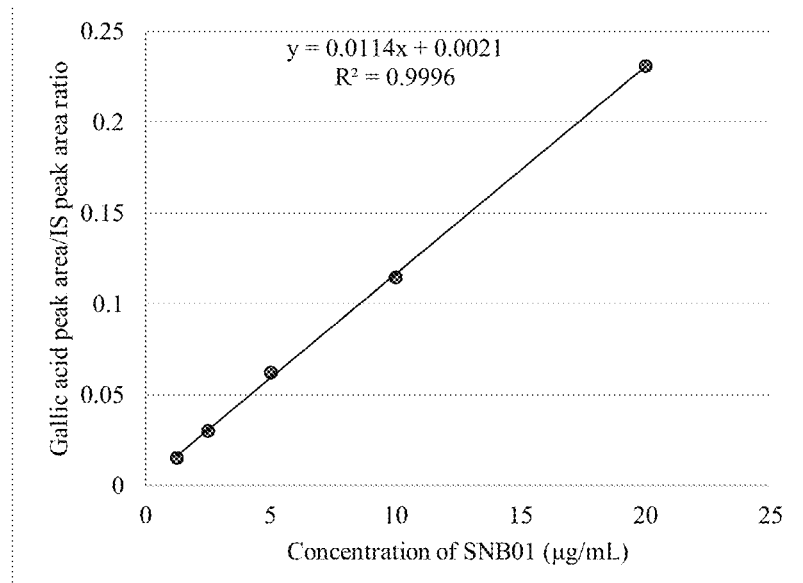
FIGS. 15A and 15B shows standard curves of SNB01 in rat plasma.
Figure 15B:
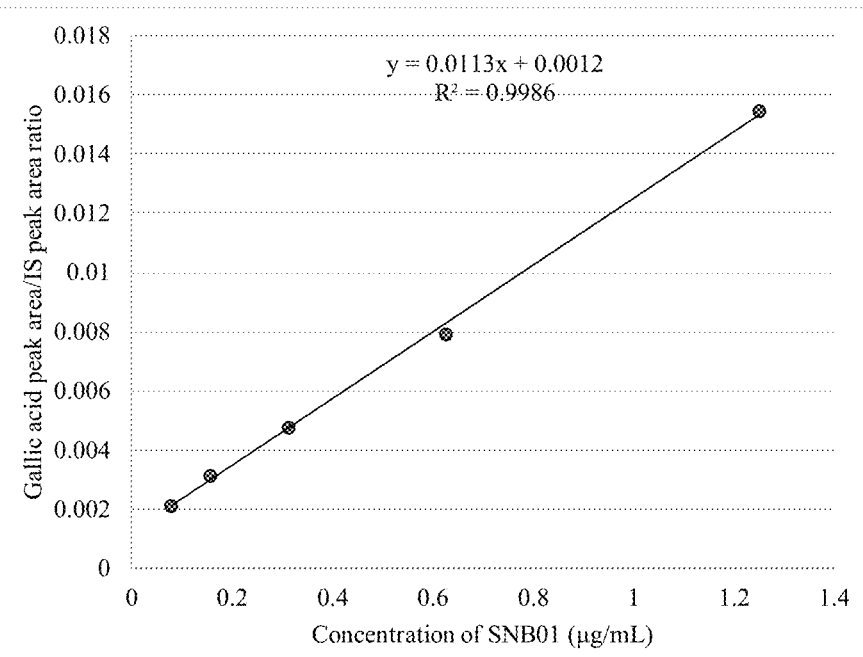

SIM of Analyte: 169 (gallic acid)
  SIM of IS: 153 (3,5-dihydroxybenzoic acid)
  The parameters of mass spectrum:
  Nebulizing gas flow: 1.5 L/min
  Drying gas flow: 20 L/min
  Interface temperature: 350° C.
  DL temperature: 250° C.
  Heat block temperature: 400° C.
  Standard curve calculation
  Response: Gallic acid peak area/IS peak area ratio
  Equation: y=bx+a Results Data of the Standard Curve Data of the standard curve of SNB01 in rat plasma was presented in FIG. 15 and Table 19. The standard curve of SNB01 was linear within the range of 0.078 to 20 μg/mL. The % CVs of the back-calculated concentrations of the standards ranged from 2.52% to 11.25%; the relative error (% RE) values were from −4.64% to 10.93%. The correlation coefficients (R) were greater than 0.99.

Data of the Plasma Concentration-Time

Figure 16:
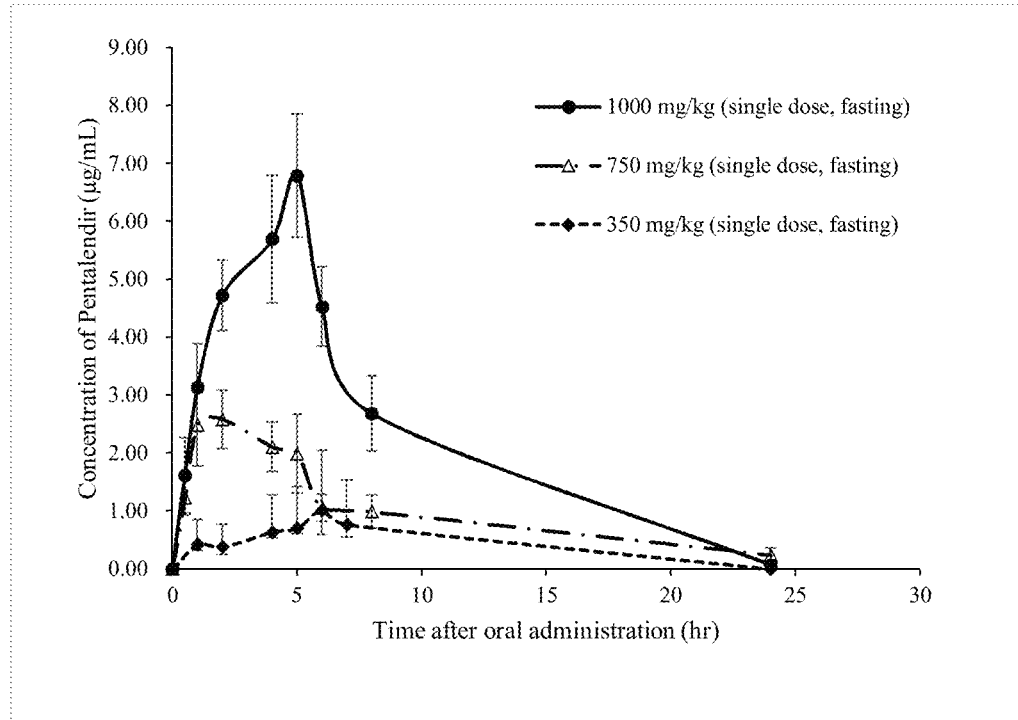
FIG. 16 shows the Mean Concentration-time Curve of SNB01 (m/mL) of Group 1 (●, 1000 mg/kg), Group 2 (Δ, 750 mg/kg), and Group 3 (♦, 350 mg/kg) after a Single Oral Administration of SNB01 under Fasting Condition.

SNB01 plasma concentration-time curve and data after single oral administration (350, 750 and 1000 mg/kg) in rats were shown in FIG. 16, Tables 20-22. The $C_{max}$ (7.80±2.32, 3.60±1.10, 1.17±0.97 μg/mL for 1000, 750, 350 mg/kg dosing group respectively) and $AUC_{0-t}$ (44.33±16.29, 23.50±12.94, 4.06±2.23 μg*hr/mL for 1000, 750, 350 mg/kg dosing group respectively) are in proportion to the administered dosages ($r^2$=0.92 for $C_{max}$, 0.98 for $AUC_{0-t}$).

Figure 17:
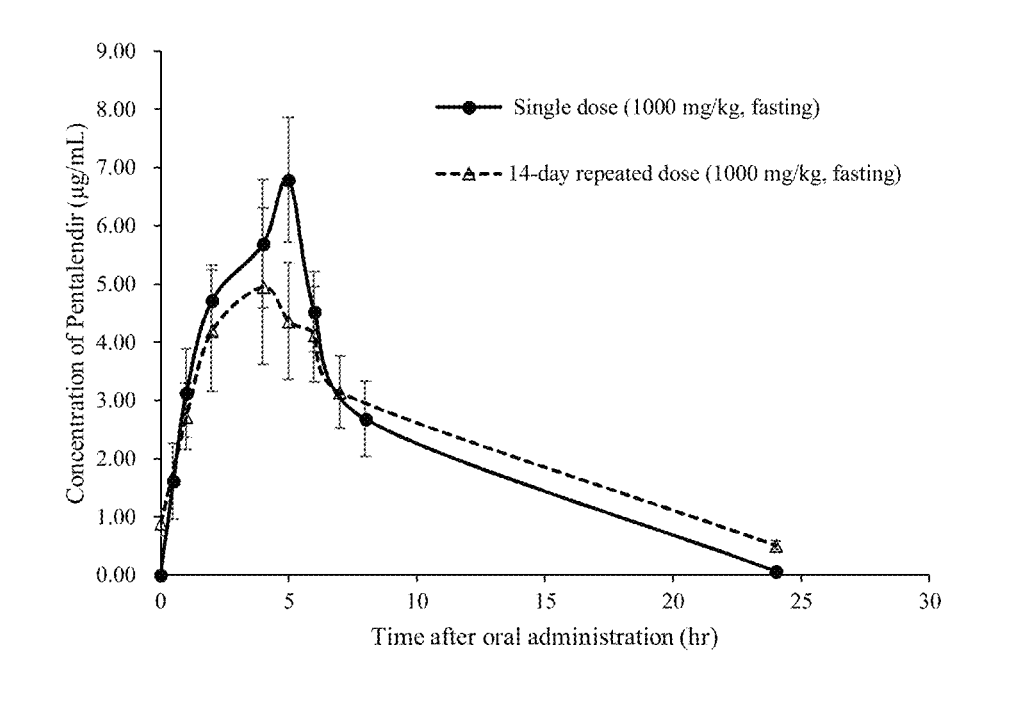
FIG. 17 shows the mean concentration-time curve of SNB01 (µg/mL) of Group 1 (●, single dose) and Group 4 (Δ, 14-day repeated dose) after Oral Administration of SNB01 (1000 mg/kg) under fasting condition. Data was presented as mean±SEM.

In addition, the concentration-time curve and data of SNB01 in single vs. 14-day repeated oral administration in rats are shown in FIG. 17 and Table 23. 14-day administration of 1000 mg/kg SNB01 led to higher, but insignificant, $AUC_{0-t}$ (58.06±9.38 vs. 44.33±16.29 μg*hr/mL, p=0.19) than single administration, while did not increase the $C_{max}$ (6.16±2.96 vs. 7.80±2.32 μg/mL). Low level of SNB01 (0.52±0.19) remained after 24 hrs.

Figure 18:
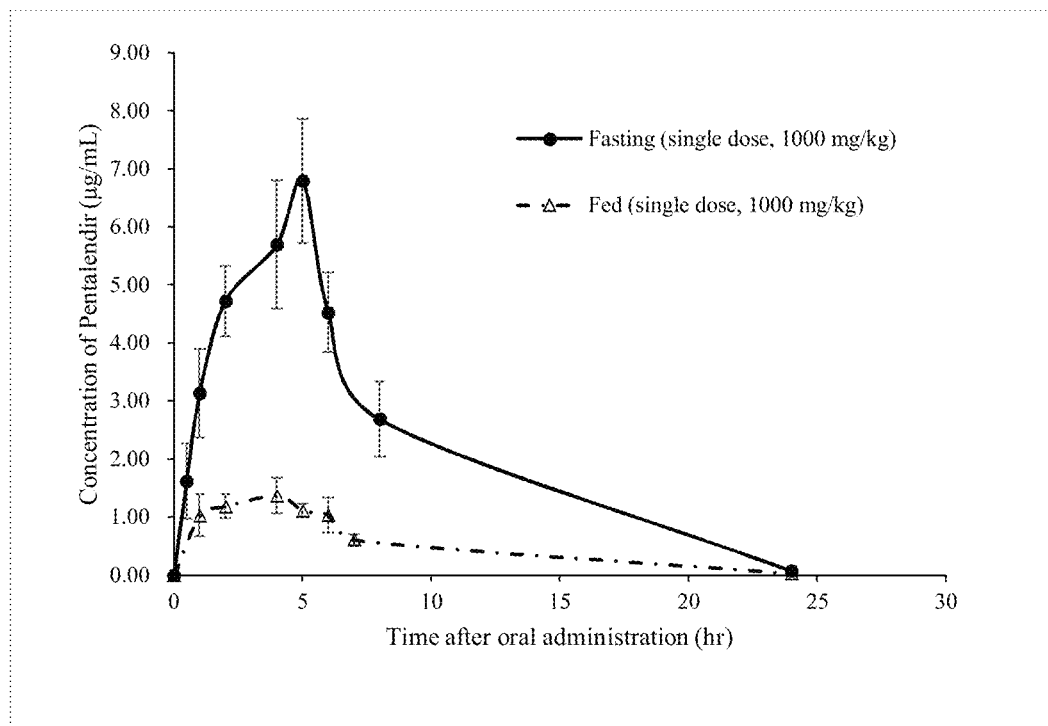
FIG. 18 shows the mean concentration-time curve of SNBOI (µg/mL) of Group 1 (●, fasting) and Group 5 (Δ, fed) after a single oral administration of SNB01 (1000 mg/kg). Data is presented as mean±SEM.

The concentration-time curve and data of single oral administration under fasting vs. fed conditions are shown in FIG. 18 and Table 24. Fasting significantly enhanced the $C_{max}$ (7.80±2.32 vs. 1.54±0.60 μg/mL, p<0.01) and $AUC_{0-t}$ (44.33±16.29 vs. 8.23±3.27 μg*hr/mL, p<0.01).

Pharmacokinetic Parameters

Lamda z calculation method of SNB01 was in Table 25. The key pharmacokinetic (PK) parameters of SNB01 for Group 1 (single dose, 1000 mg/kg, fasting), Group 2 (single dose, 750 mg/kg, fasting), Group 3 (single dose, 350 mg/kg, fasting), Group 4 (14-day repeated dose, 1000 mg/kg, fasting), and Group 5 (single dose, 1000 mg/kg, fed) are presented in Table 26.

In summary, the results demonstrated that after single oral administration at dose 350, 750 and 1000 mg/kg, the exposure of tannic acid increased in proportion to the doses of SNB01. In addition, administration for 14 days did not increase the pharmacokinetic parameters as compared to the single dose administration. Furthermore, the $C_{max}$ and AUC values of SNB01 under fasting were about 5 times of those under fed conditions.

CONCLUSION

In conclusion, SNB01 reaches the $C_{max}$ within 1-6 hrs following the oral administration. Plasma half-life of SNB01 is 1.00-7.78 hours and it is almost completely eliminated in 24 hours after a single oral administration. In addition, oral administration of SNB01 generates a linear (proportional) increase of plasma concentrations and AUC exposures with respect to the dose amount.

Mild COVID-19 is an illness, which lasts for one to two weeks. In this study, there is no significant accumulation of SNB01 after 14-day administration, which supports its safety for the duration. The pharmacokinetic findings in this study were extrapolated to humans for the oral route administration every 8 hours to keep a sustained level of SNB01 in the system for treating COVID-19. The capsule formation would allow quick release of SNB01.

In addition, SNB01 is well absorbed under fasting. Clinical administration of SNB01 will be with empty stomach postprandially.

TABLE 19

Standard Curve for SNB01 in Rat Plasma

| Run number | Nominal Concentration (μg/mL) | | | | | Slope | intercept | r |
| --- | --- | --- | --- | --- | --- | --- | --- | --- |
| | 20 | 10 | 5 | 2.5 | 1.25 | | | |
| | Back-calculated Concentration (μg/mL) | | | | | | | |
| 1 | 21.06 | 10.02 | 5.83 | 2.77 | 1.32 | 0.0118 | 0.0039 | 0.9978 |
| 2 | 20.67 | 10.04 | 5.15 | 2.24 | 1.14 | 0.0119 | −0.0006 | 0.9997 |
| 3 | 18.57 | 9.60 | 4.88 | 2.38 | 1.06 | 0.0106 | 0.0031 | 0.9994 |
| Mean | 20.10 | 9.88 | 5.29 | 2.47 | 1.17 | 0.0114 | 0.0021 | 0.9990 |
| SD | 1.34 | 0.25 | 0.49 | 0.28 | 0.13 | 0.0007 | 0.0024 | 0.0010 |
| CV (%) | 6.67 | 2.52 | 9.29 | 11.21 | 11.25 | | | |
| RE (%) | 0.49 | −1.16 | 5.75 | −1.35 | −6.22 | | | |
| | Nominal Concentration (μg/mL) | | | | | | | |
| | 1.250 | 0.615 | 0.113 | 0.116 | 0.078 | | | |
| Run number | Back-calculated Concentration (μg/mL) | | | | | Slope | intercept | r |
| 1 | 1.41 | 0.66 | 0.33 | 0.17 | 0.09 | 0.0127 | 0.001 | 0.9987 |
| 2 | 1.23 | 0.51 | 0.31 | 0.18 | 0.07 | 0.0109 | 0.0012 | 0.9947 |
| 3 | 1.15 | 0.58 | 0.32 | 0.17 | 0.09 | 0.0102 | 0.00015 | 0.9995 |
| Mean | 1.26 | 0.60 | 0.32 | 0.17 | 0.08 | 0.0113 | 0.0008 | 0.9976 |
| SD | 0.13 | 0.06 | 0.01 | 0.01 | 0.01 | 0.0013 | 0.0006 | 0.0025 |
| CV(%) | 10.54 | 10.09 | 3.34 | 3.05 | 10.21 | | | |
| RE (%) | 0.98 | −4.64 | 1.44 | 10.93 | 7.01 | | | |

TABLE 20

SNB01 Concentration in Rat Plasma of Group 1 Animals (1000 mg/kg, Single Dose, Fasting)

Group 1 (1000 mg/kg, single dose, fasting)

| Sample No. Time (hr) | Rat#1 | Rat#2 | Rat#3 | Rat#4 | Rat#5 | Rat#6 | Rat#7 |
| --- | --- | --- | --- | --- | --- | --- | --- |
| | SNB01 Content (ug/mL) | | | | | | |
| 0 | 0 | 0 | 0 | 0 | 0 | 0 | 0 |
| 0.5 | 0* | 0* | 2.33 | 0.26 | 1.66 | 4.70 | 2.36 |
| 1 | 2.09 | 6.54 | 2.61 | 0.48 | 1.72 | 4.42 | 4.02 |
| 2 | 5.11 | 7.64 | 3.78 | 3.76 | 3.02 | 5.87 | 3.85 |
| 4 | 8.80 | 10.40 | 5.05 | 4.93 | 5.30 | 2.53 | 2.85 |
| 6.94 | 6.93 | 9.07 | 8.23 | 7.02 | 10.15 | 3.92 | 2.22 |
| 6 | 4.50 | 7.82 | 4.32 | 4.61 | 4.90 | 3.91 | 1.63 |
| 8 | 2.66 | 5.29 | 1.42 | 1.75 | 1.25 | 4.91 | 1.50 |
| 24 | 0* | 0* | 0* | 0* | 0.15 | 0.22 | 0.10 |

*The calculated concentration is below LOQ (0.078 μg/mL).

TABLE 21

SNB01 Concentration in Rat Plasma of Group 2 Animals (750 mg/kg, Single Dose, Fasting)

Group 2 (750 mg/kg, single dose fasting)

| Sample No. Time (hr) | Rat#8 | Rat#9 | Rat#10 | Rat#11 | Rat#12 |
| --- | --- | --- | --- | --- | --- |
| | SNB01 Content (μg/mL) | | | | |
| 0 | 0 | 0 | 0 | 0 | 0 |
| 0.5 | 0.35 | 1.47 | 2.18 | 1.11 | 1.01 |

TABLE 21-continued

SNB01 Concentration in Rat Plasma of Group 2 Animals (750 mg/kg, Single Dose, Fasting)

Group 2 (750 mg/kg, single dose fasting)

| Sample No. Time (hr) | Rat#8 | Rat#9 | Rat#10 | Rat#11 | Rat#12 |
|---|---|---|---|---|---|
| | | | SNB01 Content (µg/mL) | | |
| 1 | 1.17 | 1.74 | 3.11 | 5.01 | 1.40 |
| 1 | 1.25 | 1.17 | 2.10 | 4.20 | 2.20 |
| 4 | 2.28 | 0.97 | 1.26 | 4.02 | 2.99 |
| 5 | 1.63 | 0.57 | 0.94 | 2.37 | 4.41 |
| 6 | 1.26 | 0.53 | 0.72 | N/A | 1.69 |
| 8 | 1.04 | 0.50 | 0.52 | 2.08 | 0.81 |
| 24 | 0.50 | 0* | 0.02 | 0.55 | 0.15 |

*The calculated concentration is below LOQ (0.078 µg/mL).

TABLE 22

SNB01 Concentration in Rat Plasma of Group 3 Animals (350 mg/kg, Single Dose, Fasting)

Group 3 (350 mg/kg, single dose, fasting)

| Sample No. Time (hr) | Rat#13 | Rat#14 | Rat#15 | Rat#16 | Rat#17 | Rat#18 |
|---|---|---|---|---|---|---|
| | | | SNB01 Content (µg/mL) | | | |
| 0 | 0 | 0 | 0 | 0 | 0 | 0 |
| 0.5 | 0.81 | 0.31 | 0.70 | 0.25 | 0.31 | 0.17 |
| 1 | 0.38 | 0.00 | 0.88 | 0.10 | 0.69 | 0.27 |
| 2 | 0.72 | 0.89 | 0.58 | 0.35 | 0.89 | 0.39 |
| 4 | 0.47 | 0.84 | 1.04 | 0.53 | 0.88 | 0.49 |
| 5 | 1.10 | 0.30 | 1.09 | 0.29 | 0.94 | 0.41 |
| 6 | 0.80 | 0.74 | 1.76 | 0.22 | 0.78 | 0.30 |
| 8 | 0* | 0* | 0* | 0* | 0* | 0* |
| 24 | 0* | 0* | 0* | 0* | 0* | 0* |

*The calculated concentration is below LOQ (0.078 µg/mL).

TABLE 23

SNB01 Concentration in Plasma of Group 4 Animals (1000 mg/kg, 14-Day Repeated Dose, Fasting)

Group 4 (1000 mg/kg, 14-day repeated dose, fasting)

| Sample No. Time (hr) | Rat#19 | Rat#20 | Rat#21 | Rat#22 | Rat#23 | Rat#24 |
|---|---|---|---|---|---|---|
| | | | SNB01 Content (µg/mL) | | | |
| 0 | 0.80 | 1.80 | 0.25 | 0.37 | 1.13 | 1,03 |
| 1 | 3.09 | 0.99 | 1.30 | 2.61 | 3.91 | 4.47 |
| 3 | 2.80 | 2.84 | 1.92 | 3.99 | 9.04 | 4.62 |
| 4 | 3.52 | 4.92 | 2.70 | 4.11 | 11.49 | 3.03 |
| 5 | 3.52 | 2.42 | 4.83 | 3.48 | 9.10 | 2.85 |
| 6 | 3.23 | 5.41 | 2.14 | 3.39 | 3.07 | 7.58 |
| 7 | 2.01 | 4.40 | 1.91 | 2.57 | 2.33 | 5.65 |
| 24 | 0.37 | 0.68 | 0.29 | 0.40 | 0.76 | 0.59 |

TABLE 24

SNB01 Concentration in Plasma of Group 5 Animals (1000 mg/kg, Single Dose, Fed)

Group 5 (1000 mg/kg, single dose, fed)

| Sample No. Time (hr) | Rat#25 | Rat#26 | Rat#27 | Rat#28 | Rat#29 |
|---|---|---|---|---|---|
| | | | SNB01 Content (µg/mL) | | |
| 0 | 0 | 0 | 0 | 0 | 0 |
| 1 | 0.68 | 2.44 | 0.90 | 0.35 | 0.78 |
| 2 | 1.06 | 1.92 | 1.33 | 0.76 | 0.84 |
| 4 | 1.85 | N/A | N/A | N/A | 0.89 |
| 5 | 1.29 | 1.42 | 0.76 | 1.01 | 1.07 |
| 6 | 1.34 | 2.06 | 0.67 | 0.37 | 0.72 |
| 7 | 0.95 | 0.58 | 0.56 | 0.35 | 0.58 |
| 24 | 0* | 0* | 0* | 0* | 0.13 |

*The calculated concentration is below LOQ (0.078 µg/mL).

TABLE 25

Lambda z Calculations for the Pharmacokinetic Study of SNB01

| Group | Res | Start Time (hr) | End time (hr) | Group | Res | Start time (hr) | End time (hr) |
|---|---|---|---|---|---|---|---|
| 1 | Rat#1 | 4 | 8 | 3 | Rat#16 | 5 | 24 |
| | Rat#2 | 4 | 8 | | Rat#17 | 6 | 24 |
| | Rat#3 | 5 | 8 | | Rat#18 | 5 | 24 |
| | Rat#4 | 5 | 8 | 4 | Rat#19 | 4 | 24 |
| | Rat#5 | 5 | 8 | | Rat#20 | 6 | 24 |
| | Rat#6 | 2 | 24 | | Rat#21 | 5 | 24 |
| | Rat#7 | 1 | 8 | | Rat#22 | 4 | 24 |
| 2 | Rat#8 | 4 | 8 | | Rat#23 | 4 | 24 |
| | Rat#9 | 2 | 6 | | Rat#24 | 6 | 24 |
| | Rat#10 | 1 | 8 | 5 | Rat#25 | 4 | 24 |
| | Rat#11 | 1 | 5 | | Rat#26 | 1 | 24 |
| | Rat#12 | 5 | 8 | | Rat#27 | 2 | 24 |
| 3 | Rat#13 | 6 | 24 | | Rat#28 | 5 | 24 |
| | Rat#14 | 4 | 24 | | Rat#29 | 5 | 24 |
| | Rat#15 | 6 | 24 | | | | |

TABLE 26

The PK Parameters of SNB01 in Each Animal Group

| Parameters | $AUC_{0-1}$ (µg*hr/mL) | $AUC_{0-\infty}$ (µg*hr/mL) | $C_{max}$ (µg/mL) | $T_{max}$ (hr) | $MRT_{0-t}$ (hr) | $T_{1/2}$ (hr) |
|---|---|---|---|---|---|---|
| Group 1 (1000 mg/kg, single dose, fasting) | | | | | | |
| Rat#1 | 38.77 | 47.29 | 8.80 | 4.00 | 4.28 | 2.26 |
| Rat#2 | 58.06 | 89.71 | 10.40 | 4.00 | 4.28 | 4.07 |
| Rat#3 | 32.50 | 34.91 | 8.23 | 5.00 | 4.17 | 1.19 |
| Rat#4 | 29.21 | 33.00 | 7.02 | 5.00 | 4.51 | 1.49 |
| Rat#5 | 44.55 | 44.55 | 10.15 | 5.00 | 5.75 | 1.00 |
| Rat#6 | 74.00 | 75.77 | 5.87 | 2.00 | 6.59 | 4.80 |
| Rat#7 | 33 21 | 33.90 | 4.02 | 1.00 | 5.58 | 4.36 |
| Mean | 44.13 | 51.30 | 7.80 | 3.71 | 5.02 | 2.74 |
| SD | 16.29 | 22.52 | 2.32 | 1.60 | 0.95 | 1.63 |
| CV (%) | 36.75 | 43.89 | 29.74 | 43.17 | 18.88 | 59.42 |
| Group 2 (750 mg/kg, single dose, fasting) | | | | | | |
| Rat#8 | 23.23 | 23.47 | 2.28 | 4.00 | 8.99 | 3.65 |
| Rat#9 | 10.12 | 10.47 | 3.17 | 2.00 | 2.83 | 1.47 |
| Rat#10 | 15.32 | 15.35 | 3.11 | 1.00 | 4.52 | 2.69 |
| Rat#11 | 44.05 | 44.47 | 5.01 | 1.00 | 7.31 | 3.79 |
| Rat#12 | 24.78 | 24.78 | 4.41 | 5.00 | 6.06 | 1.29 |
| Mean | 23.50 | 23.71 | 3.60 | 2.60 | 5.94 | 2.58 |
| SD | 12.94 | 13.01 | 1.82 | 2.39 | 2.39 | 1.17 |
| CV (%) | 55.07 | 54.89 | 30.50 | 69.87 | 40.25 | 45.55 |
| Group 3 (350 mg/kg, single dose, fasting) | | | | | | |
| Rat#13 | 4.43 | 6.94 | 1.10 | 6.00 | 4.07 | 2.18 |
| Rat#14 | 3.16 | 6.33 | 0.89 | 4.00 | 4.51 | 4.38 |

TABLE 26-continued

The PK Parameters of SNB01 in Each Animal Group

| Parameters | $AUC_{0-t}$ (μg*hr/mL) | $AUC_{0-\infty}$ (μg*hr/mL) | $C_{max}$ (μg/mL) | $T_{max}$ (hr) | $MRT_{0-t}$ (hr) | $T_{1/2}$ (hr) |
|---|---|---|---|---|---|---|
| Rat#15 | 7.90 | 11.03 | 3.09 | 6.00 | 4.65 | 1.23 |
| Rat#16 | 1.86 | 2.33 | 0.53 | 5.00 | 4.21 | 1.58 |
| Rat#17 | 4.89 | 9.07 | 0.94 | 6.00 | 4.19 | 3.71 |
| Rat#18 | 2.16 | 6.18 | 0.49 | 5.00 | 4.18 | 7.78 |
| Mean | 4.06 | 6.98 | 1.17 | 5.13 | 4.30 | 3.48 |
| SD | 2.23 | 2.95 | 0.97 | 0.82 | 0.23 | 2.44 |
| CV (%) | 54.89 | 42.23 | 82.58 | 15.31 | 5.26 | 70.11 |
| Group 4 (1000 mg/kg, 14-day repeated dose, fasting) | | | | | | |
| Rat#19 | 40.95 | 44.14 | 3.52 | 4.00 | 6.63 | 6.07 |
| Rat#20 | 66.74 | 74.20 | 5.41 | 6.00 | 7.48 | 7.33 |
| Rat#21 | 34.98 | 37.18 | 4.83 | 5.00 | 6.85 | 5.47 |
| Rat#22 | 48.35 | 51.79 | 4.11 | 4.00 | 6.63 | 6.01 |
| Rat#23 | 74.57 | 80.52 | 11.49 | 4.00 | 6.23 | 6.16 |
| Rat#24 | 82.76 | 87.02 | 7.58 | 6.00 | 6.92 | 5.03 |
| Mean | 58.06 | 62.47 | 6.16 | 4.83 | 6.79 | 6.01 |
| SD | 19.38 | 20.76 | 2.96 | 0.98 | 0.42 | 0.78 |
| CV (%) | 33.38 | 33.23 | 48.14 | 20.34 | 6.13 | 12.94 |
| Group 5 (1000 mg/kg, single dose, fed) | | | | | | |
| Rat#25 | 8.15 | 13.22 | 1.85 | 4.40 | 4.02 | 3.57 |
| Rat#26 | 11.48 | 17.68 | 2.44 | 1.00 | 3.37 | 4.40 |
| Rat#27 | 6.04 | 9.26 | 1.34 | 2.00 | 3.28 | 4.01 |
| Rat#28 | 4.07 | 4.40 | 1.01 | 5.00 | 3.58 | 0.65 |
| Rat#29 | 11.42 | 12.67 | 1.07 | 5.00 | 7.06 | 6.88 |
| Mean | 8.23 | 11.45 | 1.54 | 3.40 | 4.26 | 3.90 |
| SD | 3.27 | 4.95 | 0.60 | 1.82 | 1.59 | 2.23 |
| CV (%) | 39.75 | 43.22 | 39.09 | 53.43 | 37.28 | 57.01 |

The Pharmacokinetic Studies of SNB01-Inhalation Administration in Sprague-Dawley Rats by LC-MS Analysis The pharmacokinetics profile of inhaled SNB01 was also assessed. A single dose (26.32 mg/kg) of SNB01 was inhaled-administrated to male 10-week-old Sprague-Dawley (SD) rats by a nebulizer (BlueEchoCare, N.Y., USA). SNB01 was successful detected in the circulation system within 24 hours after treatment. This result indicates that inhalation route is a feasible delivery approach for SNB01.

Example 13. Pharmacokinetic Study of SNB01 in the Pulmonary Tissue of Sprague-Dawley Rats by LC-MS/MS Analysis The objective of this study is to evaluate and determine the pharmacokinetic parameters of SNB01 in the pulmonary tissue of Sprague-Dawley rats after either a single or 14-day repeated oral administration.

The test article and control article, as well as formulations thereof are as disclosed in Example 12 above. Study animals, their housing condition, and quarantine/acclimation are also as provided in Example 12 above. Specific pathogens, frequency and methods of examination are provided in Table 15 above.

Experimental Design
Randomization and Group Assignment

Animals were randomized into study groups before first-dosing. After randomization, rats were assigned to one of six groups as shown in the table below:

| Group | Test Article | Dose Level (mg/kg) | Conc. (mg/mL) | Tissue Collection Time | Number | Animal ID |
|---|---|---|---|---|---|---|
| 1 Fasting- | SNB01 | 1000 | 200 | 4 hrs | 7 | #1~7 |
| 2 single | | | | 7 hrs | 7 | #8~14 |
| 3 oral dose | | | | 24 hrs | 7 | #15~21 |
| 4 Fasting- | | | | 4 hrs | 9 | #22~30 |
| 5 14-day | | | | 7 hrs | 9 | #30~38 |
| 6 repeated oral dose | | | | 24 hrs | 9 | #39~48 |

Dosing Procedure
  Dosing route: Oral gavage
  Dose frequency and duration: Single and 14-day repeated administration
  Dose: 1000 mg/kg
  Dosing volume: 10 mL/kg
  Dosing method: Administer the dose by a sterile disposable syringe with a 16-gauge ball-tipped stainless steel tube for oral gavage. The dosing volume was calculated based upon the body weight most recently measured and rounded to 2 decimal places. The division value is 0.02 mL for a 1 mL one-time-use sterile syringe, therefore, when the dosing volume was between two division value lines, the dosing volume was the larger one.
  Justification for route of administration: The oral route of administration was selected for test article because it would be the intended clinical route of administration for the convenience of patients with COVID-19.
  Justification for dosage of administration: The dosage for this PK experiments was determined based on our previous research data. The results indicated that 2000 mg/kg of SNB01 is well tolerated in mice. Based on the conversion by body surface area, the equivalent dose for SNB01 in rat would be 1000 mg/kg. Furthermore, 1000 mg/kg was chosen because tannic acid has lower absorption rate in rat (*J. Agric. Food Chem.* 2003, 51, 331-339).
  Groups 4-6 received 14 days repeated administration to explore the pharmacokinetic effects in long-term administration.

Fasting Requirement
  Rats were allocated into 6 groups, animals in the first to third groups were fasted overnight, animals in the fourth to sixth group were fasted 3 hrs every day before the administration of the test article during the experimental period. This arrangement is due to the finding that gastrointestinal feed greatly affects absorption of SNB01 (see example 11).

Collection and Processing of the Lung Samples
  Lung samples were collected from the animals at 4, 7, and 24 hrs after the dosing. The pulmonary tissues were frozen rapidly in liquid nitrogen and stored at −80° C. until analysis.

Animal Welfare
  Procedures used in this study were approved by the Institutional Animal Care and Use Committee (IACUC) at SyneuRx International (Taiwan) Corp. IACUC number of the study: SR109002.

Analysis of the Lung Samples by LC-MS/MS
Internal Standard (IS)
  Name: 4-hydroxybenzoic acid
  Manufacture: ACROS, USA
  Purity: >99%
  Storage condition: Stored in a cool place. Kept the container tightly closed in a dry and well-ventilated place.

Instruments and Apparatus
  Mass spectrometer: AB SCIEX 3200 QTRAP LC-MS/MS System, USA
  Pump: Agilent 1260 LC Quaternary Pump, US Mass spectrometer detector: AB SCIEX 3200 QTRAP, USA
Automatic sampler: Agilent 1260 Infinity autosampler, US
Column oven: Agilent 1100 Column Oven, US
Column: Kinetex® C8, 5 μm, 100*4.6 mm, Phenomenex, US
Handheld tissue homogenizer: BT Lab Systems, USA Solution Preparation
1. Preparation of Mobile Phase
   Mobile phase A: Accurately transferred 1 mL of formic acid into a container with 1 L of water and mixed well.
   Mobile phase B: Accurately transferred 200 mL of MeOH into a container with 800 mL of ACN and mixed well.
2. Preparation of Enzyme Reaction Solution
   Acetate buffer (0.02 M): Prepared 0.02 M acetic acid and 0.02 M sodium acetate aqueous solutions. Mixed them together to adjust the pH to 4.7.
   Tannase reaction solution (2.5 mg/mL): Accurately weighed 75 mg of tannase into centrifuge tubes to which 30 mL of 0.02 M acetic acid buffer was added. Mixed well by vortex.
3. Preparation of Internal Standard Stock Solution
   Internal standard solution (4 μg/mL): Accurately weighed 4 mg of internal standard into a tube containing 10 mL of deionized water (ddH$_2$O) and mixed well to obtained IS stock solution (400 μg/mL). Accurately transferred 1 mL of IS stock solution into a container with 99 mL of ddH$_2$O and mixed well.
4. Preparation of Extraction Reagent
   Extraction reagent: ACN solution containing 1.5% (w/w) formic acid
5. Preparation of the Standard Curve for SNB01 in Lung Tissue
   Preparation of the Samples for SNB01's Standard Curve:
   Thirty mg of SNB01 and about 2/3 volume of diluent were added into a 200 mL volumetric flask and vortexed until well-mixed. Then, appropriate amount of diluent was added to the flask to achieve the final desired volume. The same was mixed well to obtain SNB01 stock solution (TA-B-5-1) with the concentration of 150 μg/mL to prepare for the solutions for standard curve with a serial 1:2 dilution by ddH$_2$O according to Table 27 below:

TABLE 27

TA Samples Tested

| Solution | Volume of ddH$_2$O (μL) | Final volume (μL) | SNB01 concentration (μg/mL) |
|---|---|---|---|
| TA-B-5-1 | — | 400 | 150.0 |
| TA-B-4-1 | 200 | 400 | 75.0 |
| TA-B-3-1 | 200 | 400 | 37.5 |
| TA-B-2-1 | 200 | 400 | 18.75 |
| TA-B-1-1 | 200 | 400 | 9.375 |
| Blank-1 | 400 | 400 | — |

Enzyme Hydrolysis:
The solutions (TA-B-1-1~TA-B-5-1) were used to prepare for the samples of standard curve to analyze the pulmonary tissue according to the scheme shown in Table 28 below. Each tissue sample (50 mg) was homogenized with 100 μL of homogenization media (0.02 M acetate buffer) using a handheld tissue homogenizer. The homogenate was mixed well with 300 μL of tannase (15 mg/mL) and incubated at 30° C. for 4 hours to complete the hydrolysis. The hydrolysate was extracted with 2000 μL of extraction reagent (1.5% (w/w) formic acid in ACN) and centrifuged at 15,000×g for 10 min at 2-8° C.

TABLE 28

Examination Scheme for Analyzing TA Samples in Pulmonary Tissues

| Sample name | Volume of internal standard (μL) | Volume of homogenization media (μL) | Tannase reaction solution (μL) | Extraction reagent (μL) | Final volume (μL) |
|---|---|---|---|---|---|
| TA-B-5 | 50 | 100 | 300 | 2250 | 2750 |
| TA-B-4 | 50 | 100 | 300 | 2250 | 2750 |
| TA-B-3 | 50 | 100 | 300 | 2250 | 2750 |
| TA-B-2 | 50 | 100 | 300 | 2250 | 2750 |
| TA-B-1 | 50 | 100 | 300 | 2250 | 2750 |
| Blank | 50 | 100 | 300 | 2250 | 2750 |

The supernatant was collected and evaporated to dryness under N$_2$. The dried extract was re-constituted in 300 μL of mobile phase A and filtered through a 0.22 μm membrane filter. The final concentrations of the SNB01 of the standard curve for the pulmonary samples were shown in Table 29 below.

TABLE 29

Final Concentrations of SNB01 for Standard Curve Determination

| Sample name | Reconstituted solution volume (μL) | SNB01 concentration (μg/mL) |
|---|---|---|
| TA-B-5 | 300 | 25 |
| TA-B-4 | 300 | 12.5 |
| TA-B-3 | 300 | 6.25 |
| TA-B-2 | 300 | 3.125 |
| TA-B-1 | 300 | 1.5625 |
| Blank | 300 | — |

Extraction Procedure of the Lung Samples
The frozen lung tissues were completely thawed at room temperature. Each sample was accurately weighed and transferred into 15 mL tubes. One set of samples was used to determine free gallic acid in the lung tissue; the other was used to determine the total gallic acid content in the same lung tissue. The experimental procedures were shown as the following.

Determination of the Free Gallic Acid in the Rat Lung:
Free gallic acid in the lung was analyzed without enzymatic hydrolysis. Each lung sample was mixed with 50 μL of IS (4 μg/mL) and homogenized with 4 mL of homogenization media (0.02 M acetate buffer) using a handheld tissue homogenizer. Each sample was extracted with 60 mL of extraction reagent (1.5% (w/w) formic acid in ACN), and centrifuged at 15,000×g for 10 min at 2-8° C. The supernatants were collected, mixed well and evaporated to dryness under N$_2$. The dried extract from the lung samples containing free gallic acid was re-constituted with 300 μL of mobile phase A and filtered through a 0.22 μm membrane filter. The samples were stored at −20° C. prior to LC-MS/MS analysis.

Determination of the Total Gallic Acid in the Rat Lung:
Total tannic acid content in rat lung was analyzed after the completion of the enzymatic hydrolysis. Each lung sample was mixed with 50 μL of IS (4 μg/mL) and homogenized with 4 mL of homogenization media (0.02 M acetate buffer)

using a handheld tissue homogenizer. Immediately thereafter, the homogenate was mixed well with 8 mL of tannase solution (2.5 mg/mL). The mixtures were incubated at 30° C. for 4 hours to complete the hydrolysis. Then, the hydrolysates were extracted with 60 mL of extraction reagent (1.5% (w/w) formic acid in ACN), and centrifuged at 15,000×g for 10 min at 2-8° C. The supernatants were collected, mixed and evaporated to dryness under $N_2$. The dried extract containing total gallic acid was re-constituted with 300 μL of the mobile phase A and filtered through a 0.22 μm membrane filter. The samples were stored at −20° C. prior to LC-MS/MS analysis.

Parameters of the Instruments
LC-MS/MS Parameters:
  Flow rate: 0.15 mL/min
  Column temperature: 30° C.
  Autosampler temperature: 4° C.
  Run time: 9 min
  Injection volume: 20 μL
  Mobile phase gradient elution:

| Time (min) | % M.P. A | % M.P. B |
|---|---|---|
| 0 | 95 | 5 |
| 4.0 | 50 | 50 |
| 4.1 | 0 | 100 |
| 6.0 | 0 | 100 |
| 7.0 | 95 | 5 |
| 9.0 | 95 | 5 |

LC-MS/MS Conditions:
AB SCIEX 3200 QTRAP with ESI ion source was used in a negative ion mode with multiple reaction monitoring.

Ion Source Parameters:

| Ion Source | Curtain Gas Flow (L/min) | Ion Source Gas 1 (L/min) | Ion Source Gas 2 (L/min) | Ion Spray Voltage | Temperature (° C.) |
|---|---|---|---|---|---|
| Turbo Spray | 10 | 50 | 50 | −4500 | 500 |

Compound Related Parameters:

| Compound | Precursor m/z | Product m/z | Dwell Time (ms) | DP (v) | EP (v) | CE (v) | CXP (v) |
|---|---|---|---|---|---|---|---|
| Gallic acid | 168.9 | 125.2 | 200.0 | −53.0 | −10 | −20 | −1 |
| IS | 137.0 | 93.2 | 200.0 | −16.0 | −10 | −24.5 | −1 |

Figure 19:
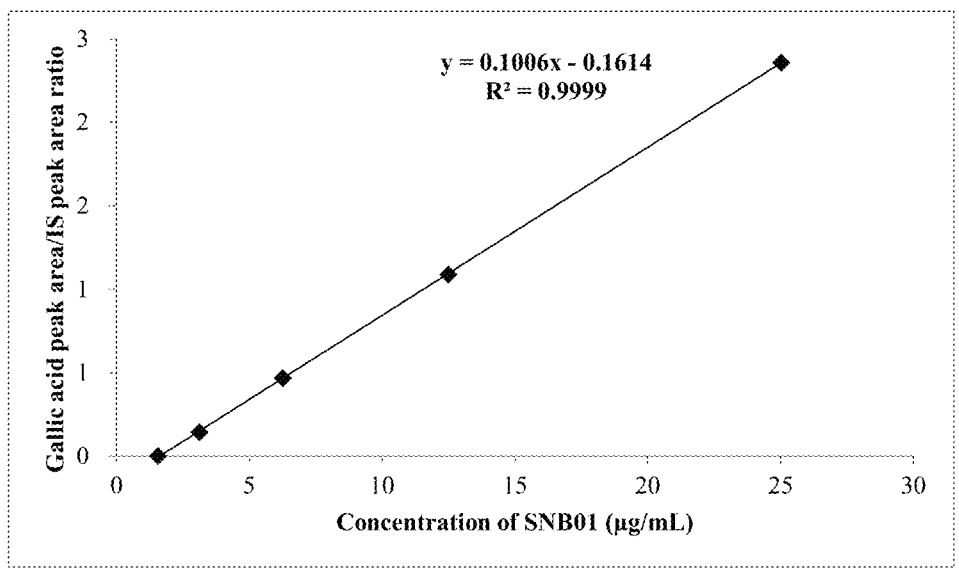
FIG. 19 shows a standard curve for SNB01 in the rodent lung. Linear regression of the peak area ratios versus concentrations is fitted over the concentration range of 1.56 to 25 µg/mL for SNB01 in the rodent lung.

Standard curve calculation
Response: Gallic acid peak area/IS peak area ratio
Equation: y=bx+a
Results
Data of the Standard Curve
The standard curve of SNB01 in the lung tissue was demonstrated to be linear in the range of 1.5625 to 25 μg/mL (FIG. 19 and Table 30). The relative error (% RE) values of the back-calculated concentrations of standards are from −2.63% to 6.78%. The correlation coefficients (R) were greater than 0.99.

Data of the Lung Concentration-Time
The concentration-time data of SNB01 by single vs. 14-day repeated oral administration in the lung tissue are shown in Table 31. The results demonstrated that:

1) SNB01 can reach similar high level in the lung tissue as in the plasma (see example 11). The concentration of SNB01 in the lung tissue reached the highest level at 4-7 hrs after either the single or 14-day repeated oral administration (1.06±1.03, 0.90±0.68 μg/gram respectively).

2) At 4- and 24-hr after oral administration, the 14-day repeated treatment gave rise to higher, but not statistically significant, level of SNB01 in the lung.

3) However, after 14-day repeated oral administration, SNB01 did not significantly accumulate in the lung.

CONCLUSION

SNB01 is well absorbed orally and distributed into the rodent lung tissue with high level after oral administration. There is no significant accumulation of SNB01 after 14-day administration, which supports its safety for the duration of treatment.

The findings support that the oral route of administration of SNB01. SNB01 can reach the pulmonary tissue well, which is an essential requirement for any clinical therapeutic to treat the respiratory infection of SARS-CoV-2 that can give rise to grave outcome.

TABLE 30

Standard Curve for SNB01 in the Rodent Lung

| Nominal Concentration (μg/mL) | | | | | | | |
|---|---|---|---|---|---|---|---|
| 25.000 | 12.5 | 6.25 | 3.125 | 1.5625 | | Intercept | |
| Back-calculated Concentration (μg/mL) | | | | | Slope | | r |
| 25.050 | 12.421 | 6.273 | 3.043 | 1.668 | 0.1006 | −0.1614 | 0.9999 |
| RE (%) | | | | | | | |
| 0.200 | −0.633 | 0.364 | −2.631 | 6.779 | | | |

TABLE 31

The Concentration of SNB01 versus Time by Single (Groups 1 to 3) vs. 14-Day Repeated (Groups 4 to 6) Oral Administration in the Rodent Lung

| Group | | Collect) on time (hour) | SNB01 content in rat lung (μg/g) | | | | | | | | | Average | SD |
|---|---|---|---|---|---|---|---|---|---|---|---|---|---|
| | | | Rat-1 | Rat-2 | Rat-3 | Rat-4 | Rat-5 | Rat-6 | Rat-7 | Rat-8 | Rat-9 | | |
| 1 | Single | 4 | 1.51 | 0.47 | 0.97 | 0.36 | 0.40 | 0.68 | 0.53 | N/A | N/A | 0.70 | 0.41 |
| 2 | dose | 7 | 3.34 | 0.76 | 1.07 | 0.74 | 0.58 | 0.54 | 0.38 | N/A | N/A | 1.06 | 1.03 |
| 3 | | 24 | 0.67 | 0.87 | 0.47 | 0.53 | 0.44 | 0.58 | 0.43 | N/A | N/A | 0.57 | 0.16 |
| 4 | 14- | 4 | 0.85 | 4.37 | 4.08 | 0.50 | 0.90 | 0.74 | 0.52 | 0.55 | 1.64 | 1.57 | 1.55 |
| 5 | day | 7 | 1.11 | 0.69 | 0.49 | 0.77 | 0.43 | 0.68 | 0.66 | 2.63 | 0.61 | 0.90 | 0.68 |

TABLE 31-continued

The Concentration of SNB01 versus Time by Single (Groups 1 to 3) vs. 14-Day Repeated (Groups 4 to 6) Oral Administration in the Rodent Lung

| Group | | Collect) on time (hour) | SNB01 content in rat lung (μg/g) | | | | | | | | | |
|---|---|---|---|---|---|---|---|---|---|---|---|---|
| | | | Rat-1 | Rat-2 | Rat-3 | Rat-4 | Rat-5 | Rat-6 | Rat-7 | Rat-8 | Rat-9 | Average | SD |
| 6 | repeated dose | 24 | 0.49 | 0.71 | 0.59 | 0.42 | 0.35 | 0.64 | 1.30 | 0.66 | 3.89 | 1.01 | 1.12 |

Example 14. Molecular Modelling of Binding of SNB01 to the 3CL Protease of SARS-CoV-2

SARS-CoV-2 or 2019-nCoV has caused the most rampant pandemic worldwide in the centennial during the last half year. Its Severe Acute Respiratory (SARI) symptoms, including fever, asthenia, dyspnea and pneumonia can bring forth catastrophic morbidity and mortality in the infected population, particularly in elder population and in patients with existing conditions.

Like other coronaviruses, the SARS-CoV-2 virus requires self-cleavage by the main protease ($M^{pro}$), a protease of ~306 amino acids. It is a critical enzyme for viral replication. The $M^{pro}$ has similar cleavage site to that of picornavirus 3C protease ($3C^{pro}$). Thus, the $M^{pro}$ of SARS-CoV-2 is also known as 3C-like protease (3CLPro). With the conserved molecular features and pathologic significance, 3CLPro is an attractive target to develop therapeutics.

SNB01 was found herein to potently inhibit 3CLPro in vitro and viral production in Vero E6 cells. To further understand the molecular underpinning of its inhibition, the complex crystal 6LU7 disclosed in Jin et al., 2020 was used, in association with a computational method, to investigate the conformation and ligand-enzyme interaction with several confirmed components of SNB01.

Computational Method
Software
UCSF Dock 6 for complex simulation
Avogadro Ver. 1.2 for conformation minimization
UCSF Chimera Ver. 1.12 for results viewing and editing.
Materials The 3CLPro enzyme was modified by the complex 6LU7, a crystal structure of 3CLPro in complex with an inhibitor, N3). The inhibitor N3 and water was removed from 6LU7 to get naked 3CLPro enzyme for docking using the software, UCSF Chimera. The docking molecules were the components that had been confirmed and isolated from SNB01, including the main component, (2S,3R,4S,5R,6R)-3,4,5-tris (3,4-dihydroxy-5-(3,4,5-tri hydroxybenzoyloxy)benzoyloxy)-6-((3,4-dihydroxy-5-(3,4,5-trihydroxy benzoyloxy) benzoyloxy)methyl)oxan-2-yl 3,4-dihydroxy-5-(3,4,5-tri-hydr oxybenzoyl oxy)benzoate, abbreviated as β-10G (Tsai et al., 2017) (Nishizawa et al., 1982). Four other analogues of tannic acid were also studied (Table 22).

The stereo conformation was minimized by Avogadro using MMFF94 force field etc. on the default setting.

Method

The inhibitor N3's docking site was chosen, and the grid generation followed the Rizzo Lab tutorial (2018 DOCK tutorial 1 with PDBID 2NNQ) with its default setting.
Results The findings of the molecular docking of the 3CLPro with the inhibitors, tannic acid analogues in SNB01, were shown by the most stable conformation with the grid score based upon Van der Waals energy and electrostatic energy as well as the hydrogen bonds in Table 23.

The indicated amino acid residues, $His^{41}$, $Asn^{142}$, $Ser^{144}$, $Cys^{145}$, $His^{163}$, $Glu^{166}$, and $Pro^{168}$, formed multiple hydrogen bonds to those inhibitors with length of 2.0-2.6 Å (Table 23). The simulation results from Table 23 showed that all these 3CLPro inhibitors of tannic acid analogues could form 4 to 5 hydrogen bonds with the 3CLPro of SARS-CoV-2. In addition, all the inhibitors could properly fit the cleavage site to geometrically prohibit other plausible substrates.

Among the residues that formed hydrogen bonds, $Cys^{145}$ and $His^{41}$ are critical for the proteolytic process of the 3CLPro (Pillaiyar et al., 2016). The inhibitors docked with the 3CLPro of SARS-CoV-2 were found to form at least one hydrogen bond with $Cys^{145}$ and/or $His^{41}$, which could evidently prohibit the proteolytic process of the plausible substrates of 3CLPro in our molecular simulation. These findings support the potent inhibitory activity of SNB01 on both in vitro protease assay and in vivo virucidal assay in Vero E6 cells (see Example 5 and Example 7)

CONCLUSION

The results from this molecular simulation assay demonstrate a plausible mechanism of active site inhibition of the 3CLPro of SARS-CoV-2 by SNB01, which can be accounted for by the formation of at least one hydrogen bond with the critical cleavage amino acid residues of $Cys^{145}$ and/or $His^{41}$. Taken together with our other studies of the mechanism of action, such as the virucidal study in Vero E6 cells, the protease assay, the native-PAGE (polyacrylamide gel electrophoresis) analysis, and the ITC (isothermal titration calorimetry) study (see example 7, example 8, example 9), those amino acid residues, which formed multiple hydrogen bonds, likely play a significant role in regulating of the activity of the 3CLPro of SARS-CoV-2.

In summary, the findings reported herein support the hypothesis that SNB01 is a potent 3CLPro inhibitor that can help curtail the morbidity and mortality of the pandemic of SARS-CoV-2.

TABLE 32

The Chemical Structures of the Analogues of Tannic Acid

| Compound name (IUPAC; Abbr.) | Chemical structure |
|---|---|
| (2S,3R,4S,5R,6R)-3,4,5-tris(3,4-dihydroxy-5-(3,4,5-trihydroxybenzoyloxy)benzoyloxy)-6-((3,4-dihydroxy-5-(3,4,5-trihydroxybenzoyloxy)benzoyloxy)methyl)oxan-2-yl 3,4-dihydroxy-5-(3,4,5-trihydroxybenzoyloxy)benzoate; β-10G | 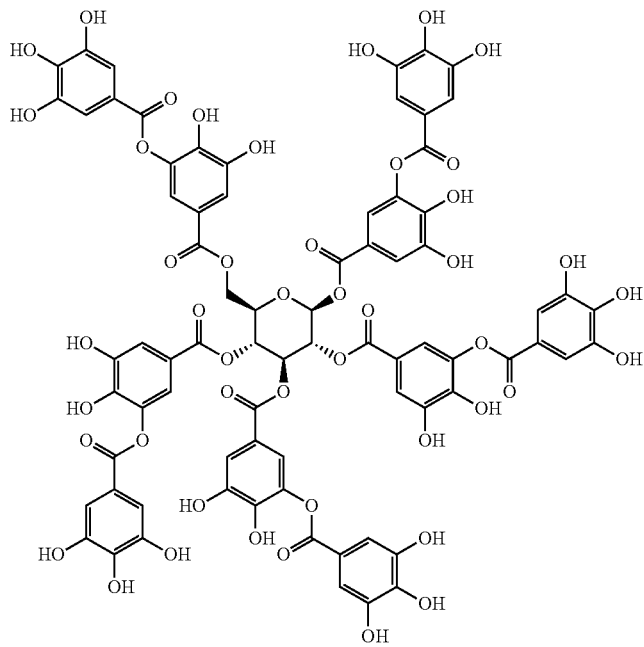 [SMILES: O=C(OC[C@H]1O[C@@H](OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1] |
| (2S,3R,4S,5R,6R)-3,4,5-tris(3,4,5-trihydroxybenzoyloxy)-6-((3,4,5-trihydroxybenzoyloxy)methyl)oxan-2-yl 3,4,5-trihydroxybenzoate; β-5G | 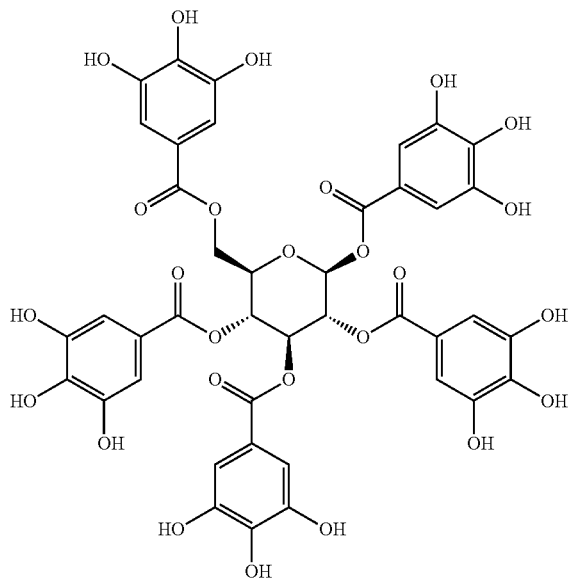 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1] |

TABLE 32-continued

The Chemical Structures of the Analogues of Tannic Acid

| Compound name (IUPAC; Abbr.) | Chemical structure |
|---|---|
| (2S,3R,4S,5R,6R)-4-(3,4-dihydroxy-5-(3,4,5-trihydroxybenzoyloxy)benzoyloxy)-5-hydroxy-3-(3,4,5-trihydroxybenzoyloxy)-6-((3,4,5-trihydroxybenzoyloxy)methyl)oxan-2-yl 3,4,5-trihydroxybenzoate; β-5G_m | 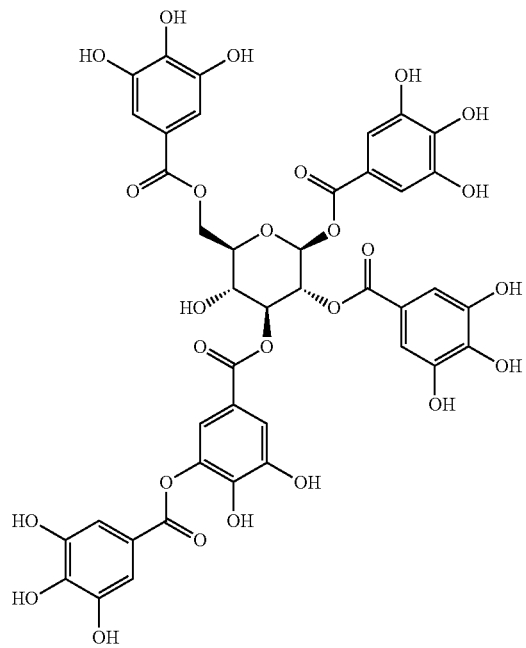 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(OC(=O)c3cc(O)c(O)c(O)c3)c2)[C@@H]1O)c1cc(O)c(O)c(O)c1] |
| (2S,3R,4S,5R,6R)-4-(3,5-dihydroxy-4-(3,4,5-trihydroxybenzoyloxy)benzoyloxy)-5-hydroxy-3-(3,4,5-trihydroxybenzoyloxy)-6-((3,4,5-trihydroxybenzoyloxy)methyl)oxan-2-yl 3,4,5-trihydroxybenzoate; β-5G_p | 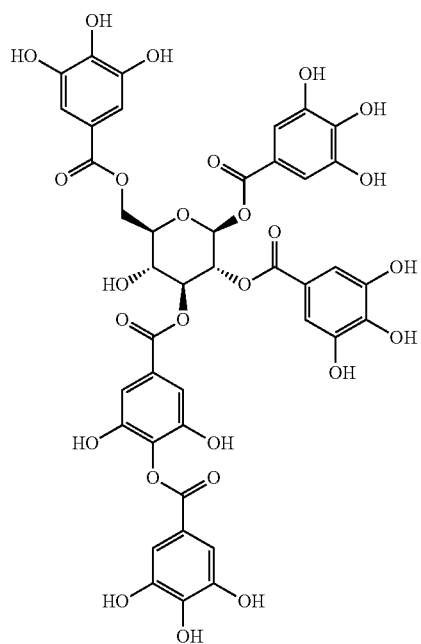 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(OC(=O)c3cc(O)c(O)c(O)c3)c(O)c2)[C@@H]1O)c1cc(O)c(O)c(O)c1] |

TABLE 32-continued

The Chemical Structures of the Analogues of Tannic Acid

| Compound name (IUPAC; Abbr.) | Chemical structure |
|---|---|
| (2S,3R,4S,5R,6R)-4-(3,5-dihydroxy-4-(3,4,5-trihydroxybenzoyloxy)benzoyloxy)-3,5-bis(3,4,5-trihydroxybenzoyloxy)-6-((3,4,5-trihydroxybenzoyloxy)methyl)oxan-2-yl 3,4,5-trihydroxybenzoate; β-6G_p | (structure) |

TABLE 33

The Findings of Simulated Interaction of 3CLPro with Analogues of Tannic Acid in SNB01

| Abbr. | Grid Score | Number of H-Bond | H-Bonds (Å) |
|---|---|---|---|
| β-10G | −82.89 | 5 | Pro$^{168}$ (2.5 Å); Glu$^{166}$ (2.6 Å); Asn$^{142}$ (2.5 Å); Cys$^{145}$ (2.4 Å); Cys$^{145}$ (2.3 Å) |
| β-5G | −73.19 | 5 | Pro$^{168}$ (2.4Å); Gln$^{189}$ (2.3 Å); His$^{163}$ (2.1 Å); Ser$^{144}$ (2.2 Å); Cys$^{145}$ (2.6 Å) |
| β-5G_m | −75.44 | 5 | Glu$^{166}$ (2.0 Å); Phe$^{140}$ (2.5 Å); His$^{163}$ (2.4 Å); Cys$^{145}$ (2.1 Å); His$^{41}$ (2.3 Å); |
| β-5G_p | −84.01 | 4 | Glu$^{166}$ (2.3 Å); Leu$^{141}$ (2.7 Å); Asn$^{142}$ (2.5 Å); Cys$^{145}$ (2.2 Å) |
| β-6G_p | −81.79 | 5 | Glu$^{166}$ (2.0 Å); His$^{163}$ (2.2 Å); Ser$^{144}$ (2.2 Å); Cys$^{145}$ (2.6 Å); His$^{41}$ (2.5 Å) |

Example 15 Inhibition of 3CL Protease (3CLPro) of SARS-CoV-2 by Test Compounds

To study the inhibitory activities against SARS-CoV-2 3CLPro of the test compounds shown in Table 34 below, an assay was determined in vitro by measuring the enhanced fluorescence due to cleavage of the fluorogenic substrate (Dabcyl-KTSAVLQSGFRKME-Edans). For analyzing the inhibition potential, various compounds were dissolved in 1 or 8% dimethyl sulfoxide (DMSO) aqueous solution as the compound stocks. Different concentration of each stocks (5 μl) was pre-incubated with 45 μl reaction mixture (50 nM SARS-CoV-2 viral 3CL protease in 20 mM Bis-Tris, pH 7.4) at 37° C. for 30 minutes. Afterwards, 50 μl of the fluorogenic peptide substrate (6 μM) was added into the mixture and gently mixed to get the final DMSO concentration 0.05 or 0.4% solution. The difference of fluorescence intensity resulting from the reaction was measured at 485 nm with excitation at 360 nm using a fluorescence plate reader at 37° C. for 4 min. The protease activity was presented as fluorescence intensity and calculated by the following equation:

Inhibition (%)=1−[(fluorescence$_{sample,\ 4\ min}$−fluorescence$_{sample,\ 0\ min}$)/(fluorescence$_{ddH_2O,\ 4\ min}$−fluorescence$_{ddH_2O,\ 0\ min}$)]×100%.

The 50% inhibition concentration (IC$_{50}$) of the test compounds against SARS-CoV-2 3CLPro was shown in Table 34. Among these samples, Samples 5 displayed half maximal inhibition (IC$_{50}$) at the lowest concentration (1.037 μg/mL). In addition, Samples 1, 2, 3, 4 and 6 showed good inhibitory activities against SARS-CoV-2 3CLPro. The IC$_{50}$ of these samples was below 1.5 μg/mL. In sum, all test compounds had inhibition against proteolytic activity of SARS-CoV-2 3CLPro.

TABLE 34

Inhibitory Activities of Exemplary Formula (I) Compounds Against 2019-nCoV 3CLPro

| Sample | Cpd. name | IC$_{50}$ (μM) | IC$_{50}$ (μg/mL) | Final DMSO concentration (%) |
|---|---|---|---|---|
| 1 | α5G | 1.5670 | 1.474 | 0.05 |
| 2 | β5G | 1.5880 | 1.494 | 0.05 |
| 3 | α10G | 0.6657 | 1.132 | 0.05 |

TABLE 34-continued

Inhibitory Activities of Exemplary Formula (I) Compounds Against 2019-nCoV 3CLPro

| Sample | Cpd. name | $IC_{50}$ (μM) | $IC_{50}$ (μg/mL) | Final DMSO concentration (%) |
|---|---|---|---|---|
| 4 | β10G | 0.8063 | 1.372 | 0.05 |
| 5 | α15G | 0.4213 | 1.037 | 0.05 |
| 6 | β15G | 0.6018 | 1.481 | 0.05 |
| 7 | α20G | 0.7014 | 2.260 | 0.40 |
| 8 | β20G | 0.8380 | 2.700 | 0.40 |
| 9 | α25G | 0.4336 | 1.727 | 0.40 |
| 10 | β25G | 0.6824 | 2.718 | 0.40 |
| 11 | phenol 3G | 6.439 | 3.544 | 0.40 |
| 12 | Phloroglucinol 9G | 1.452 | 2.171 | 0.05 |
| 13 | phenol 5G | 2.6530 | 2.267 | 0.40 |
| 14 | Resorcin 10G | 1.1550 | 1.884 | 0.40 |
| 15 | Phloroglucinol 15G | 0.9340 | 2.249 | 0.40 |
| 16 | phenol 7G | 1.8710 | 2.168 | 0.40 |
| 17 | Resorcin 14G | 1.1330 | 2.537 | 0.40 |
| 18 | Phloroglucinol 21G | 0.7164 | 2.379 | 0. |
| 19 | The Enriched tannic acid (SNB01) | 0.9236 | 1.571 | 0.05 |
| 20 | The Enriched tannic acid (SNB01) | 0.9759 | 1.660 | 0.40 |
| 21 | Merck tannic acid Product No.:1.00773.1000 | 1.7400 | 1.959 | 0.05 |
| 22 | CCBiotech tannic acid | 1.3420 | 1.844 | 0.05 |

Structures of phenol 3G, Phloroglucinol 9G, and Phloroglucinol 15G are shown below. Structures of the other compounds are provided in Table 1 above.

(phenol 3G)

(Phloroglucinol 9G)

(Phloroglucinol 15G)

Additional compounds of Formula (I) have been tested for their inhibitory activity against 2019-nCoV 3CLPro and the results are shown in Table 35 below.

TABLE 35

Inhibitory Activities of Additional Exemplary Formula (I) Compounds Against 2019-nCoV 3CLPro

| Cpd. name | $IC_{50}$ (μM) | $IC_{50}$ (μg/mL) | Final DMSO concentration (%) |
|---|---|---|---|
| Compound 103 | 1.925 | 3.371 | 0.4 |
| Compound 117 | 1.238 | 1.692 | 0.05 |
| Compound 119 | 0.526 | 1.039 | 0.05 |
| Compound 121 | 0.585 | 1.510 | 0.4 |
| Compound 123 | 0.380 | 1.212 | 0.4 |
| Compound 126 | 0.706 | 1.395 | 0.4 |
| Compound 128 | 0.604 | 1.560 | 0.4 |
| Compound 134 | 1.016 | 1.389 | 0.4 |
| Compound 136 | 0.841 | 1.661 | 0.05 |
| Compound 138 | 0.552 | 1.425 | 0.4 |
| Compound 140 | 0.658 | 2.100 | 0.4 |
| Compound 142 | 1.699 | 2.322 | 0.4 |
| Compound 144 | 0.870 | 1.718 | 0.4 |
| Compound 146 | 1.528 | 3.948 | 0.4 |
| Compound 148 | 0.724 | 2.310 | 0.4 |
| Compound 149 | 4.659 | 2.919 | 0.4 |

Structures of the compounds listed in Table 35 above are shown in FIG. 20.

Structures of Compound 14 and Compound 18 are provided below:

14

18

The $IC_{50}$ values of Compound 14 and Compound 18 for inhibiting human D-amino acid oxidase are 299 nM and 121 nM, respectively. Further, Compound 18 shows a 44% inhibition activity against 2019-nCoV $3CL^{pro}$ (56% of residual protease activity) at the concentration of 3 μM.

Example 16. Preparation of Pressurized Metered-Dose Inhaler Comprising SNB01

Pressurized metered-dose inhaler (pMDI) comprising SNB01 was prepared and inhaler performance of which was tested by aerodynamic particle size distribution (APSD) and delivered dose uniformity (DDU).

Preparation: Micronization and Filling

First, SNB01 was micronized using a high-pressure air jet mill. The mass median diameter ($D_{50}$) of the particle size distribution (PSD) was 2.17 μm after micronization. Then, the micronized SNB01 was suspended in a liquid propellant, hydrofluoroalkanes (HFA-134a). The mixture of SNB01 and HFA-134a was filled in a 19 mL canister composed of uncoated Aluminium. The metering chamber in the valve defined the maximum amount of the formulation to be dispensed as the next dose, was 50 pt. The SNB01 amount in one puff was 250 μg.

1. Aerodynamic Particle Size Distribution

The APSD was performed based on the USP method for pMDIs using a multistage cascade impactor described in USP apparatus 6: Next Generation Impactor (NGI). The NGI simulates the route of inhalation from mouth to alveoli in lung. It includes an actuator, an L-tube, an impactor body with 8 stages, each set with a cut-off diameter, and one airflow pump. The mixture of SNB01 and HFA-134a was released from the canister to NGI under 30 L/min air flow regulated by the airflow valve. The content flowed through the actuator, L-tube and the 8 stages, in which the content with different particle sizes was collected. 10 puffs were tested and collected. The content (SNB01) in each stage was analyzed as shown in Table 36.

TABLE 36

| The content in each stage and the parameter of APSD | | | |
|---|---|---|---|
| Stage of NGI | Cut-off Diameters (μm) | Amount of SNB01 (μg) | Ratio of SNB01 amount/ the total SNB01 amount (%) |
| Actuator | N/A | 344.91 | 14.23 |
| L-tube | N/A | 777.39 | 32.06 |
| Stage 1 | >11.72 | 118.86 | 4.90 |
| Stage 2 | 6.40~11.72 | 138.22 | 5.70 |
| Stage 3 | 3.99~6.40 | 363.23 | 14.98 |
| Stage 4 | 2.30~3.99 | 484.61 | 19.99 |
| Stage 5 | 1.36~2.30 | 156.00 | 6.43 |
| Stage 6 | 0.83~4.36 | 25.80 | 1.06 |
| Stage 7 | 0.54~0.83 | 5.04 | 0.21 |
| Stage 8 | <0.54 | 10.57 | 0.44 |
| The parameter of APSD | | | |
| Fine Particle Dose | | 87.18 μg | |
| Fine Particle Fraction | | 41.92% | |
| MMAD | | 3.87 μm | |
| GSD | | 1.99 | |

This parameter of APSD was analyzed and reported by Copley Inhaler Testing Data Analysis Software (CITDAS) Version 3.10. The Mass Median Aerodynamic Diameter (MMAD) of SNB01 released was 3.87 μm. Geometric Standard Deviation (GSD) of MMAD was 1.99. Fine particle dose (FPD) provides a direct measurement of the aerosol particles considered suitable for deposition and retention in the respiratory tract. The FPD, indicating the amount of particles of which the size were less than 5 μm, was 87.18 μg. The Fine Particle Fraction (FPF), as an expression of the FPD in percentage over the delivered dose, was 41.92%. As shown in the APSD result, about 41.92% of the delivered dose is estimated to able to reach the lung successfully.

2. Delivered Dose Uniformity

The delivered dose uniformity (DDU) is a critical requirement of in vitro testing to ensure that the correct and accurate dose is delivered to the patient. The mixture in a canister was released to a Dosage Unit Sampling Apparatus (DUSA) and washed by water to collect and calculate the amount of SNB01. 10 individual puffs were collected and analyzed as shown in Table 37. The results complied with the regulation of USP41<601> that not less than 9 of the 10 doses are between 75% and 125% of the specified target-delivered dose and none is outside the range of 65% to 135% of the specified target-delivered dose.

$$DDU(\%) = \frac{\text{experimental value}}{\text{mean}} * 100\%$$

TABLE 37

| 10 individual doses of DDU. | | |
|---|---|---|
| No. | DDU (%) | RSD (%) |
| 1 | 100 | 9.2% |
| 2 | 81 | |
| 3 | 102 | |
| 4 | 98 | |
| 5 | 109 | |
| 6 | 110 | |
| 7 | 91 | |
| 8 | 101 | |
| 9 | 111 | |
| 10 | 98 | |

What is claimed is:

1. A method of treating coronavirus infection, comprising administering to a subject in need thereof an effective amount of a composition, wherein the composition comprises a compound of a formula selected from the group consisting of:

(a) Formula (Ic)]

(Ic)

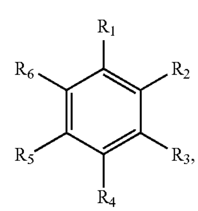

in which $R_1$, $R_2$, $R_3$, $R_4$, $R_5$, and $R_6$ are each, independently, selected from the group consisting of:

-continued
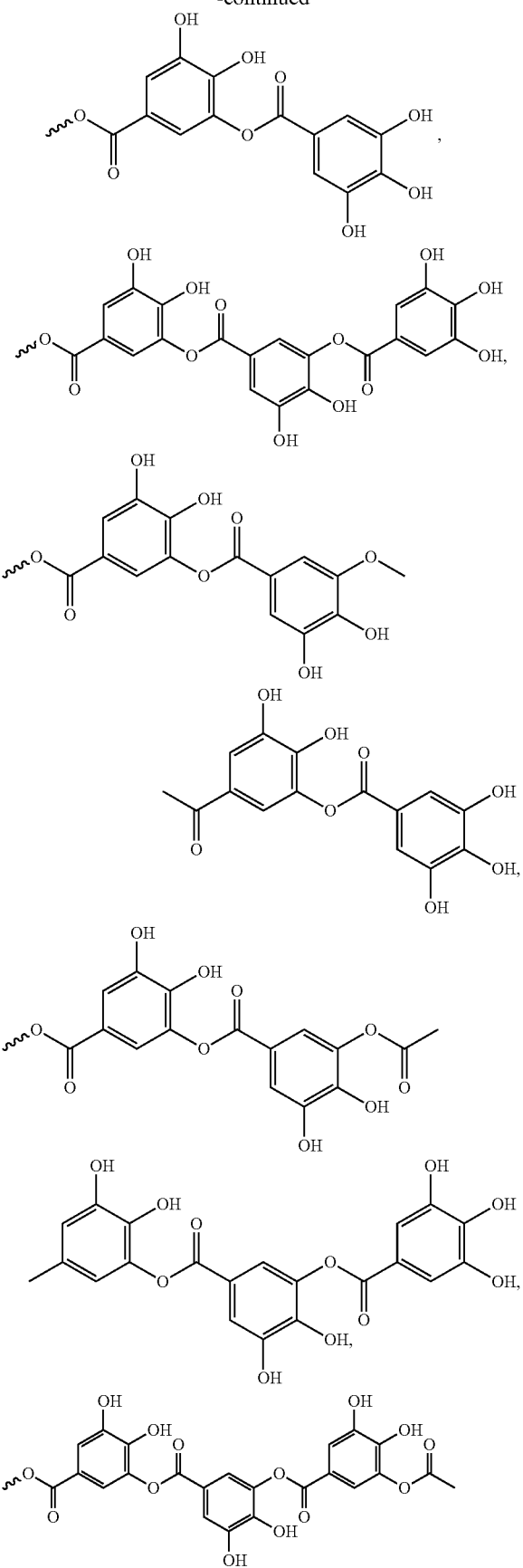
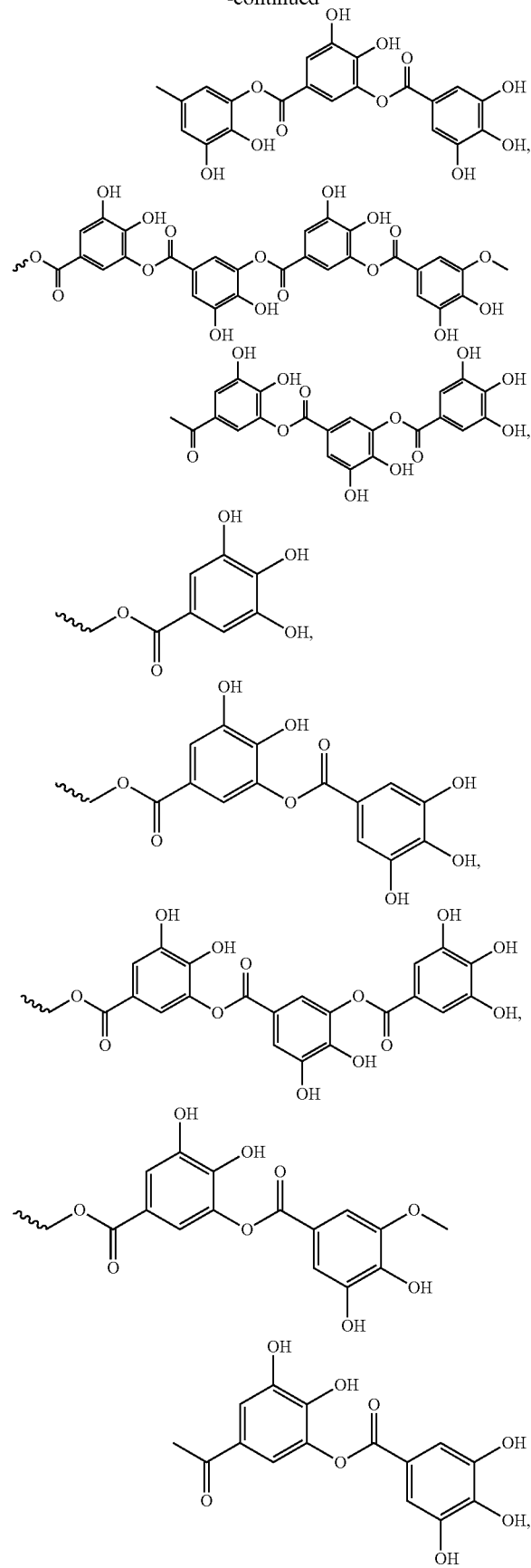

-continued
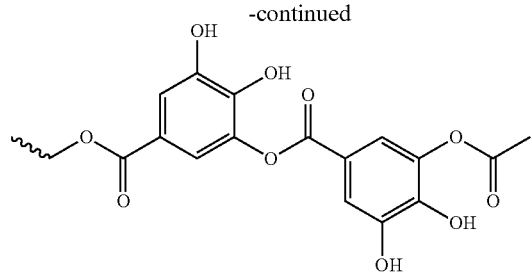
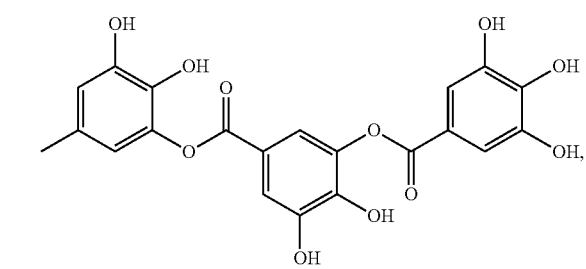
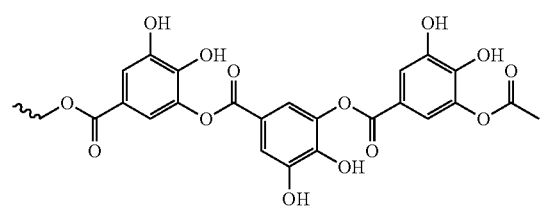
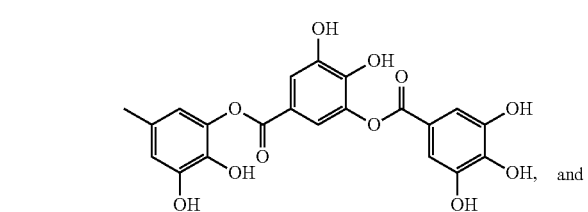
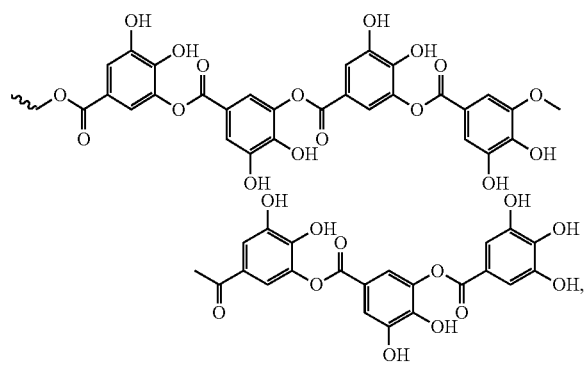
(b) Formula (Id)
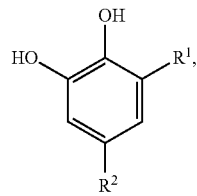
(Id)
in which R¹ is
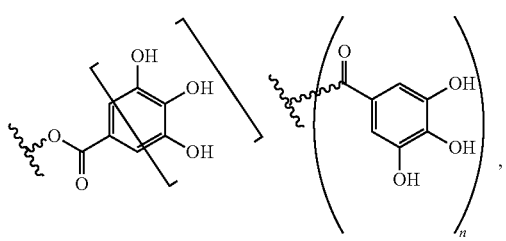
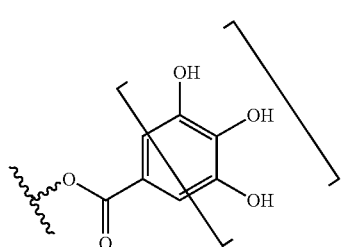
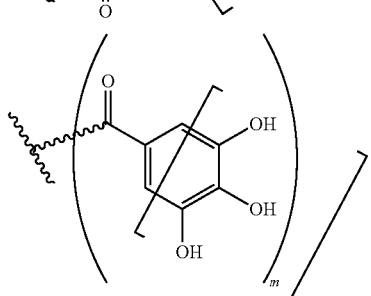
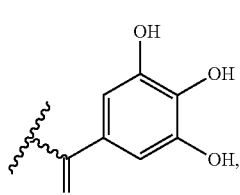
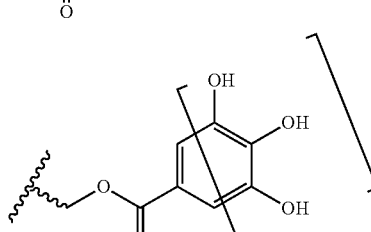
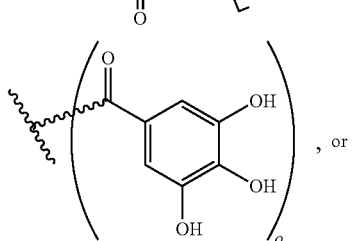, or
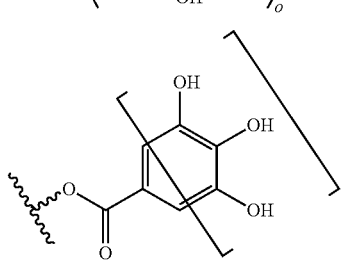

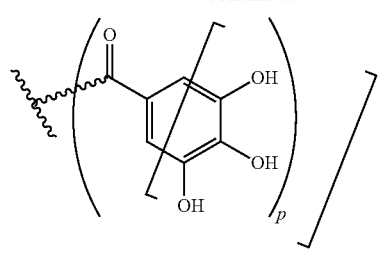
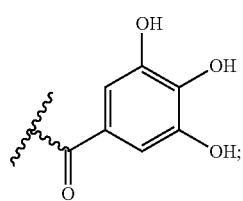
and R² is —COOH or
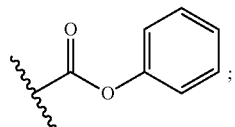 [SMILES: *C(=O)Oc1ccccc1]
(c) Formula (Ie)
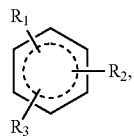
(Ie)
in which at least one of R¹, R², and R³ is
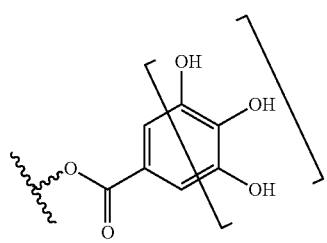
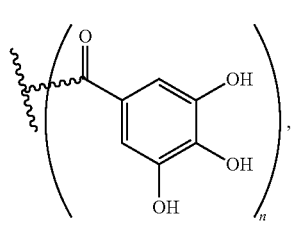
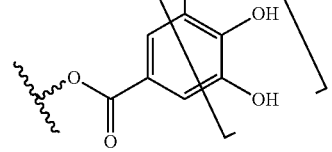
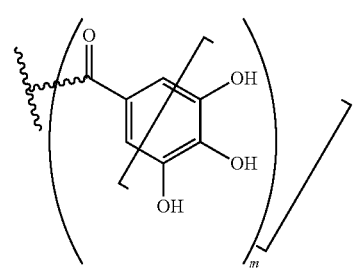
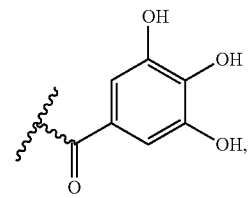
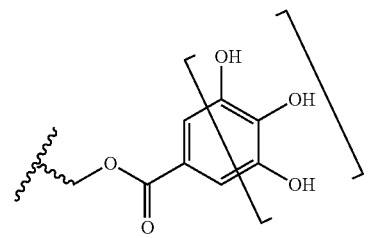
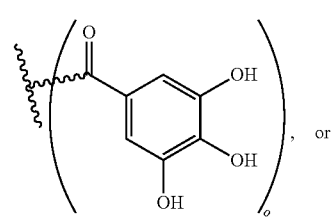, or
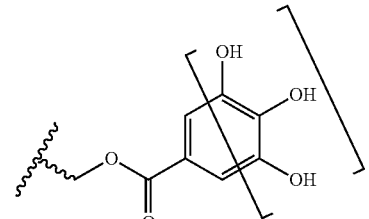
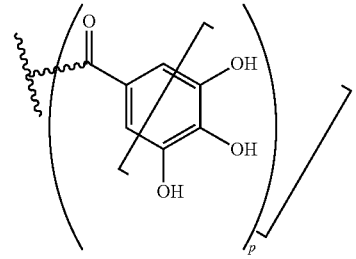

155
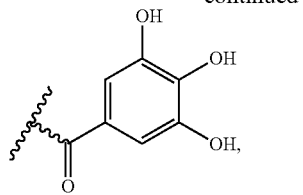
and the remaining of $R^1$, $R^2$, and $R^3$ each independently are selected from the group consisting of
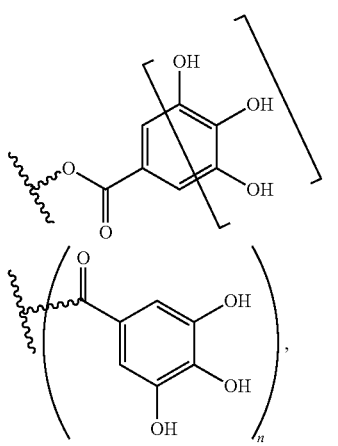
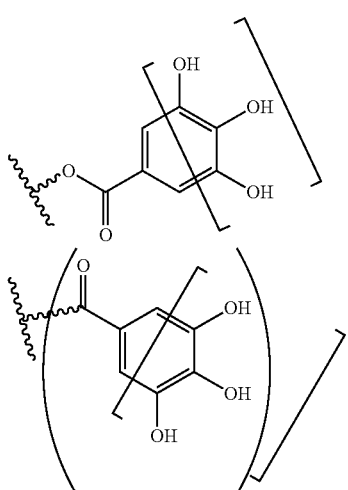
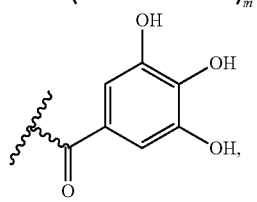
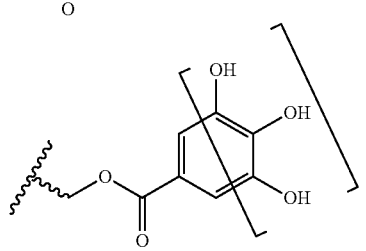
156
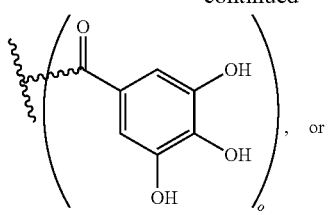, or
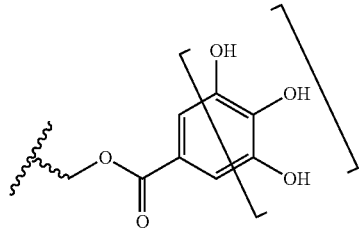
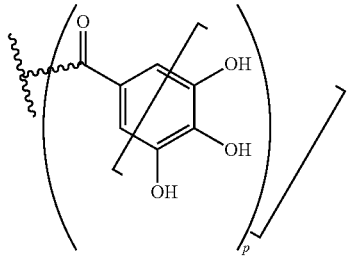
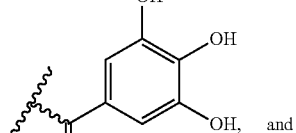, and
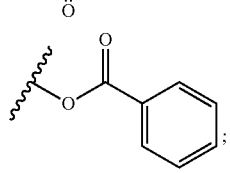;
(d) Formula (If):
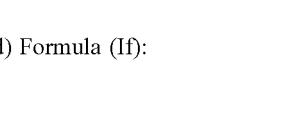 (If)
in which each of $R^1$ and $R^2$, independently, is
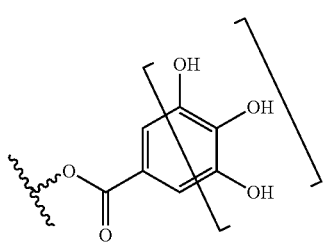

-continued
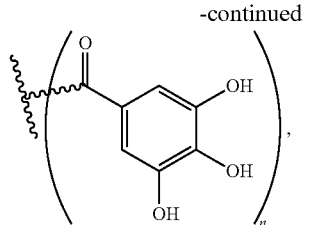
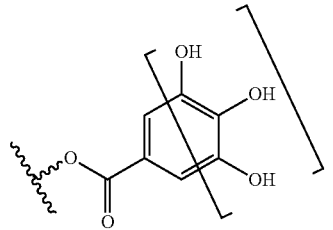
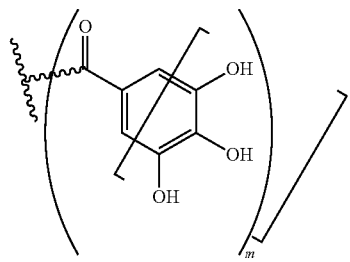
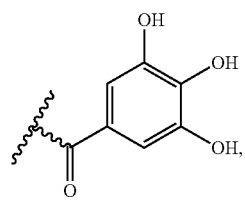
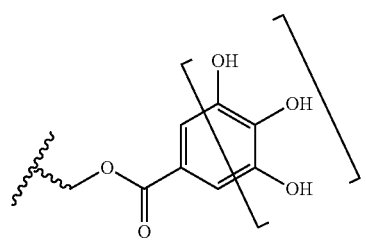
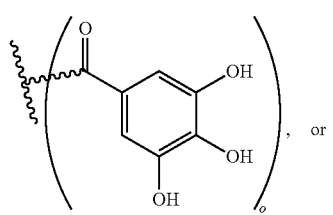, or
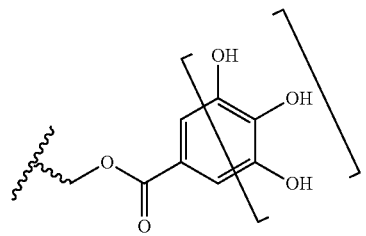
-continued
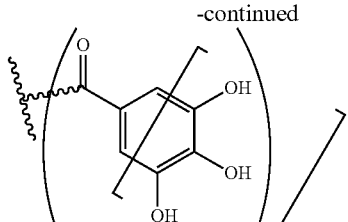
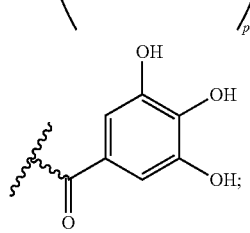
(e) Formula (Ig)
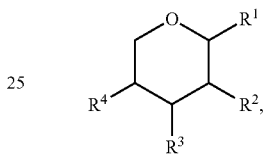
in which each of $R^1$, $R^2$, $R^3$, and $R^4$, independently, is
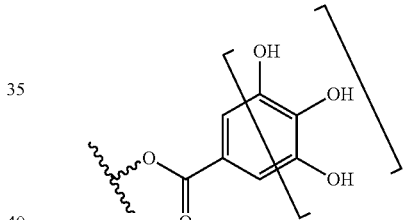
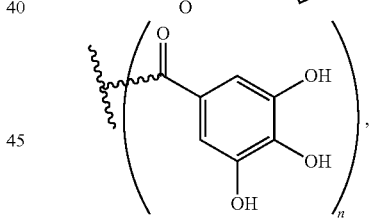
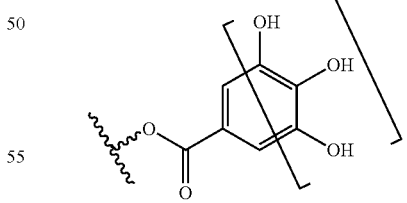
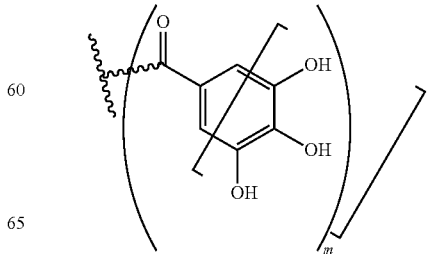

-continued
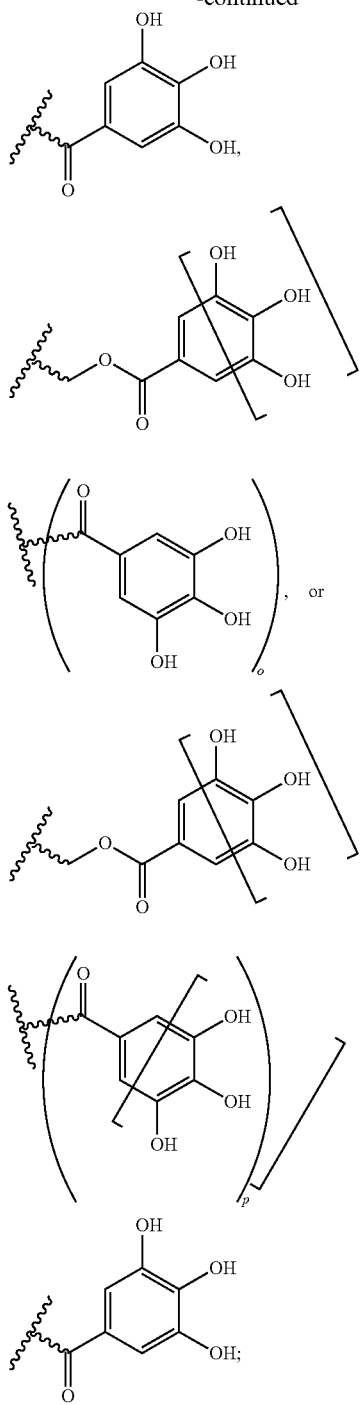
and
(f) Formula (Ih):
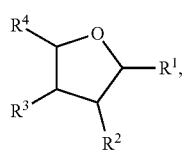
in which each of $R^1$, $R^2$, $R^3$, and $R^4$, independently, is
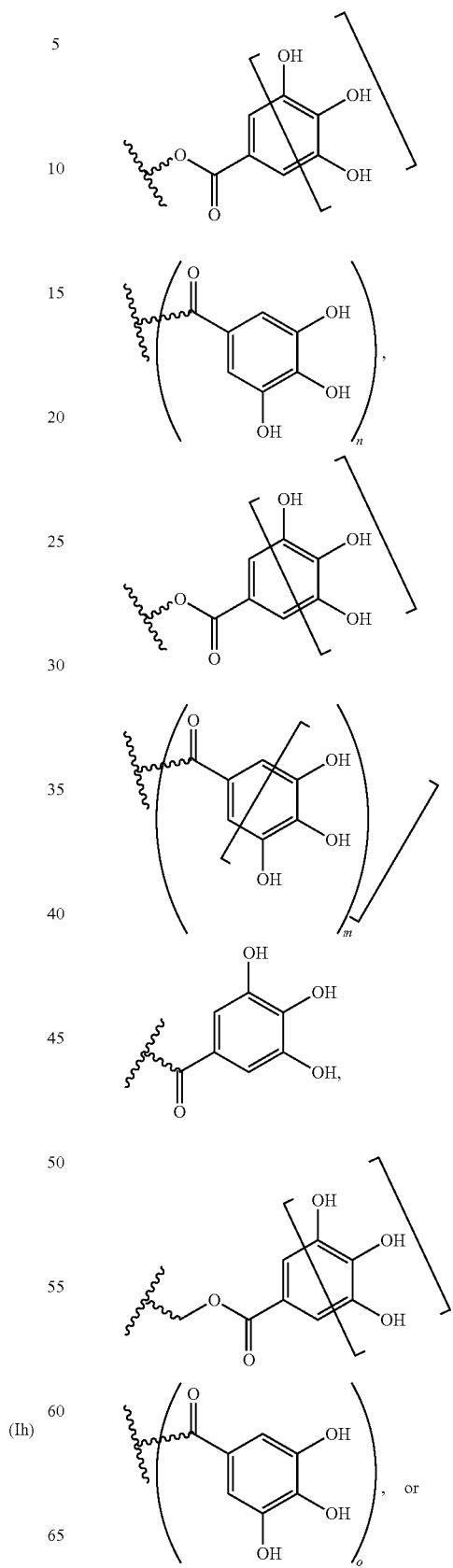

-continued
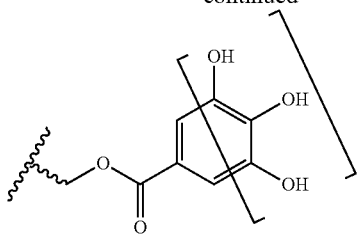
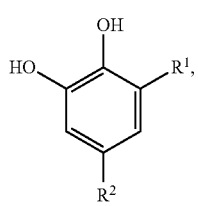
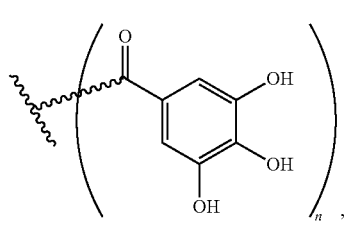
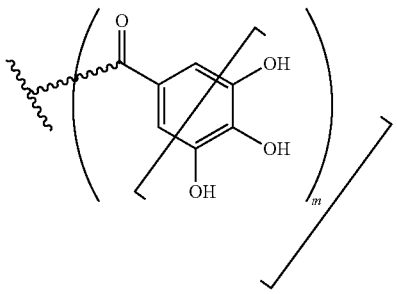
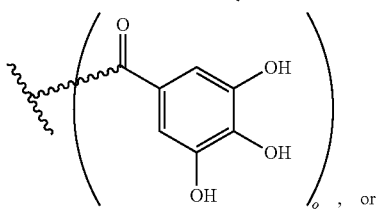
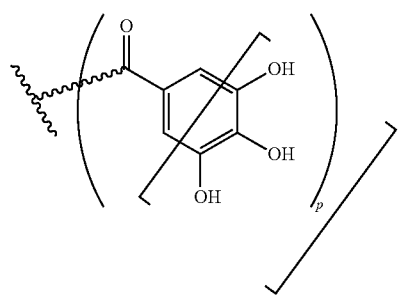
-continued
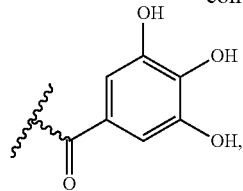
wherein n and o are independently 0 or 1 and wherein p and m are independently 1, 2, 3, 4 or 5.
2. The method of claim 1, wherein the compound is of the Formula (Id):
(Id)
$$\text{structure with } R^1, R^2$$
in which $R^1$ is
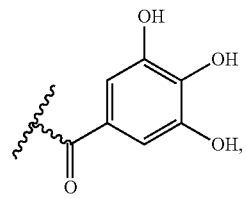
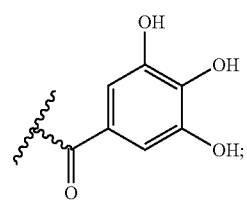

and $R^2$ is —COOH or
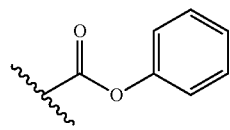
3. The method of claim 2, wherein $R^1$ is selected from the group consisting of:
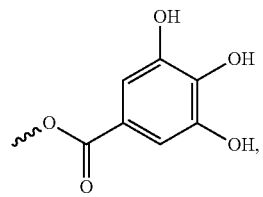
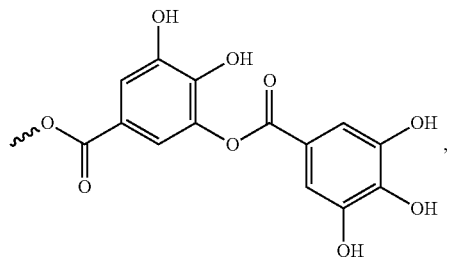
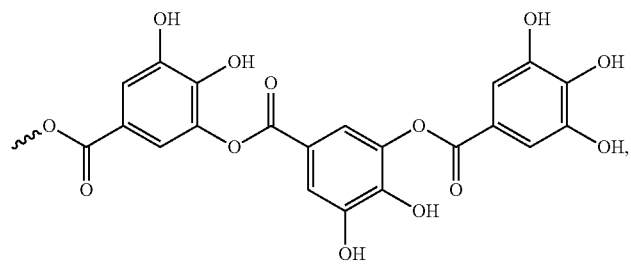
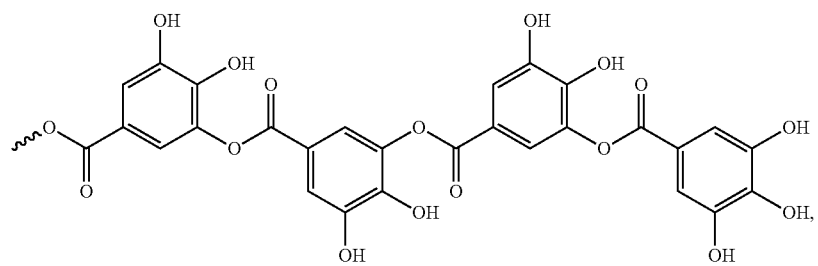
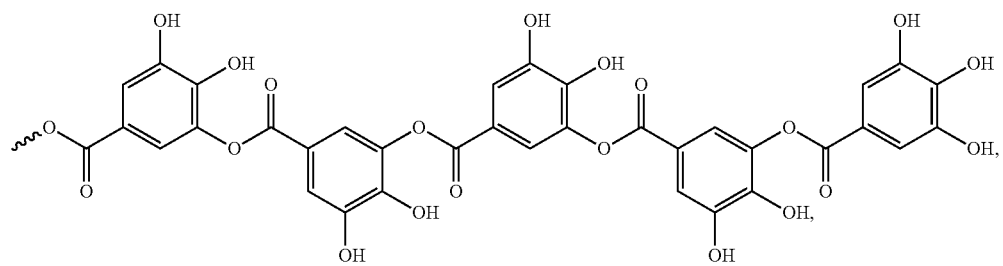
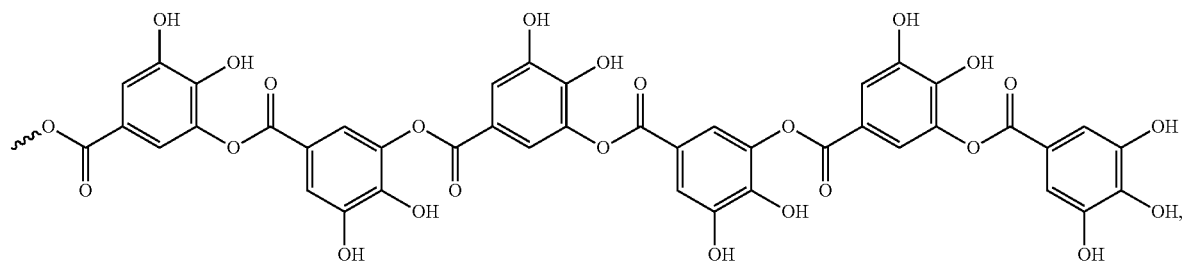

165 166
-continued
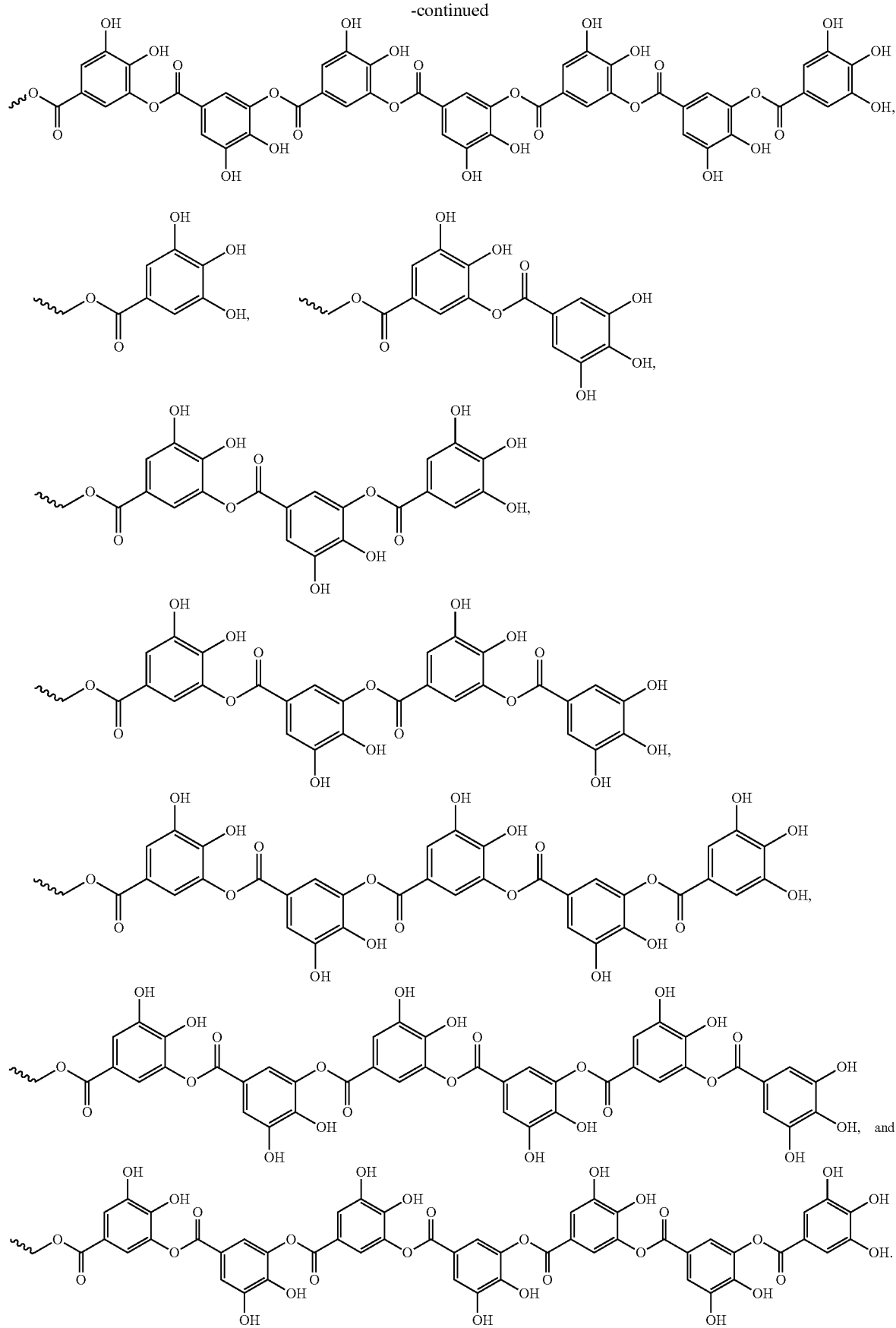

4. The method of claim 3, wherein the compound of Formula (Id) is phenol 3G, phenol 5G, phenol 7G, Compound 14, Compound 18, or Compound 149.
5. The method of claim 1, wherein the compound is of the Formula (Ie)
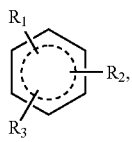
in which at least one of $R^1$, $R^2$, and $R^3$ is
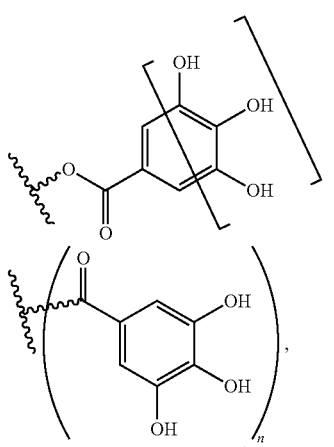
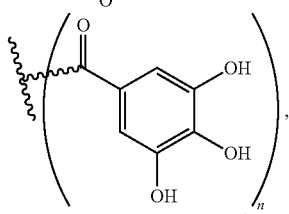
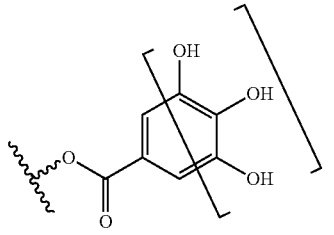
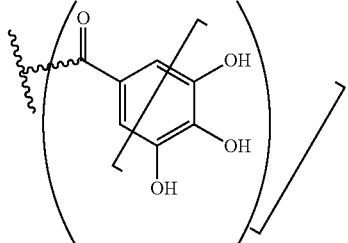
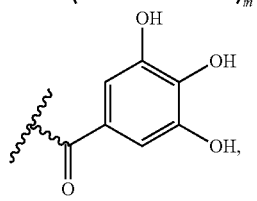
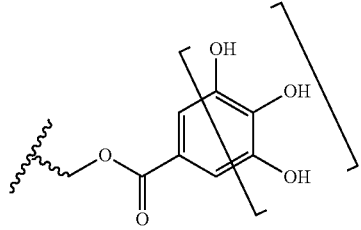
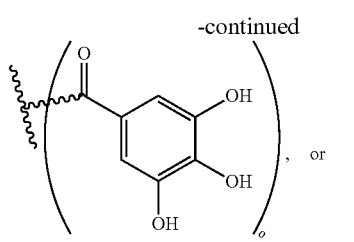
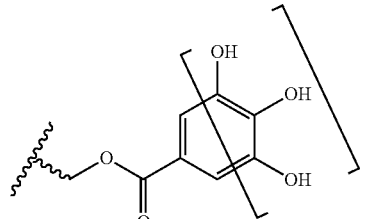
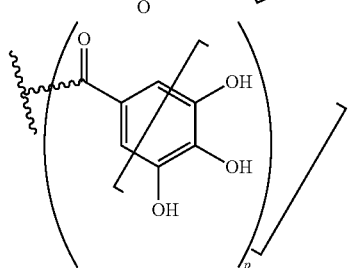
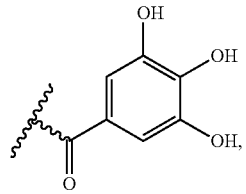
and the remaining of $R^1$, $R^2$, and $R^3$ each independently are selected from the group consisting
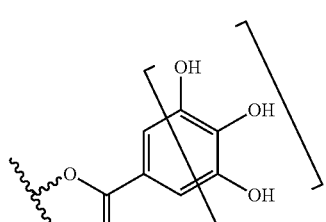
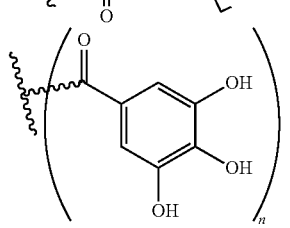
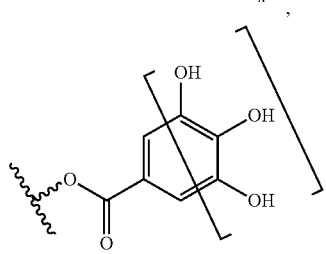

169
-continued
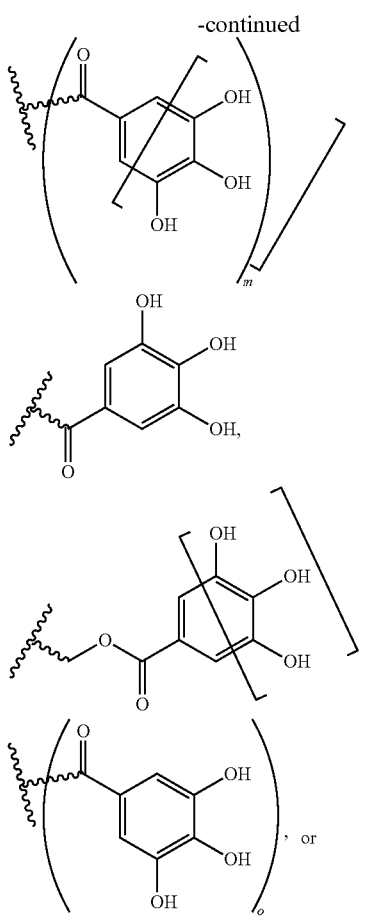
, or
170
-continued
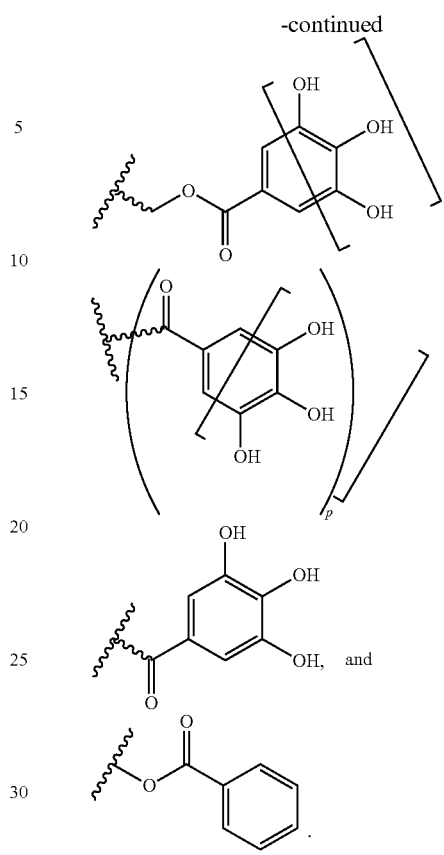
6. The method of claim 5, wherein each of $R^1$, $R^2$, and $R^3$, independently, is selected from the group consisting of:
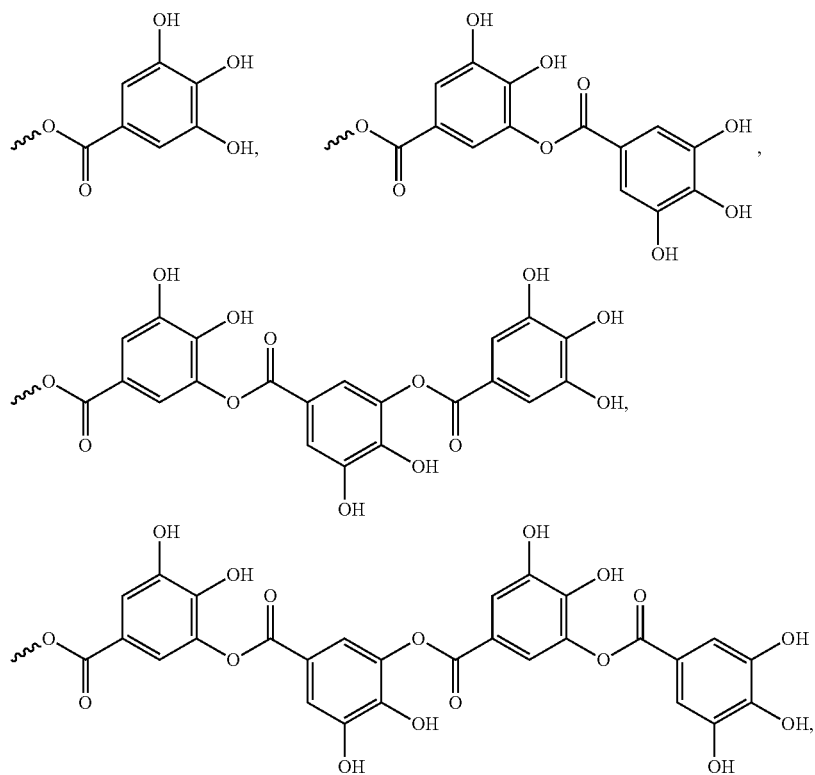

-continued
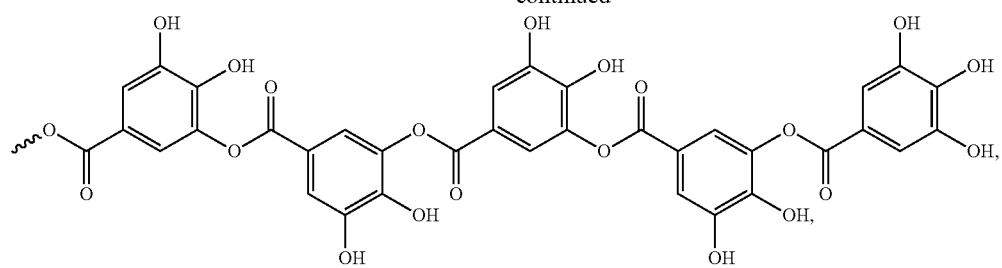
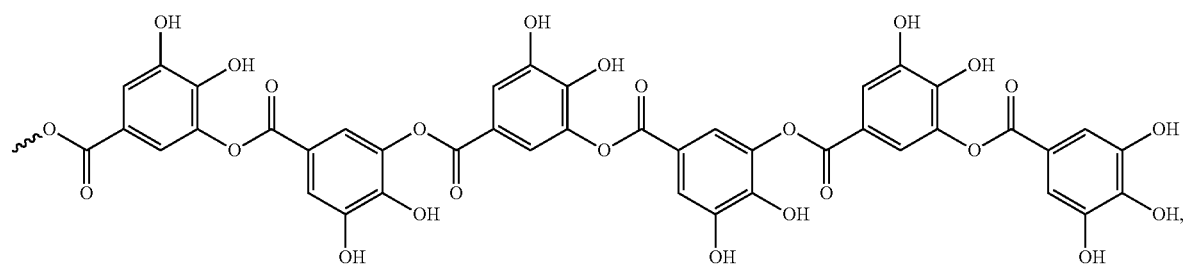
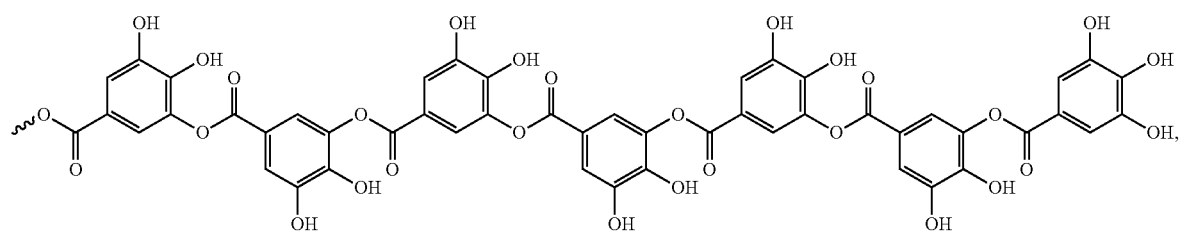
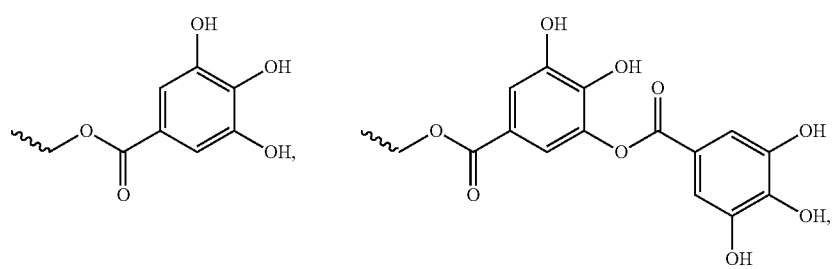
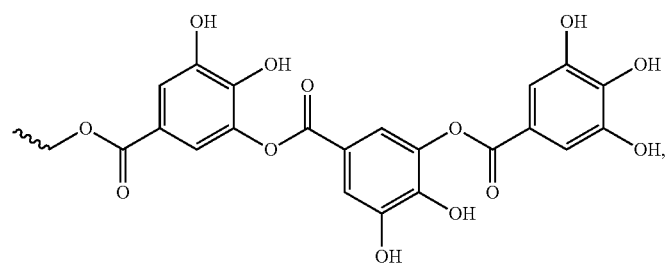
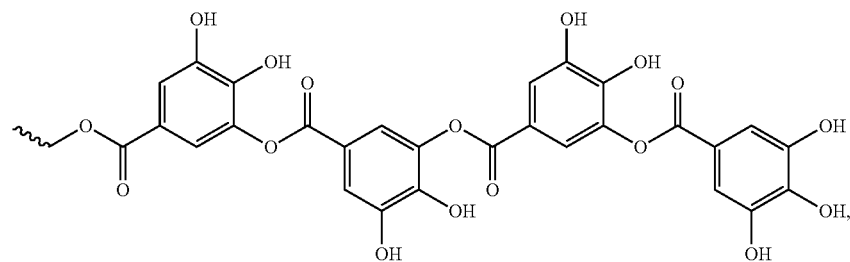

-continued
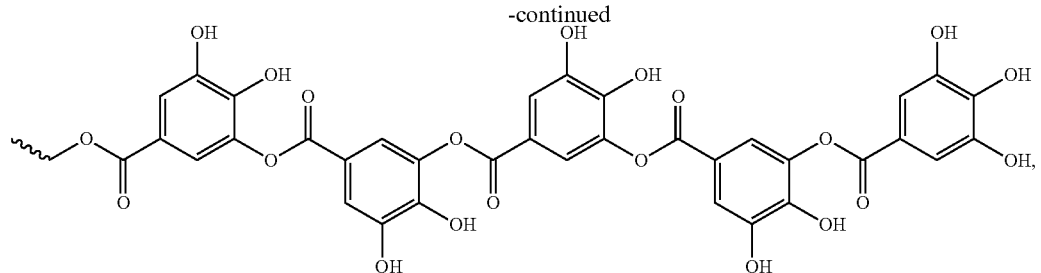
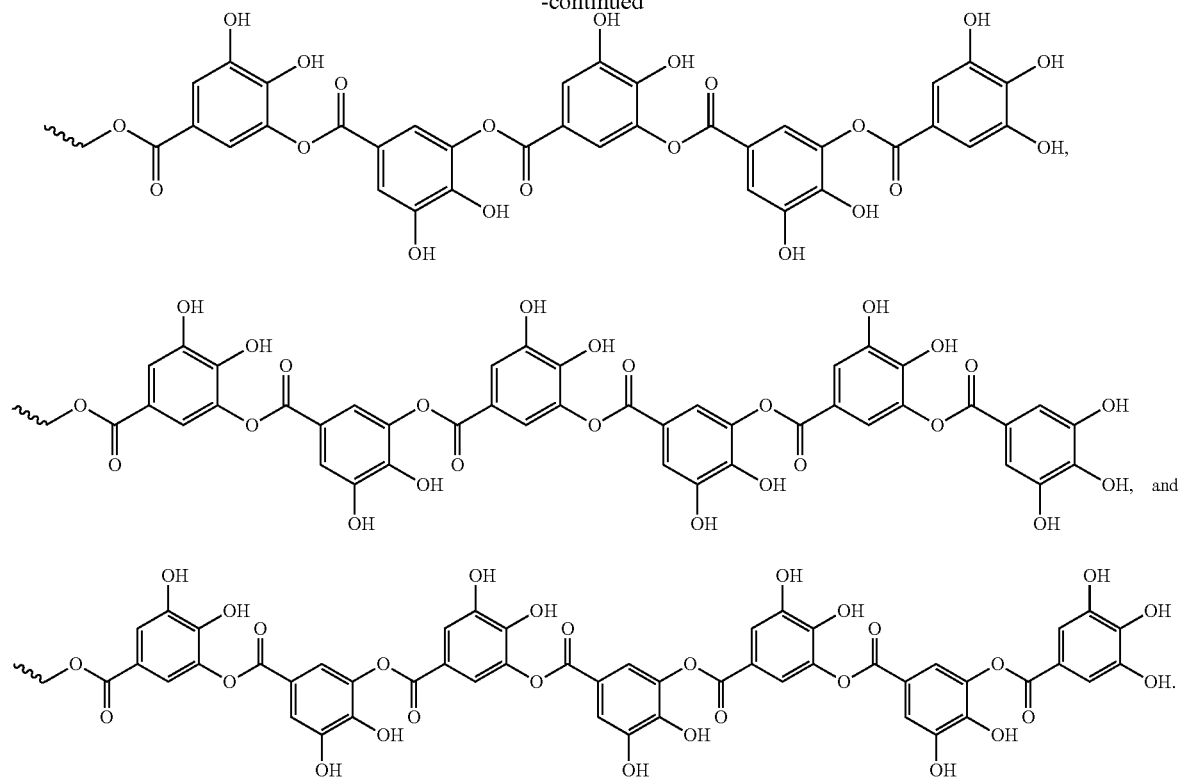
7. The method of claim 5, wherein the compound of Formula (Ie) is phloroglucinol 6G, phloroglucinol 9G, phloroglucinol 12G, phloroglucinol 15G, phloroglucinol 21G, or Compound 103.
8. The method of claim 1, wherein the compound is of the Formula (If)
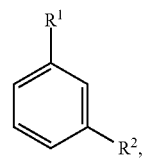
(If)
in which each of $R^1$ and $R^2$, independently, is
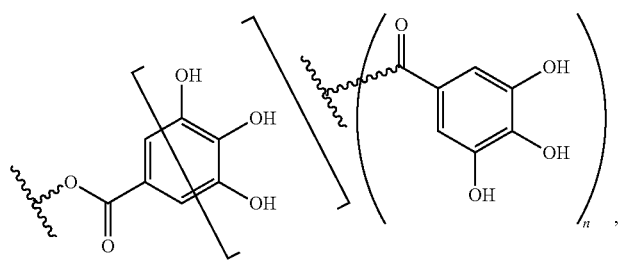
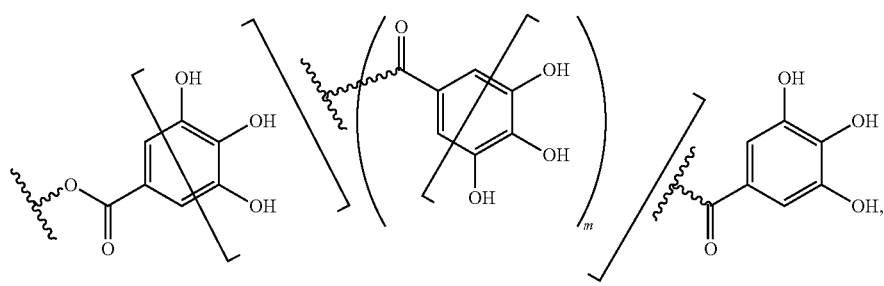

-continued
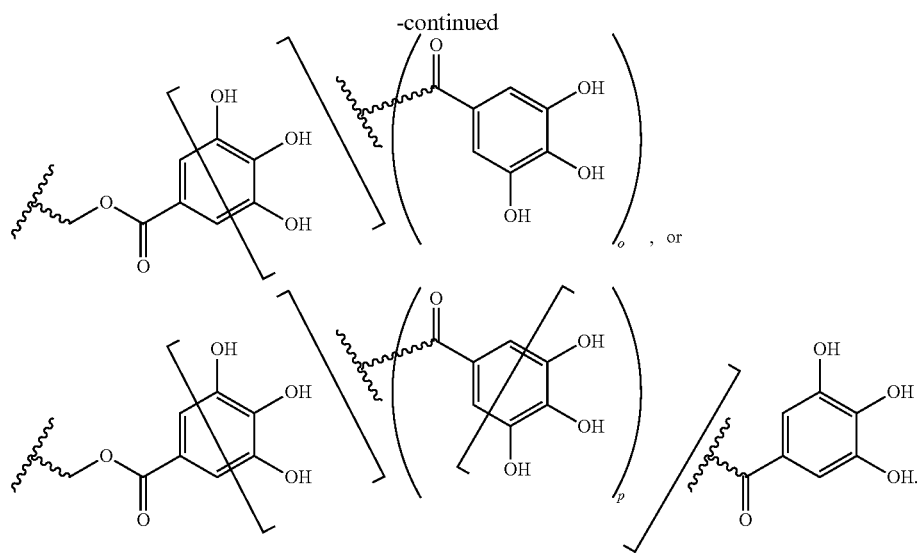
9. The method of claim 8, wherein each of $R^1$ and $R^2$, independently, is selected from the group consisting of:
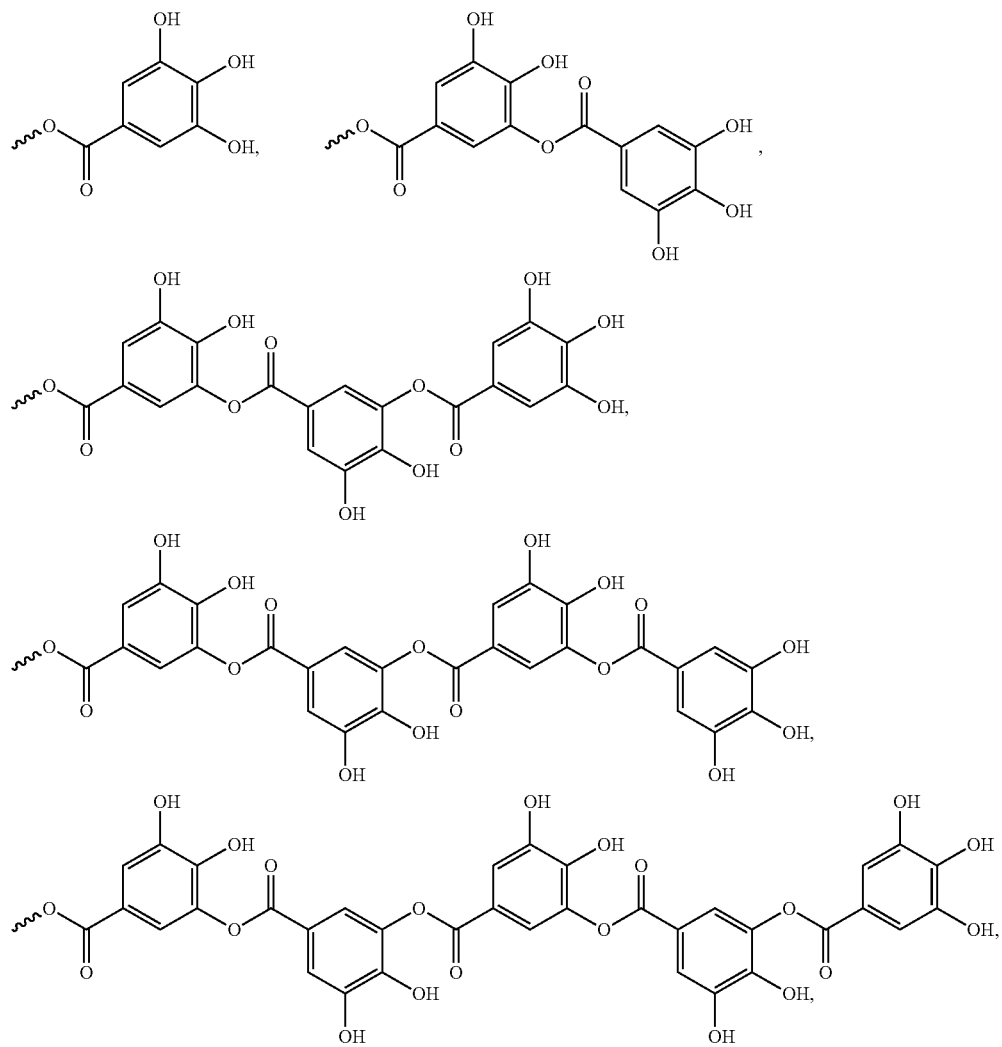

177 178
-continued
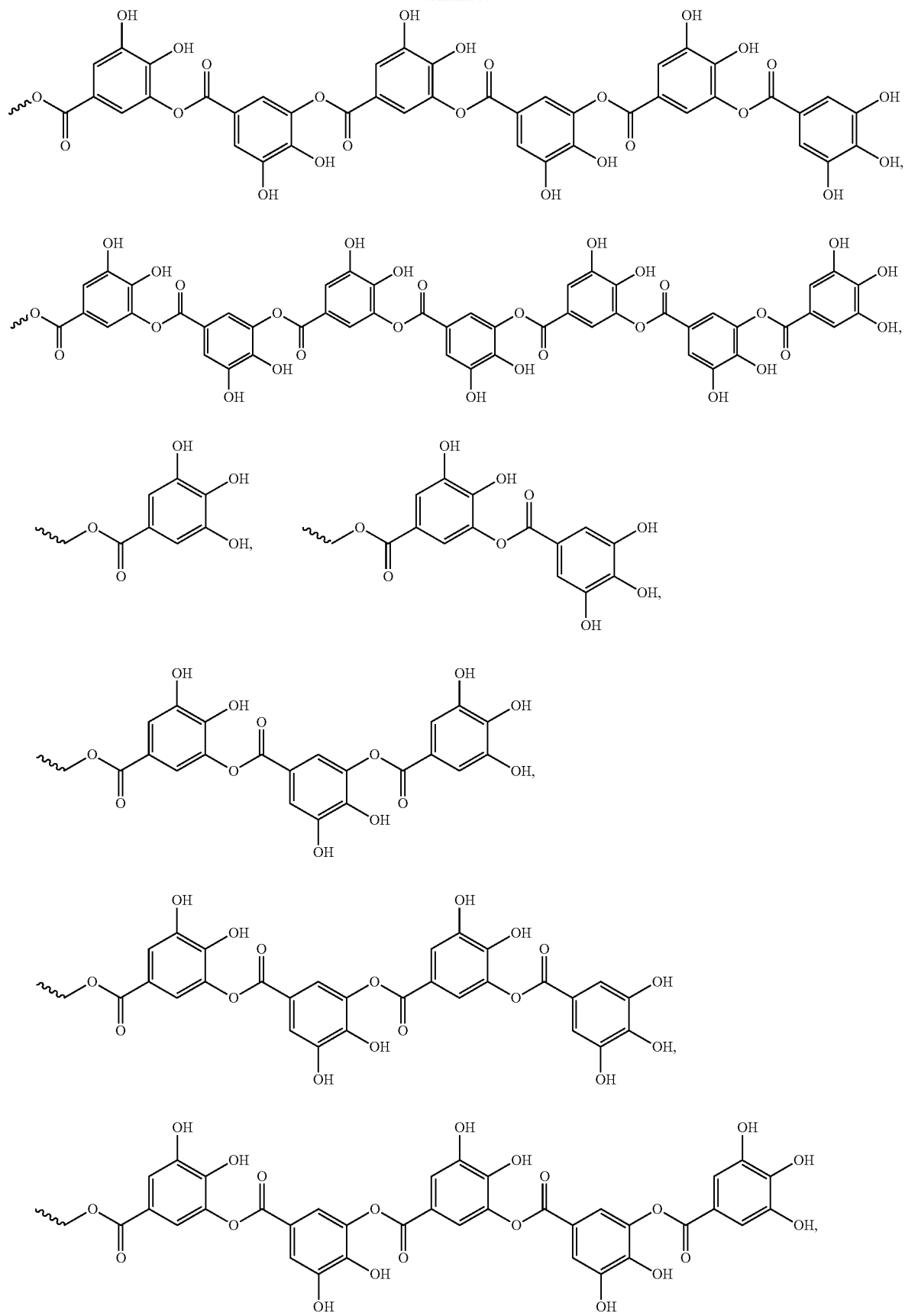

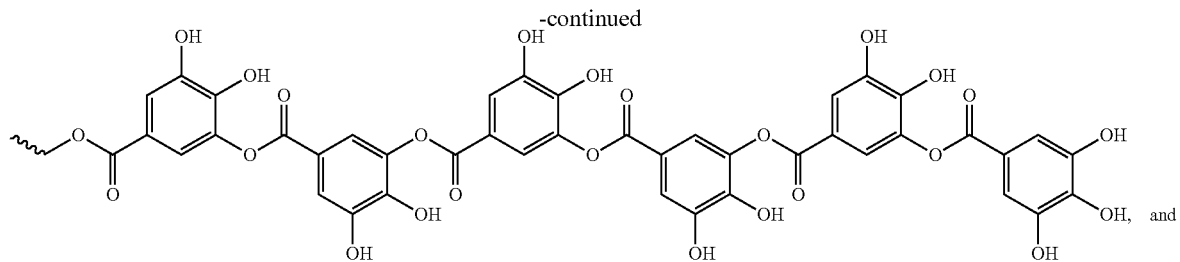
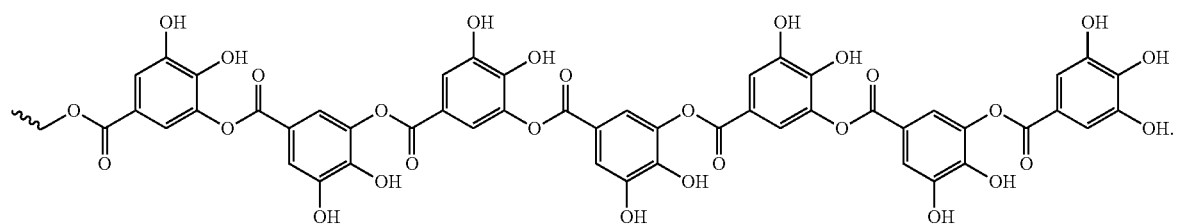
10. The method of claim 9, wherein the compound of Formula (If) is Resorcin 10G or Resorcin 14G.
11. The method of claim 1, wherein the compound is of the Formula (Ig)
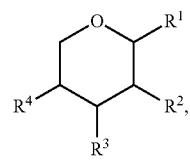
in which each of $R^1$, $R^2$, $R^3$, and $R^4$, independently, is
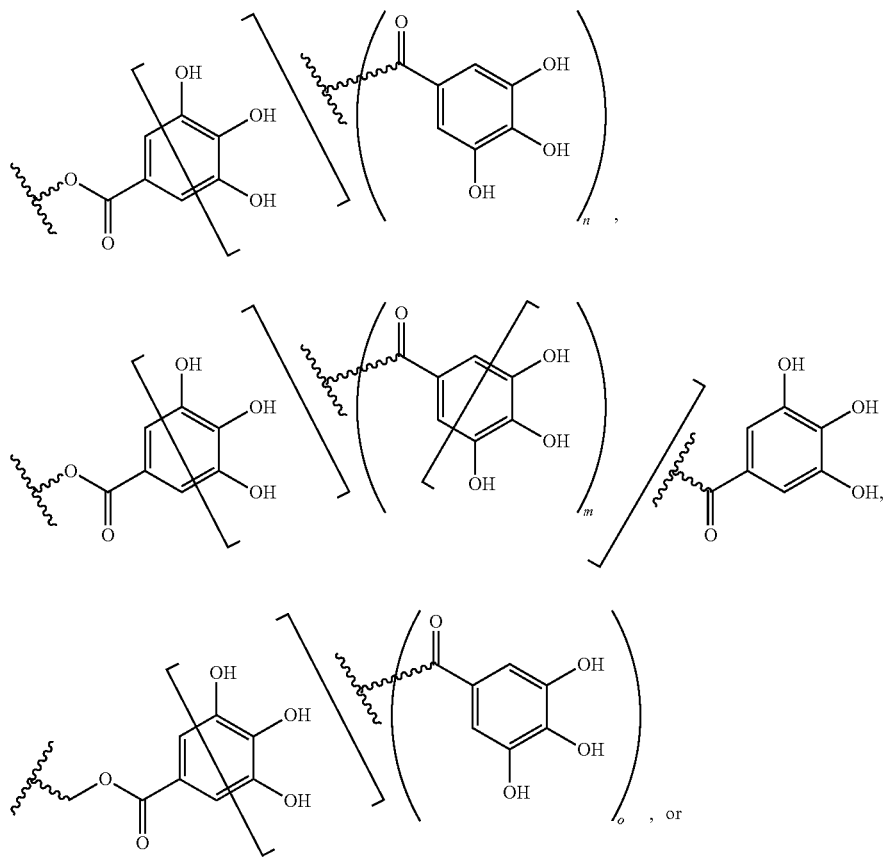

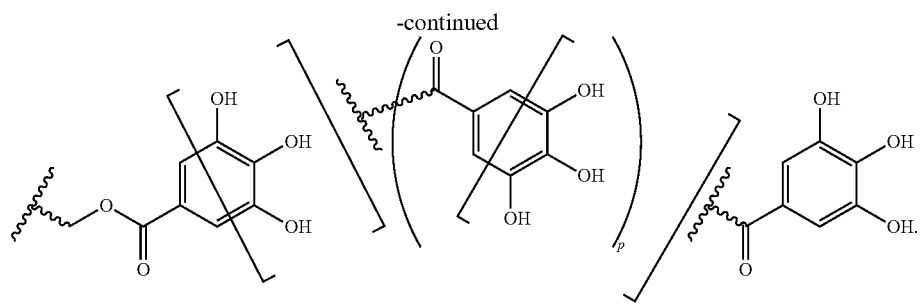
12. The method of claim 11, wherein each of $R^1$, $R^2$, $R^3$, and $R^4$, independently, is selected from the group consisting of:
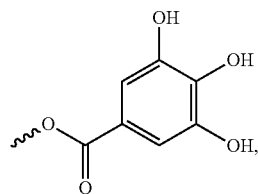
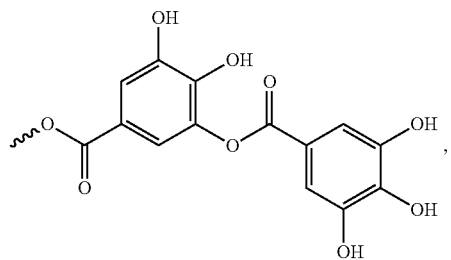
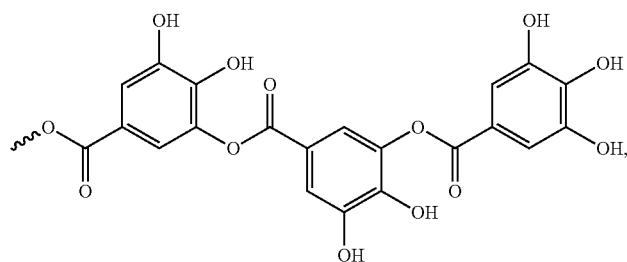
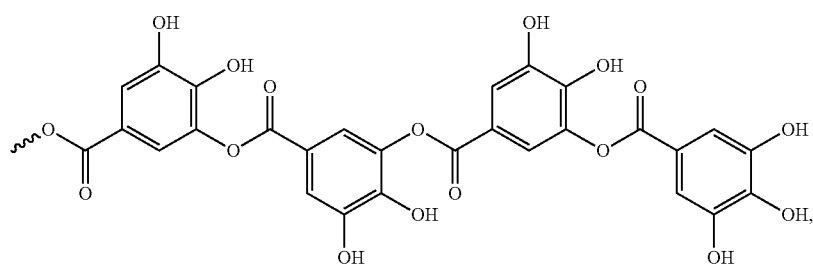
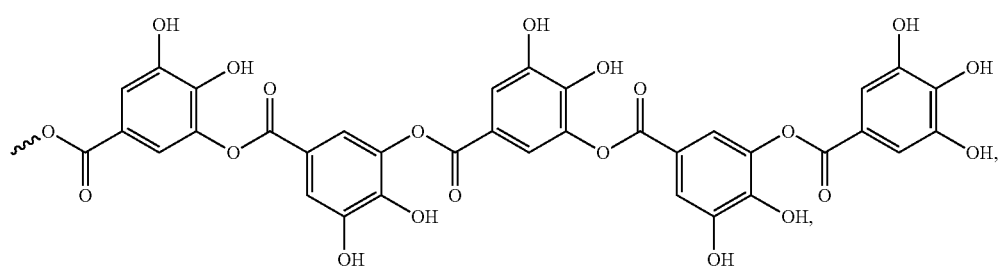

183                                    184
-continued
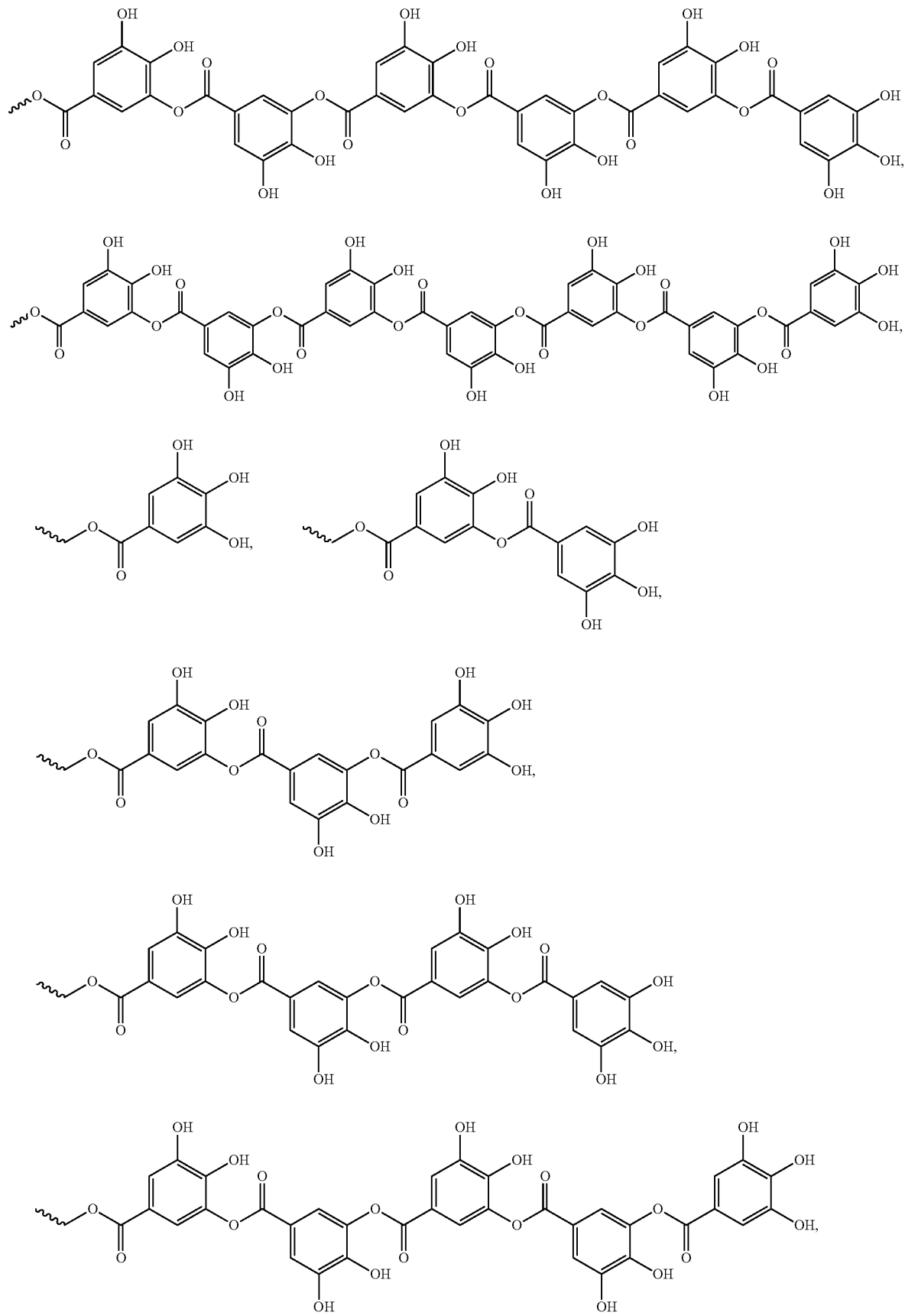

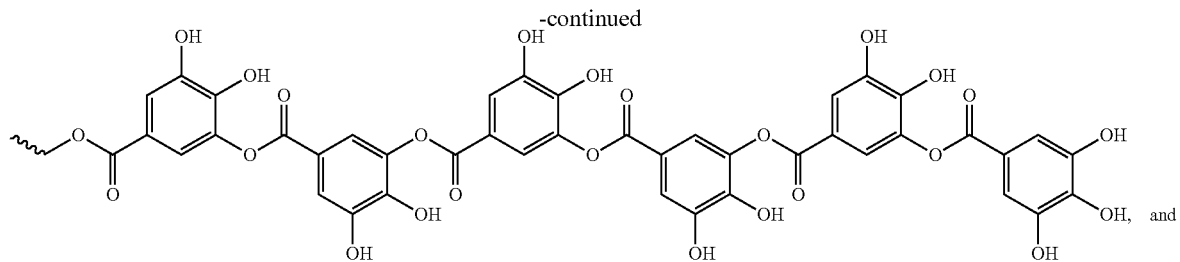
-continued
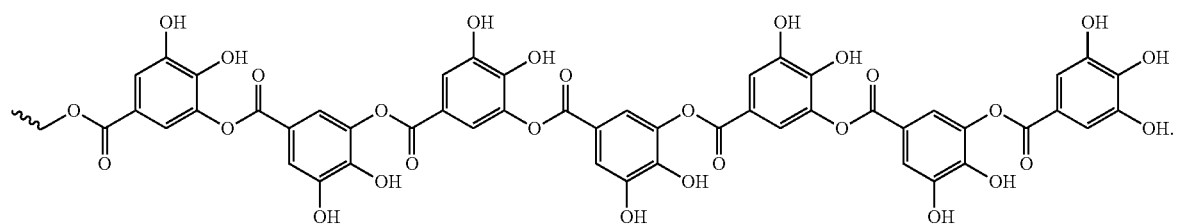
13. The method of claim 12, wherein the compound of Formula (Ig) is Compound 117, 119, 121, 123, 126, or 128.
14. The method of claim 1, wherein the compound is of the Formula (Ih)
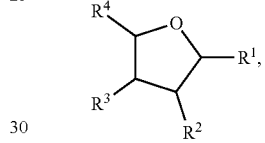
in which each of $R^1$, $R^2$, $R^3$, and $R^4$, independently, is
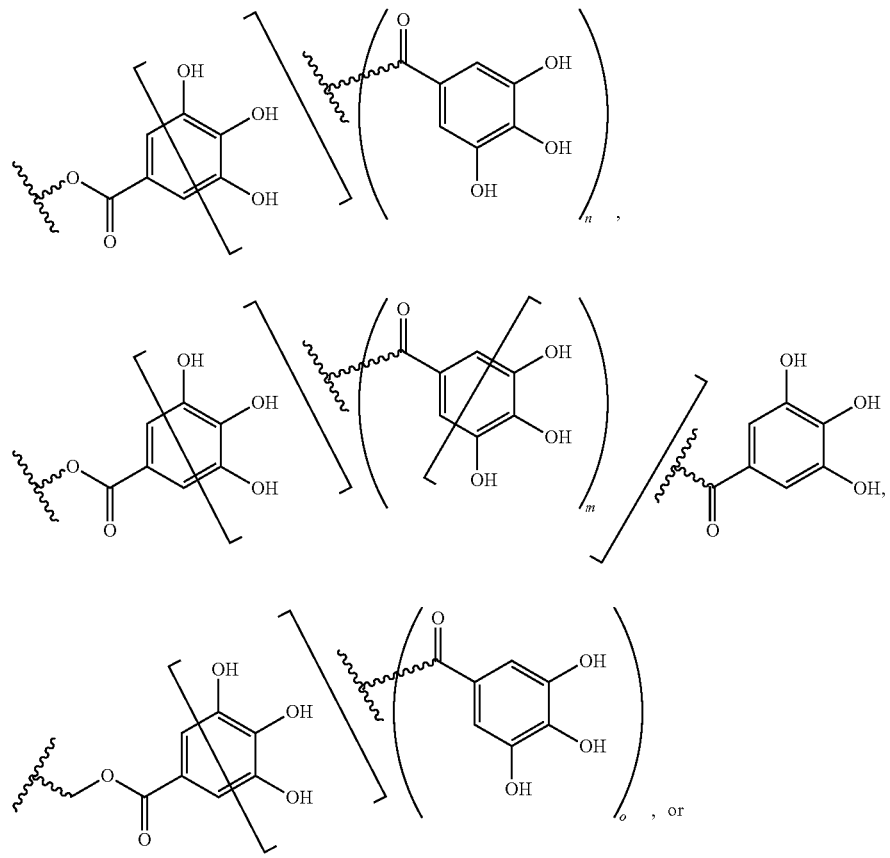

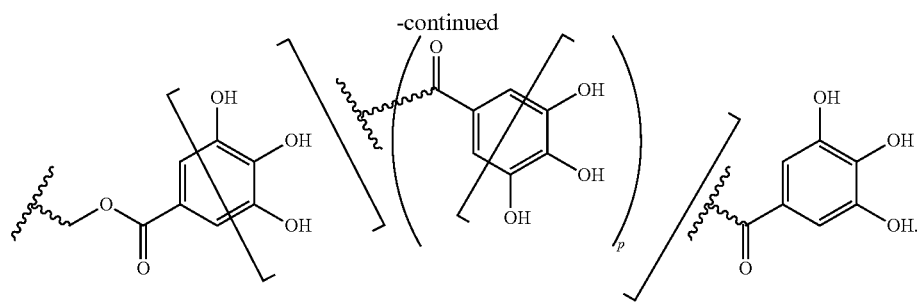
15. The method of claim 14, wherein each of $R^1$, $R^2$, $R^3$, and $R^4$, independently, is selected from the group consisting of:
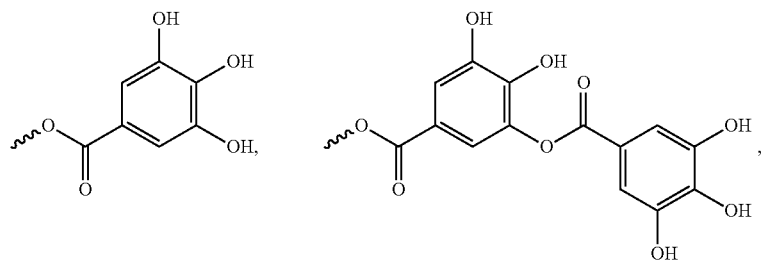
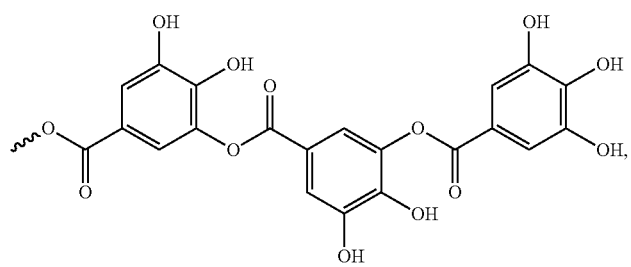
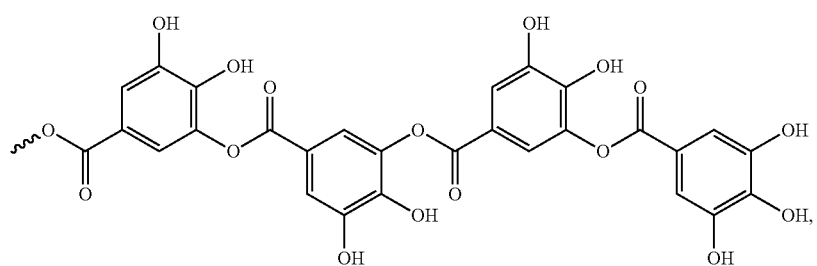
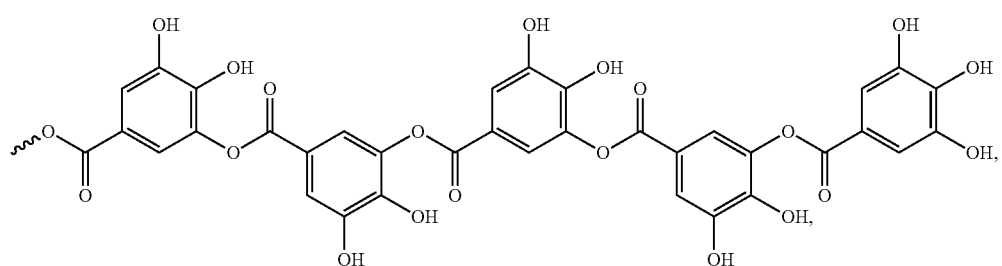

189 190
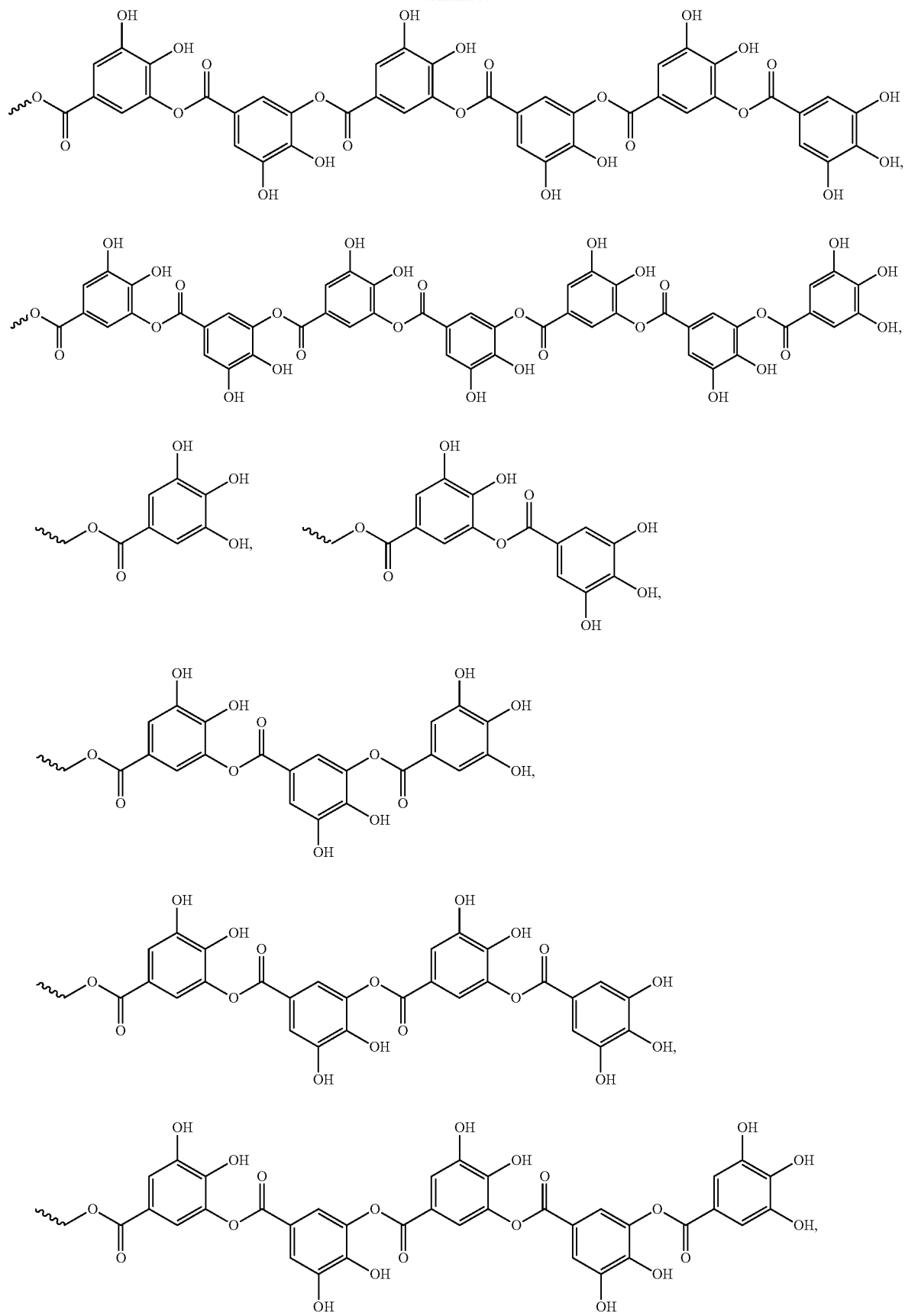

-continued
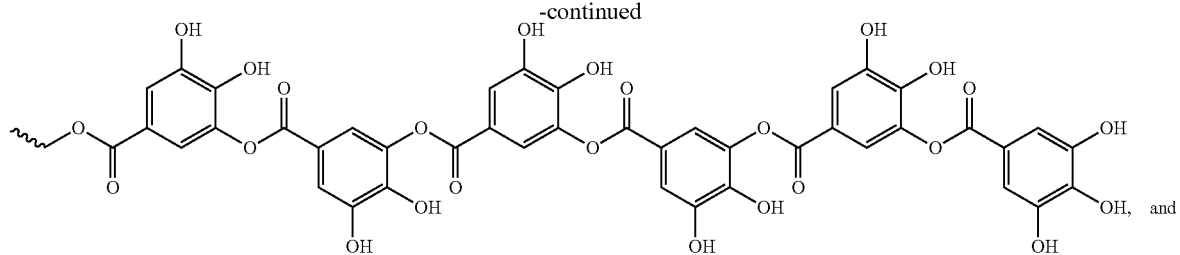
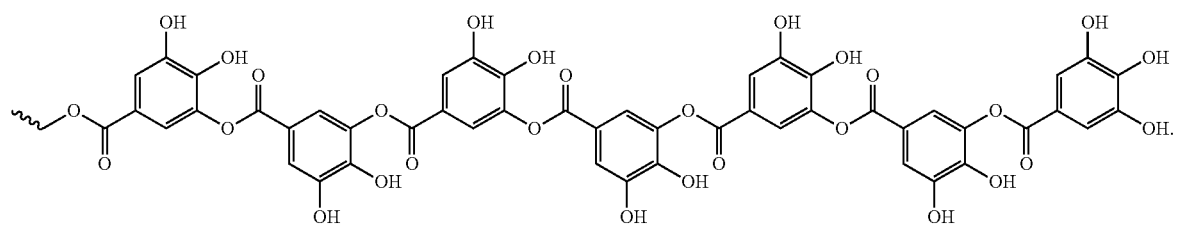
16. The method of claim 15, wherein the compound of Formula (Ij) is Compound 134, 136, 138, 140, 142, 144, 146, or 148.
17. The method of claim 1, wherein the compound is of the Formula (Ic)
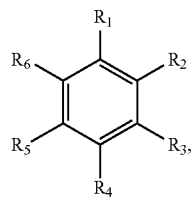
(Ic)
in which $R_1$, $R_2$, $R_3$, $R_4$, $R_5$, and $R_6$ are each, independently, selected from the group consisting of:
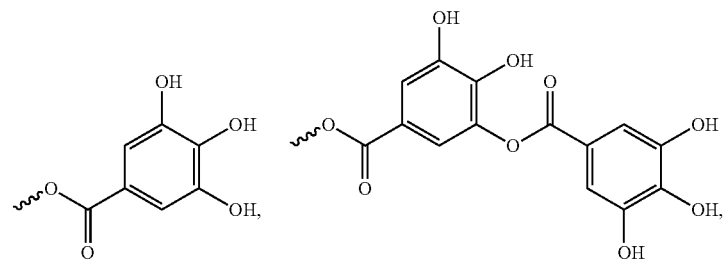
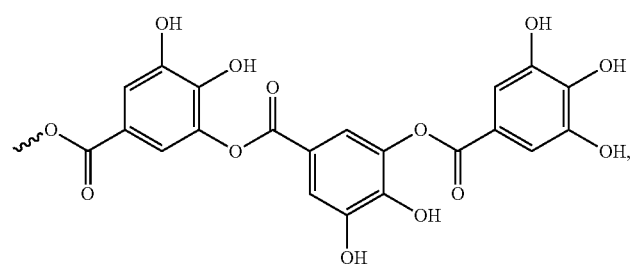
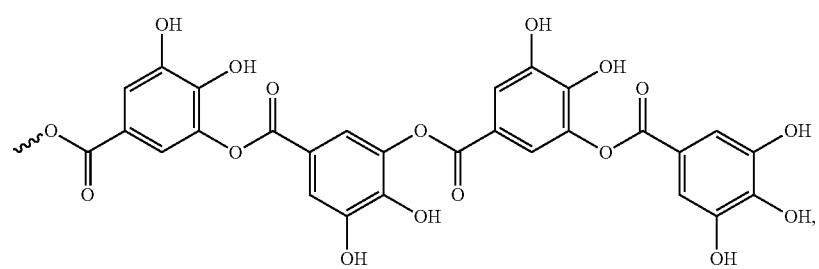

193 194
-continued
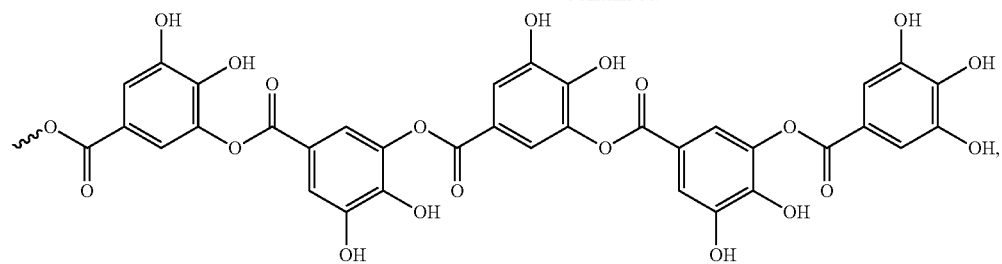
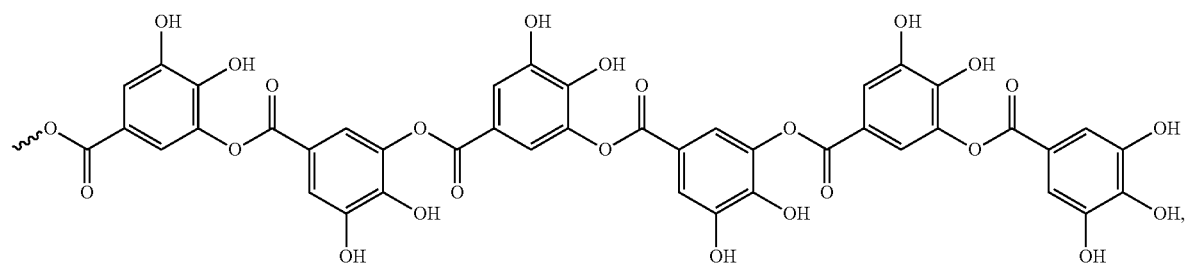
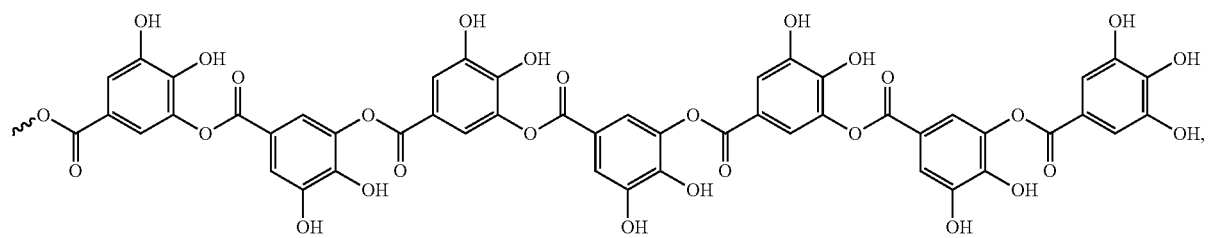
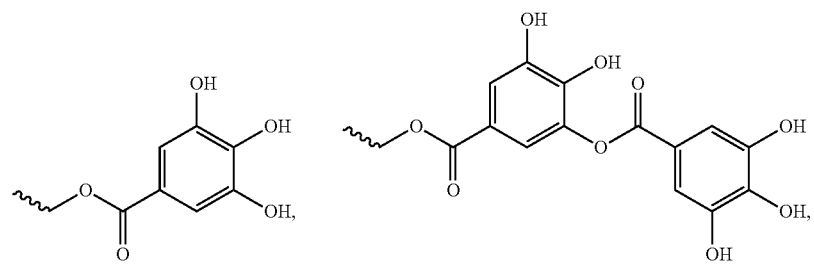
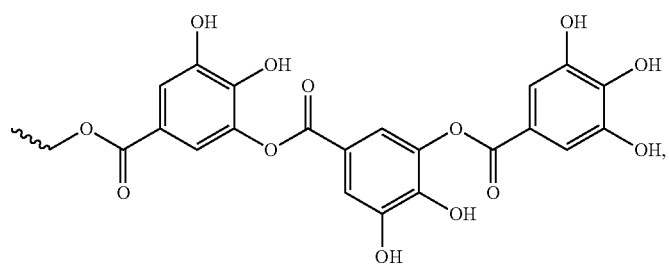
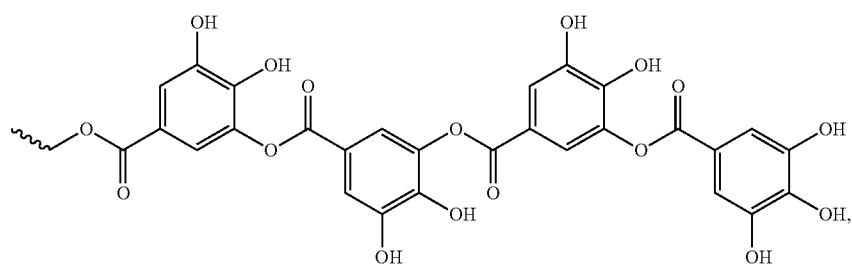

-continued

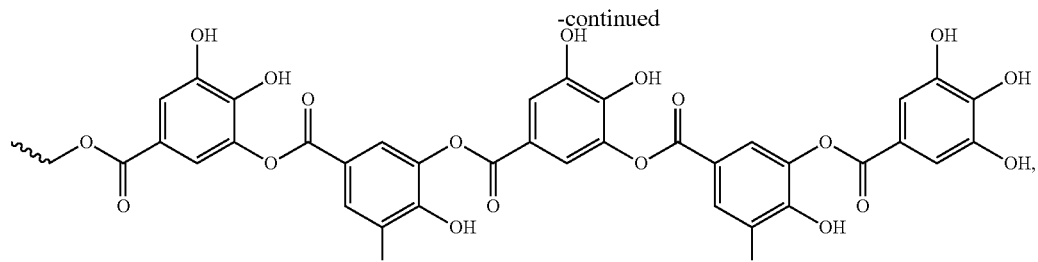

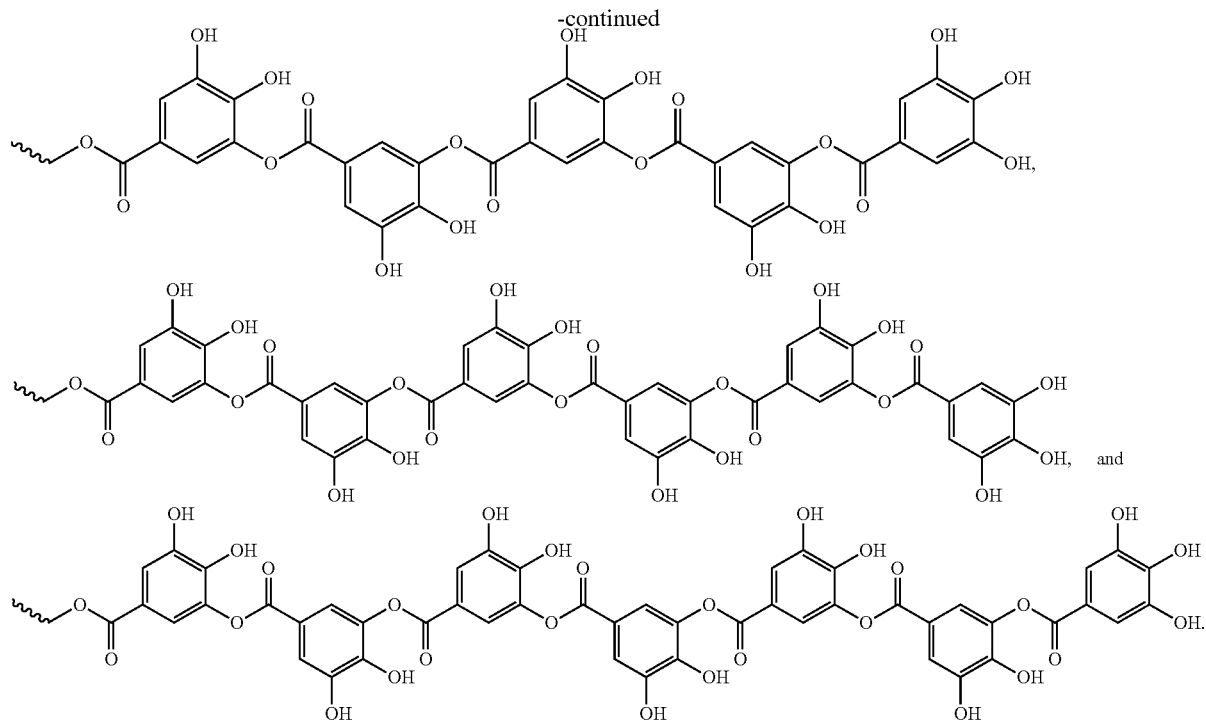

18. The method of claim 1, wherein the composition is a nutraceutical composition, a health food, or a medical food.

19. The method of claim 1, wherein the coronavirus infection is an infection caused by a coronavirus SARS-CoV-2.

20. The method of claim 1, wherein the composition is administered to the subject by oral administration, by injection, by topical administration, or by inhalation.

21. The method of claim 1, wherein the composition is placed in a medical device selected from the group consisting of an inhaler, a nebulizer, a nasal spray, and a vaporization aerosol device for administration to the subject.

22. The method of claim 1, wherein the subject is a human subject.

23. The method of claim 1, wherein the subject is administered the composition continuously or at a frequency of every five minutes to one time every three months.

24. The method of claim 1, wherein the human subject is treated concurrently with, prior to, or subsequent to, one or more additional anti-viral agents.

* * * * *